United States Patent
Kim et al.

(10) Patent No.: US 12,421,207 B2
(45) Date of Patent: Sep. 23, 2025

(54) PYRIMIDINEDIONE-BASED COMPOUNDS AS AXL, C-MET, AND MER INHIBITORS AND METHODS OF USE THEREOF

(71) Applicant: CMG Pharmaceutical Co., Ltd., Seongnam (KR)

(72) Inventors: Jin Sung Kim, Seoul (KR); Young Sang Kim, Goyang (KR); Sungmoo Kim, Seongnam (KR); Ju Hui Jeong, Seongnam (KR); Hyun Sook An, Seongnam (KR); Soojeong Kim, Yongin (KR)

(73) Assignee: CMG Pharmaceutical Co., Ltd., Seongnam (KR)

( * ) Notice: Subject to any disclaimer, the term of this patent is extended or adjusted under 35 U.S.C. 154(b) by 0 days.

(21) Appl. No.: 18/161,678

(22) Filed: Jan. 30, 2023

(65) Prior Publication Data
US 2023/0348423 A1    Nov. 2, 2023

Related U.S. Application Data

(60) Provisional application No. 63/310,840, filed on Feb. 16, 2022.

(51) Int. Cl.
| | |
|---|---|
| *C07D 401/12* | (2006.01) |
| *A61K 31/513* | (2006.01) |
| *A61K 31/53* | (2006.01) |
| *A61K 31/5377* | (2006.01) |
| *A61P 11/06* | (2006.01) |
| *A61P 35/00* | (2006.01) |
| *C07D 401/14* | (2006.01) |
| *C07D 413/14* | (2006.01) |
| *C07D 417/14* | (2006.01) |

(52) U.S. Cl.
CPC .......... *C07D 401/12* (2013.01); *A61K 31/513* (2013.01); *A61K 31/53* (2013.01); *A61K 31/5377* (2013.01); *A61P 11/06* (2018.01); *A61P 35/00* (2018.01); *C07D 401/14* (2013.01); *C07D 413/14* (2013.01); *C07D 417/14* (2013.01)

(58) Field of Classification Search
CPC .. C07D 401/12; C07D 401/14; C07D 413/14; C07D 417/14; C07D 405/14; A61K 31/33; A61K 31/513; A61K 31/53; A61K 31/5377; A61P 11/06; A61P 17/00; A61P 29/00; A61P 35/00
See application file for complete search history.

(56) References Cited

U.S. PATENT DOCUMENTS 11,623,923 B2 *  4/2023  Li ................... A61P 35/00
                                              514/210.18
2021/0371395 A1  12/2021  Li et al.

FOREIGN PATENT DOCUMENTS

| CN | 112457295 A | 3/2021 |
|---|---|---|
| WO | WO 2019/213340 A1 | 11/2019 |

OTHER PUBLICATIONS

Patani et al. (1996) Bioisosterism A rational approach in drug design, Chem. Rev., 96, 3147-3176 (Year: 1996).*
Janssen et al., "A Novel Putative Tyrosine Kinase Receptor with Oncogenic Potential," *Oncogene*, 6(11): 2113-2120 (Nov. 1, 1991).
Jiang et al., "Hepatocyte Growth Factor, its Receptor, and Their Potential Value in Cancer Therapies," *Critical Reviews in Oncology/Hematology*, 53(1): 35-69 (Jan. 2005).
Bauer et al., "Identification of Axl as a Downstream Effector of TGF-β1 During Langerhans Cell Differentiation and Epidermal Homeostasis," *J Exp Med.*, 209(11): 2033-2047 (Oct. 22, 2012).
Holland et al., "Multiple Roles for the Receptor Tyrosine Kinase Axl in Tumor Formation," *Cancer Res.*, 65(20): 9294-9303 (Oct. 15, 2005).
Inoue et al., "Discovery of a Potent and Selective Axl Inhibitor in Preclinical Model," *Bioorganic & Medicinal Chemistry*, 39 (116137), 17 pp. (Jun. 1, 2021).
Korean Intellectual Property Office, International Search Report in International Patent Application No. PCT/IB2023/050810, 4 pp. (May 1, 2023).

(Continued)

*Primary Examiner* — Juliet C Switzer
*Assistant Examiner* — Dawanna Shar-Day White
(74) *Attorney, Agent, or Firm* — Leydig, Voit & Mayer, Ltd.

(57) ABSTRACT

Provided is an inhibitor of AXL, Mer, and/or c-Met of Formula (I) or a pharmaceutically acceptable salt thereof:

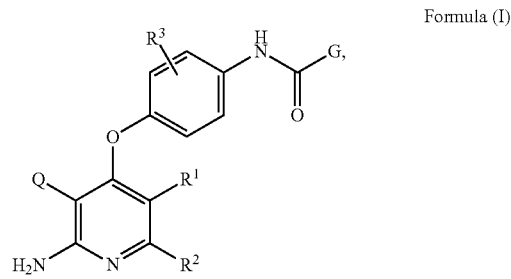

Formula (I)

in which $R^1$, $R^2$, $R^3$, G, and Q are described herein. Further provided is a method of treating or preventing an AXL-, Mer-, and/or c-Met-mediated disease using an effective amount of the compound of Formula (I) or a pharmaceutically acceptable salt thereof. When AXL, MER, and/or c-Met is inhibited, the compound or pharmaceutically acceptable salt thereof can re-sensitize cancer cells, such as non-small cell lung cancer cells, that have grown resistant to an anti-cancer agent.

20 Claims, 34 Drawing Sheets

(56) References Cited

OTHER PUBLICATIONS

Korean Intellectual Property Office, Written Opinion in International Patent Application No. PCT/IB2023/050810, 6 pp. (May 1, 2023).

Li et al., "Axl as a Potential Therapeutic Target in Cancer: Role of Axl in Tumor Growth, Metastasis and Angiogenesis," *Oncogene*, 28(39): 3442-3455 (Oct. 1, 2009).

Liang et al., "AXL Signaling in Primary Sensory Neurons Contributes to Chronic Compression of Dorsal Root Ganglion-Induced Neuropathic Pain in Rats," *Mol Pain.*, 16: 1-13 (Jan.-Dec. 2020).

Mudduluru et al., "Myeloid Zinc Finger 1 Induces Migration, Invasion, and In vivo Metastasis through Axl Gene Expression in Solid Cancer," *Mol Cancer Res.*, 8(2): 159-169 (Feb. 2010).

O'Bryan et al., "axl, a Transforming Gene Isolated from Primary Human Myeloid Leukemia Cells, Encodes a Novel Receptor Tyrosine Kinase," *Mol Cell Biol.*, 11(10): 5016-5031 (Oct. 1991).

Shibata et al., "Axl Receptor Blockade Ameliorates Pulmonary Pathology Resulting from Primary Viral Infection and Viral Exacerbation of Asthma," *J Immunol.*, 192(8): 3569-3581 (Apr. 15, 2014).

Tai et al., "Axl Promotes Cell Invasion by Inducing MMP-9 Activity Through Activation of NF-kappaB and Brg-1," *Oncogene*, 27(29): 4044-4055 (Jul. 3, 2008).

Zhang et al., "Discovery of a Pyrimidinedione Derivative as a Potent and Orally Bioavailable Axl Inhibitor," *Journal of Medicinal Chemistry*, 64 (7): 3956-3975 (Mar. 18, 2021).

\* cited by examiner

PYRIMIDINEDIONE-BASED COMPOUNDS AS AXL, C-MET, AND MER INHIBITORS AND METHODS OF USE THEREOF

CROSS-REFERENCE TO PRIOR APPLICATIONS

This application claims benefit to U.S. Provisional Patent Application No. 63/310,840, filed Feb. 16, 2022, which is hereby incorporated by reference in its entirety.

BACKGROUND OF THE INVENTION

Receptor tyrosine kinases (RTKs) are transmembrane proteins that transduce signals from the extracellular environment to the cytoplasm and nucleus to regulate normal cellular processes, including survival, growth, differentiation, adhesion, and mobility. Over expression or activation of RTKs has been implicated in the pathogenesis of various cancers, linked with cell transformation, tumor formation, and metastasis.

TAM receptors are expressed in various cells and tissues. AXL is a member of the TAM RTK family, which also includes TYR03 and Mer, originally identified as a transforming gene expressed in cells from patients with chronic myelogenous leukemia (O'Bryan et al, Mol. Cell Biol., 1991, 11, 5016-5031) and chronic myeloproliferative disorder (Janssen et al., Oncogene, 1991, 6 (11), 2113-2120). AXL contributes to at least three of the six fundamental mechanisms of malignancy in cancer, by promoting cancer cell migration and invasion, involving in tumor angiogenesis, and facilitating cancer cell survival and tumor growth (Holland et al., Cancer Res., 2005, 65 (20), 9294-9303, Tai et al., Oncogene, 2008, 27, 4044-4055; Li et al., Oncogene, 2009, 28, 3442-3455; and Mudduluru et al., Mol. Cancer Res., 2010, 8 (2), 159-169).

In addition, over expression of AXL also has been implicated in asthma, pain, and dermatitis (Shibata et al., J Immunol, 2014, 192 (8), 3569-3581; Liang et al., Molecular Pain, 2020, 16, 1-13; and Bauer et al., J Exp Med, 2012, 209 (11), 2033-2047).

Over expression of c-MET is associated with the development and poor prognosis of a wide range of solid tumors, including breast, prostate, thyroid, lung, stomach, colorectal, pancreatic, kidney, ovarian, and uterine carcinoma, malignant glioma, uveal melanoma, and osteo- and soft-tissue sarcoma (Jiang et al, Critical Reviews in Oncology Hematology, 2005, 53 (1), 35-69).

Given the roles of AXL, Mer, and c-MET in a variety of diseases, there remains a need for the development of agents that act as inhibitors of AXL, Mer, and/or C-Met to therapeutically treat such diseases.

BRIEF SUMMARY OF THE INVENTION

The present invention provides a compound of Formula (I) or a pharmaceutically acceptable salt thereof:

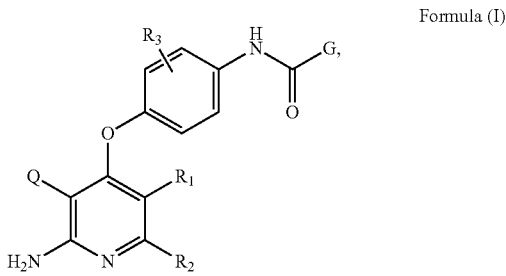

Formula (I)

in which $R^1$, $R^2$, $R^3$, G, and Q are as described herein.

The invention further provides a method of treating or preventing an AXL-, Mer-, and/or c-Met-mediated disease in a subject comprising administering to the subject an effective amount of the compound of Formula (I) or a pharmaceutically acceptable salt thereof.

The invention provides a method of inhibiting an AXL, Mer, and/or c-Met enzyme in a cell comprising administering a compound of Formula (I) or a pharmaceutically acceptable salt thereof to the cell.

pyridin-4-yloxy)-3-fluorophenyl)-2,4-dioxo-1,2,3,4-tetrahydropyrimidine-5-carboxamide in an aspect of the invention.

Figure 66:
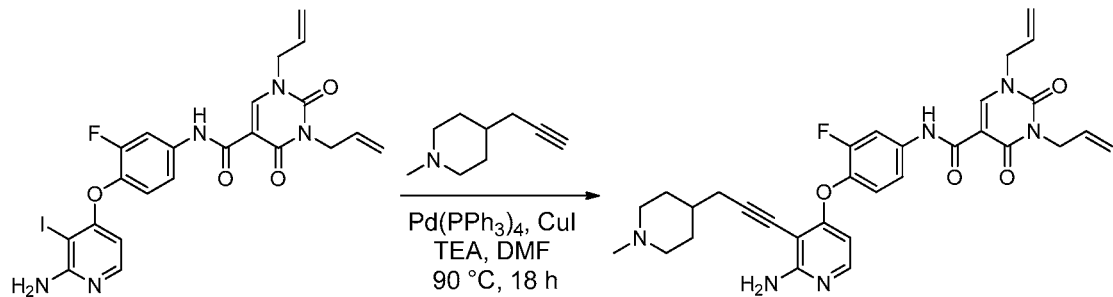

FIG. 66 is a chemical synthesis of 1,3-diallyl-N-(4-(2-amino-3-(3-(1-methylpiperdin-4-yl)prop-1-ynyl)pyridin-4-yloxy)-3-fluorophenyl)-2,4-dioxo-1,2,3,4-tetrahydropyrimidine-5-carboxamide in an aspect of the invention.

Figure 67:
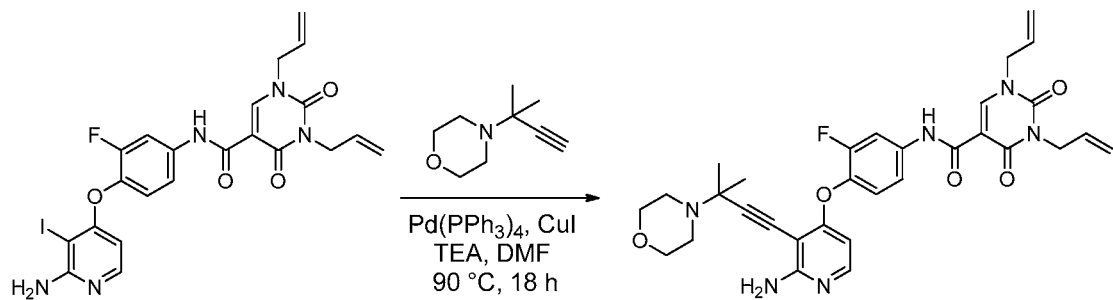

FIG. 67 is a chemical synthesis of 1,3-diallyl-N-(4-(2-amino-3-(3-methyl-3-morpholinobut-1-ynyl)pyridin-4-yloxy)-3-fluorophenyl)-2,4-dioxo-1,2,3,4-tetrahydropyrimidine-5-carboxamide in an aspect of the invention.

Figure 68:
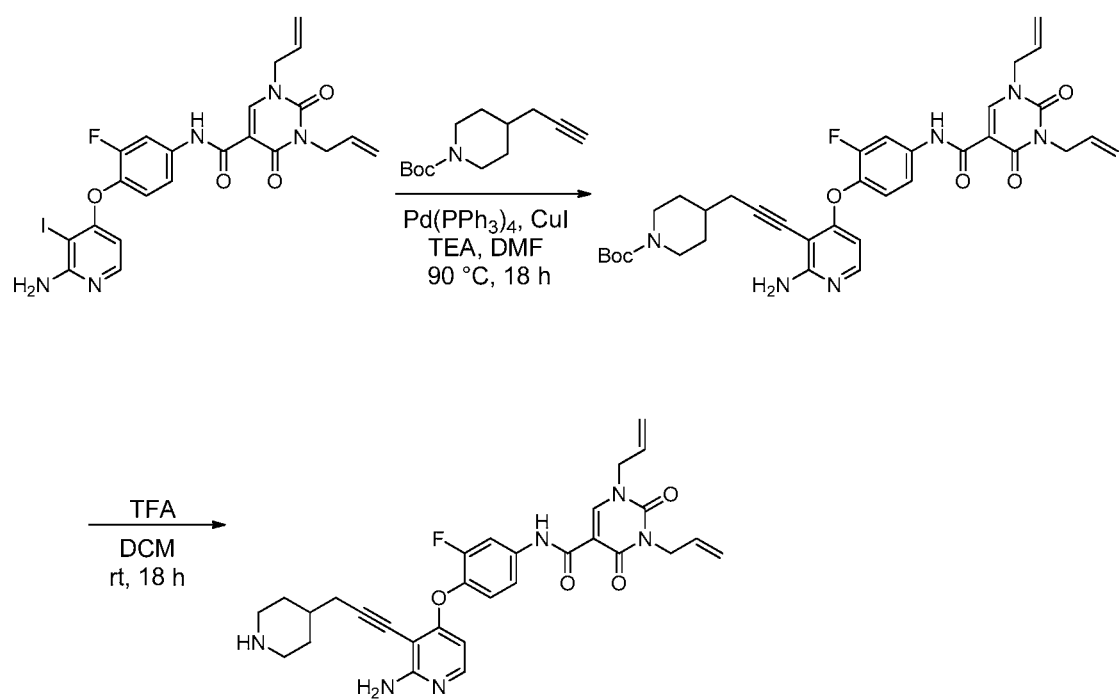

FIG. 68 is a chemical synthesis of 1,3-dialyl-N-(4-(2-amino-3-(3-(piperidin-4-yl)prop-1-ynyl)pyridin-4-yloxy)-3-fluorophenyl)-2,4-dioxo-1,2,3,4-tetrahydropyrimidine-5-carboxamide in an aspect of the invention.

DETAILED DESCRIPTION OF THE INVENTION

A compound of Formula (I) or a pharmaceutically acceptable salt thereof:

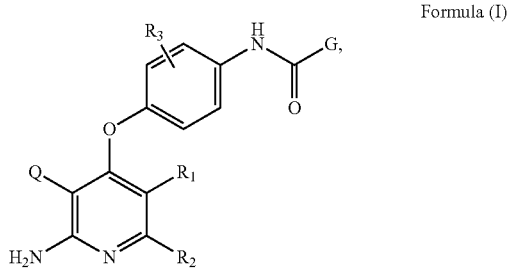

Formula (I)

wherein:
$R^1$ is H, alkyl, haloalkyl, halo, or CN;
$R^2$ is H, alkyl, haloalkyl, halo, or CN;
$R^3$ is H or halo;
Q is H, CN, halo, alkyl, alkenyl, alkynyl, cycloalkyl, heterocyclyl, heteroaryl, or aryl, wherein said alkenyl or alkynyl is selected from the group consisting of
—CH=CR$^4$(CX')$_m$(CH$_2$)$_n$NR$^5$R$^6$, —C≡C(CX')$_m$(CH$_2$)$_n$NR$^5$R$^6$,
—CH=CR$^4$(CX')$_m$(CH$_2$)$_n$CHR$^5$R$^6$, —C≡C(CX')$_m$(CH$_2$)$_n$CHR$^5$R$^6$,
—CH=CR$^4$(CX')$_m$(CH$_2$)$_n$NR$^7$OR$^8$, and —C≡C(CX')$_m$(CH$_2$)$_n$NR$^7$OR$^8$;
wherein
$R^4$ is hydrogen or halo;
X' is H$_2$, (C$_{1-6}$ alkyl)$_2$, or =O;
m is 0 or 1;
n is 0 or 1-3;
—NR$^5$R$^6$ either forms a 4-7 membered heterocyclic ring or does not form a ring structure, the heterocyclic ring being either heteroaryl or heterocyclyl ring,
when —NR$^5$R$^6$ forms a 4-7 membered heterocyclic ring, the 4-7 membered heterocyclic ring includes an optional second heteroatom in addition to the nitrogen of —NR$^5$R$^6$ and is optionally substituted with one or more substituent groups independently selected from the group consisting of linear C$_1$-C$_6$ alkyl, branched C$_3$-C$_6$ alkyl, hydroxy, C$_1$-C$_6$ alkoxyalkyl, carboxylic acid, linear C$_1$-C$_4$ alkyl carboxylic acid, and branched C$_3$-C$_4$ alkyl carboxylic acid;
when —NR$^5$R$^6$ does not form a ring structure, R$^5$ is selected from the group consisting of hydrogen, linear C$_1$-C$_6$ alkyl, and branched C$_3$-C$_6$ alkyl, and R$^6$ is selected from the group consisting of hydrogen, linear C$_1$-C$_6$ alkyl optionally substituted with at least one fluoro or at least one hydroxy, branched C$_3$-C$_6$ alkyl optionally substituted with at least one fluoro or at least one hydroxy, and cycloalkyl optionally substituted with at least one fluoro or at least one hydroxy;
—CHR$^5$R$^6$ either forms a 4-7 membered heterocyclic ring or does not form a ring structure, the heterocyclic ring being either heteroaryl or heterocyclyl ring,
when —CHR$^5$R$^6$ forms a 4-7 membered heterocyclic ring, the 4-7 membered heterocyclic ring includes one or two heteroatoms and is optionally substituted with one or more substituent groups independently selected from the group consisting of linear C$_1$-C$_6$ alkyl, branched C$_3$-C$_6$ alkyl, hydroxy, C$_1$-C$_6$ alkoxyalkyl, carboxylic acid, linear C$_1$-C$_4$ alkyl carboxylic acid, and branched C$_3$-C$_4$ alkyl carboxylic acid;
when —CHR$^5$R$^6$ does not form a ring structure, R$^5$ is selected from the group consisting of hydrogen, linear C$_1$-C$_6$ alkyl, and branched C$_3$-C$_6$ alkyl, and R$^6$ is selected from the group consisting of hydrogen, linear C$_1$-C$_6$ alkyl optionally substituted with at least one fluoro or at least one hydroxy, branched C$_3$-C$_6$ alkyl optionally substituted with at least one fluoro or at least one hydroxy, and cycloalkyl optionally substituted with at least one fluoro or at least one hydroxy;
—NR$^7$OR$^8$ does not form a ring structure, R$^7$ is selected from the group consisting of hydrogen, linear C$_1$-C$_6$ alkyl, and branched C$_3$-C$_6$ alkyl, and R$^1$ is selected from the group consisting of hydrogen, linear C$_1$-C$_6$ alkyl optionally substituted with at least one fluoro, hydroxy, or alkoxy group, branched C$_3$-C$_6$ alkyl optionally substituted with at least one fluoro, hydroxy, or alkoxy group, and cycloalkyl optionally substituted with at least one fluoro, hydroxy, or alkoxy group;
G is

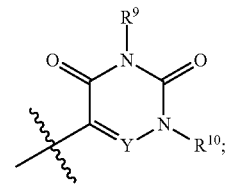

wherein
$R^9$ is H, alkyl, substituted alkyl, alkenyl, substituted alkenyl, alkynyl, substituted alkynyl, cycloalkyl, aryl, substituted aryl, heteroaryl, substituted heteroaryl, heterocyclyl or heteroarylalkyl, where the heteroaryl group of heteroarylalkyl may be substituted or unsubstituted;
$R^{10}$ is H, aryl, substituted aryl, heteroaryl, substituted heteroaryl, heterocyclyl, alkyl or cycloalkyl, cycloalkylalkyl, alkenyl or alkynyl, where alkyl, alkenyl or cycloalkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, substituted heteroaryl, carboxyl, oxo, carbamoyl, alkylcarbamoyl, dialkylcarbamoyl, where the alkyl groups of dialkylcarbamoyl may be the same or different and heterocyclylcarbonyl; and Y is N, C—H, or C-alkyl.

The pyrimidinedione-based inhibitors are useful in treating a variety of diseases and disorders associated with AXL, Mer, and/or c-Met without the need for specialized mode of administration.

In some aspects of Formula (I), both $R^1$ and $R^2$ are hydrogen.

In some aspects of Formula (I), $R^3$ is a halo.

In some aspects of Formula (I), Q is CN, halo, optionally substituted phenyl, optionally substituted heterocyclyl, or an alkenyl or alkynyl moiety selected from the group consisting of —CH=CR$^4$(CX')$_m$(CH$_2$)$_n$NR$^5$R$^6$, —C≡C(CX')$_m$(CH$_2$)$_n$NR$^5$R$^6$, —CH=CR$^4$(CX')$_m$(CH$_2$)$_n$CHR$^5$R$^6$, —C≡C(CX')$_m$(CH$_2$)$_n$CHR$^5$R$^6$, —CH=CR$^4$(CX')$_m$(CH$_2$)$_n$NR$^7$OR$^8$, and —C≡C(CX')$_m$(CH$_2$)$_n$NR$^7$OR$^8$, wherein $R^4$ is hydrogen or halo;

X' is H$_2$, (C$_{1-6}$ alkyl)$_2$, or =O;

m is 0 or 1;

n is 0 or 1;

—NR$^5$R$^6$ is morpholinyl, piperazinyl, or piperidinyl, each of which is optionally substituted with one or more substituent groups independently selected from the group consisting of a nitrogen protecting group, alkyl, hydroxy, alkoxy, and alkoxyalkyl, —CHR$^5$R$^6$ is tetrahydropyranyl, morpholinyl, piperazinyl, or piperidinyl, each of which is optionally substituted with one or more substituent groups independently selected from the group consisting of a nitrogen protecting group, alkyl, hydroxy, alkoxy, and alkoxyalkyl, $R^7$ is selected from the group consisting of hydrogen, linear C$_1$-C$_6$ alkyl, and branched C$_3$-C$_6$ alkyl, and $R^8$ is selected from the group consisting of linear C$_1$-C$_6$ alkyl optionally substituted with at least one alkoxy group and branched C$_3$-C$_6$ alkyl optionally substituted with at least one alkoxy group.

In some aspects of Formula (I), $R^9$ is phenyl substituted with alkyl, haloalkyl, halogen, and/or CN; and either (i) Y is C—H or (ii) Y is N.

In some aspects, the compound of Formula (I) is a compound Formula (Ib):

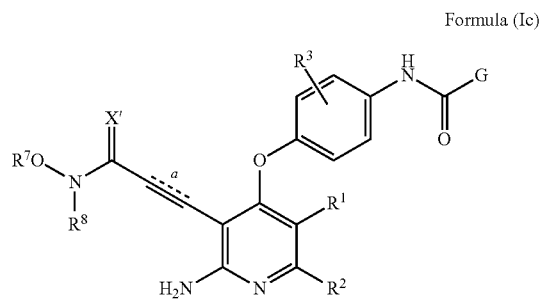

Formula (Ib)

wherein ⩵ is —C≡C— or —CH=CH—.

In some aspects of Formula (Ib), both $R^1$ and $R^2$ are hydrogen.

In some aspects of Formula (Ib), $R^3$ is halo.

In some aspects of Formula (Ib), X' is H$_2$, (C$_{1-6}$ alkyl)$_2$, or =O; and —NR$^5$R$^6$ is morpholinyl, piperazinyl, or piperidinyl, each of which is optionally substituted with one or more substituent groups independently selected from the group consisting of a nitrogen protecting group (e.g., tert-butyloxycarbonyl (Boc), fluorenylmethyloxycarbonyl (Fmoc), carboxybenzyl (Cbz), acetyl, trifluoroacetamide, phthalimide, benzyl, trityl, benzylideneamine, or tosyl), alkyl, hydroxy, alkoxy, and alkoxyalkyl.

In some aspects of Formula (Ib), $R^9$ is phenyl substituted with alkyl, haloalkyl, halo, and/or CN; and either (i) Y is C—H or (ii) Y is N.

In some aspects, the compound of Formula (I) is a compound Formula (Ic):

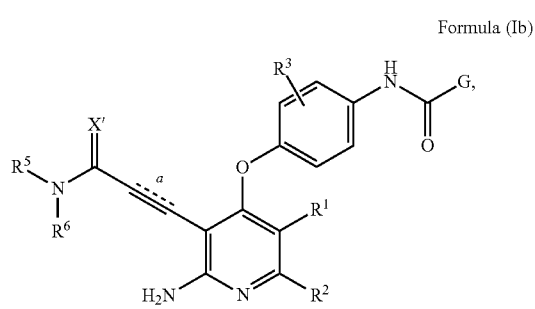

Formula (Ic)

wherein ⩵ is —C≡C— or —CH=CH—.

In some aspects of Formula (Ic), both $R^1$ and $R^2$ are hydrogen.

In some aspects of Formula (Ic), $R^3$ is a halo.

In some aspects of Formula (Ic), X' is H$_2$, (C$_{1-6}$ alkyl)$_2$, or =O; $R^7$ is selected from the group consisting of linear C$_1$-C$_6$ alkyl and branched C$_3$-C$_6$ alkyl, and $R^1$ is selected from the group consisting of linear C$_1$-C$_6$ alkyl and branched C$_3$-C$_6$ alkyl.

In some aspects of Formula (Ic), $R^9$ is phenyl substituted with alkyl, haloalkyl, halo, and/or CN; and either (i) Y is C—H or (ii) Y is N.

Exemplary compounds of Formula (I), including compounds of Formulas (Ib) and (Ic), are set forth below in the examples. Pharmaceutically acceptable salts of these exemplary compounds are also envisioned. In particular, the compound of Formula (I) is selected from

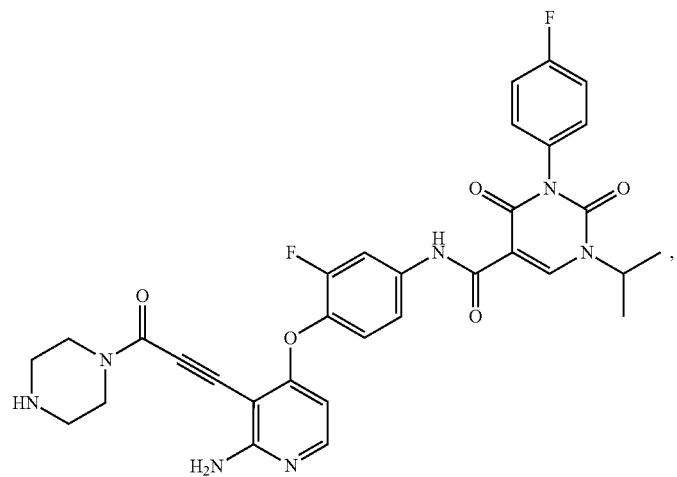
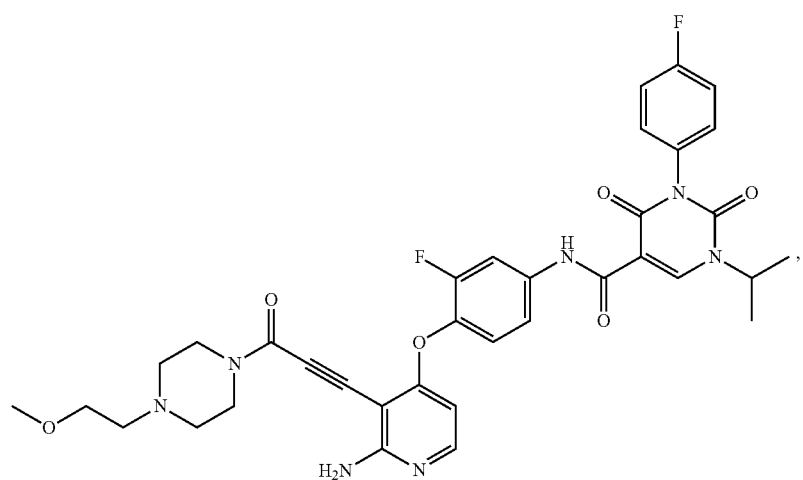
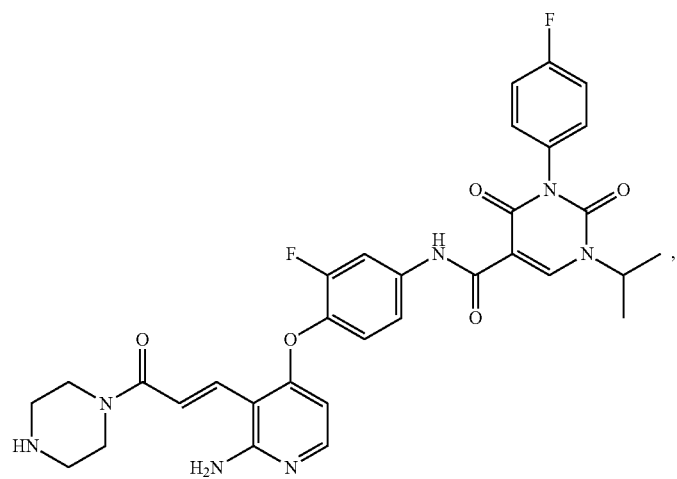

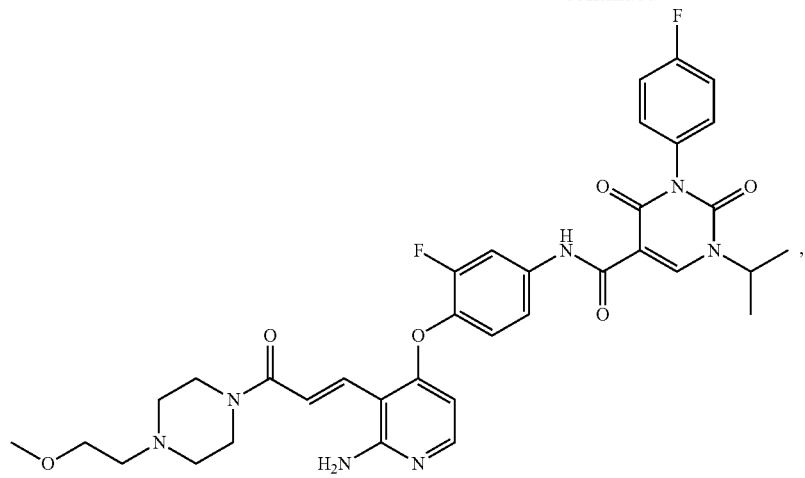
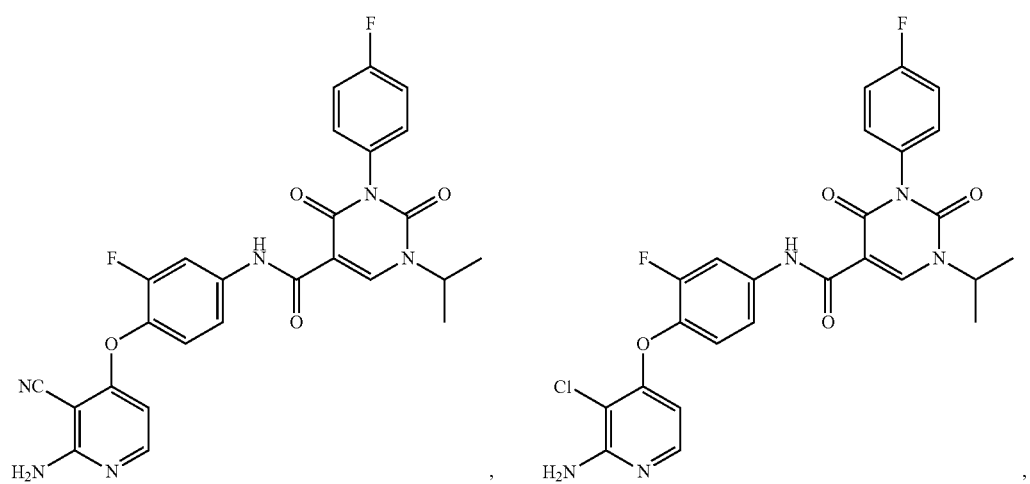
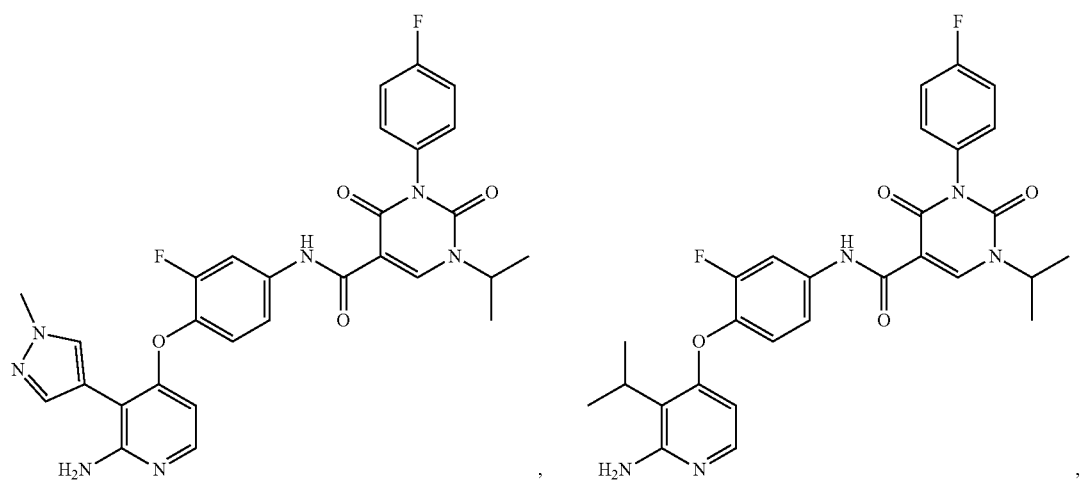

-continued
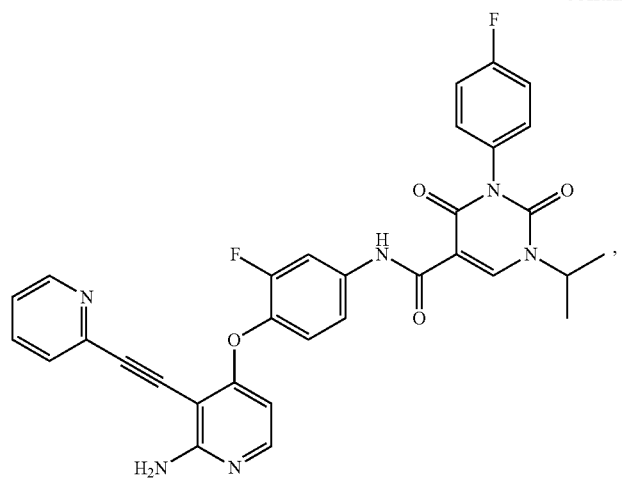
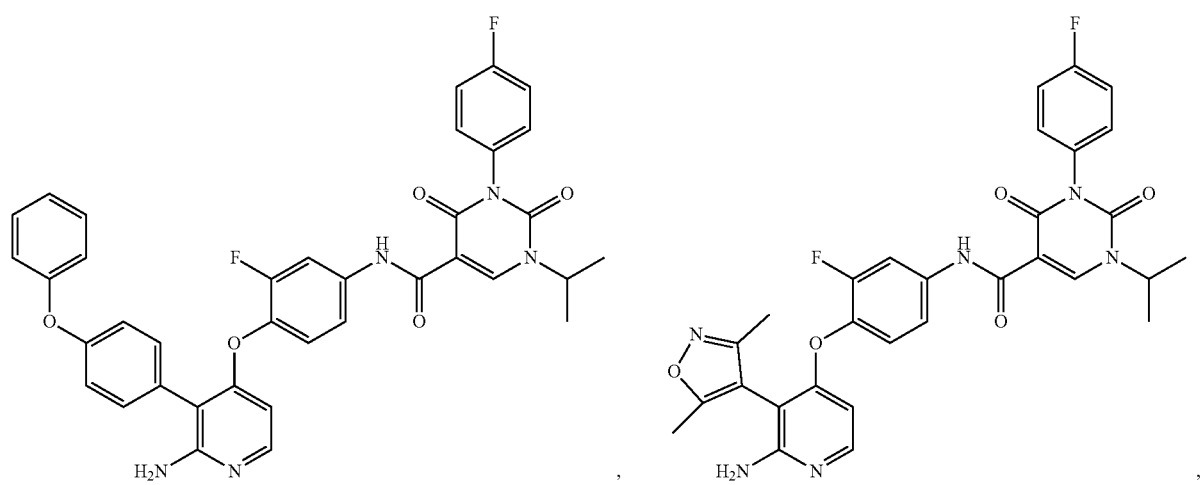
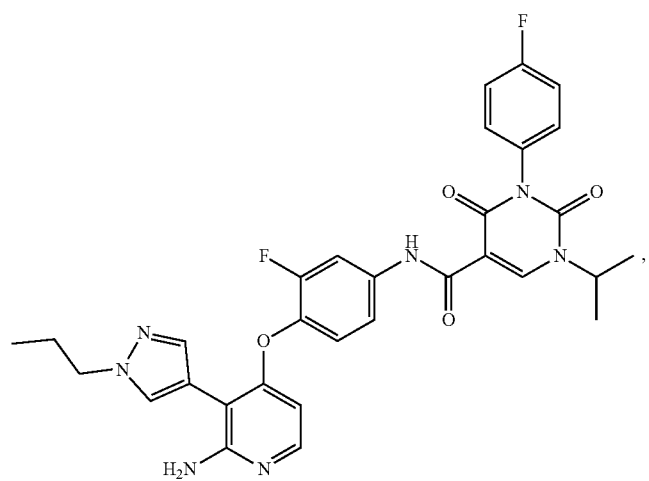

-continued
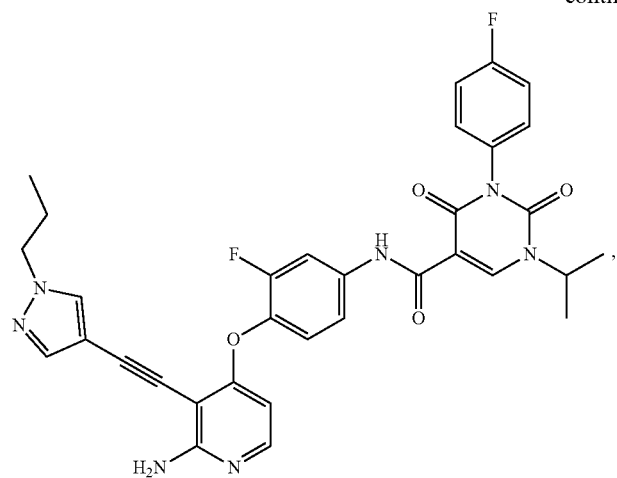
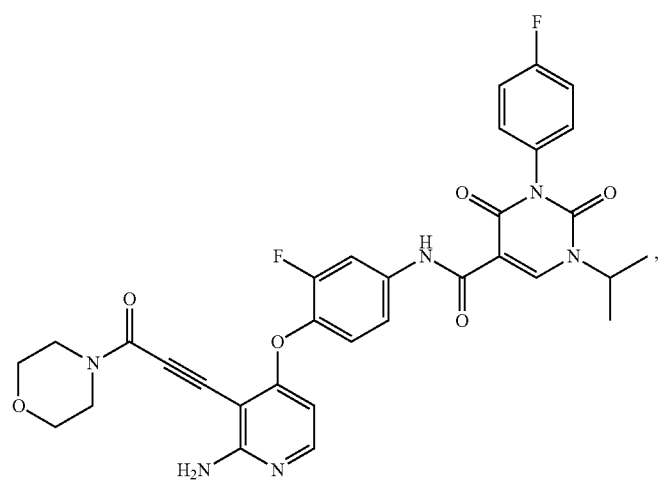
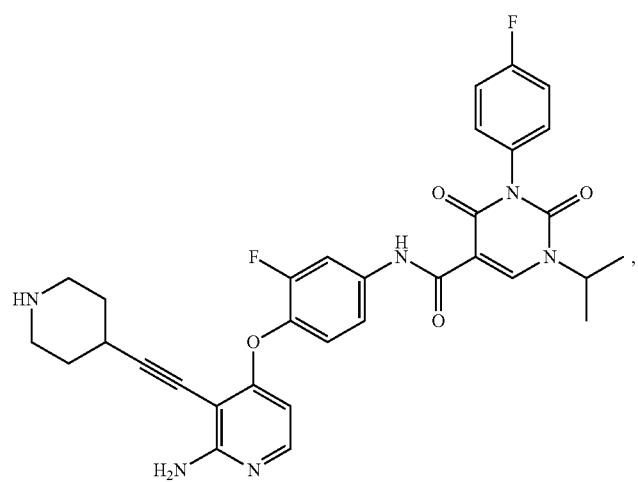

-continued
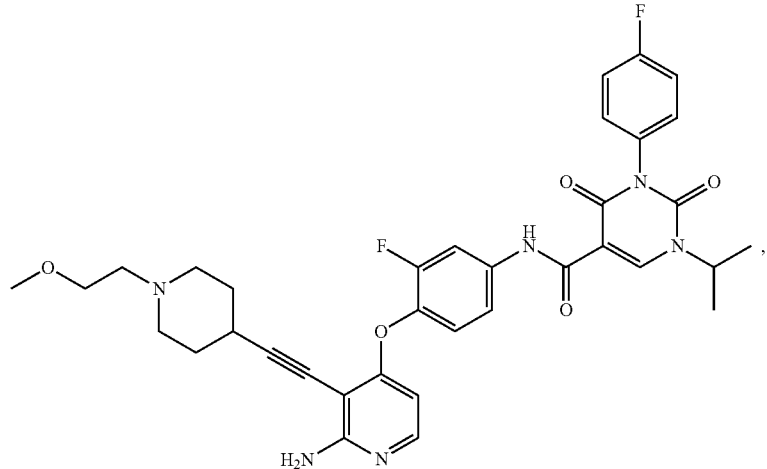
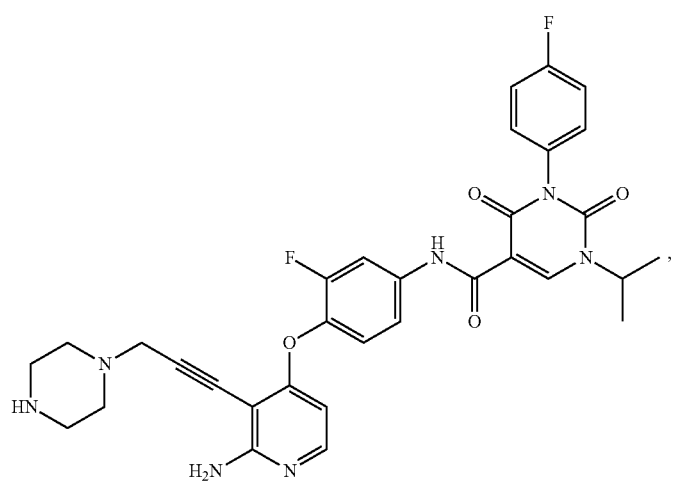
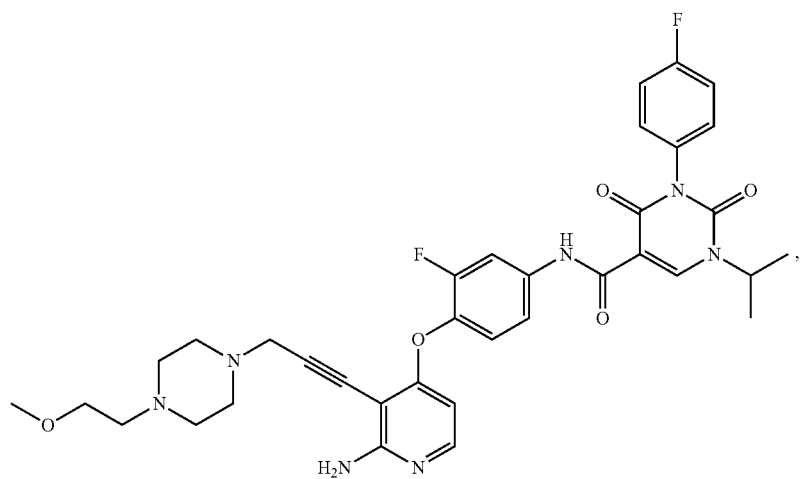

-continued
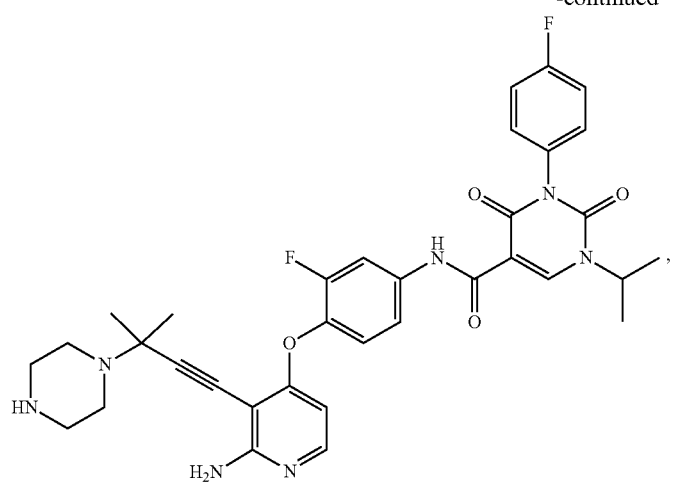
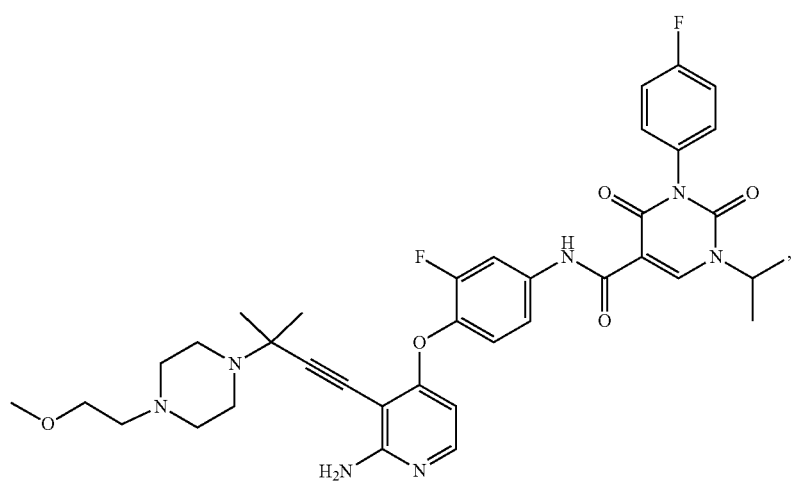
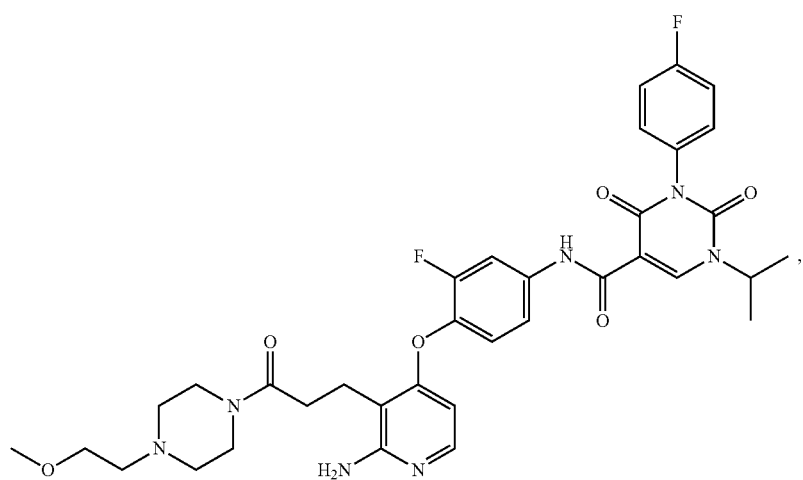

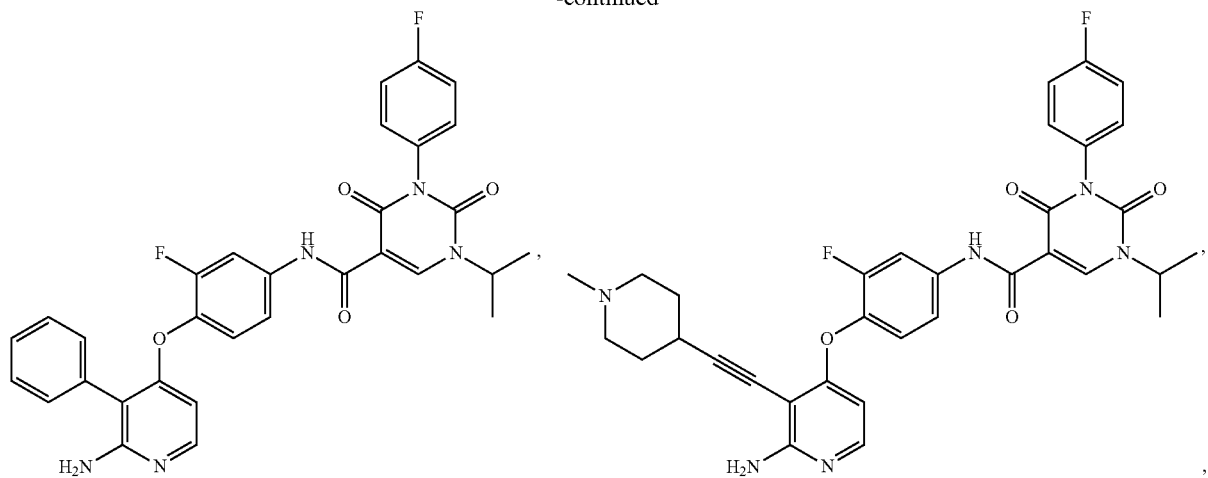
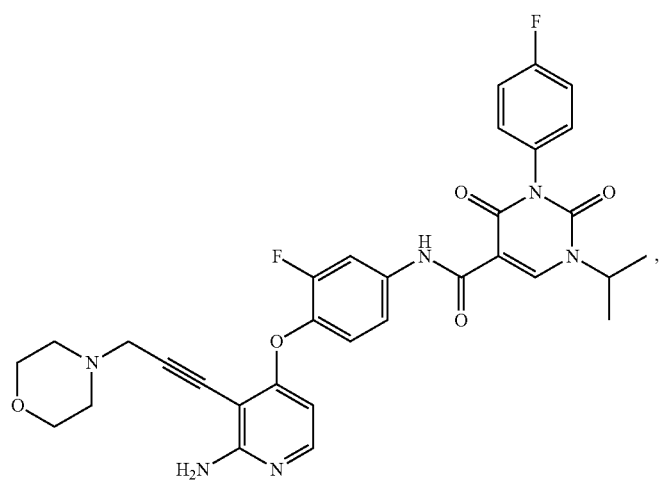
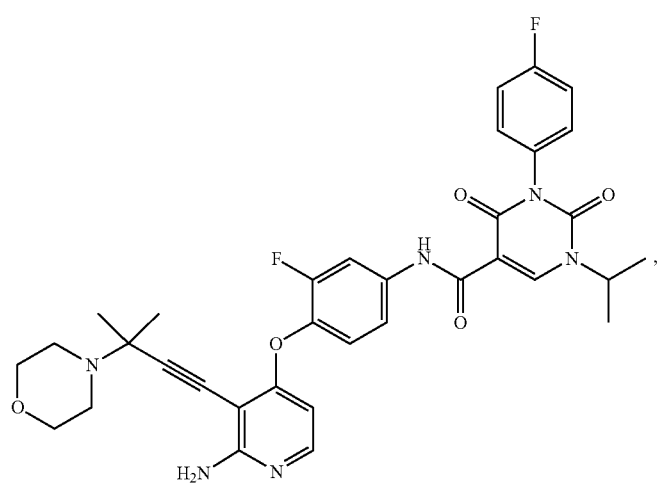

-continued
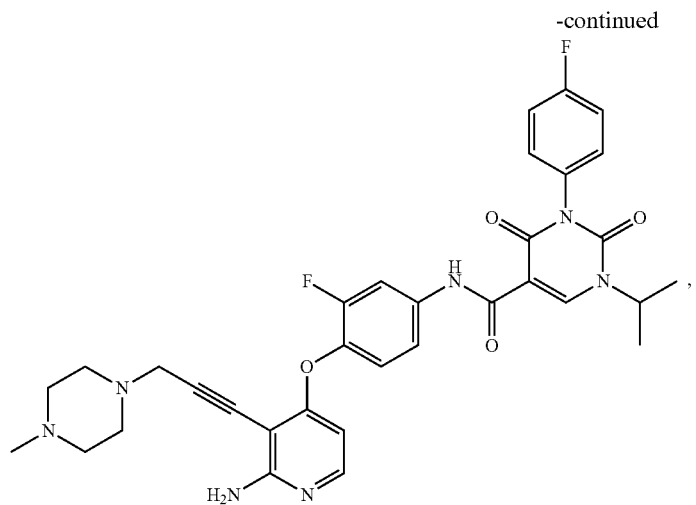
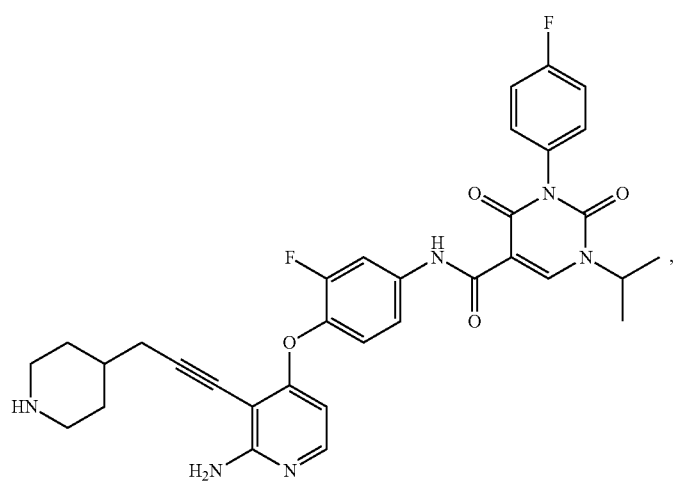
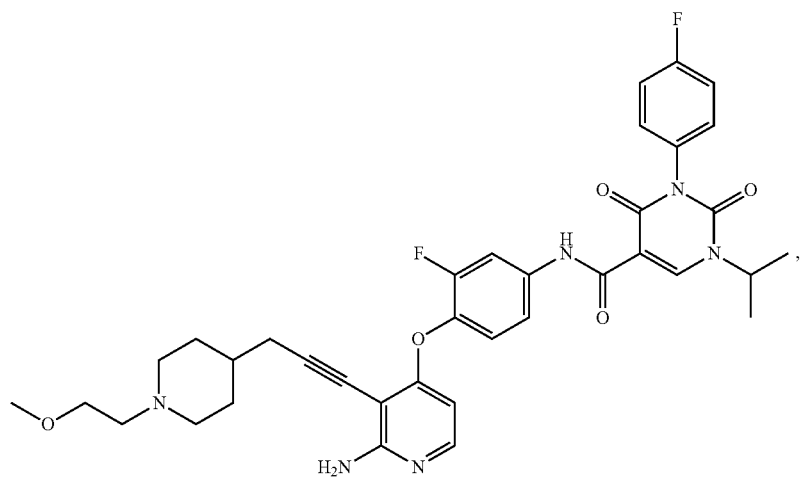

-continued
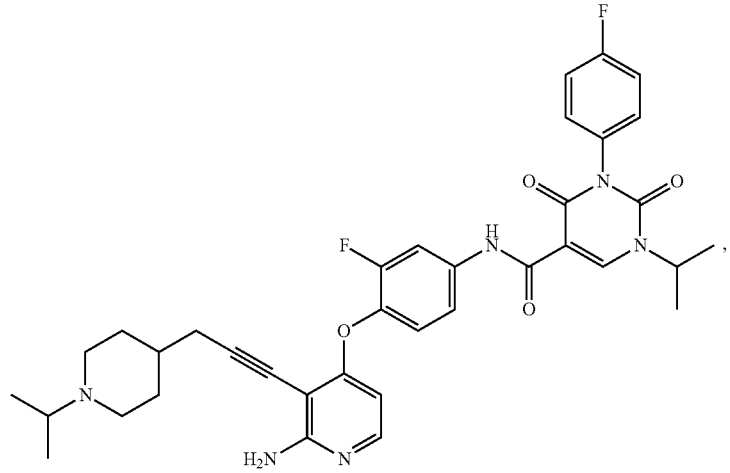
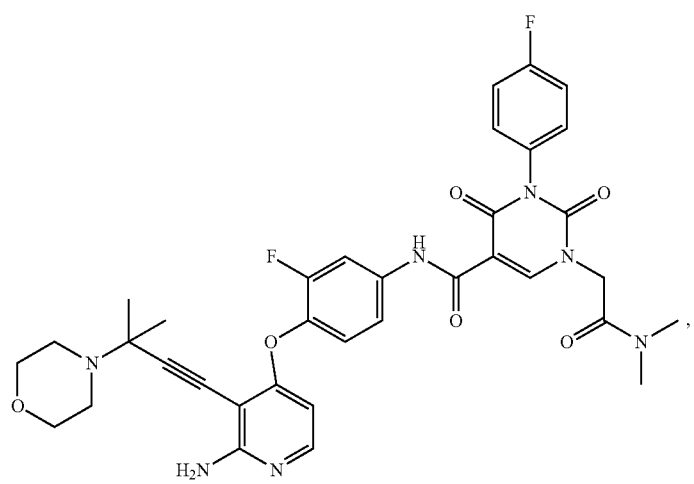
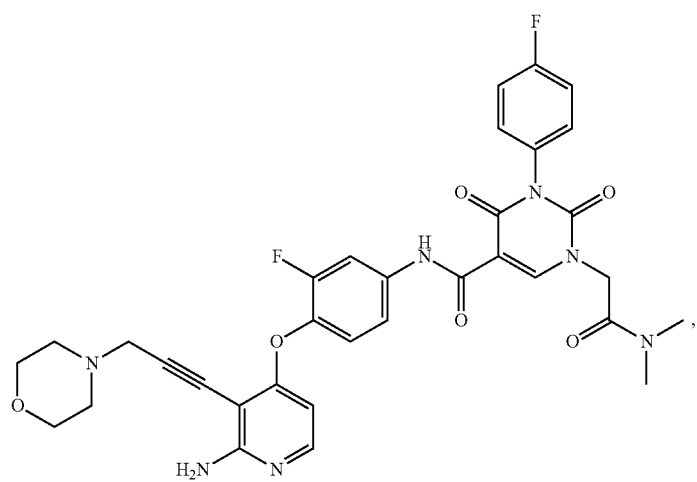

-continued
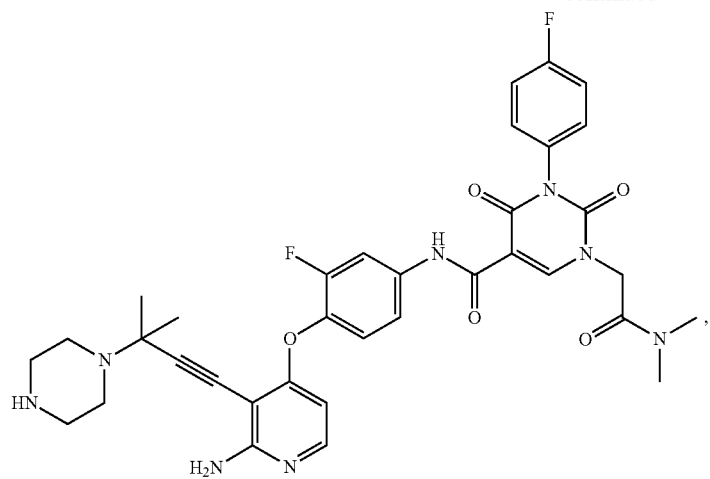
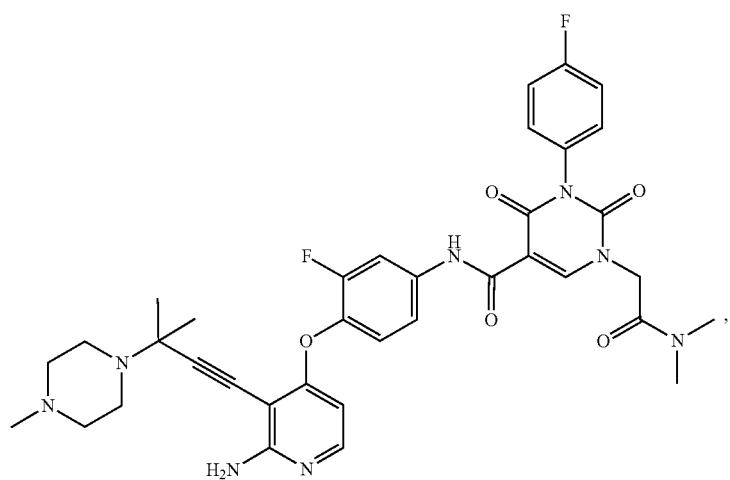
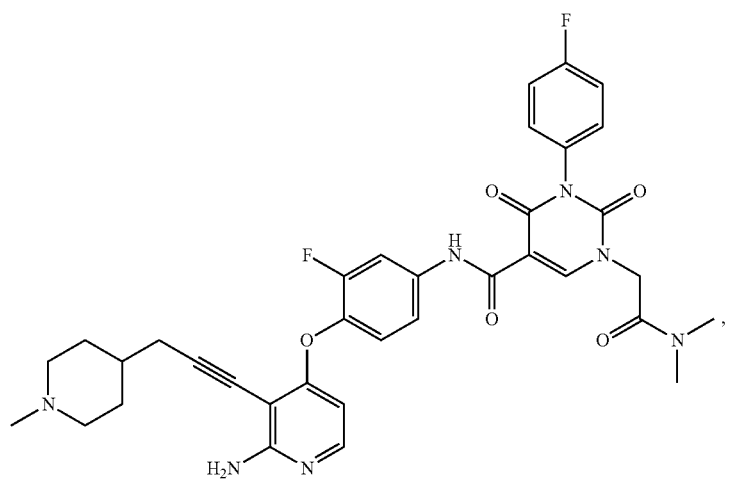

-continued
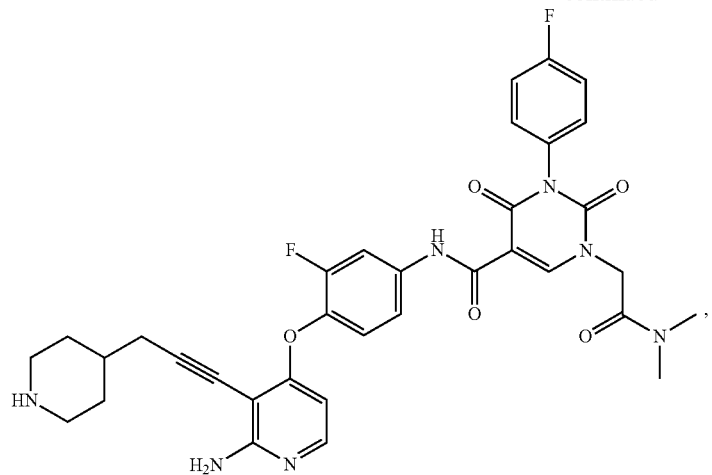
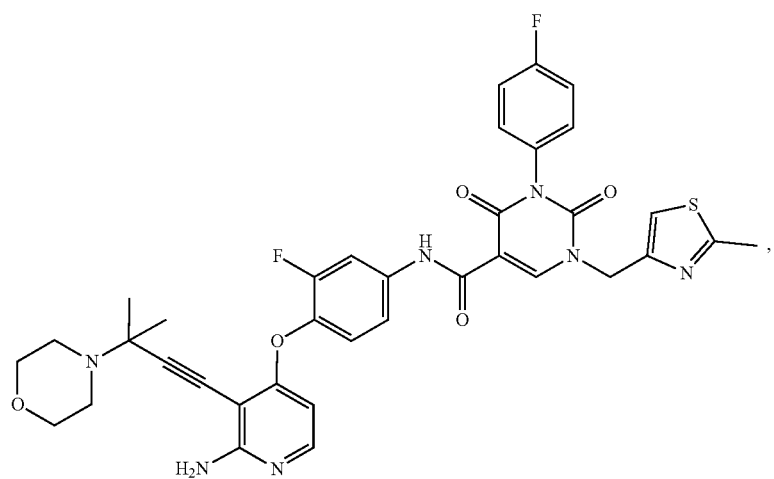
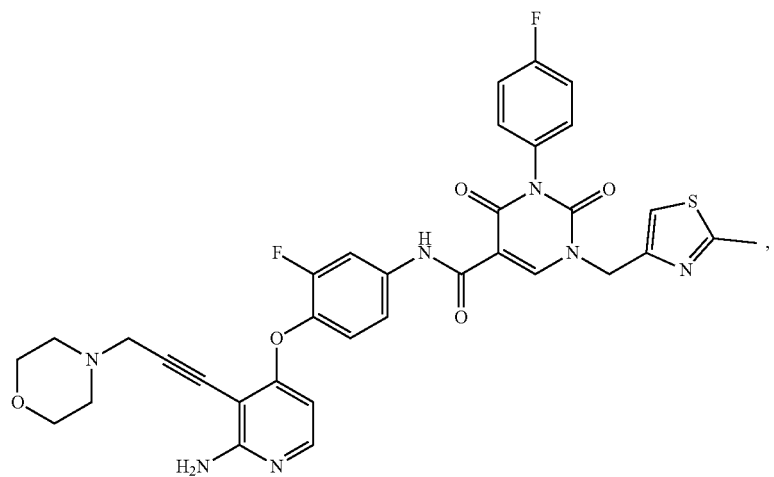

-continued
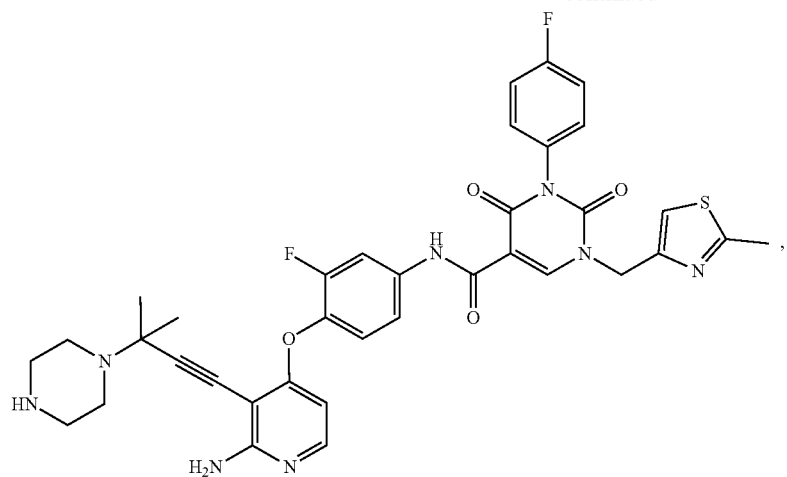
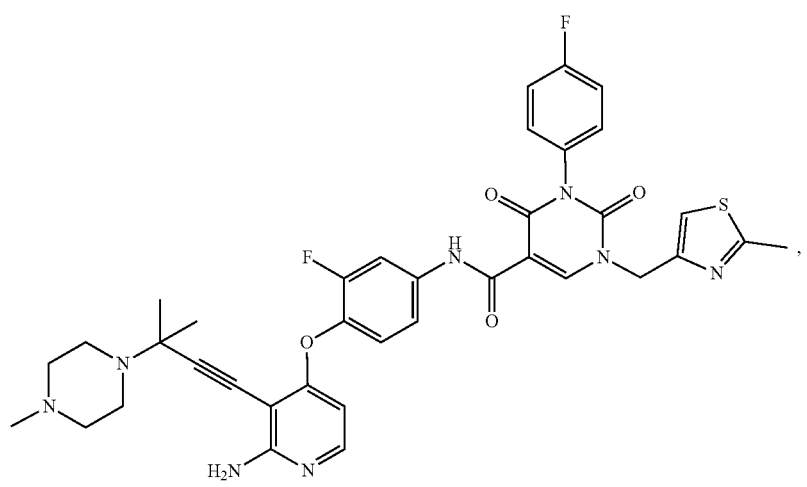
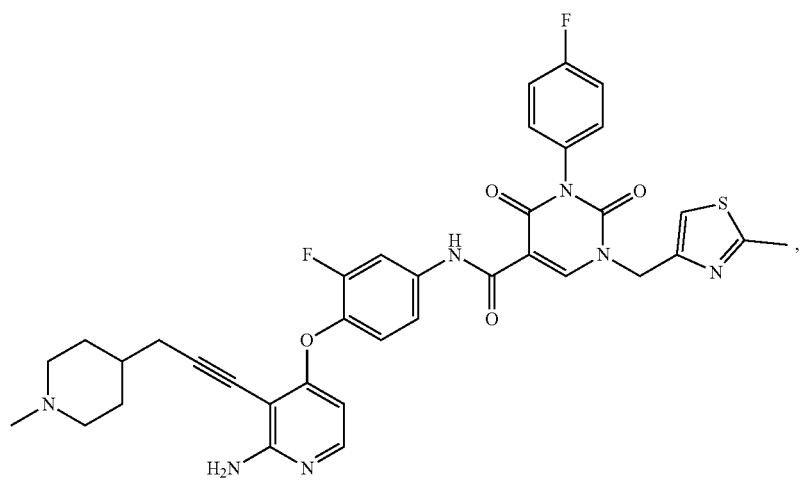

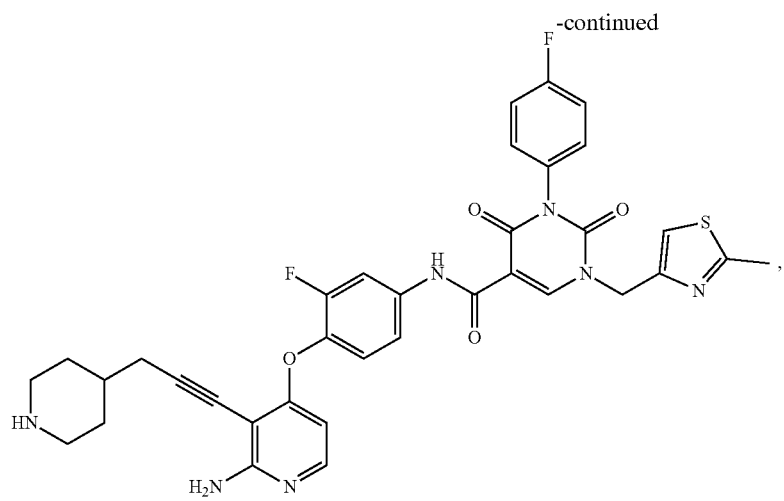
-continued
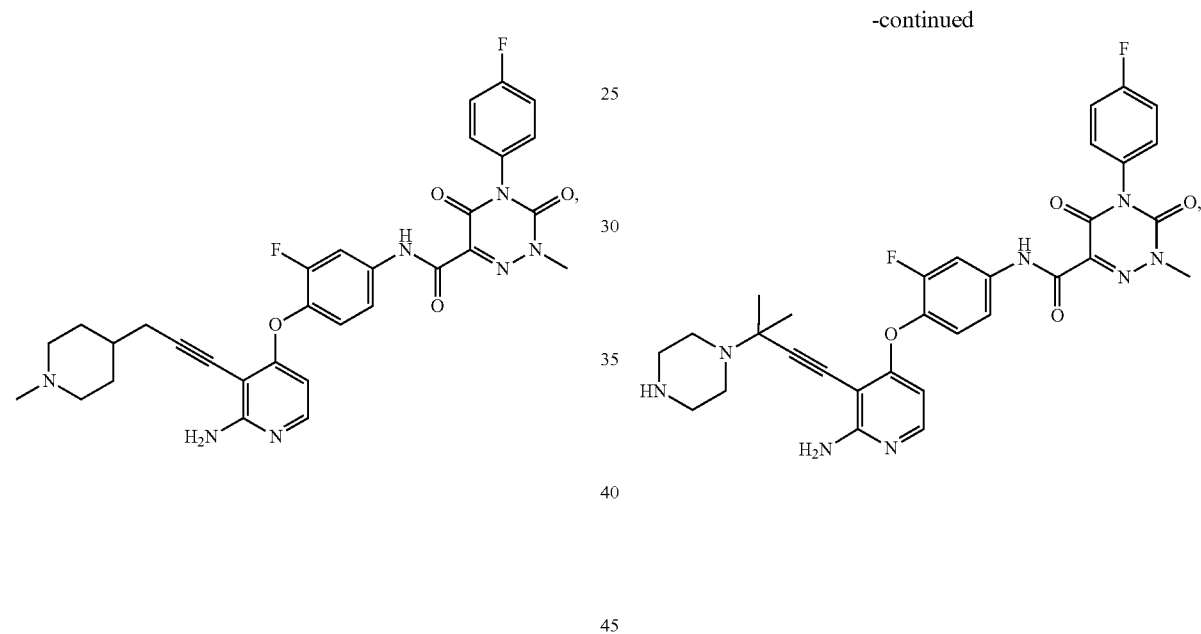
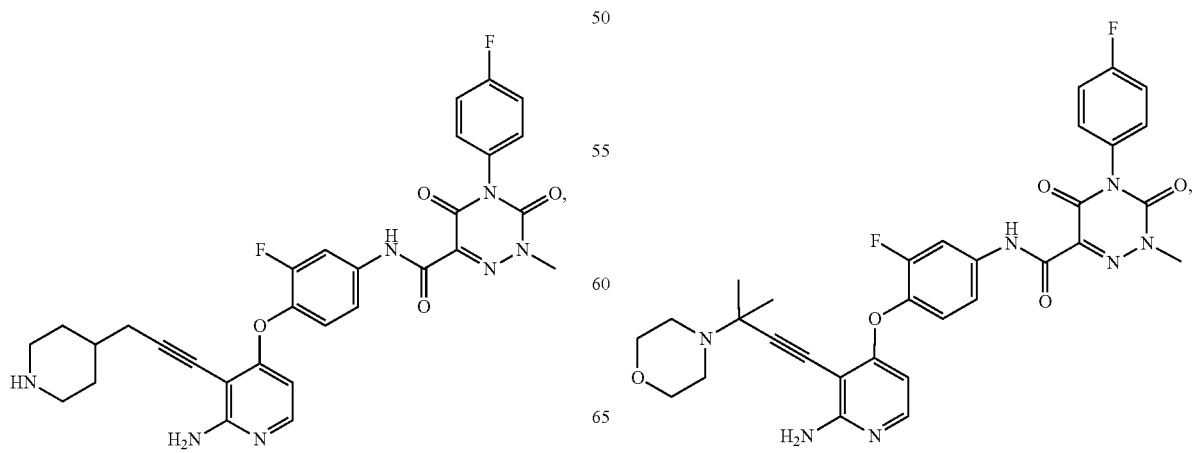

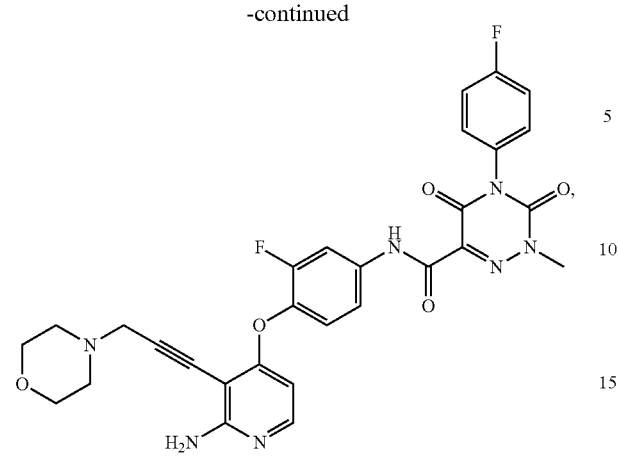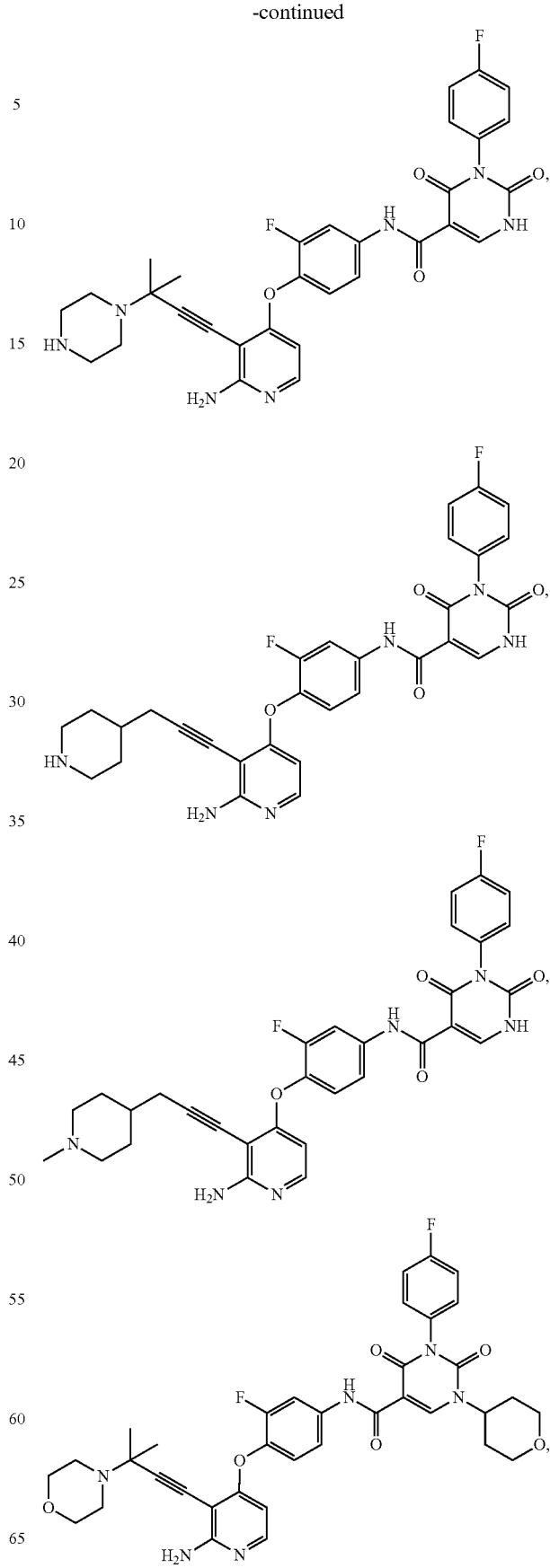

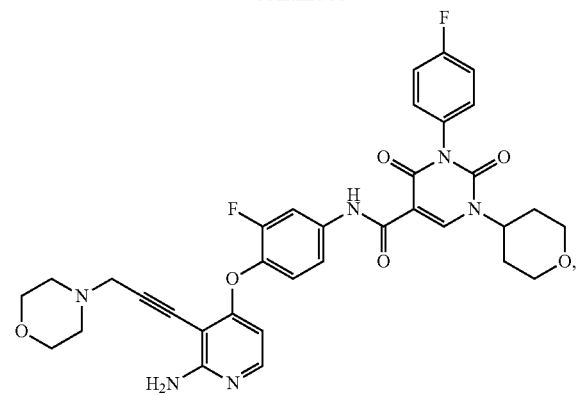
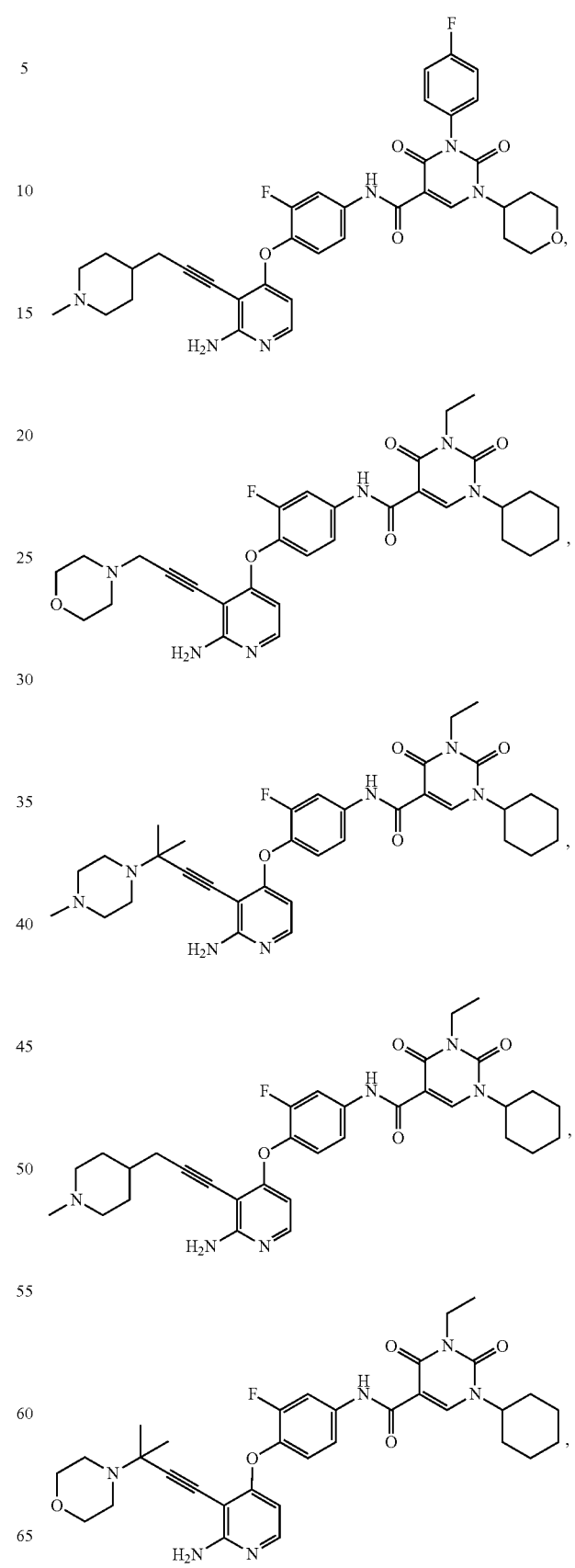

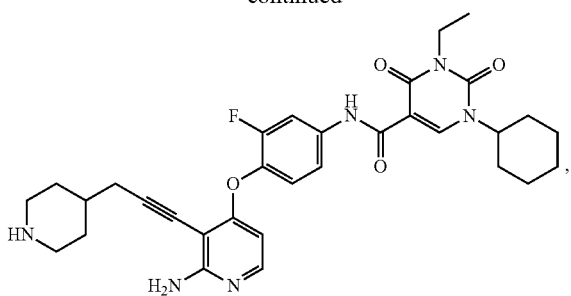
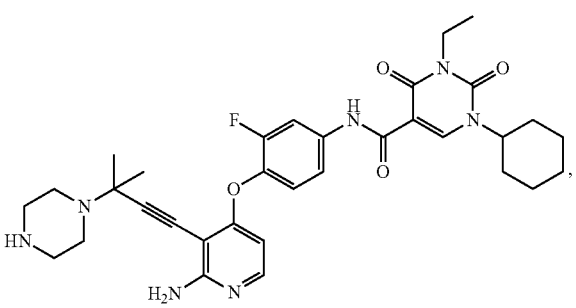
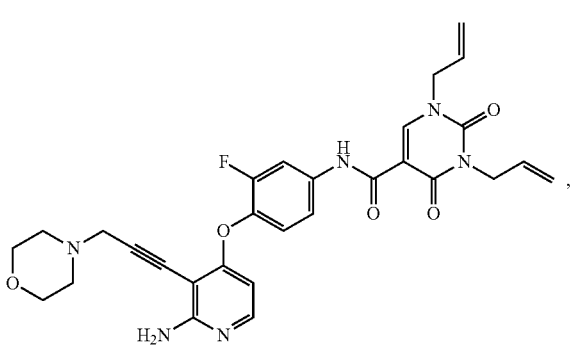
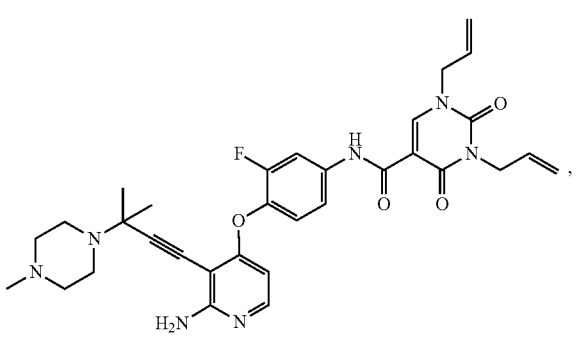
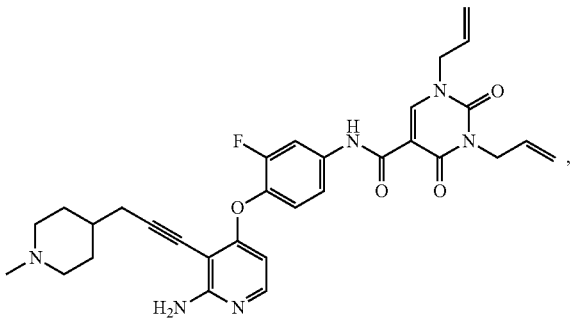
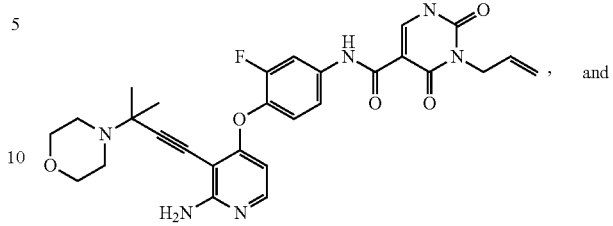
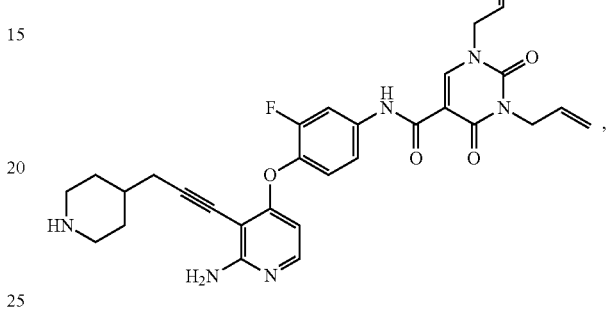

, and

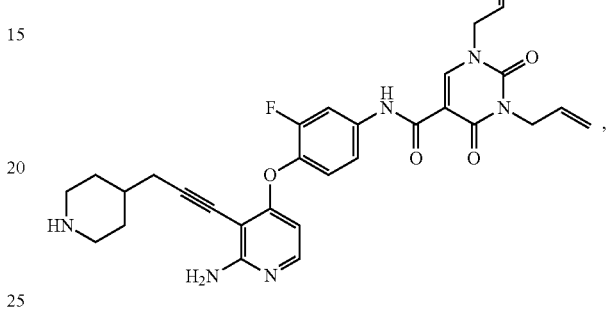

, or a pharmaceutically acceptable salt thereof.

In any of the aspects above, the term "alkyl" implies a straight-chain or branched alkyl substituent containing from, for example, from about 1 to about 8 carbon atoms, e.g., from about 1 to about 6 carbon atoms. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs as part of a group, such as, e.g., in $C_3$-$C_6$ cycloalkylalkyl, hydroxyalkyl, haloalkyl (e.g., monohaloalkyl, dihaloalkyl, and trihaloalkyl), cyanoalkyl, aminoalkyl, alkylamino, dialkylamino, arylalkyl, etc. The alkyl can be substituted or unsubstituted, as described herein. Even in instances in which the alkyl is an alkylene chain (e.g., —$(CH_2)_n$—), the alkyl group can be substituted or unsubstituted. An example of a substituted alkylene chain includes —$CH_2CH_2$-methoxy.

In any of the aspects above, the term "alkenyl," as used herein, means a linear alkenyl substituent containing from, for example, about 2 to about 8 carbon atoms (branched alkenyls are about 3 to about 8 carbons atoms), e.g., from about 3 to about 6 carbon atoms (branched alkenyls are about 3 to about 6 carbons atoms). In accordance with an aspect, the alkenyl group is a $C_2$-$C_4$ alkenyl. Examples of alkenyl group include ethenyl, allyl, 2-propenyl, 1-butenyl, 2-butenyl, 1-pentenyl, 2-pentenyl, 3-pentenyl, 1-hexenyl, and the like. The alkenyl can be substituted or unsubstituted, as described herein.

In any of the aspects above, the term "alkynyl," as used herein, means a linear alkynyl substituent containing at least one carbon-carbon triple bond and from, for example, about 2 to about 8 carbon atoms (branched alkynyls are about 4 to about 12 carbons atoms), e.g., from about 2 to about 6 carbon atoms (branched alkynyls can be from about 4 to about 8 carbon atoms), e.g., from about 2 to about 4 carbon atoms. Examples of such substituents include propynyl, propargyl, n-butynyl, pentynyl, isopentynyl, hexynyl, octynyl, and the like. The alkynyl can be substituted or unsubstituted, as described herein.

In any of the aspects above, the term "cycloalkyl," as used herein, means a cyclic alkyl moiety containing from, for example, 3 to 6 carbon atoms or from 5 to 6 carbon atoms. Examples of such moieties include cyclopropyl, cyclobutyl, cyclopentyl, cyclohexyl, and the like. The cycloalkyl can be substituted or unsubstituted, as described herein.

In any of the aspects above, the term "hydroxy" refers to the group —OH.

In any of the aspects above, the terms "alkoxy" embrace linear or branched alkyl groups that are attached to a divalent oxygen. The alkyl group is the same as described herein.

In any of the aspects above, the term "halo" refers to a halogen radical selected from fluoro, chloro bromo, and iodo.

In any of the aspects above, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise 4n+2 π electrons, according to Hickel's Rule, wherein n=1, 2, or 3. This definition also applies wherever "aryl" occurs as part of a group, such as, e.g., in haloaryl (e.g., monohaloaryl, dihaloaryl, and trihaloaryl), arylalkyl, etc. The aryl can be substituted or unsubstituted, as described herein.

In any of the aspects above, the term "heteroaryl" refers to aromatic 5 or 6 membered monocyclic groups, 9 or 10 membered bicyclic groups, and 11 to 14 membered tricyclic groups which have at least one heteroatom (O, S, or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized, and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furyl, pyrrolyl, thienyl, isothiazolyl, thiazolyl, isoxazolyl, and oxadiazolyl. The heteroaryl can be substituted or unsubstituted, as described herein.

The term "heterocyclyl" means a stable, saturated, or partially unsaturated monocyclic, bicyclic, and spiro ring system containing 3 to 7 ring members of carbon atoms and other atoms selected from nitrogen, sulfur, and/or oxygen. In an aspect, a heterocyclyl is a 5, 6, or 7-membered monocyclic ring and contains one, two, or three heteroatoms selected from nitrogen, oxygen, and sulfur. The heterocyclyl may be attached to the parent structure through a carbon atom or through any heteroatom of the heterocyclyl that results in a stable structure (e.g., a nitrogen atom). Examples of such heterocyclyl rings are isoxazolyl, thiazolinyl, imidazolidinyl, piperazinyl, homopiperazinyl, pyrrolyl, pyrrolinyl, pyrazolyl, pyranyl, dihydropyranyl, tetraydropyranyl, piperidinyl, oxazolyl, and morpholinyl. Preferably, the heterocyclyl is piperazinyl, piperidinyl, or morpholinyl. The heterocyclyl can be substituted or unsubstituted, as described herein.

In other aspects, any substituent that is not hydrogen (e.g., alkyl, alkenyl, alkynyl, cycloalkyl, aryl, arylalkyl, heteroaryl, heteroarylalkyl, or heterocyclyl) can be an optionally substituted moiety. The substituted moiety typically comprises at least one substituent (e.g., 1, 2, 3, 4, 5, 6, etc.) in any suitable position (e.g., 1-, 2-, 3-, 4-, 5-, or 6-position, etc.). When an aryl group is substituted with a substituent, e.g., halo, amino, alkyl, OH, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention. Suitable substituents include, e.g., halo, alkyl, alkenyl, alkynyl, hydroxy, nitro, cyano, amino, alkylamino, alkoxy, aryloxy, aralkoxy, carboxyl, carboxyalkyl, carboxyalkyloxy, amido, alkylamido, haloalkylamido, aryl, heteroaryl, and heterocyclyl, each of which is described herein.

In any of the aspects above, whenever a range of the number of atoms in a structure is indicated (e.g., a $C_{1-12}$, $C_{1-8}$, $C_{1-6}$, or $C_{1-4}$ alkyl, cycloalkyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_5$) as used with respect to any chemical group (e.g., alkyl, cycloalkyl, etc.) referenced herein encompasses and specifically describes 1, 2, 3, 4, 5, 6, 7, and/or 8 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 2-3 carbon atoms, 2-4 carbon atoms, 2-5 carbon atoms, 2-6 carbon atoms, 2-7 carbon atoms, 2-8 carbon atoms, 3-4 carbon atoms, 3-5 carbon atoms, 3-6 carbon atoms, 3-7 carbon atoms, 3-8 carbon atoms, 4-5 carbon atoms, 4-6 carbon atoms, 4-7 carbon atoms, 4-8 carbon atoms, etc., as appropriate).

The subscript "m" represents the number of (CX') repeat units. The subscript m can be either 0 or 1. When m is 0, then (CX') is not present in the molecule.

The subscript "n" represents the number of methylene ($CH_2$) repeat units. The subscript n can be either 0 or an integer from 1-3 (i.e., 1, 2, or 3). When n is 0, then the respective moiety does not contain any methylene repeat units.

In any of the aspects herein, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences*, 18th ed., Mack Publishing Company, Easton, PA, 1990, p. 1445, and *Journal of Pharmaceutical Science*, 66, 2-19 (1977). For example, the salt can be selected from the group consisting of acetate, benzoate, besylate, bitartrate, bromide, carbonate, chloride, edetate, edisylate, estolate, fumarate, gluceptate, gluconate, hydrobromide, hydrochloride, iodide, formate, lactate, lactobionate, malate, maleate, mandelate, mesylate, methyl bromide, methyl sulfate, mucate, napsylate, nitrate, oxalate, pamoate, phosphate, diphosphate, salicylate, disalicylate, stearate, succinate, sulfate, tartrate, tosylate, triethiodide, trifluoroacetate, and valerate.

The methods described herein comprise administering a compound of Formula (I) or a pharmaceutically acceptable salt thereof in the form of a pharmaceutical composition. In particular, a pharmaceutical composition will comprise at least one compound of Formula (I) or a pharmaceutically acceptable salt thereof and a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the aspects, the compound of Formula (I) or a pharmaceutically acceptable salt thereof can be administered orally to a subject in need thereof. Formulations suitable for oral administration can consist of (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of Formula (I) or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (e) mixtures thereof.

The parenteral formulations will typically contain from about 0.5 to about 25% by weight of the inhibitors in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The inhibitors can be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some aspects, the composition contains at least one active component and a suitable vehicle or carrier. It may also contain other components, such as an anti-irritant. The carrier can be a liquid, solid or semi-solid. In aspects, the composition is an aqueous solution, such as a mouthwash. Alternatively, the composition can be a dispersion, emulsion, gel, lotion or cream vehicle for the various components. In one aspect, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In aspects of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compound of Formula (I) or a pharmaceutically acceptable salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

The dose administered to the subject, particularly a human and other mammals, in accordance with the present invention should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations.

The inventive methods comprise administering an effective amount of a compound of Formula (I) or a pharmaceutically acceptable salt thereof. An "effective amount" means an amount sufficient to show a meaningful benefit in an individual, cell, or tissue to be great. A meaningful benefit means that one or more symptoms of the disease or disorder (e.g., asthma, cancer) are prevented, reduced, halted, or eliminated subsequent to administration of a compound of Formula (I), including a compound of Formula (Ib) or (Ic), or a pharmaceutically acceptable salt thereof, thereby effectively treating the disease to at least some degree. For example, the meaningful benefit can be promoting at least one aspect of tumor cell cytotoxicity (e.g., inhibition of growth, inhibiting survival of a cancer cell, reducing proliferation, reducing size and/or mass of a tumor (e.g., solid tumor)), or treatment, healing, prevention, delay of onset, halting, or amelioration of other relevant medical condition(s) associated with a particular disease or disorder. The meaningful benefit observed in the subject to be treated can be to any suitable degree (10, 20, 30, 40, 50, 60, 70, 80, 90% or more).

Effective amounts may vary depending upon the biological effect desired in the individual, condition to be treated, and/or the specific characteristics of the compound of Formula (I), including a compound of Formula (Ib) or (Ic), or a pharmaceutically acceptable salt thereof, and the individual. In this respect, any suitable dose of the compound of Formula (I) or a pharmaceutically acceptable salt thereof can be administered to the subject (e.g., human), according to the disease or disorder (e.g., asthma, cancer) to be treated. Various general considerations taken into account in determining the "effective amount" are known to those of skill in the art and are described, e.g., in Gilman et al., eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the compound of Formula (I), including a compound of Formula (Ib) or (Ic), or a pharmaceutically acceptable salt thereof desirably comprises about 0.01 mg per kilogram (kg) of the body weight of the subject (mg/kg) or more (e.g., about 0.05 mg/kg or more, 0.1 mg/kg or more, 0.5 mg/kg or more, 1 mg/kg or more, 2 mg/kg or more, 5 mg/kg or more, 10 mg/kg or more, 15 mg/kg or more, 20 mg/kg or more, 30 mg/kg or more, 40 mg/kg or more, 50 mg/kg or more, 75 mg/kg or more, 100 mg/kg or more, 125 mg/kg or more, 150 mg/kg or more, 175 mg/kg or more, 200 mg/kg or more, 225 mg/kg or more, 250 mg/kg or more, 275 mg/kg or more, 300 mg/kg or more, 325 mg/kg or more, 350 mg/kg or more, 375 mg/kg or more, 400 mg/kg or more, 425 mg/kg or more, 450 mg/kg or more, or 475 mg/kg or more) per day. Typically, the dose will be about 500 mg/kg or less (e.g., about 475 mg/kg or less, about 450 mg/kg or less, about 425 mg/kg or less, about 400 mg/kg or less, about 375 mg/kg or less, about 350 mg/kg or less, about 325 mg/kg or less, about 300 mg/kg or less, about 275 mg/kg or less, about 250 mg/kg or less, about 225 mg/kg or less, about 200 mg/kg or less, about 175 mg/kg or less, about 150 mg/kg or less, about 125 mg/kg or less, about 100 mg/kg or less, about 75 mg/kg or less, about 50 mg/kg or less, about 40 mg/kg or less, about 30 mg/kg or less, about 20 mg/kg or less, about 15 mg/kg or less, about 10 mg/kg or less, about 5 mg/kg or less, about 2 mg/kg or less, about 1 mg/kg or less, about 0.5 mg/kg or less, or about 0.1 mg/kg or less). Any two of the foregoing endpoints can be used to define a close-ended range, or a single endpoint can be used to define an open-ended range.

In an aspect, a compound of Formula (I) or a salt thereof inhibits one or more enzymes selected from AXL, Mer, and c-Met. Accordingly, the present invention provides a method of inhibiting an AXL, Mer, and/or c-Met enzyme in a cell comprising administering a pharmaceutically effective amount of a compound of Formula (I) or a pharmaceutically acceptable salt thereof to a cell in need of such inhibition (e.g., a cell that overexpresses AXL, Mer, and/or c-Met). For example, the cell can be any cell that overexpresses AXL, Mer, and/or c-Met and is associated with any suitable tissue, particularly a tissue associated with a disease such as papillary thyroid carcinoma, pancreatic cancer, lung cancer, colon cancer, breast carcinoma, neuroblastoma, pain, cachexia (wasting syndrome), dermatitis, and asthma. The tissue can be from, for example, the thyroid, pancreas, lung, colon, breast, skin, or adrenal glands. In accordance with an aspect, the cell is a cancer cell that overexpresses AXL, Mer, and/or c-Met, such as cells from papillary thyroid carcinoma, pancreatic cancer, lung cancer, colon cancer, breast carcinoma, and neuroblastoma. In another aspect, the cancer cells are non-small cell lung cancer cells.

Elevated levels of AXL, Mer, and c-Met are associated with certain diseases, and it is envisioned that inhibiting one or more of AXL, Mer, and c-Met is a viable treatment of such diseases. Thus, the invention provides a method of treating or preventing an AXL-, Mer- and/or c-Met-mediated disease in a subject with a compound of Formula (I). In general, the compound of Formula (I) will be provided to the subject in the form of a pharmaceutical composition, as described herein. The type of disease to be treated or prevented is not particularly limited, but in general, the disease is characterized as having increased expression of AXL, Mer, and c-Met relative to normal tissue of the same type. In some aspects, the disease is selected from the group consisting of papillary thyroid carcinoma, pancreatic cancer, lung cancer, colon cancer, breast carcinoma, neuroblastoma, pain, cachexia (wasting syndrome), dermatitis, and asthma. The method comprises administering a pharmaceutically effective amount of a compound of Formula (I) or a pharmaceutically acceptable salt thereof to a subject in need of such treatment. In some preferred aspects of this method, the disease is lung cancer (e.g., non-small cell lung cancer).

The invention further provides a method of treating a subject with cancer cells resistant to an anti-cancer agent, comprising administering to the subject an effective amount of the compound of Formula (I), including a compound of Formula (Ib) or (Ic), or a pharmaceutically acceptable salt thereof, and the anti-cancer agent, whereby the compound or pharmaceutically acceptable salt thereof re-sensitizes the cancer cells to the anti-cancer agent. The cancer cell is the same as described herein. In accordance with an aspect, the cancer cells are selected from papillary thyroid carcinoma, pancreatic cancer, lung cancer, colon cancer, breast carcinoma, and neuroblastoma. In another aspect, the cancer cells are non-small cell lung cancer cells.

In certain aspects of this method, the compound of Formula (I), including a compound of Formula (Ib) or (Ic), or a pharmaceutically acceptable salt thereof can be co-administered with an anti-cancer agent (e.g., a chemotherapeutic agent) and/or radiation therapy. In an aspect, the method comprises administering an amount of a compound or salt thereof, preferably in the form of a pharmaceutical composition, that is effective to sensitize the cancer cells to one or more therapeutic regimens (e.g., chemotherapy or radiation therapy). The terms "co-administered" or "co-administration" refer to simultaneous or sequential administration. A compound can be administered before, concurrently with, or after administration of another compound using any suitable time frame.

One or more than one, e.g., two, three, or more anti-cancer agents can be administered. In this regard, the present invention is directed a pharmaceutical composition comprising a pharmaceutically acceptable carrier and a combination of the compound of Formula (I), including a compound of Formula (Ib) or (Ic), or a pharmaceutically acceptable salt thereof and at least one anti-cancer agent (e.g., chemotherapeutic agent).

Examples of anti-cancer agents include platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, mitomycin C, plicamycin, dactinomycin), taxanes (e.g., paclitaxel and docetaxel), antimetabolites (e.g., 5-fluorouracil, cytarabine, pemetrexed, thioguanine, floxuridine, capecitabine, and methotrexate), nucleoside analogues (e.g., fludarabine, clofarabine, cladribine, pentostatin, nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vincristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panitumumab, tositumomab, trastuzumab, alemtuzumab, gemtuzumab ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), a CDK4/6 inhibitor (e.g., abemaciclib, palbociclib, ribociclib), anti-cancer hormonal agents (e.g., tamoxifen, fulvestrant, raloxifene, leuprolide, bicalutamide, granisetron, flutamide, goserelin), aromatase inhibitors (e.g., exemestane, letrozole, and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, immune checkpoint inhibitors (e.g., anti-PD1, anti-CTLA4, and anti-PD-L1), cellular immunotherapy (e.g., chimeric antigen receptor T cell therapy, tumor-infiltrating lymphocyte therapy), or any combination thereof.

For purposes of the present invention, the term "subject" preferably is directed to a mammal. Mammals include, but are not limited to, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perissodactyla, including Equines (horses). It is most preferred that the mammals are of the order Primates, Cebids, or Simioids (monkeys) or of the order Anthropoids (humans and apes). An especially preferred mammal is a human.

The invention is further illustrated by the following aspects.

A compound of Formula (I) or a pharmaceutically acceptable salt thereof:

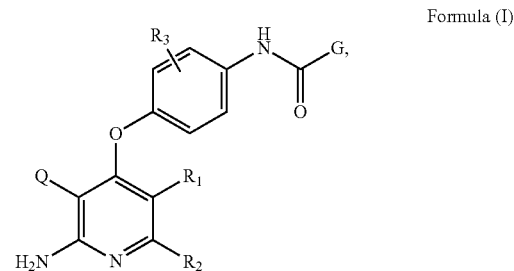

Formula (I)

wherein:
$R^1$ is H, alkyl, haloalkyl, halo, or CN;
$R^2$ is H, alkyl, haloalkyl, halo, or CN;
$R^3$ is H or halo;
Q is H, CN, halo, alkyl, alkenyl, alkynyl, cycloalkyl, heterocyclyl, heteroaryl, or aryl, wherein said alkenyl or alkynyl is selected from the group consisting of

—CH=CR⁴(CX')ₘ(CH₂)ₙNR⁵R⁶, —C≡C(CX')ₘ(CH₂)ₙNR⁵R⁶,

—CH=CR⁴(CX')ₘ(CH₂)ₙCHR⁵R⁶, —C≡C(CX')ₘ(CH₂)ₙCHR⁵R⁶,

—CH=CR⁴(CX')ₘ(CH₂)ₙNR⁷OR⁸, and —C≡C(CX')ₘ(CH₂)ₙNR⁷OR⁸;

wherein

R⁴ is hydrogen or halo;

X' is H₂, (C₁₋₆ alkyl)₂, or =O;

m is 0 or 1;

n is 0 or 1-3;

—NR⁵R⁶ either forms a 4-7 membered heterocyclic ring or does not form a ring structure, the heterocyclic ring being either heteroaryl or heterocyclyl ring, when —NR⁵R⁶ forms a 4-7 membered heterocyclic ring, the 4-7 membered heterocyclic ring includes an optional second heteroatom in addition to the nitrogen of —NR⁵R⁶ and is optionally substituted with one or more substituent groups independently selected from the group consisting of linear C₁-C₆ alkyl, branched C₂-C₆ alkyl, hydroxy, C₁-C₆ alkoxyalkyl, carboxylic acid, linear C₁-C₄ alkyl carboxylic acid, and branched C₃-C₄ alkyl carboxylic acid;

when —NR⁵R⁶ does not form a ring structure, R⁵ is selected from the group consisting of hydrogen, linear C₁-C₆ alkyl, and branched C₃-C₆ alkyl, and R⁶ is selected from the group consisting of hydrogen, linear C₁-C₆ alkyl optionally substituted with at least one fluoro or at least one hydroxy, branched C₃-C₆ alkyl optionally substituted with at least one fluoro or at least one hydroxy, and cycloalkyl optionally substituted with at least one fluoro or at least one hydroxy;

—CHR⁵R⁶ either forms a 4-7 membered heterocyclic ring or does not form a ring structure, the heterocyclic ring being either heteroaryl or heterocyclyl ring, when —CHR⁵R⁶ forms a 4-7 membered heterocyclic ring, the 4-7 membered heterocyclic ring includes one or two heteroatoms and is optionally substituted with one or more substituent groups independently selected from the group consisting of linear C₁-C₆alkyl, branched C₃-C₆ alkyl, hydroxy, C₁-C₆ alkoxyalkyl, carboxylic acid, linear C₁-C₄ alkyl carboxylic acid, and branched C₃-C₄ alkyl carboxylic acid;

when —CHR⁵R⁶ does not form a ring structure, R⁵ is selected from the group consisting of hydrogen, linear C₁-C₆ alkyl, and branched C₃-C₆ alkyl, and R⁶ is selected from the group consisting of hydrogen, linear C₁-C₆ alkyl optionally substituted with at least one fluoro or at least one hydroxy, branched C₃-C₆ alkyl optionally substituted with at least one fluoro or at least one hydroxy, and cycloalkyl optionally substituted with at least one fluoro or at least one hydroxy;

—NR⁷OR⁸ does not form a ring structure, R⁷ is selected from the group consisting of hydrogen, linear C₁-C₆ alkyl, and branched C₃-C₆ alkyl, and R¹ is selected from the group consisting of hydrogen, linear C₁-C₆ alkyl optionally substituted with at least one fluoro, hydroxy, or alkoxy group, branched C₃-C₆ alkyl optionally substituted with at least one fluoro, hydroxy, or alkoxy group, and cycloalkyl optionally substituted with at least one fluoro, hydroxy, or alkoxy group;

G is

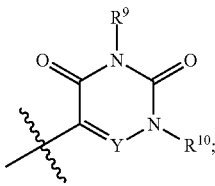

wherein

R⁹ is H, alkyl, substituted alkyl, alkenyl, substituted alkenyl, alkynyl, substituted alkynyl, cycloalkyl, aryl, substituted aryl, heteroaryl, substituted heteroaryl, heterocyclyl or heteroarylalkyl, where the heteroaryl group of heteroarylalkyl may be substituted or unsubstituted;

R¹⁰ is H, aryl, substituted aryl, heteroaryl, substituted heteroaryl, heterocyclyl, alkyl or cycloalkyl, cycloalkylalkyl, alkenyl or alkynyl, where alkyl, alkenyl or cycloalkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, substituted heteroaryl, carboxyl, oxo, carbamoyl, alkylcarbamoyl, dialkycarbamoyl, where the alkyl groups of dialkylcarbamoyl may be the same or different and heterocyclylcarbonyl; and Y is N, C—H, or C-alkyl.

2. The compound of aspect 1 or a pharmaceutically acceptable salt thereof, wherein both R¹ and R² are hydrogen.

3. The compound of aspect 1 or 2 or a pharmaceutically acceptable salt thereof, wherein R³ is a halo.

4. The compound of any one of aspects 1-3 or a pharmaceutically acceptable salt thereof, wherein Q is CN, halo, optionally substituted phenyl, optionally substituted heterocyclyl, or an alkenyl or alkynyl moiety selected from the group consisting of —CH=CR⁴(CX')ₘ(CH₂)ₙNR⁵R⁶, —C≡C(CX')ₘ(CH₂)ₙNR⁵R⁶, —CH=CR⁴(CX')ₘ(CH₂)ₙCHR⁵R⁶, —C≡C(CX')ₘ(CH₂)ₙCHR⁵R⁶, —CH=CR⁴(CX')ₘ(CH₂)ₙNR⁷OR⁸, and —C≡C(CX')ₘ(CH₂)ₙNR⁷OR⁸, wherein R⁴ is hydrogen or halo; X' is H₂, (C₁₋₆ alkyl)₂, or =O; m is 0 or 1; n is 0 or 1; —NR⁵R⁶ is morpholinyl, piperazinyl, or piperidinyl, each of which is optionally substituted with one or more substituent groups independently selected from the group consisting of a nitrogen protecting group, alkyl, hydroxy, alkoxy, and alkoxyalkyl, —CHR⁵R⁶ is tetrahydropyranyl, morpholinyl, piperazinyl, or piperidinyl, each of which is optionally substituted with one or more substituent groups independently selected from the group consisting of a nitrogen protecting group, alkyl, hydroxy, alkoxy, and alkoxyalkyl, R⁷ is selected from the group consisting of hydrogen, linear C₁-C₆ alkyl, and branched C₃-C₆ alkyl, and R¹ is selected from the group consisting of linear C₁-C₆ alkyl optionally substituted with at least one alkoxy group and branched C₃-C₆ alkyl optionally substituted with at least one alkoxy group.

5. The compound of any one of aspects 1-4 or a pharmaceutically acceptable salt thereof, wherein R⁹ is phenyl substituted with alkyl, haloalkyl, halo, and/or CN; and either (i) Y is C—H or (ii) Y is N.

6. The compound of any one of aspects 1-5 or a pharmaceutically acceptable salt thereof, wherein the compound of Formula (I) is a compound Formula (Ib):

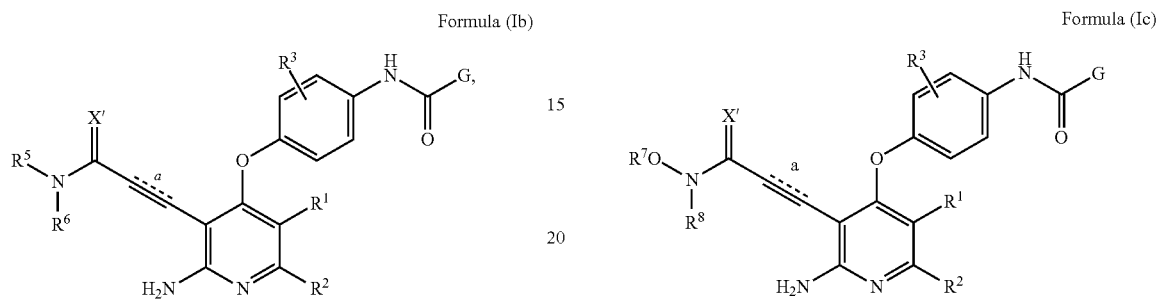

Formula (Ib)

wherein $\stackrel{a}{=\!=\!=}$ is —C≡C— or —CH=CH—.

7. The compound of aspect 6 or a pharmaceutically acceptable salt thereof, wherein both $R^1$ and $R^2$ are hydrogen.

8. The compound of aspect 6 or 7 or a pharmaceutically acceptable salt thereof, wherein $R^3$ is a halo.

9. The compound of any one of aspects 6-8 or a pharmaceutically acceptable salt thereof, wherein X' is $H_2$, $(C_{1-6}$ alkyl$)_2$, or ≡O; and —$NR^5R^6$ is morpholinyl, piperazinyl, or piperidinyl, each of which is optionally substituted with one or more substituent groups independently selected from the group consisting of a nitrogen protecting group, alkyl, hydroxy, alkoxy, and alkoxyalkyl.

10. The compound of any one of aspects 6-9 or a pharmaceutically acceptable salt thereof, wherein $R^9$ is phenyl substituted with alkyl, haloalkyl, halo, and/or CN; and either (i) Y is C—H or (ii) Y is N.

11. The compound of any one of aspects 1-5 or a pharmaceutically acceptable salt thereof, wherein the compound of Formula (I) is a compound Formula (Ic):

Formula (Ic)

wherein $\stackrel{a}{=\!=\!=}$ is —C≡C— or —CH=CH—.

12. The compound of aspect 11 or a pharmaceutically acceptable salt thereof, wherein both $R^1$ and $R^2$ are hydrogen.

13. The compound of aspect 11 or 12 or a pharmaceutically acceptable salt thereof, wherein $R^3$ is a halo.

14. The compound of any one of aspects 11-13 or a pharmaceutically acceptable salt thereof, wherein X' is $H_2$, $(C_{1-6}$ alkyl$)_2$, or ≡O; $R^7$ is selected from the group consisting of linear $C_1$-$C_6$ alkyl and branched $C_3$-$C_6$ alkyl, and $R^1$ is selected from the group consisting of linear $C_1$-$C_6$ alkyl and branched $C_3$-$C_6$ alkyl.

15. The compound of any one of aspects 11-14 or a pharmaceutically acceptable salt thereof, wherein $R^9$ is phenyl substituted with alkyl, haloalkyl, halo, and/or CN; and either (i) Y is C—H or (ii) Y is N.

16. A compound of aspect 1 selected from

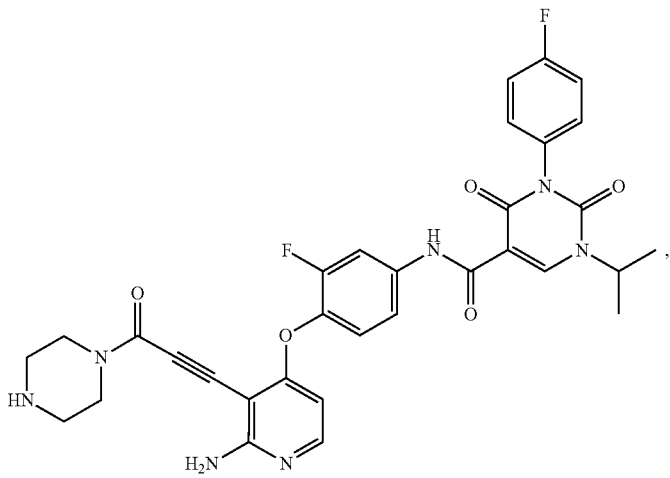

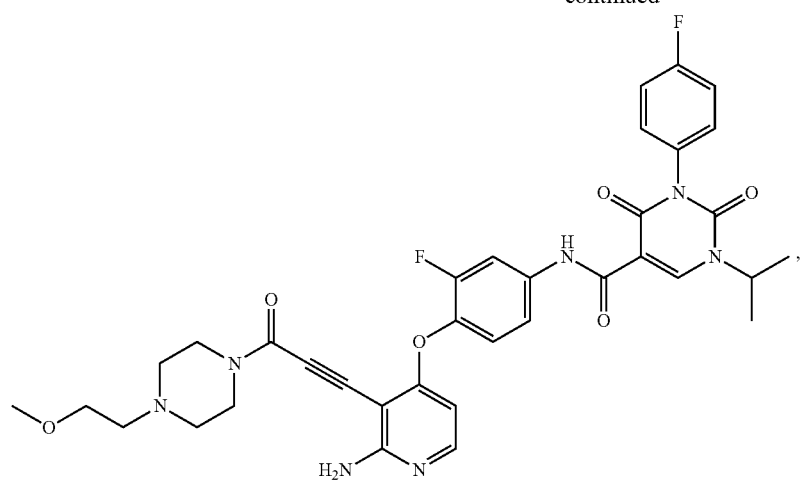
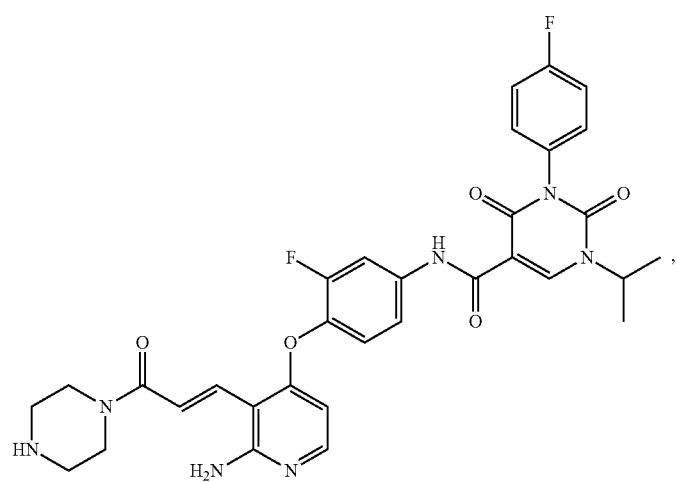
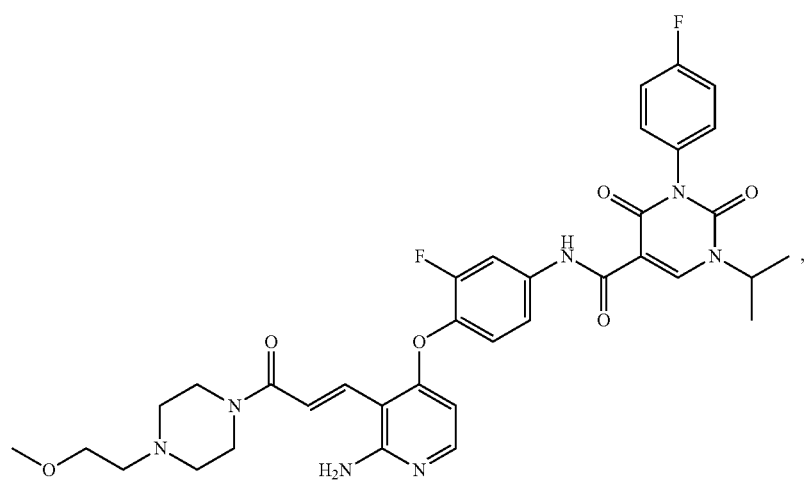

-continued
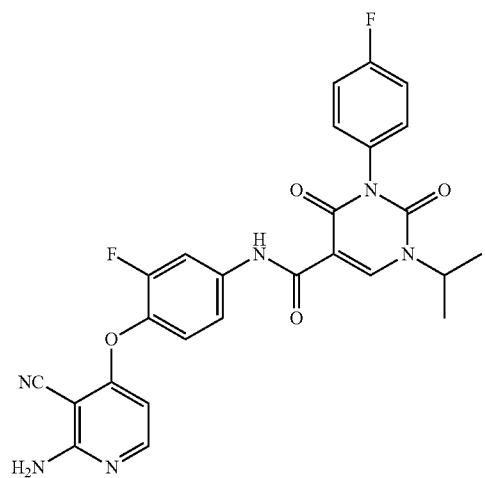
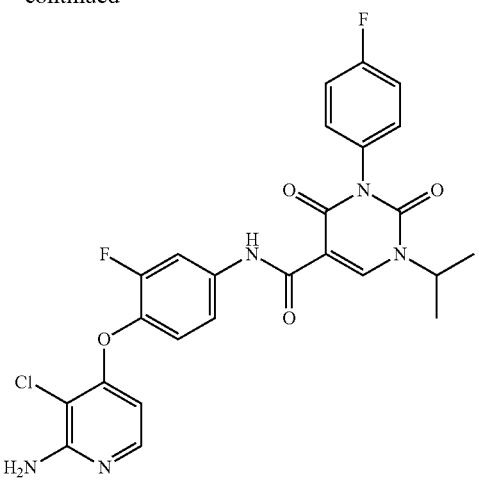
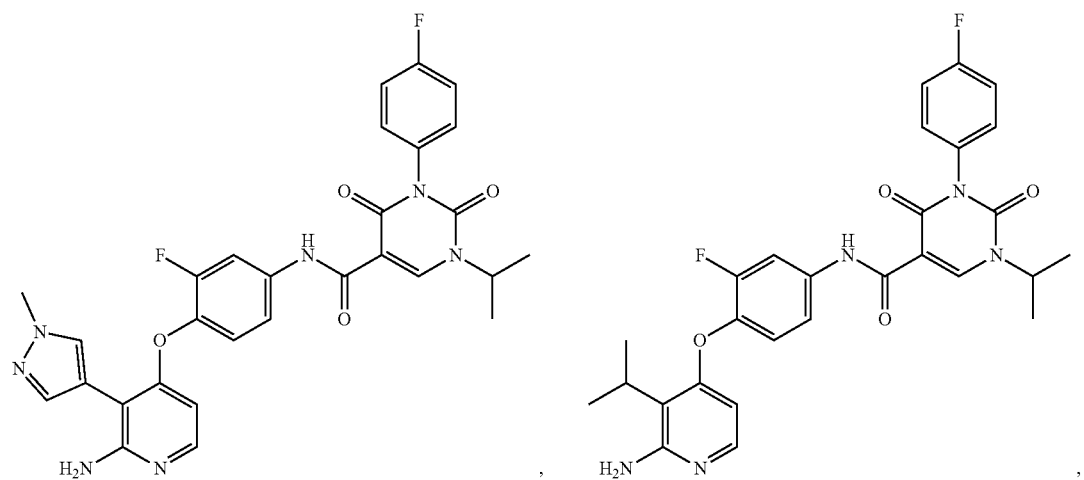
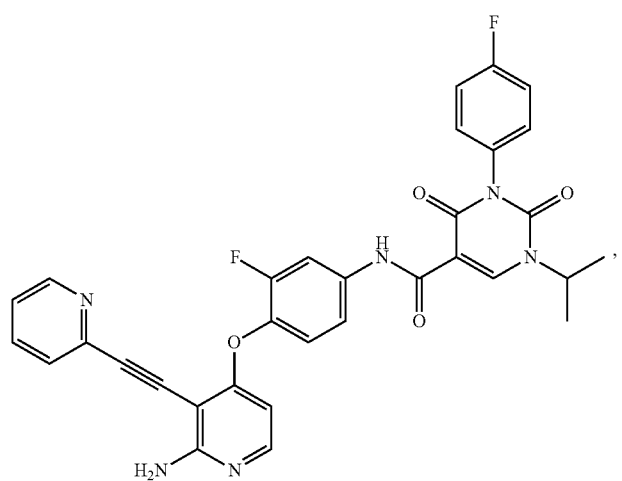

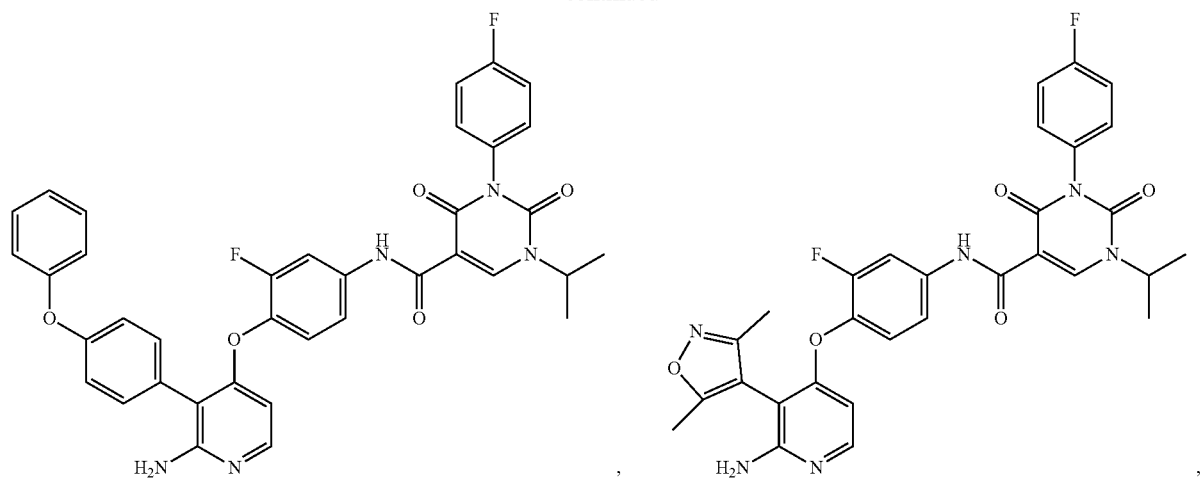
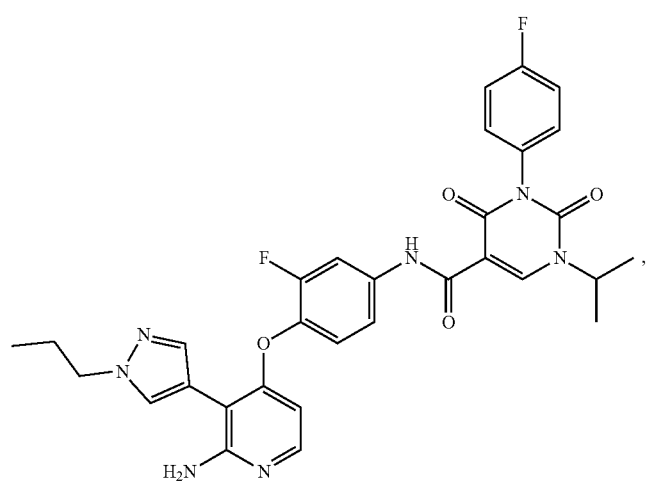
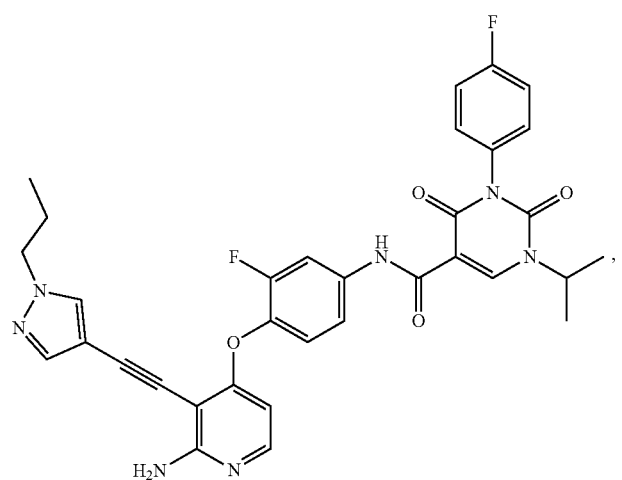

-continued
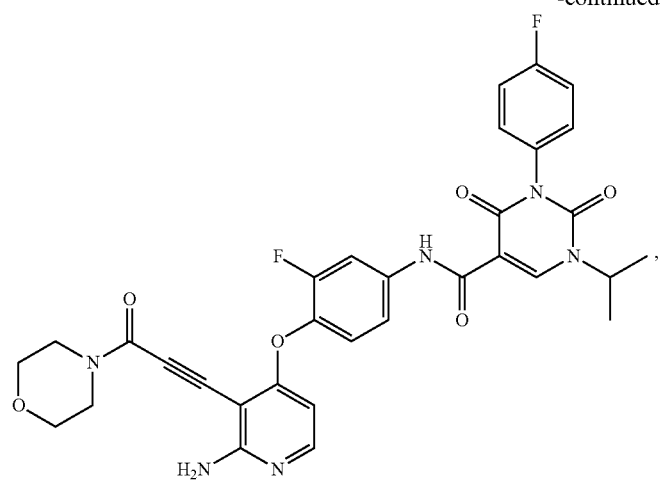
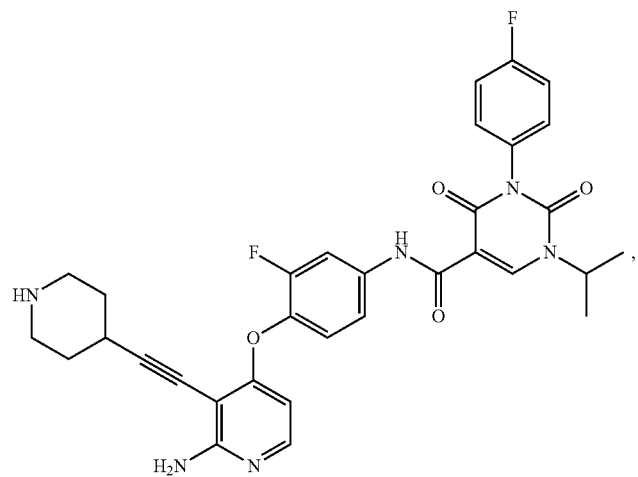
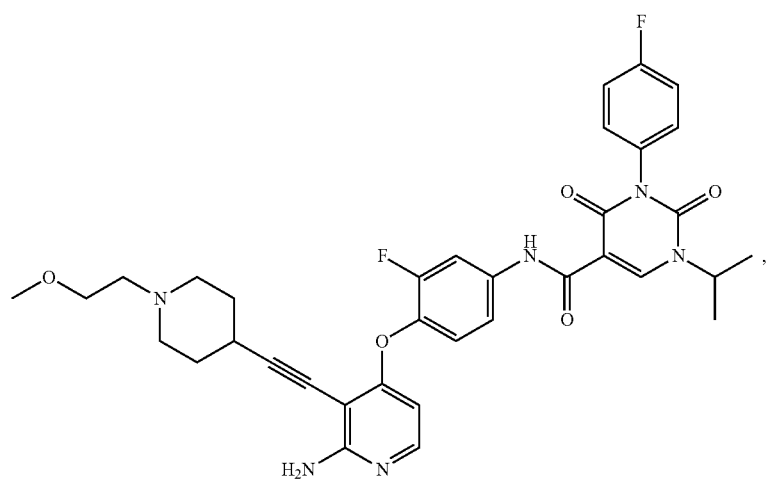

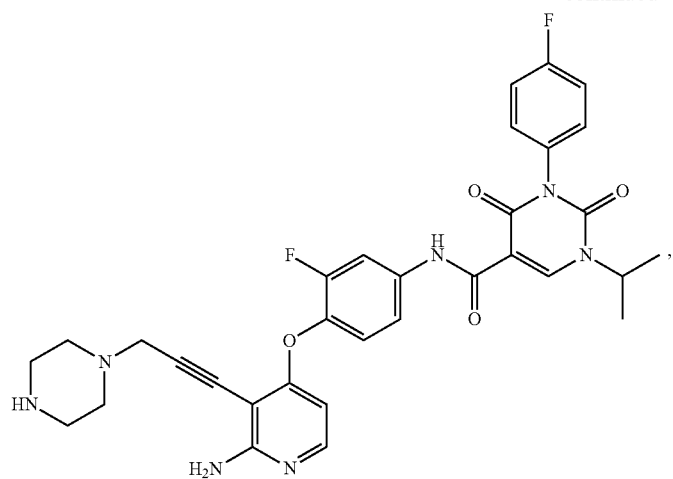
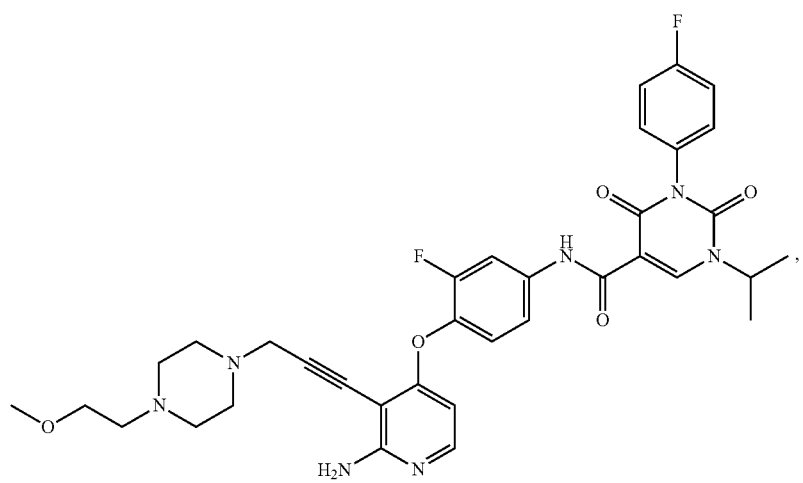
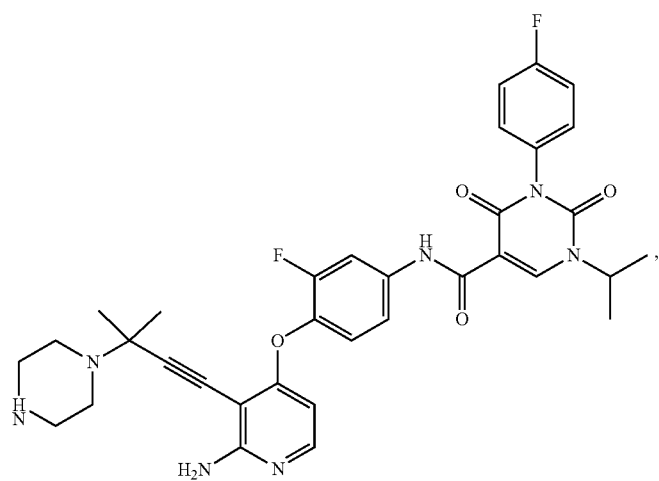

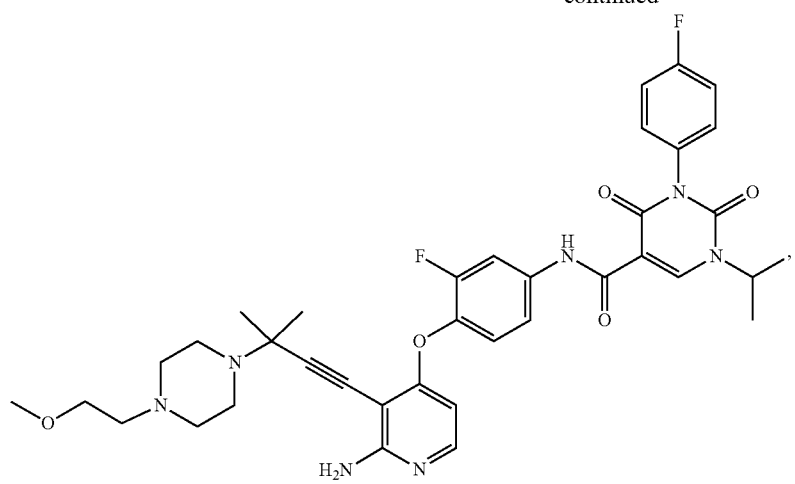
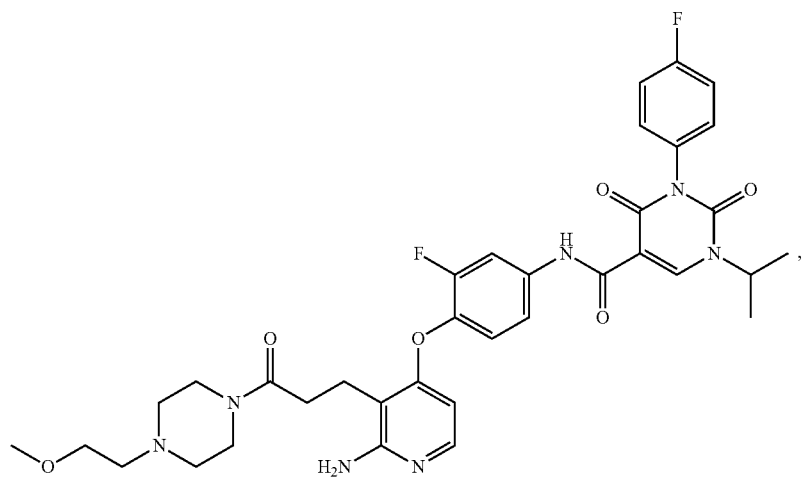
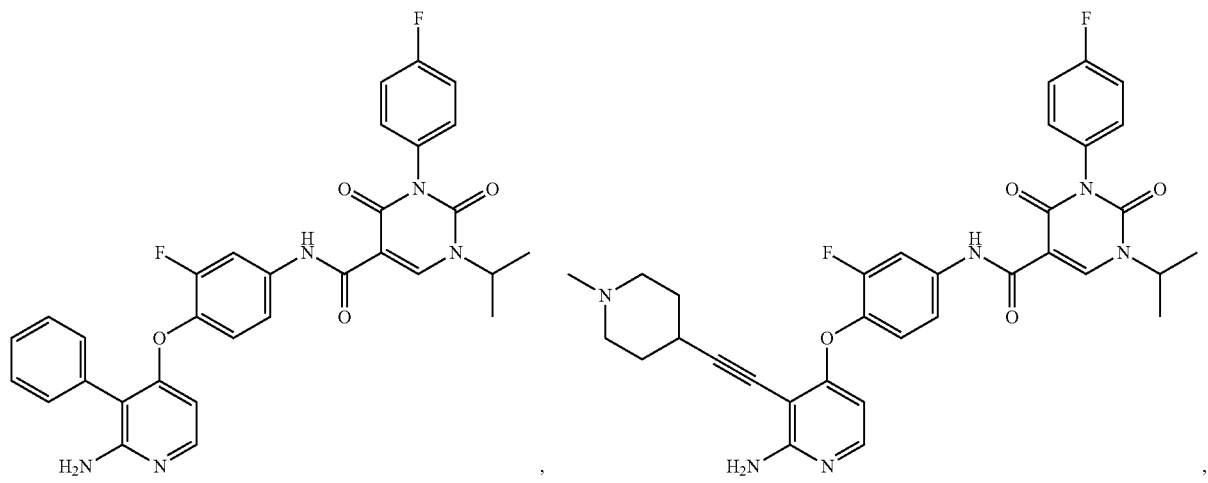

-continued
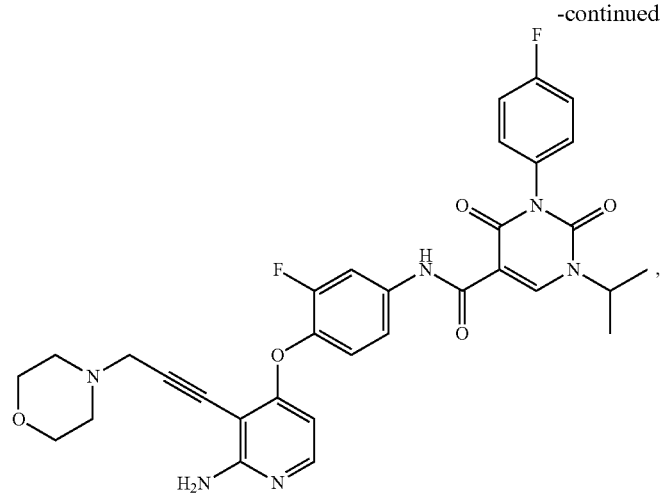
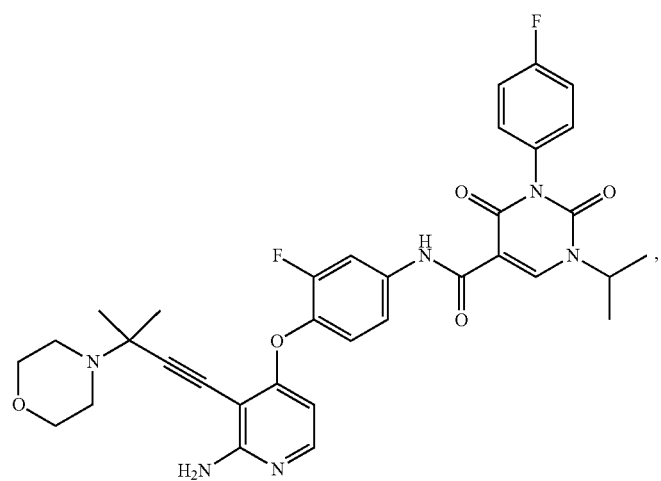
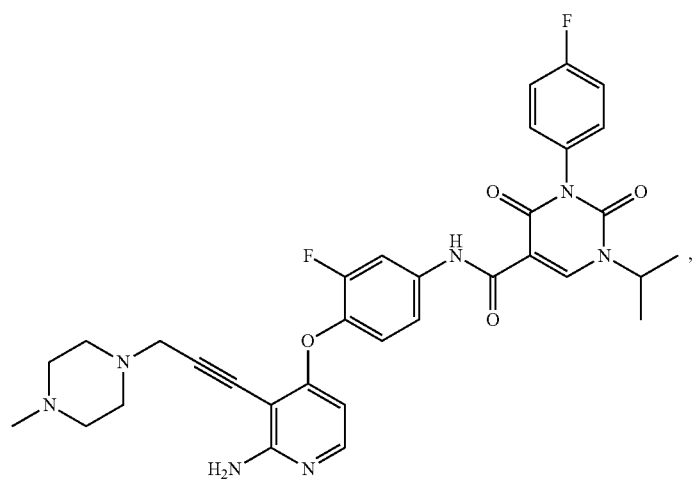

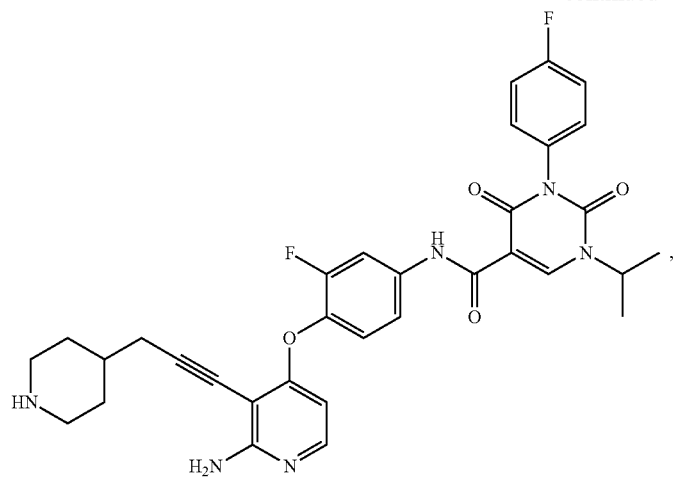
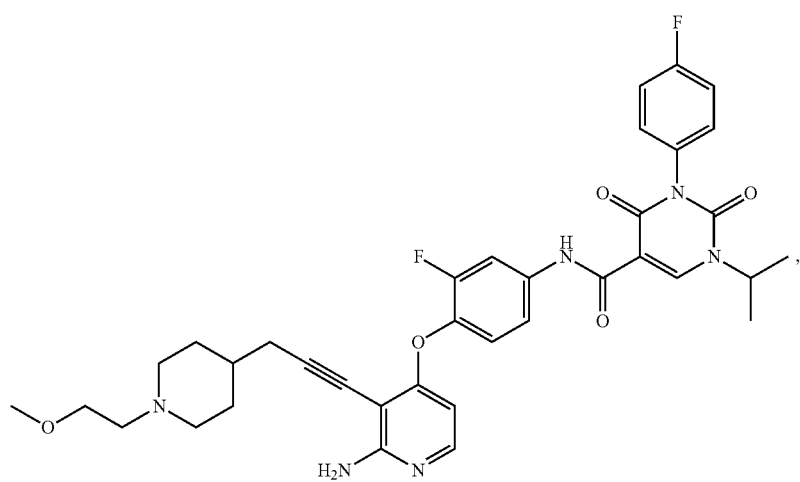
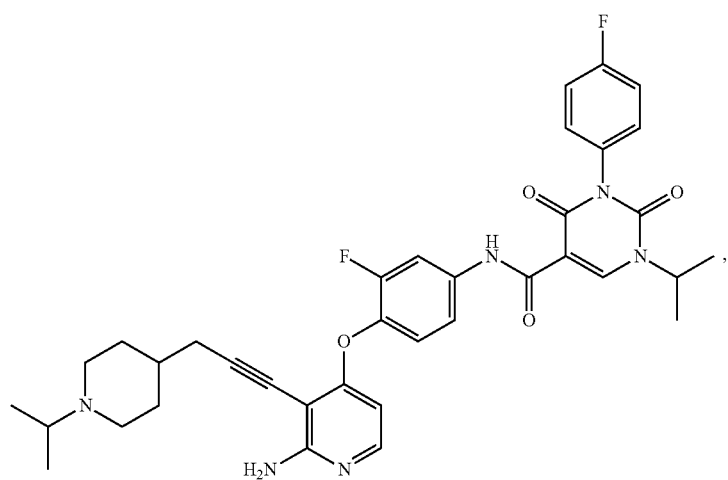

-continued
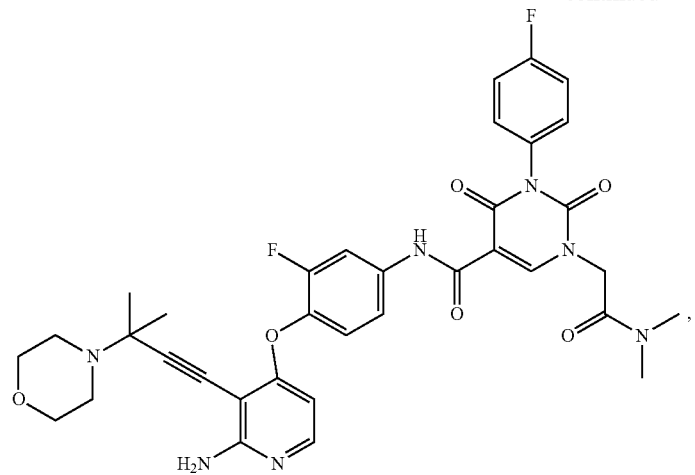
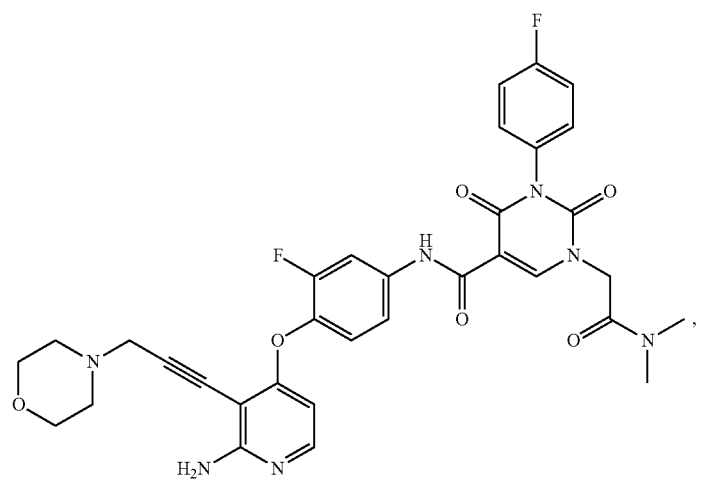
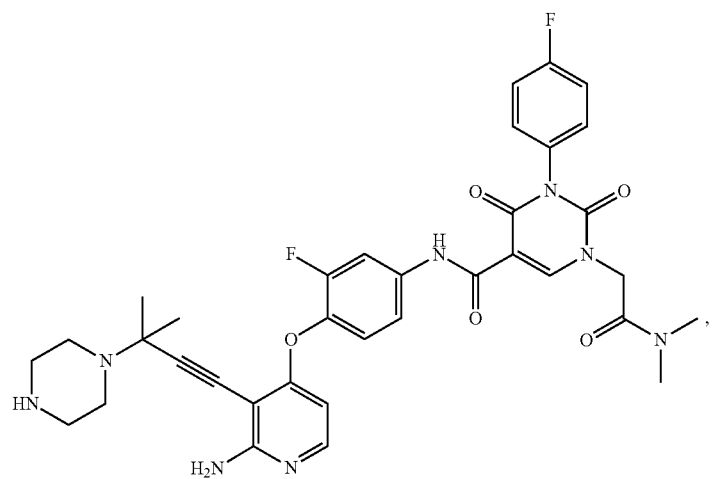

-continued
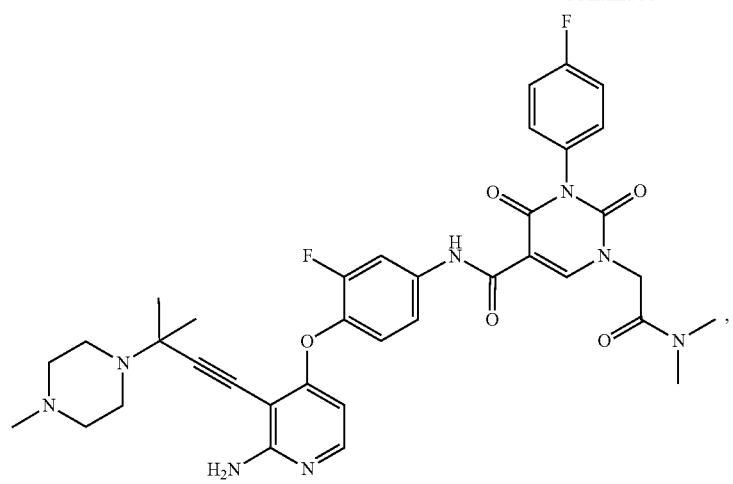
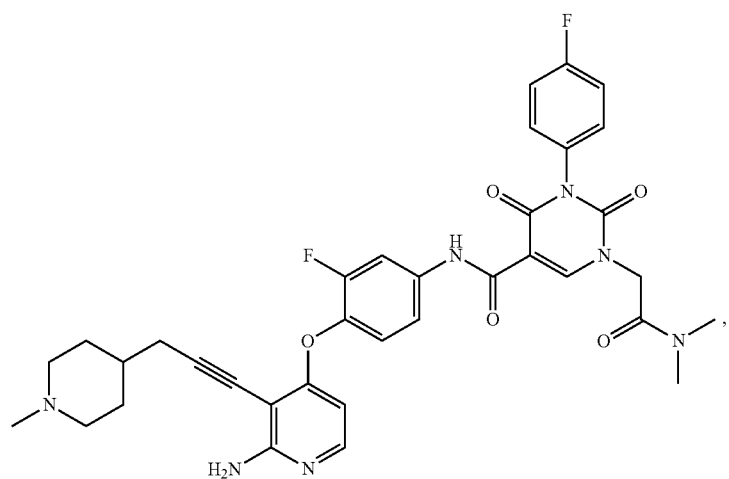
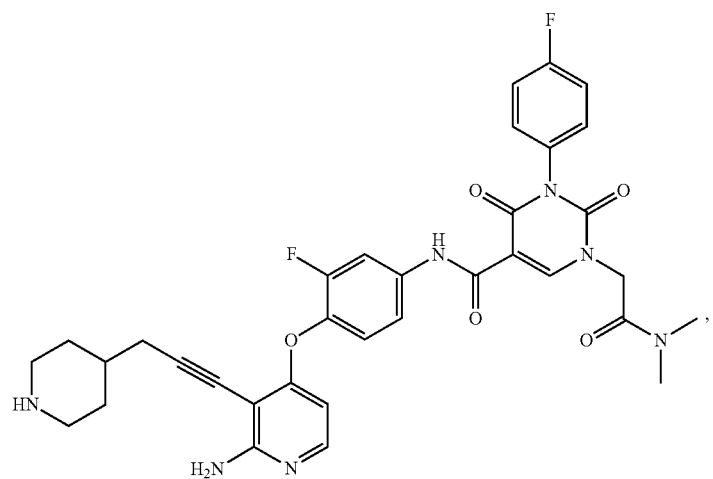

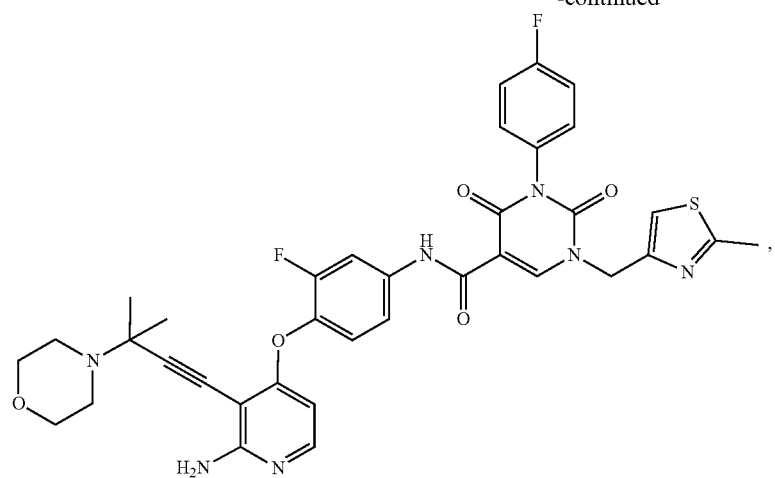
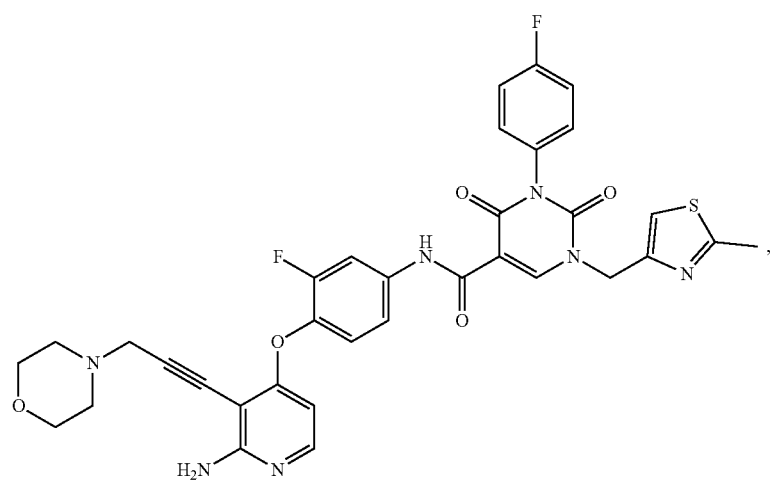
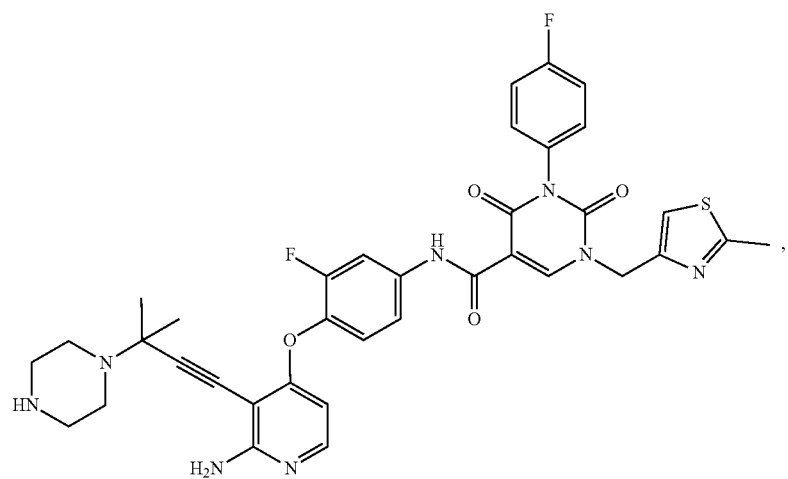

-continued
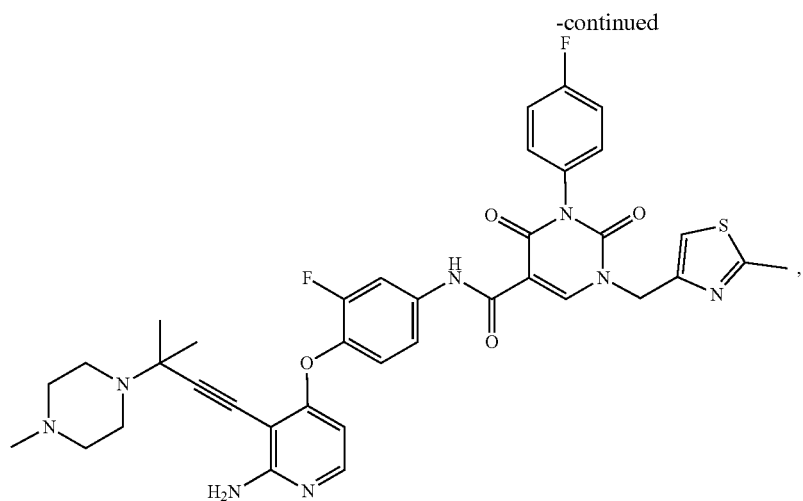
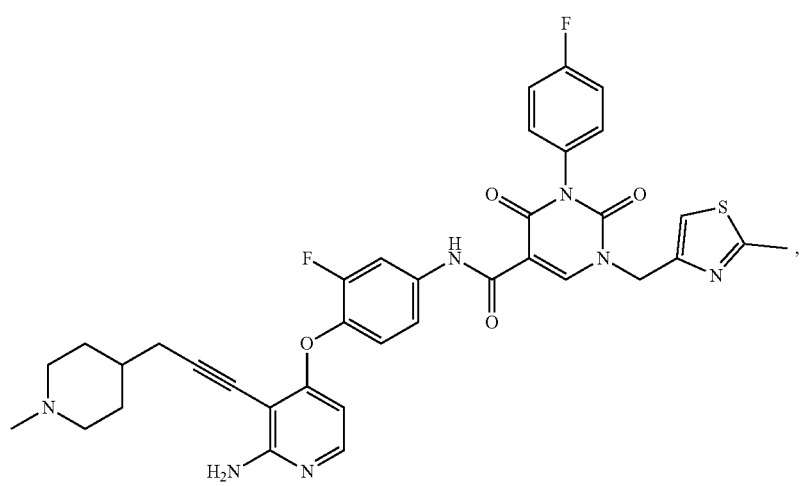
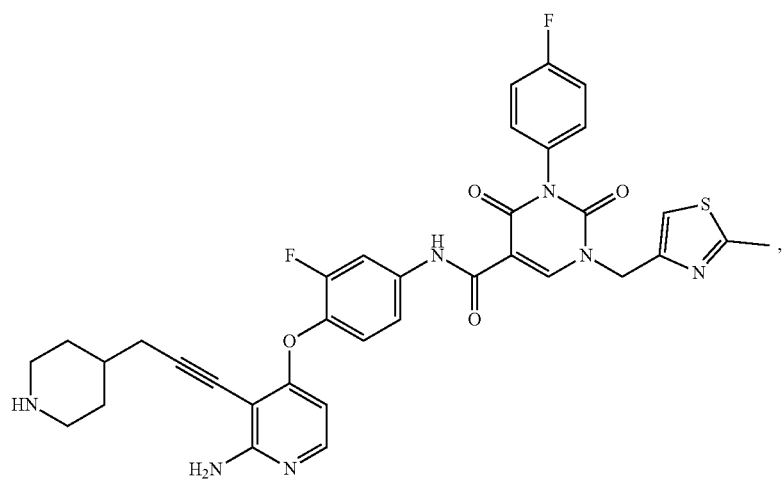

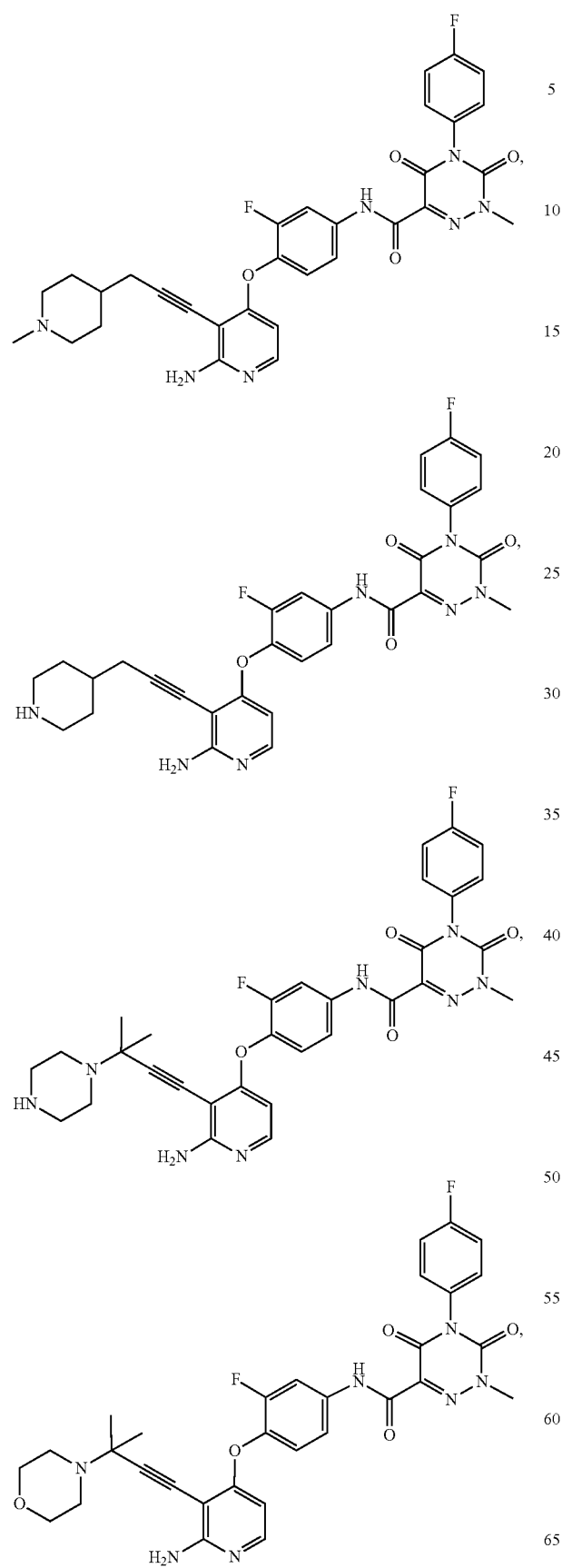

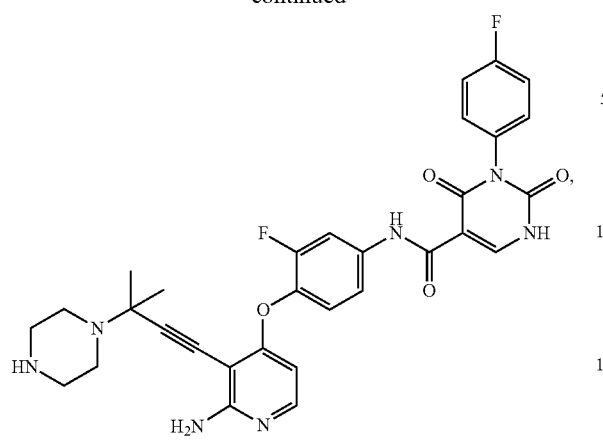
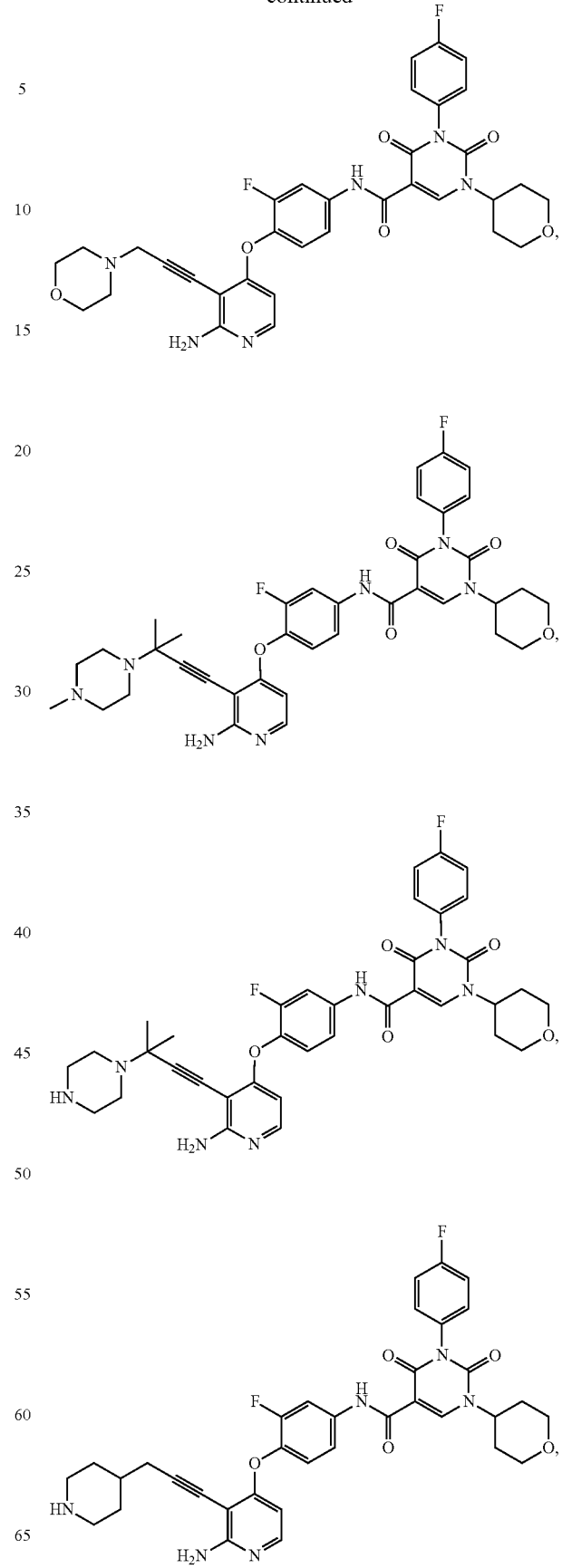

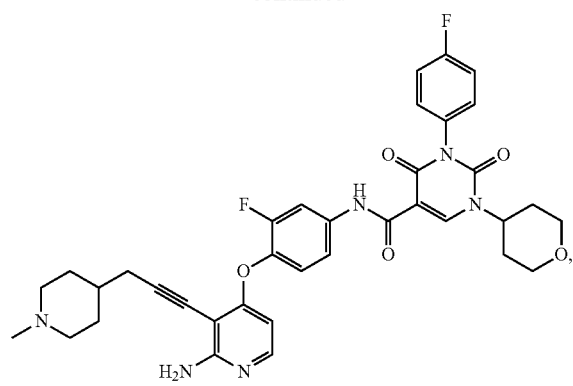
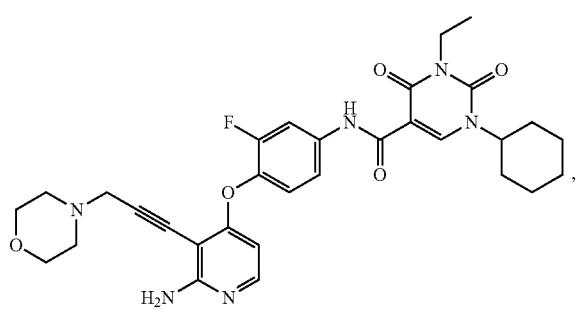
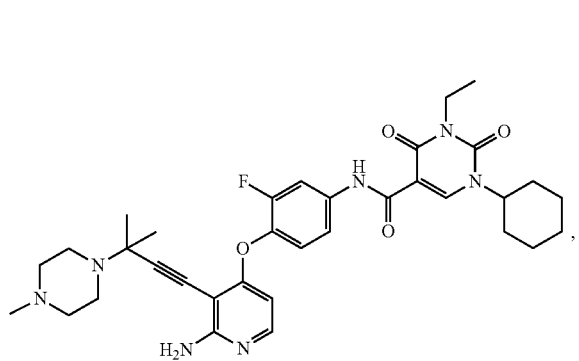
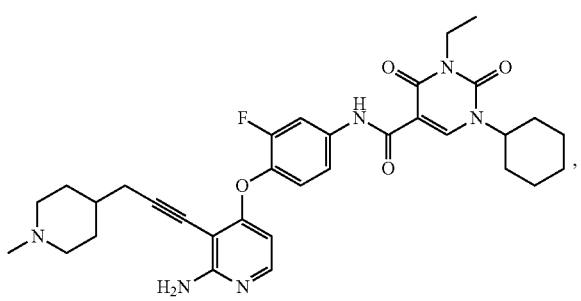
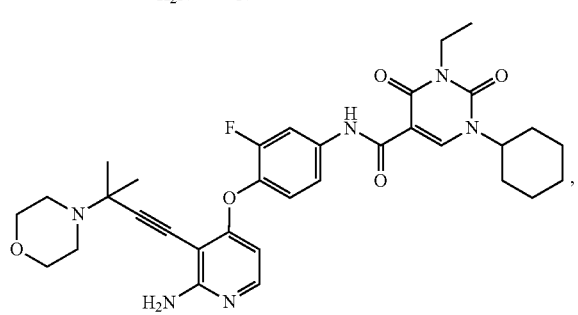
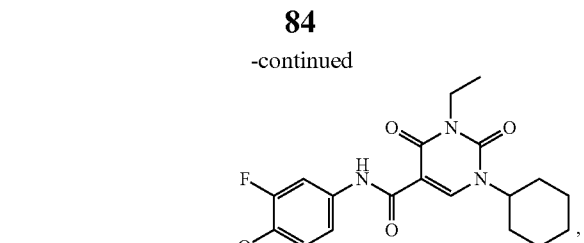
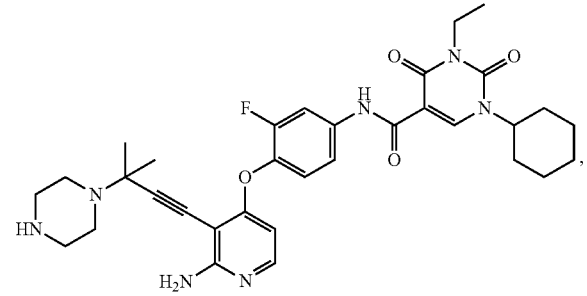
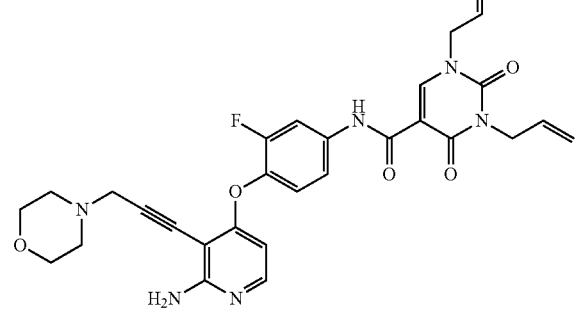
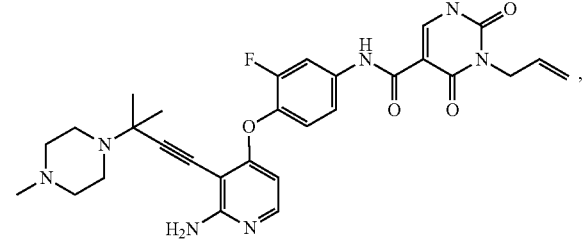
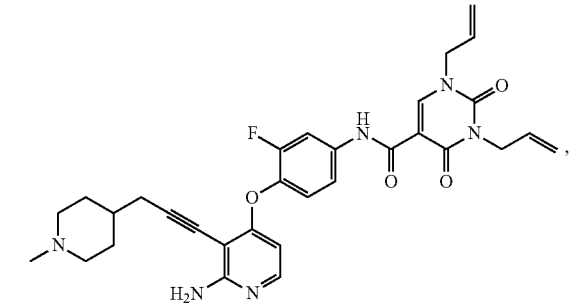

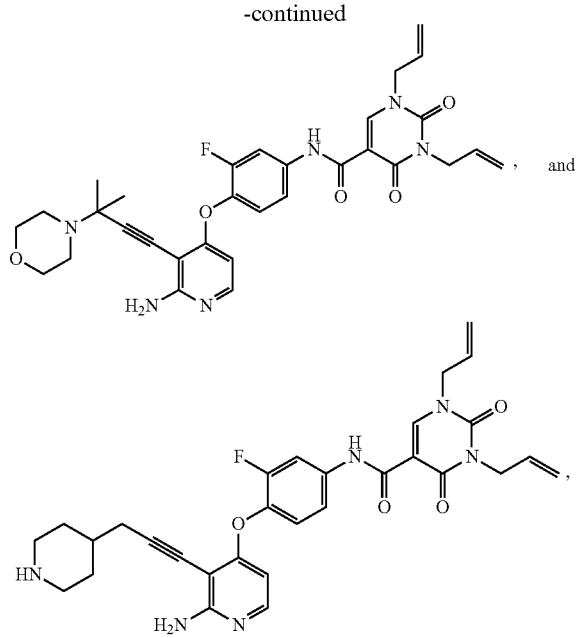

or a pharmaceutically acceptable salt thereof.

17. A pharmaceutical composition comprising at least one compound of any one of aspects 1-16 or a pharmaceutically acceptable salt thereof and a pharmaceutically acceptable carrier.

18. A method of treating or prophylaxis of an AXL-, Mer- and/or c-Met-mediated disease in a subject, wherein the disease is selected from the group consisting of papillary thyroid carcinoma, pancreatic cancer, lung cancer, colon cancer, breast carcinoma, neuroblastoma, pain, cachexia, dermatitis, and asthma, the method comprising administering a pharmaceutically effective amount of the compound of any one of aspects 1-16 or a pharmaceutically acceptable salt thereof to a subject in need of such treatment.

19. The method of aspect 18, wherein the lung cancer is non-small cell lung cancer.

20. A method of inhibiting a AXL, Mer, and/or c-Met enzyme in a cell, the method comprising administering a pharmaceutically effective amount of the compound of any one of aspects 1-16 or a pharmaceutically acceptable salt thereof to a cell in need of such inhibition.

The following examples further illustrate the invention but, of course, should not be construed as in any way limiting its scope.

EXAMPLES

NMR spectra were recorded in CDCl$_3$ and DMSO-d$_6$ solution in 5-mm o.d. tubes (Norell, Inc. 507-TIP) at 30° C. and were collected on Varian VNMRS-400 at 400 MHz for $^1$H. The chemical shifts (δ) are relative to tetramethylsilane (TMS=0.00 ppm) and expressed in ppm. LC/MS was taken on Ion-trap Mass Spectrometer on FINNIGAN Thermo LCQ Advantage MAX, Agilent LC 1200 series (Column: YMC Hydrosphere (C$_{18}$, Ø 4.6×50 mm, 3 m, 120 Å, 40° C.) operating in ESI (+) ionization mode; flow rate=1.0 mL/min., mobile phase=0.01% heptafluorobutyric acid (HFBA) and 1.0% isopropyl alcohol (IPA) in water or CH$_3$CN.

Intermediate Example 1

This example describes the synthesis of 1-morpholino-prop-2-yn-1-one (Intermediate 1).

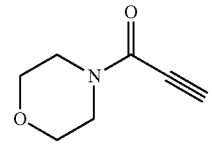

n-BuLi (2.5 M in hexane, 4.89 mL, 12.22 mmol) was slowly added to a solution of ethynyltrimethylsilane (1.45 mL, 10.18 mmol) in tetrahydrofuran (THF) (50 mL) at −78° C. The reaction mixture was stirred for 1 h at the same temperature and was added morpholine-4-carbonyl chloride (1.27 mL, 11.20 mmol). The reaction mixture was stirred additionally for 2 h at room temperature (rt). Water was added to the reaction mixture and stirred for 10 min. Ethyl acetate (EtOAc) was poured into the mixture and the separated organic layer was extracted with EtOAc. The organic layer was dried over Na$_2$SO$_4$, filtered, and concentrated in vacuo. The residue was purified by column chromatography on SiO$_2$ (Hexanes/EtOAc=1/1) to afford the 1-morpholino-prop-2-yn-1-one (1.03 g, 73%) as an off-white solid. $^1$H-NMR (CDCl$_3$, Varian, 400 MHz): δ 3.14 (1H, s), 3.64-3.69 (4H, m), 3.70-3.73 (2H, m), 3.77-3.79 (2H, m).

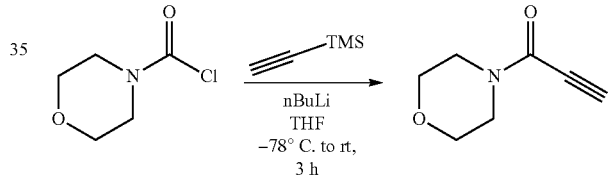

Intermediate Example 2

This example describes the synthesis of 4-(prop-2-ynyl) morpholine (Intermediate 2).

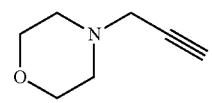

To a solution of morpholine (0.50 g, 5.74 mmol) in acetone (30.0 mL) were added 3-bromoprop-1-yne (0.82 g, 6.89 mmol) and potassium carbonate (1.03 g, 7.46 mmol). The reaction mixture was stirred for 8 h at room temperature. The mixture was filtered through a CELITE™ pad (Sigma-Aldrich, St. Louis, MO), and the filtrate was concentrated in vacuo. The residue was purified by column chromatography on SiO$_2$ (Hexanes/EtOAc=1/1) to afford the 4-(prop-2-ynyl)morpholine (370 mg, 52%) as a yellow oil. $^1$H-NMR (CDCl$_3$, Varian, 400 MHz): δ 2.27 (1H, s), 2.57 (4H, t, J=4.8 Hz), 3.29 (2H, t, J=2.0 Hz), 3.74 (4H, t, J=4.4 Hz).

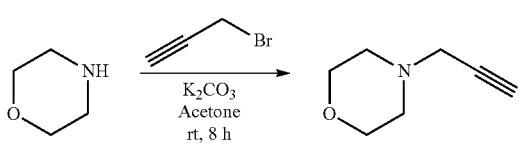

Intermediate Example 3

This example describes the synthesis of tert-butyl 4-(prop-2-ynyl)piperazine-1-carboxylate (Intermediate 3).

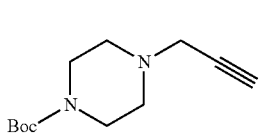

To a mixture of a tert-butyl piperazine-1-carboxylate (5.00 g, 26.8 mmol) and K$_2$CO$_3$ (7.42 g, 53.7 mmol) in CH$_3$CN (140 mL) was added dropwise 3-bromoprop-1-yne (2.63 mL, 34.9 mmol) at 0° C. The reaction mixture was stirred for 2 h at room temperature. The reaction mixture was filtered through a CELITE™ pad (Sigma-Aldrich, St. Louis, MO) and the filtrate was concentrated in vacuo. The residue was purified by column chromatography (Hexanes/EtOAc=1/1) to afford the tert-butyl 4-(prop-2-ynyl)pipearazine-1-carboxylate (5.39 g, 90%) as a yellow oil. $^1$H-NMR (CDCl$_3$, Varian, 400 MHz): δ 1.46 (9H, s), 2.26 (1H, brs), 2.51 (4H, brs), 3.32 (2H, s), 3.47 (4H, t, J=4.4 Hz).

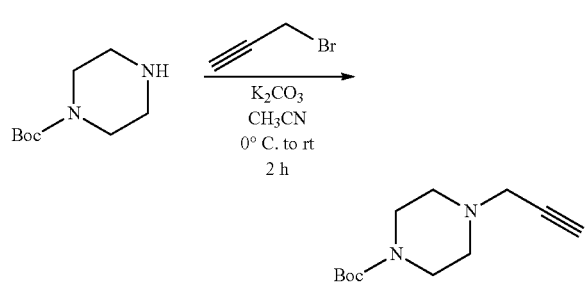

Intermediate Example 4

This example describes the synthesis of tert-butyl 4-propioloylpiperazine-1-carboxylate (Intermediate 4).

To a solution of propiolic acid (0.67 g, 9.66 mmol) in dichloromethane (DCM) (22 mL) was added N,N'-dicyclohexylcarbodiimide (DCC) (1.76 mL, 9.66 mmol) at −5° C. and stirred for 1 h. To the reaction mixture were added tert-butyl piperazine-1-carboxlate (2.0 g, 10.74 mmol) and N,N-diisopropylethylamine (DIPEA) (5.75 mL, 32.2 mmol). The reaction mixture was stirred for 1 h at room temperature. The reaction mixture was filtered through a CELITE™ pad (Sigma-Aldrich, St. Louis, MO), the filtrate was concentrated in vacuo. The residue was purified by column chromatography on SiO$_2$ (Hexanes/EtOAc=1/1) to afford the tert-butyl 4-propioloylpiperazine-1-carboxylate (1.09 g, 43%) as a white solid. $^1$H-NMR (CDCl$_3$, Varian, 400 MHz): δ 1.47 (9H, s), 3.15 (1H, s), 3.43 (2H, t, J=5.6 Hz), 3.49 (2H, t, J 5.6 Hz), 3.61 (2H, t, J=5.6 Hz), 3.74 (2H, t, J=5.6 Hz).

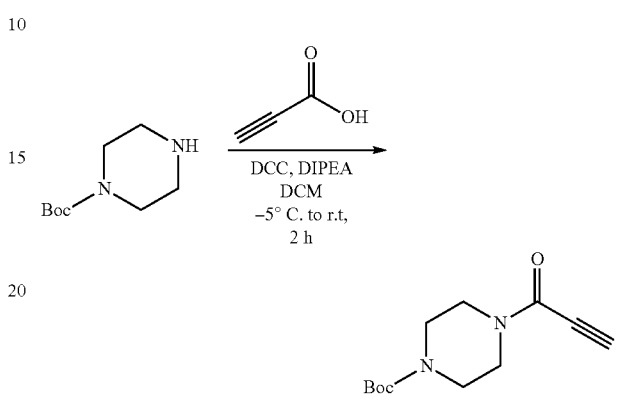

Intermediate Example 5

This example describes the synthesis of tert-butyl 4-acryloylpiperazine-1-carboxylate (Intermediate 5).

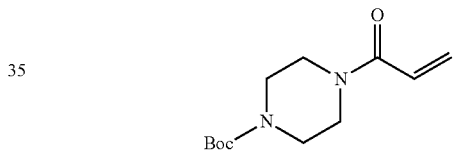

Triethylamine (TEA) (1.39 mL, 10.0 mmol) was added to a solution of acryloyl chloride (0.89 mL, 11.0 mmol) and tert-butyl piperazine-1-carboxylate in DCM (60 mL) at 0° C. The reaction mixture was stirred for 2 h at room temperature. The reaction mixture was washed with water and saturated NaHCO$_3$ (aq.). The organic layer was dried over Na$_2$SO$_4$, filtered, and concentrated in vacuo to afford the tert-butyl 4-acryloylpiperazine-1-carboxylate (2.33 g, 97%) as a pale yellow solid. $^1$H-NMR (CDCl$_3$, Varian, 400 MHz): δ 1.37 (9H, s), 3.35 (8H, brs), 5.36 (1H, dd, J=10.4 Hz), 6.19 (1H, dd, J=16.8 Hz), 6.48 (1H, dd, J=16.8 Hz).

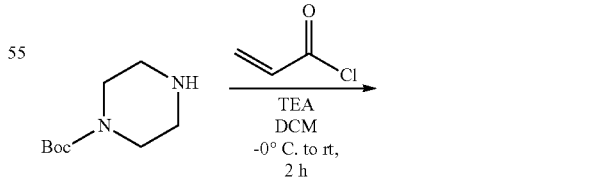
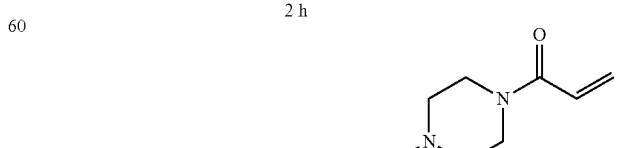

Intermediate Example 6

This example describes the synthesis of tert-butyl 4-(2-methylbut-3-yn-2-yl)piperazine-1-carboxylate (Intermediate 6).

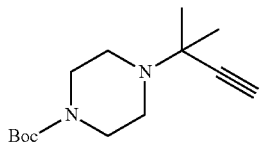 [SMILES: C#CC(C)(C)N1CCN(C(=O)OC(C)(C)C)CC1]

To a solution of tert-butyl piperazine-1-carboxylate (0.50 g, 2.68 mmol), 3-chloro-3-methylbut-1-yne (0.39 mL, 3.50 mmol) and TEA (0.48 mL, 3.50 mmol) in tetrahydrofuran (THF) (10.0 mL) was added copper(I) chloride (0.02 g, 0.19 mmol) under $N_2$ atmosphere. The reaction mixture was stirred at room temperature for 30 min. Water-1N HCl (v/v=2/1, 3.0 mL) was poured into the mixture and extracted with EtOAc. The organic layer was dried over $Na_2SO_4$, filtered and concentrated in vacuo to afford the tert-butyl 4-(2-methylbut-3-yn-2-yl)piperazine-1-carboxylate (0.66 g, 97%) as an ivory solid. $^1$H-NMR (CDCl$_3$, Varian, 400 MHz): δ 1.39 (6H, s), 1.46 (9H, s), 2.29 (1H, s), 2.58 (4H, m), 3.44-3.46 (4H, in).

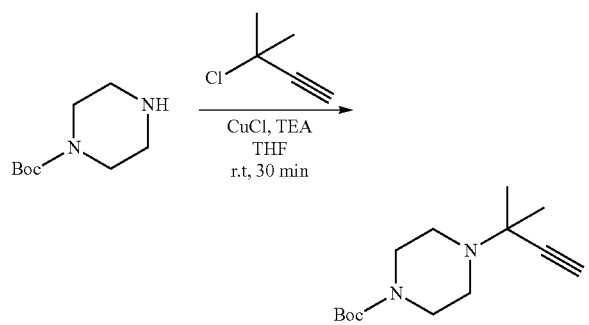

Intermediate Example 7

This example describes the synthesis of 4-(2-methylbut-3-yn-2-yl)morpholine (Intermediate 7).

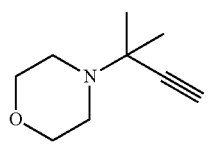

To a solution of morpholine (0.50 g, 5.74 mmol), 3-chloro-3-methylbut-1-yne (0.83 mL, 7.46 mmol) and TEA (1.0 mL, 7.46 mmol) in THE (10.0 mL) was added copper(I) chloride (0.04 g, 0.40 mmol) under $N_2$ atmosphere. The reaction mixture was stirred at room temperature for 30 min. Water-1N HCl (v/v=2/1, 3.0 mL) was poured into the mixture and extracted with EtOAc. The organic layer was dried over $Na_2SO_4$, filtered, and concentrated in vacuo to afford the 4-(2-mehtylbut-3-yn-2-yl)morpholine (0.66 g, 97%) as an ivory solid. $^1$H-NMR (CDCl$_3$, Varian, 400 MHz): δ 1.38 (6H, s), 2.30 (1H, s), 2.62-2.64 (4H, m), 3.73-3.76 (4H, m).

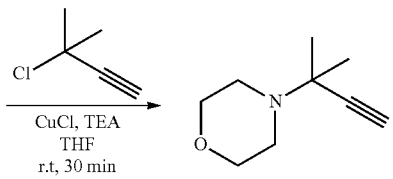

Intermediate Example 8

This example describes the synthesis of 1-methyl-4-(prop-2-ynyl)piperazine (Intermediate 8).

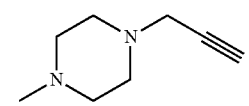

To a solution of 1-methylpiperazine (3.80 mL, 33.7 mmol) and $K_2CO_3$ (4.70 g, 33.7 mmol) in acetone (40 mL) was added to a solution of 3-bromoprop-1-yne (1.70 mL, 22.5 mmol) in acetone (10 mL) at 0° C. The reaction mixture was stirred at room temperature for 4 h and concentrated in vacuo. Water was poured into the residue and extracted with DCM. The organic layer was dried over $Na_2SO_4$, filtered and concentrated in vacuo to afford the 1-methyl-4-(prop-2-ynyl)piperazine (2.10 g, 45%) as a dark yellow oil. $^1$H-NMR (CDCl$_3$, Varian, 400 MHz): δ 2.14-2.16 (1H, m), 2.19 (3H, s), 2.74-2.48 (8H, m), 3.17 (1H, d, J=2.4 Hz).

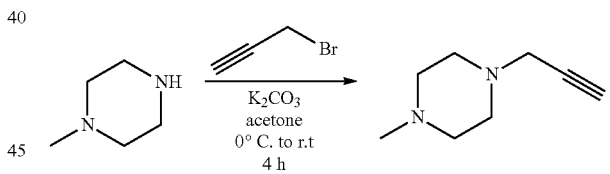

Intermediate Example 9

This example describes the synthesis of 4-ethynyl-1-propyl-1H-pyrazole (Intermediate 9).

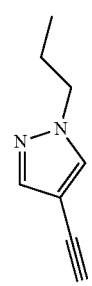

Step A: 4-iodo-1-propy-1H-pyrazole

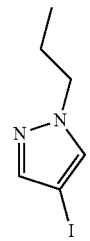

A mixture of 4-iodo-1H-pyrazole (500 mg, 2.58 mmol), and K$_2$CO$_3$ (430 mg, 3.09 mmol) in dimethylfuran (DMF) (10 mL) was stirred for 5 min at room temperature. 1-Iodopropane (0.28 mL, 2.84 mmol) was added to the mixture and stirred for 17 h at room temperature. The reaction mixture was filtered through a CELITE™ pad (Sigma-Aldrich, St. Louis, MO), and the filtrate was concentrated in vacuo. Water was added to the residue, and aqueous layer was extracted with EtOAc. The combined organic layers were dried over Na$_2$SO$_4$, filtered, and concentrated in vacuo. The residue was purified by column chromatography on SiO$_2$ (Hexanes/EtOAc=7/3) to afford the -iodo-1-propy-1H-pyrazole (430 mg, 71%) as a brown solid. $^1$H-NMR (CDCl$_3$, Varian, 400 MHz): δ 0.61-0.67 (3H, m), 1.57-1.67 (2H, m), 3.81-3.86 (2H, m), 7.22 (1H, d, J=6.8 Hz), 7.75 (1H, d, J=6.4 Hz).

Step B: 1-propyl-4-((trimethylsilyl)ethynyl)-1H-pyrazole

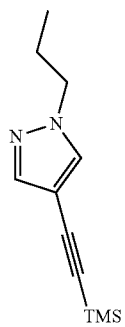

A mixture of 4-iodo-1-propy-1H-pyrazole (430 mg, 1.82 mmol), ethynyltrimethylsilane (0.36 mL, 2.55 mmol), DIPEA (0.41 mL, 2.37 mmol), copper(I) iodide (21 mg, 0.11 mmol), PPh$_3$ (96 mg, 0.36 mmol), and Pd(OAc)$_2$ (29 mg, 0.13 mmol) in DMF (4 mL) was heated at 60° C. under Ar atmosphere for 3 h. After cooling at room temperature, water was poured into the mixture and then extracted with EtOAc. The combined organic layers were dried over Na$_2$SO$_4$, filtered, and concentrated in vacuo. The residue was purified by column chromatography on SiO$_2$ (Hexanes/EtOAc=9/1) to afford the 1-propyl-4-((trimethylsilyl)ethynyl)-1H-pyrazole (260 mg, 69%) as a brown oil. $^1$H-NMR (CDCl$_3$, Varian, 400 MHz): δ 0.09 (9H, s), 0.66 (3H, t, J=5.4 Hz), 1.59-1.68 (2H, m), 3.81 (2H, t, J=6.8 Hz), 7.29 (1H, s), 7.37 (1H, s).

Step C: 4-ethynyl-1-propyl-1H-pyrazole

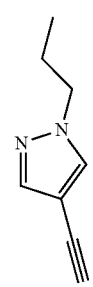

To a solution of 1-propyl-4-((trimethylsilyl)ethynyl)-1H-pyrazole (260 mg, 1.26 mmol) in MeOH (8 mL) was added K$_2$CO$_3$ (192 mg, 1.39 mmol) at room temperature. The reaction mixture was for 10 mins stirred at room temperature and the solvent was removed in vauco. The residue was dissolved with EtOAc and washed with water. The organic layer was dried over Na$_2$SO$_4$, filtered, and concentrated in vacuo to afford the 4-ethynyl-1-propyl-1H-pyrazole (120 mg, 71%) as a dark brown oil. $^1$H-NMR (CDCl$_3$, Varian, 400 MHz): δ 0.90 (3H, t, J=7.6 Hz), 1.84-1.90 (2H, m), 3.01 (1H, s), 4.05 (2H, t, J=7.2 Hz), 7.54 (1H, s), 7.61 (1H, s).

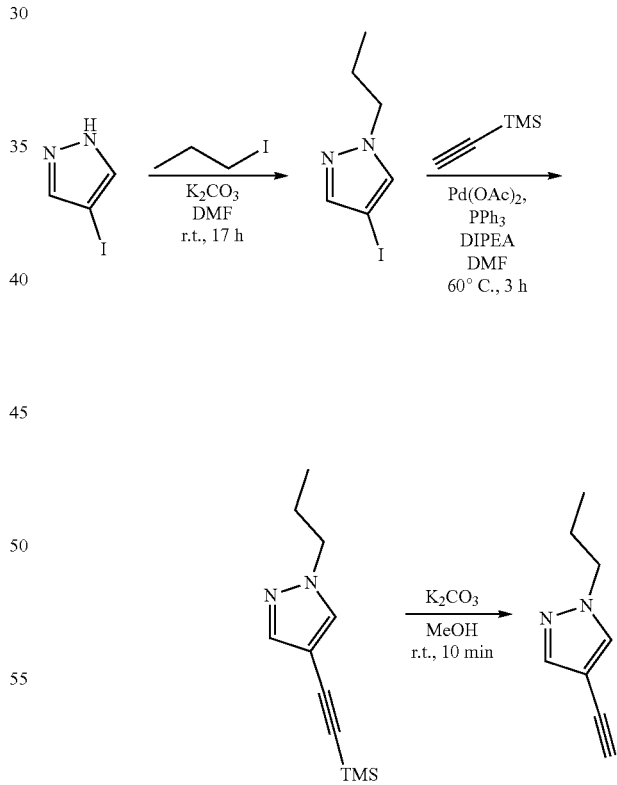

Intermediate Example 10

This example describes the synthesis of 3-(4-fluorophenyl)-1-isopropyl-2,4-dioxo-1,2,3,4-tetrahydropyrimidine-5-carboxylic acid (Intermediate 10).

Step A: diethyl 2-((3-(4-fluorophenyl)ureido)methylene)malonate

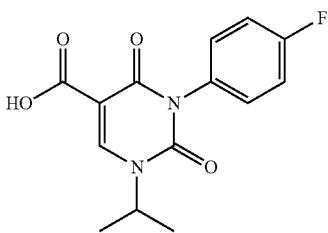 [SMILES: CC(C)n1cc(C(=O)O)c(=O)n(-c2ccc(F)cc2)c1=O]

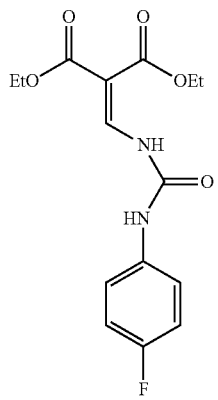 [SMILES: CCOC(=O)C(=CNC(=O)Nc1ccc(F)cc1)C(=O)OCC]

To a solution of diethyl 2-(aminoethylene)malonate (500 mg, 2.67 mmol) in dichloroethane (13 mL) was added 1-fluro-4-isocyanatobenzene (318 μL, 2.80 mmol), followed by DIPEA (513 μL, 2.94 mmol) at room temperature. The reaction mixture was stirred for 8 h at 100° C., and cooled to room temperature. The resulting precipitate was collected by filtration, washed with Et$_2$O, and dried under vacuum to afford the diethyl 2-((3-(4-fluorophenyl)ureido)methylene)malonate (465 mg, 54%) as a yellow solid. $^1$H-NMR (DMSO-d$_6$, Varian, 400 MHz): δ 1.22-1.29 (6H, m), 4.15 (2H, q, J=7.2 Hz), 4.24 (2H, q, J=7.2 Hz), 7.17-7.21 (2H, m), 7.49-7.53 (2H, m), 8.46 (1H, d, J=12.8 Hz), 10.41 (1H, s), 10.58 (1H, d, J=12.4 Hz).

Step B: ethyl 3-(4-fluorophenyl)-2,4-dioxo-1,2,3,4-tetrahydropyrimidine-5-carboxylate

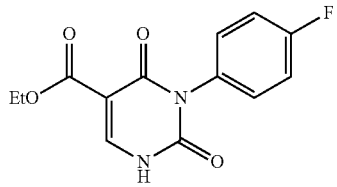 [SMILES: CCOC(=O)c1c[nH]c(=O)n(-c2ccc(F)cc2)c1=O]

To a solution of diethyl 2-((3-(4-fluorophenyl)ureido)methylene)malonate (465 mg, 1.43 mmol) in EtOH (7 mL) was added NaOEt (156 mg, 2.29 mmol) at room temperature. The reaction mixture was stirred for 2 h at room temperature, and concentrated in vacuo. The residue was partitioned with EtOAc and 30% citric acid (aq.), extracted with EtOAc. The combined organic layers were washed with brine, dried over Na$_2$SO$_4$, and concentrated in vacuo. The residue was triturated with DCM and isopropyl ether (IPE) to afford the ethyl 3-(4-fluorophenyl)-2,4-dioxo-1,2,3,4-tetrahydropyrimidine-5-carboxylate (342 mg, 86%) as a yellow solid. $^1$H-NMR (DMSO-d$_6$, Varian, 400 MHz): δ 1.23 (3H, t, J=7.2 Hz), 4.18 (2H, q, J=7.2 Hz), 7.29-7.31 (4H, m), 8.25 (1H, s). * NH peak was not observed.

Step C: ethyl 3-(4-fluorophenyl)-1-isopropyl-2,4-dioxo-1,2,3,4-tetrahydropyrimidine-5-carboxylate

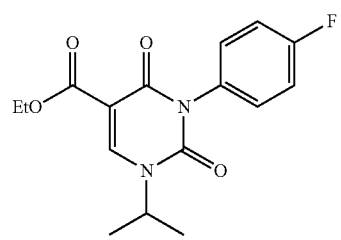 [SMILES: CCOC(=O)c1cn(C(C)C)c(=O)n(-c2ccc(F)cc2)c1=O]

To a solution of ethyl 3-(4-fluorophenyl)-2,4-dioxo-1,2,3,4-tetrahydropyrimidine-5-carboxylate (342 mg, 1.23 mmol) in DMF (3 mL) was added K$_2$CO$_3$ (340 mg, 2.46 mmol), followed by 2-iodopropane (246 μL, 2.46 mmol) at room temperature. The reaction mixture was stirred overnight at 70° C., and quenched with saturated NH$_4$Cl solution (aq.). The aqueous layer was extracted with EtOAc. The combined organic layers were washed with water and brine, dried over Na$_2$SO$_4$, and concentrated in vacuo. The residue was purified by column chromatography on SiO$_2$ (Hexanes/EtOAc=3/2) to afford the ethyl 3-(4-fluorophenyl)-1-isopropyl-2,4-dioxo-1,2,3,4-tetrahydropyrimidine-5-carboxylate (276 mg, 70%) as a yellow solid. $^1$H-NMR (CDCl$_3$, Varian, 400 MHz): δ 1.36 (3H, t, J=7.2 Hz), 1.45 (6H, d, J=6.8 Hz), 4.35 (2H, q, J=7.2 Hz), 4.89-4.95 (1H, m), 7.17-7.18 (4H, m), 8.36 (1H, s).

Step D: 3-(4-fluorophenyl)-1-isopropyl-2,4-dioxo-1,2,3,4-tetrahydropyrimidine-5-carboxylic acid

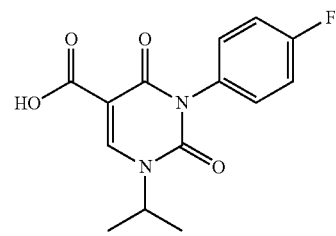

A mixture of ethyl 3-(4-fluorophenyl)-1-isopropyl-2,4-dioxo-1,2,3,4-tetrahydropyrimidine-5-carboxylate (276 mg, 0.86 mmol) and HCl (1.08 mL, 4.31 mmol; 4 M solution in dioxane) in water (0.25 mL) was stirred overnight at 70° C. After cooling at room temperature, the reaction mixture was added water. The resulting precipitate was collected by filtration, washed with water and hexane, dried under vacuum to afford the 3-(4-fluorophenyl)-1-isopropyl-2,4-dioxo-1,2,3,4-tetrahydropyrimidine-5-carboxylic acid (202 mg, 80%) as a white solid. $^1$H-NMR (DMSO-d$_6$, Varian, 400

MHz): δ 1.38 (6H, d, J=6.8 Hz), 4.69-4.74 (1H, m), 7.30-7.35 (4H, m), 8.58 (1H, s). * COOH peak was not observed.

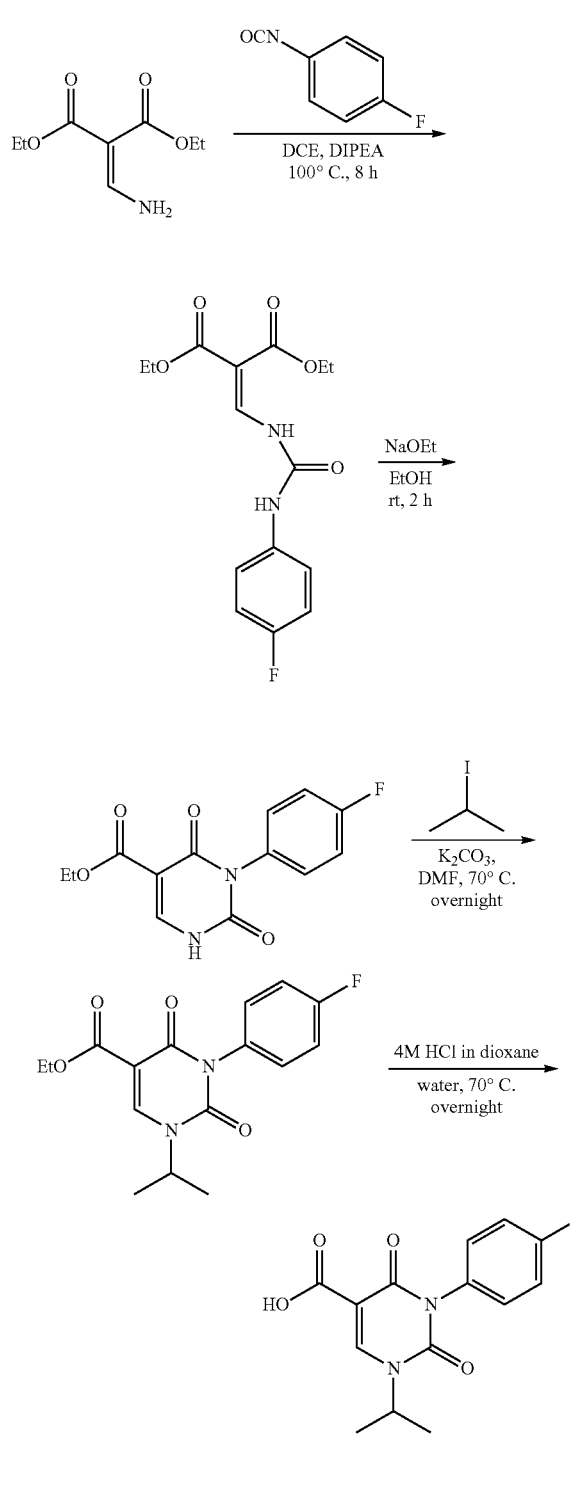

Intermediate Example 11

This example describes the synthesis of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (Intermediate 11).

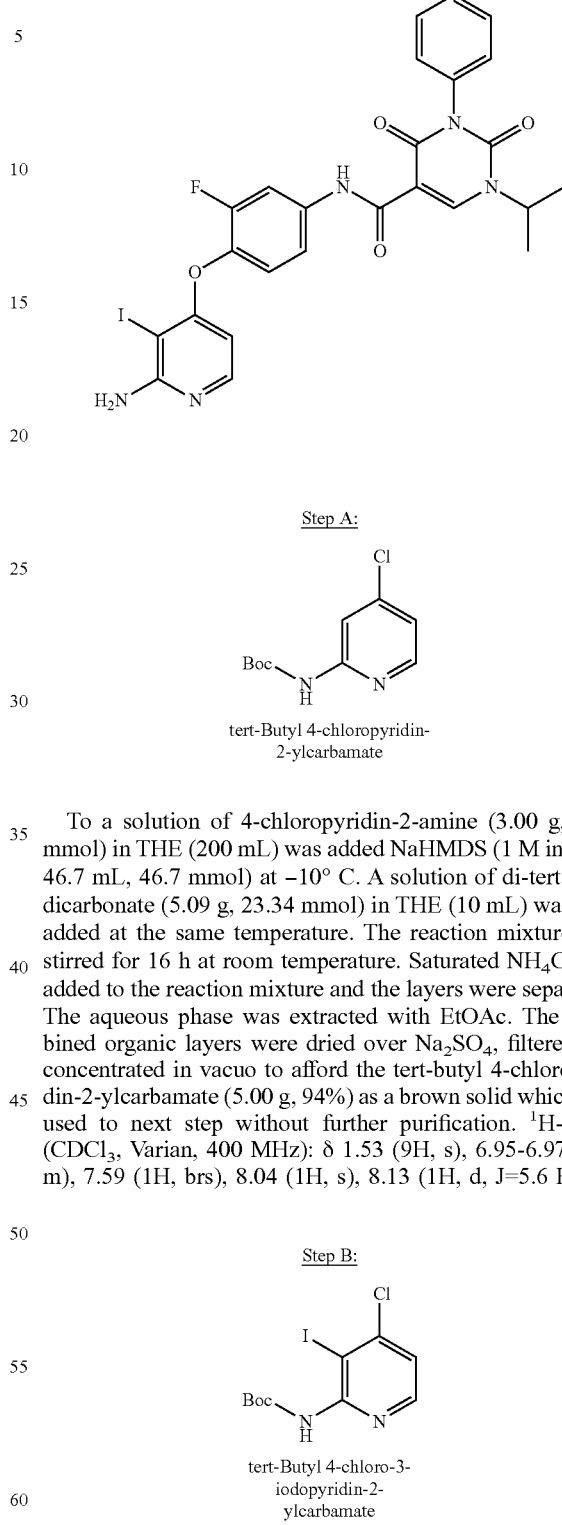

Step A:

tert-Butyl 4-chloropyridin-2-ylcarbamate

To a solution of 4-chloropyridin-2-amine (3.00 g, 23.3 mmol) in THF (200 mL) was added NaHMDS (1 M in THF, 46.7 mL, 46.7 mmol) at −10° C. A solution of di-tert-butyl dicarbonate (5.09 g, 23.34 mmol) in THF (10 mL) was then added at the same temperature. The reaction mixture was stirred for 16 h at room temperature. Saturated NH₄Cl was added to the reaction mixture and the layers were separated. The aqueous phase was extracted with EtOAc. The combined organic layers were dried over Na₂SO₄, filtered and concentrated in vacuo to afford the tert-butyl 4-chloropyridin-2-ylcarbamate (5.00 g, 94%) as a brown solid which was used to next step without further purification. ¹H-NMR (CDCl₃, Varian, 400 MHz): δ 1.53 (9H, s), 6.95-6.97 (1H, m), 7.59 (1H, brs), 8.04 (1H, s), 8.13 (1H, d, J=5.6 Hz).

Step B:

tert-Butyl 4-chloro-3-iodopyridin-2-ylcarbamate n-BuLi (2 M in hexane, 8.75 mL, 21.9 mmol) was dropwise added to a solution of tert-butyl 4-chloropyridin-2-ylcarbamate (2.00 g, 8.75 mmol) and tetramethylethylenediamine (TMEDA) (3.27 mL, 21.87 mmol) in THF (292 mL) at −78° C. for 30 min. The mixture was stirred for 1 h at the same temperature, and then I₂ (11.1 g, 43.7 mmol) in THF (100 mL) was added. After the addition was completed, the reaction mixture was stirred at for 30 min −78° C., and then allowed to warm up to room temperature. The mixture was treated with a solution of sodium hydrogensulfite (16.0 g) in H₂O (100 mL) and stirred for 30 min, and then extracted with EtOAc. The extracts were washed with brine, dried over Na₂SO₄, and concentrated in vacuo. The residue was purified by column chromatography on SiO₂ (Hexanes/EtOAc=1/1) to afford the tert-butyl 4-chloro-3-iodopyridin-2-ylcarbamate (2.10 g, 68%) as a white solid. ¹H-NMR (DMSO-d₆, Varian, 400 MHz): δ 1.45 (9H, s), 7.48 (1H, d, J=4.8 Hz), 8.30 (1H, d, J=4.8 Hz), 9.48 (1H, s).

Step C:

4-Chloro-3-iodopyridin-2-amine

A suspension of tert-butyl 4-chloro-3-iodopyridin-2-ylcarbamate (2.10 g, 5.92 mmol) in HBr (10 mL, 5.92 mmol) was heated for 10 min at 0° C. to give a clear solution. After cooling at 0° C., the reaction mixture was treated with crushed ice and basified with 6 M NaOH (aq.). The precipitated product was collected by vacuum filtration, washed with water and sucked partially on the funnel to give a white solid. The product was dissolved in THF and the solution dried over Na₂SO₄ and concentrated in vacuo to afford the 4-chloro-3-iodopyridin-2-amine (1.50 g, quant.) as a white solid. ¹H-NMR (DMSO-d₆, Varian, 400 MHz): δ 6.43 (2H, s), 6.72 (1H, d, J=5.2 Hz), 7.84 (1H, d, J=5.2 Hz).

Step D:

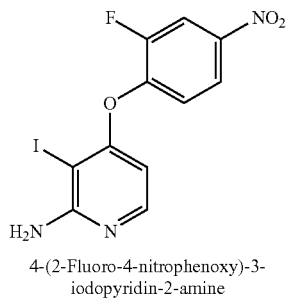

4-(2-Fluoro-4-nitrophenoxy)-3-iodopyridin-2-amine

A mixture of 4-chloro-3-iodopyridin-2-amine (1.50 g, 5.89 mmol), 2-fluoro-4-nitrophenol (1.85 g, 11.8 mmol), DIPEA (1.54 mL, 8.84 mmol) and N-methylpyrrolidone (NMP) (8 mL) was placed in a glass pressure vessel and heated rapidly to 170° C. The heating was continued for 18 h. After cooling at room temperature, the reaction mixture was dissolved with EtOAc and washed with saturated NaHCO₃ solution (aq.). The organic layer was dried over Na₂SO₄, filtered, and concentrated in vacuo. The residue was purified by column chromatography on SiO₂ (Hexanes/EtOAc=3/1) to afford the 4-(2-fluoro-4-nitrophenoxy)-3-iodopyridin-2-amine (1.48 g, 67%) as a pale yellow solid. ¹H-NMR (DMSO-d₆, Varian, 400 MHz): δ 6.19 (1H, d, J=5.6 Hz), 6.41 (2H, s), 7.33 (1H, t, J=8.6 Hz), 7.87 (1H, d, J=5.6 Hz), 8.11-8.14 (1H, m), 8.40 (1H, dd, J=2.4, 10.4 Hz).

Step E:

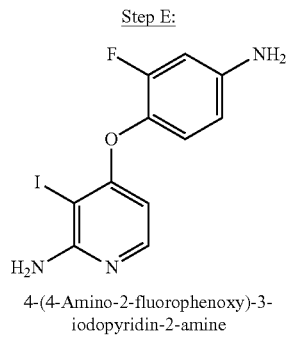

4-(4-Amino-2-fluorophenoxy)-3-iodopyridin-2-amine

A mixture of 4-(2-fluoro-4-nitrophenoxy)-3-iodopyridin-2-amine (150 mg, 0.40 mmol) and SnCl₂ (361 mg, 1.60 mmol) in EtOH (10 mL) was stirred vigorously for 2 h at 90° C. After cooling at room temperature, the solvent was removed under reduced pressure, EtOAc was poured into the residue. The mixture was neutralized with saturated NaHCO₃ (aq.) and 2N NaOH until pH 9, and then filtered through a CELITE™ pad (Sigma-Aldrich, St. Louis, MO). The filtrate was extracted with EtOAc, dried over Na₂SO₄, and concentrated in vacuo to afford the 4-(4-amino-2-fluorophenoxy)-3-iodopyridin-2-amine (130 mg, 94%) as a yellow solid which was used to next step without further purification. ¹H-NMR (CDCl₃, Varian, 400 MHz): δ 3.78 (2H, brs), 5.08 (2H, brs), 5.87 (1H, d, J=5.6 Hz), 6.44-6.53 (2H, m), 6.97 (1H, t, J=8.8 Hz), 7.76 (1H, d, J=5.6 Hz)

Step F:

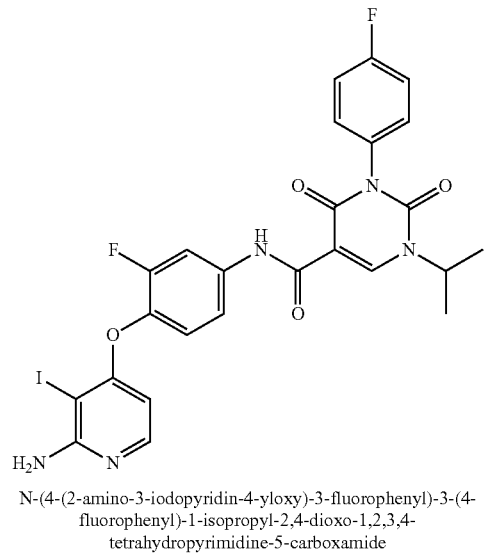

N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide To a mixture of 3-(4-fluorophenyl)-1-isopropyl-2,4-dioxo-1,2,3,4-tetrahydropyrimidine-5-carboxylic acid (intermediate 11, 2.12 g, 7.24 mmol), hexafluorophosphate (HATU) (3.03 g, 7.97 mmol), DIPEA (3.15 mL, 18.1 mmol) in DMF (18 mL) was added and stirred for 1 h at room temperature. The reaction mixture was added 4-(4-amino-2-fluorophenoxy)-3-iodopyridin-2-amine (2.50 g, 7.24 mmol) and was stirred for 3 h at room temperature. The water was poured into the reaction mixture. The resulting solid was collected by filtration, washed with water, and ether, and dried under vacuum to afford the N-(4-(2-amino-3-iodopyridin-4-yloxy)-3-fluorophenyl)-3-(4-fluorophenyl)-1-isopropyl-2,4-dioxo-1,2,3,4-tettahydropyrimidine-5-carbpxamide (3.60 g, 80%) as a beige solid which was used to next step without further purification. $^1$H-NMR (CDCl$_3$, Varian, 400 MHz): δ 10.9 (1H, s), 8.68 (1H, s), 7.82-7.79 (2H, m), 7.26-7.25 (4H, m), 7.19 (1H, d, J=9.2 Hz), 6.95 (1H, t, J=8.4 Hz), 6.02 (1H, d, J=6.0 Hz), 5.09 (2H, s), 5.01-4.94 (1H, m), 1.49 (6H, d, J=6.4 Hz).

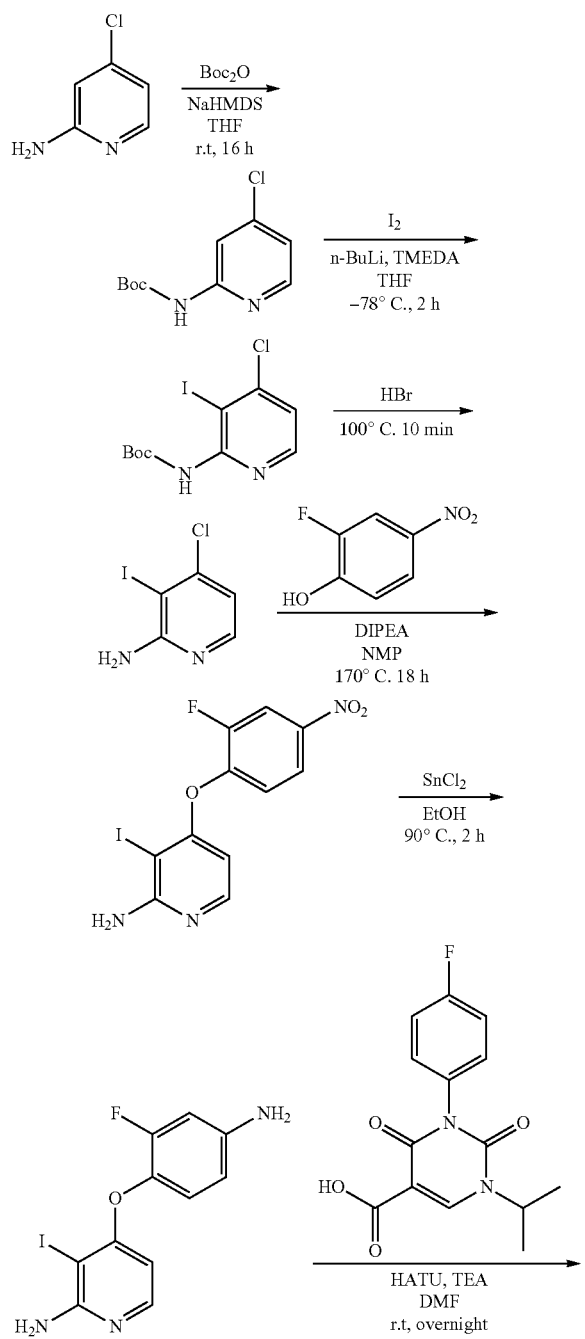

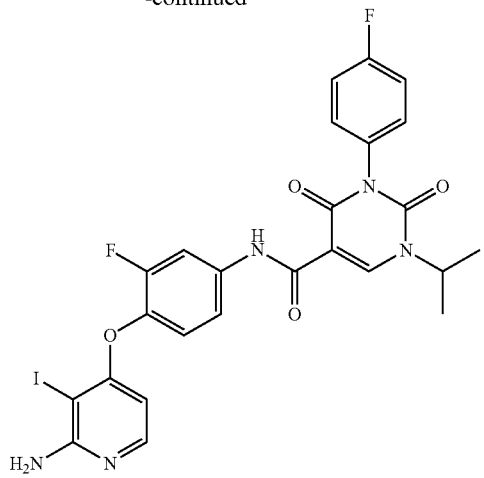

Intermediate Example 12

This example describes the synthesis of tert-butyl 4-(3-(2-amino-4-(4-amino-2-fluorophenoxy)pyridin-3-yl)propioloyl)piperazine-1-carboxylate (Intermediate 12).

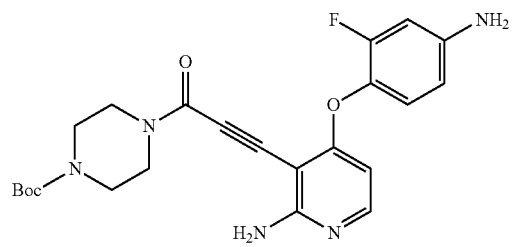 [SMILES: CC(C)(C)OC(=O)N1CCN(C(=O)C#Cc2c(Oc3ccc(N)cc3F)ccnc2N)CC1]

Step A:

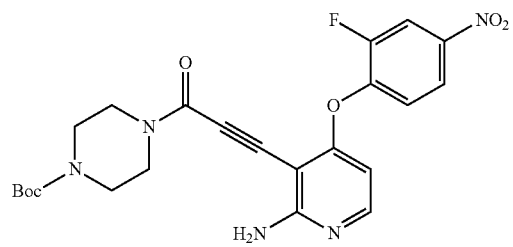

tert-Butyl 4-(3-(2-amino-4-(2-fluoro-4-nirtophenoxy)pyridin-3-yl)propioloyl)piperazine-1-carboxylate To a solution of 4-(2-fluoro-4-nitrophenoxy)-3-iodopyridin-2-amine (step D of intermediate 11, 1.00 g, 2.67 mmol), tert-butyl 4-propioloylpiperazine-1-carboxylate (intermediate 4, 953 mg, 4.00 mmol) and TEA (1.49 mL, 10.7 mmol) in DMF (9 mL) were added copper (I) iodide (102 mg, 0.53 mmol) and Pd(PPh$_3$)$_4$ (308 mg, 0.27 mmol) under N$_2$ at room temperature. The reaction mixture was subjected to microwave irradiation for 1 h at 90° C. The mixture was concentrated in vacuo, and the residue was purified by column chromatography on SiO$_2$ (EtOAc/MeOH=97/3) to afford the tert-butyl 4-(3-(2-amino-4-(2-fluoro-4-nitrophenoxy)pyridin-3-yl)propioloyl)piperazine-1-carboxylate (1.04 g, 80%) as a brown solid. ¹H-NMR (CDCl₃, Varian, 400 MHz): δ 1.47 (9H, s), 3.43 (4H, brs), 3.64 (2H brs), 3.73 (2H, brs), 5.35 (2H, brs), 6.10 (1H, d, J=6.0 Hz), 7.29 (1H, d, J=8.4 Hz), 8.03 (1H, d, J=6.0 Hz), 8.14 (2H, t, J=10.4 Hz).

Step B:

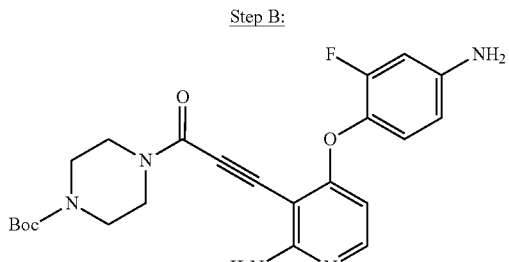

tert-butyl 4-(3-(2-amino-4-(4-amino-2-fluorophenoxy)pyridin-3-yl)propioloyl)piperazine-1-carboxylate A mixture of tert-butyl 4-(3-(2-amino-4-(2-fluoro-4-nitrophenoxy)pyridin-3-yl)propioloyl)piperazine-1-carboxylate (1.04 g, 2.14 mmol), zinc (1.40 g, 21.4 mmol), and ammonium chloride (1.15 g, 21.4 mmol) in THF/MeOH (v/v=1/1, 22 mL) was stirred for 45 min at 60° C. The reaction mixture was filtered and the filtrate was partitioned between EtOAc and saturated NaHCO₃ (aq.). The aqueous layer was extracted with EtOAc. The combined organic layer was washed with brine, dried over Na₂SO₄, and concentrated in vacuo. The residue was purified by column chromatography (EtOAc/MeOH=95/5) to afford the tert-butyl 4-(3-(2-amino-4-(4-amino-2-fluorophenoxy)pyridin-3-yl)propioloyl)piperazine-1-carboxylate (636 mg, 65%) as a yellow solid. ¹H-NMR (CDCl₃, Varian, 400 MHz): δ 1.46 (9H, s), 3.45 (4H, brs), 3.65 (2H brs), 3.81 (2H, brs), 3.85 (2H, brs), 5.22 (2H, brs), 5.98 (1H, d, J=6.0 Hz), 6.45 (1H, d, J=8.4 Hz), 6.51 (1H, dd, J=11.6, 2.4 Hz), 6.93 (1H, t, J=8.4 Hz), 7.90 (1H, d, J=6.0 Hz).

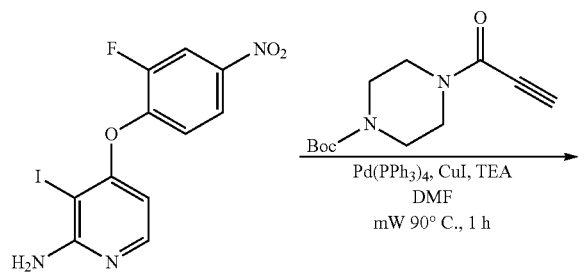

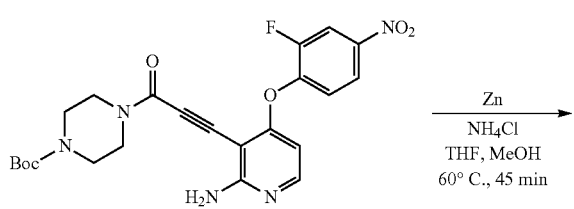

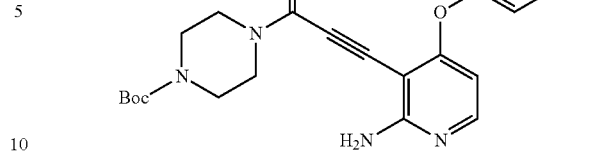

Intermediate Example 13

This example describes the synthesis of tert-butyl 4-(prop-2-ynyl)piperidine-1-carboxylate (Intermediate 13).

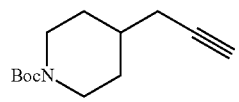

Step A: 4-methylbenzenesulfonyl azide

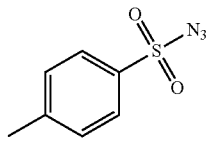

To a solution of 4-methylbenzene-1-sulfonyl chloride (5.0 g, 26.2 mmol) in acetone (65 mL) was added a solution of sodium azide (2.56 g, 39.3 mmol) in water (65 mL) at 0° C. The reaction mixture was allowed to warm up to room temperature and stirred for 3 h. The acetone was removed in vacuo and the mixture was extracted with DCM. The combined organic layer was dried over Na₂SO₄, filtered and concentrated in vacuo to afford 4-methylbenzenesulfonyl azide (4.9 g, 95%) as a colorless oil. ¹H-NMR (CDCl₃, Varian, 400 MHz): δ 2.46 (3H, s), 7.39 (2H, d, J=8.4 Hz), 7.82 (2H, d, J=8.0 Hz).

Step B: dimethyl 1-diazo-2-oxopropylphosphonate

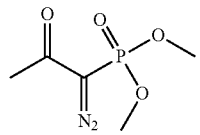

To a stirred suspension of sodium hydride (4.9 g, 24.9 mmol) in toluene (50 mL) and THF (16 mL) was added a solution of dimethyl 2-oxopropylphosphonate (3.78 mL, 27.3 mmol) in toluene (6 mL) at 0° C. A white solid was formed and the stirring was continued for 1 h. A solution of 4-methylbenzenesulfonyl azide (1.19 g, 27.3 mmol) in toluene (10 mL) was added. The reaction mixture was stirred at room temperature for 12 h, and then filtered through a pad of celite. The filtrates was evaporated in vacuo to remove the volatile materials. The residue was purified by column chromatography on SiO₂ (Hexane/EtOAc=1/1) to afford dimethyl 1-diazo-2-oxopropylphosphonate (3.4 g, 71%) as a yellow oil. ¹H-NMR (CDCl₃, Varian, 400 MHz): δ 2.16 (3H, s), 3.73 (3H, s), 3.76 (3H, s).

Step C: tert-butyl 4-(prop-2-ynyl)piperidine-1-carboxylate

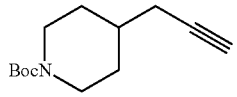

To a solution of tert-butyl 4-(2-oxoethyl)piperidine-1-carboxylate (3.3 g, 14.5 mmol) and potassium carbonate (4.01 g, 29.0 mmol) in MeOH (48 mL) was added dimethyl 1-diazo-2-oxopropylphosphonate (3.35 g, 17.4 mmol) at 0° C. The reaction mixture was stirred at room temperature for 12 h. Then the mixture was extracted with EtOAc, dried over Na₂SO₄, filtered and concentrated in vacuo. The residue was purified by column chromatography on SiO₂ (Hexane/EtOAc=2/1) to afford tert-butyl 4-(prop-2-ynyl)piperidine-1-carboxylate (2.9 g, 89%) as a pale yellow solid. ¹H-NMR (CDCl₃, Varian, 400 MHz): δ 1.02-1.16 (2H, m), 1.32 (9H, s), 1.38-1.56 (1H, m), 1.63 (2H, d, J=12.8 Hz), 1.87 (1H, t, J=2.4 Hz), 2.01 (2H, dd, J=2.2, 6.6 Hz), 2.56 (2H, s), 3.98 (2H, s).

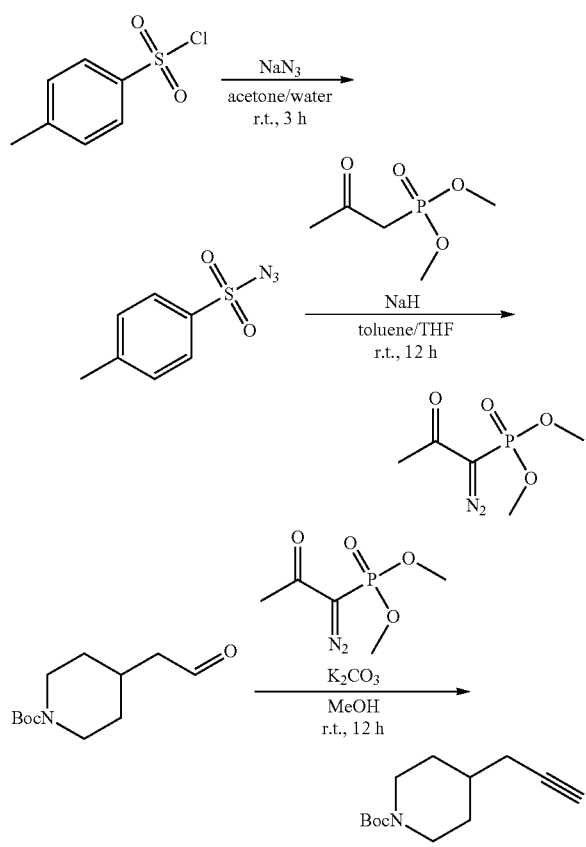

Intermediate Example 14

This example describes the synthesis of 1-methyl-4-(prop-2-ynyl)piperidine hydrochloride (Intermediate 14).

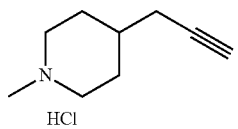

Step A: 4-(prop-2-ynyl)piperidine hydrochloride

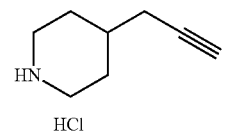

A mixture of tert-butyl 4-(prop-2-ynyl)piperidine-1-carboxylate (1.2 g, 5.37 mmol) and HCl (4 M in dioxane, 8.0 mL, 269 mmol) in DCM (20 mL) was stirred at room temperature for 3 h. The solvent was removed in vacuo, the residue was triturated with ether. A precipitated solid was collected by filtration to afford the 4-(prop-2-ynyl)piperidine hydrochloride (739 mg, 86%) as a white solid. ¹H-NMR (CDCl₃, Varian, 400 MHz): δ 1.34-1.44 (2H, m), 1.66-1.71 (1H, m), 1.79 (2H, d, J=13.6 Hz), 2.14 (2H, dd, J=2.4, 6.0 Hz), 2.79 (2H, t, J=12.2 Hz), 2.88 (1H, d, J=2.4 Hz), 3.20 (2H, d, J=12.8 Hz), 8.78 (1H, s).

Step B: 1-methyl-4-(prop-2-ynyl)piperidine hydrochloride

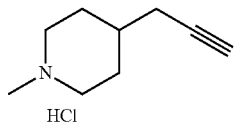

A mixture of 4-(prop-2-ynyl)piperidine hydrochloride (739 mg, 4.63 mmol), formaldehyde (37 wt. % in water, 0.26 mL, 6.94 mmol), sodium cyanoborohydride (582 mg, 9.26 mmol) and acetic acid (0.53 mL, 9.26 mmol) in MeOH (23 mL) was stirred at room temperature for 18 h. The reaction mixture was quenched with NaHCO₃ (aq.) and extracted with DCM, dried over Na₂SO₄, filtered and concentrated in vacuo. The residue was triturated with HCl in ether. A precipitated solid was collected by filtration to afford the 1-methyl-4-(prop-2-ynyl)piperidine hydrochloride (410 mg, 51%) as a white solid. ¹H-NMR (CDCl₃, Varian, 400 MHz): δ 1.73-1.83 (2H, m), 1.93-1.96 (1H, m), 1.98-2.09 (3H, m), 2.22-2.24 (2H, m), 2.68-2.76 (2H, m), 2.78 (3H, s), 3.54 (2H, d, J=12.0 Hz).

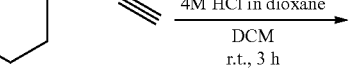

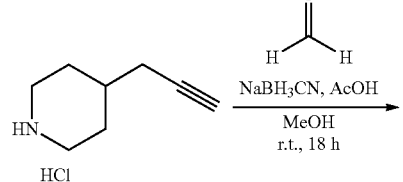

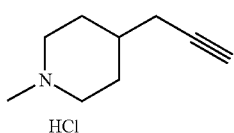

Intermediate Example 15

This example describes the synthesis of 1-(2-(dimethylamino)-2-oxoethyl)-3-(4-fluorophenyl)-2,4-dioxo-1,2,3,4-tetrahydropyrimidine-5-carboxylic acid (Intermediate 15).

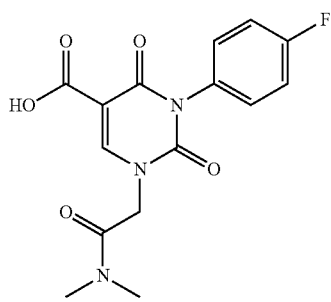

Step A: Diethyl 2-((3-(4-fluorophenyl)ureido)methylene)malonate

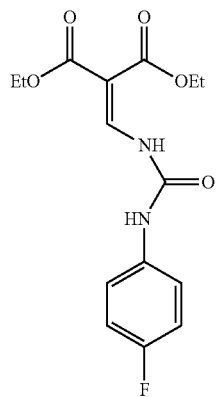

To a solution of diethyl 2-(aminoethylene)malonate (1.0 g, 5.34 mmol) in dichloroethane (1.5 mL) was added 1-fluro-4-isocyanatobenzene (0.64 mL, 5.61 mmol), followed by DIPEA (1.03 mL, 2.94 mmol) at room temperature. The reaction mixture was stirred for 6 h at 100° C., and cooled to room temperature. The solvent was removed in vacuo. The resulting precipitate was collected by filtration, washed with Et$_2$O, and dried under vacuum to afford the diethyl 2-((3-(4-fluorophenyl)ureido)methylene)malonate (776 mg, 44%) as a brown solid. $^1$H-NMR (DMSO-d$_6$, Varian, 400 MHz): δ 1.22-1.29 (6H, m), 4.15 (2H, q, J=7.2 Hz), 4.24 (2H, q, J=7.2 Hz), 7.17-7.21 (2H, m), 7.49-7.53 (2H, m), 8.46 (1H, d, J=12.8 Hz), 10.41 (1H, s), 10.58 (1H, d, J=12.4 Hz).

Step B: Ethyl 3-(4-fluorophenyl)-2,4-dioxo-1,2,3,4-tetrahydropyrimidine-5-carboxylate

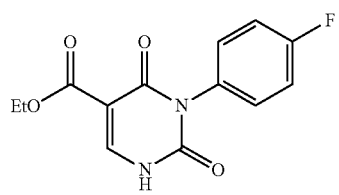

To a solution of diethyl 2-((3-(4-fluorophenyl)ureido)methylene)malonate (776 mg, 2.39 mmol) in EtOH (6 mL) was added NaOEt (261 mg, 3.83 mmol) at 0° C. The reaction mixture was stirred for 2 h at room temperature, and concentrated in vacuo. The residue was partitioned with EtOAc and 1M citric acid (aq.), extracted with EtOAc. The combined organic layers were washed with brine, dried over Na$_2$SO$_4$, and concentrated in vacuo. The residue was triturated with diethylether and hexane to afford the ethyl 3-(4-fluorophenyl)-2,4-dioxo-1,2,3,4-tetrahydropyrimidine-5-carboxylate (562 mg, 85%) as a yellow solid. $^1$H-NMR (DMSO-d$_6$, Varian, 400 MHz): δ 1.23 (3H, t, J=7.2 Hz), 4.18 (2H, q, J=7.2 Hz), 7.29-7.31 (4H, m), 8.25 (1H, s). * NH peak was not observed.

Step C: Ethyl 1-(2-(dimethylamino)-2-oxoethyl)-3-(4-fluorophenyl)-2,4-dioxo-1,2,3,4-tetrahydropyrimidine-5-carboxylate

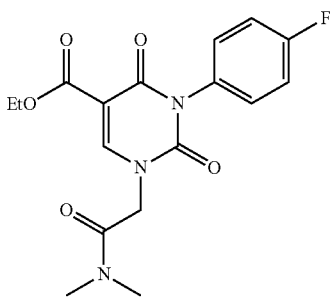

To a solution of ethyl 3-(4-fluorophenyl)-2,4-dioxo-1,2,3,4-tetrahydropyrimidine-5-carboxylate (510 mg, 1.83 mmol) in DMF (5 mL) was added K$_2$CO$_3$ (507 mg, 3.67 mmol), followed by 2-chloro-N,N-dimethylacetamide (0.38 mL, 3.67 mmol) at room temperature. The reaction mixture was heated at 70° C. for overnight in a sealed tube. The reaction mixture was diluted with EtOAc and then filtered through Celite pad. The filtrate was washed with brine, dried over Na$_2$SO$_4$, filtered and concentrated in vacuo. The residue was purified by column chromatography on SiO$_2$ (EtOAc only) to afford the Ethyl 1-(2-(dimethylamino)-2-oxoethyl)-3-(4-fluorophenyl)-2,4-dioxo-1,2,3,4-tetrahydropyrimidine-5-carboxy (560 mg, 84%) as a yellowish withe solid. $^1$H-NMR (CDCl$_3$, Varian, 400 MHz): δ 1.33 (3H, t, J=6.8 Hz), 3.01 (3H, s), 3.06 (3H, s), 4.29-4.35 (2H, m), 4.65 (2H, s), 7.12-7.25 (4H, m), 8.25 (1H, s).

Step D: 1-(2-(dimethylamino)-2-oxoethyl)-3-(4-fluorophenyl)-2,4-dioxo-1,2,3,4-tetrahydropyrimidine-5-carboxylic acid

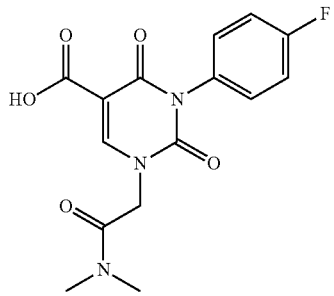 [SMILES: CN(C)C(=O)Cn1cc(C(=O)O)c(=O)n(-c2ccc(F)cc2)c1=O]

A mixture of Ethyl 1-(2-(dimethylamino)-2-oxoethyl)-3-(4-fluorophenyl)-2,4-dioxo-1,2,3,4-tetrahydropyrimidine-5-carboxylate (560 mg, 1.54 mmol) and HCl (4 M in dioxane, 1.93 mL, 7.71 mmol) in water (0.5 mL) was stirred for overnight at 70° C. After cooling at room temperature, the reaction mixture was added water. The reaction mixture was extracted with DCM, washed with brine, dried over Na$_2$SO$_4$, filtered and concentrated in vacuo. The resulting residue was triturated with hexane to afford the 1-(2-(dimethylamino)-2-oxoethyl)-3-(4-fluorophenyl)-2,4-dioxo-1,2,3,4-tetrahydropyrimidine-5-carboxylic acid (419 mg, 81%) as a white solid. $^1$H-NMR (DMSO-d$_6$, Varian, 400 MHz): δ 2.84 (3H, s), 2.97 (3H, s), 4.85 (2H, s), 7.29-7.31 (4H, m), 8.65 (1H, s), 12.58 (1H, s).

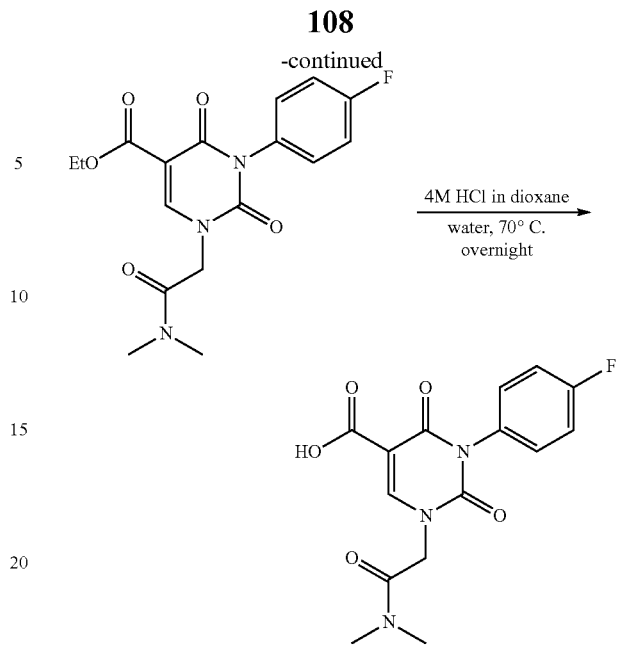

Intermediate Example 16

This example describes the synthesis of N-(4-((2-amino-3-iodopyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (Intermediate 16).

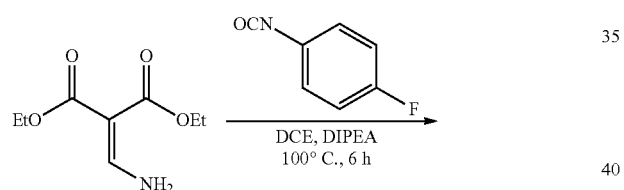

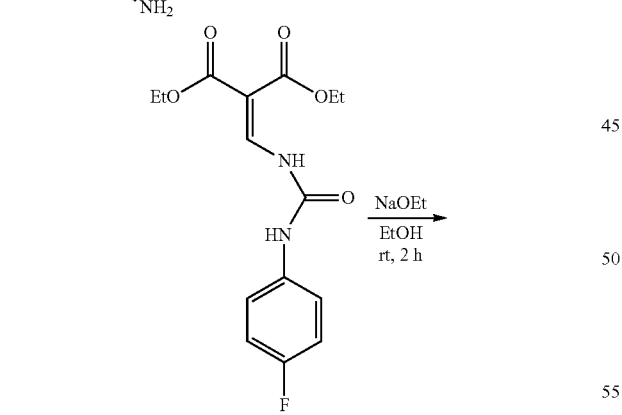

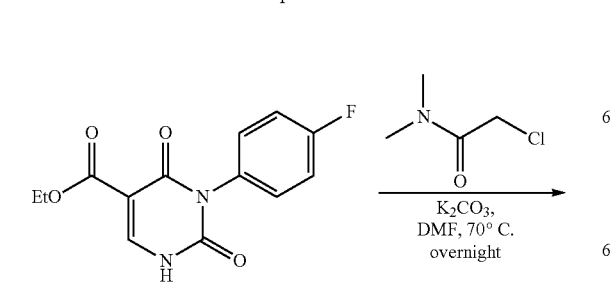

Step A: 4-(4-Amino-2-fluorophenoxy)-3-iodopyridin-2-amine

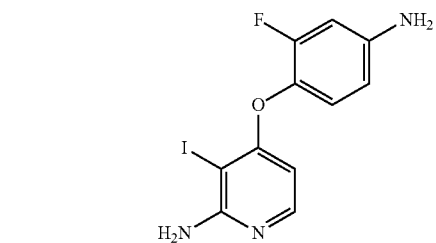

A mixture of 4-(2-fluoro-4-nitrophenoxy)-3-iodopyridin-2-amine (1.04 g, 2.77 mmol) and SnCl$_2$ (2.1 g, 11.09 mmol) in EtOH (27 mL) was stirred vigorously for 2 h at 90° C. After cooling at room temperature, the solvent was removed under reduced pressure, EtOAc was poured into the residue. The mixture was neutralized with 2N NaOH solution until pH 9, and then filtered through Celite pad. The filtrate was extracted with EtOAc, dried over Na$_2$SO$_4$, and filtered and concentrated in vacuo to afford the 4-(4-amino-2-fluorophenoxy)-3-iodopyridin-2-amine (914 mg, 96%) as a yellow solid, which was used to next step without further purification. $^1$H-NMR (CDCl$_3$, Varian, 400 MHz): δ 3.78 (2H, brs), 5.08 (2H, brs), 5.87 (1H, d, J=5.6 Hz), 6.44-6.53 (2H, m), 6.97 (1H, t, J=8.8 Hz), 7.76 (1H, d, J=5.6 Hz)

Step B: N-(4-((2-amino-3-iodopyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide

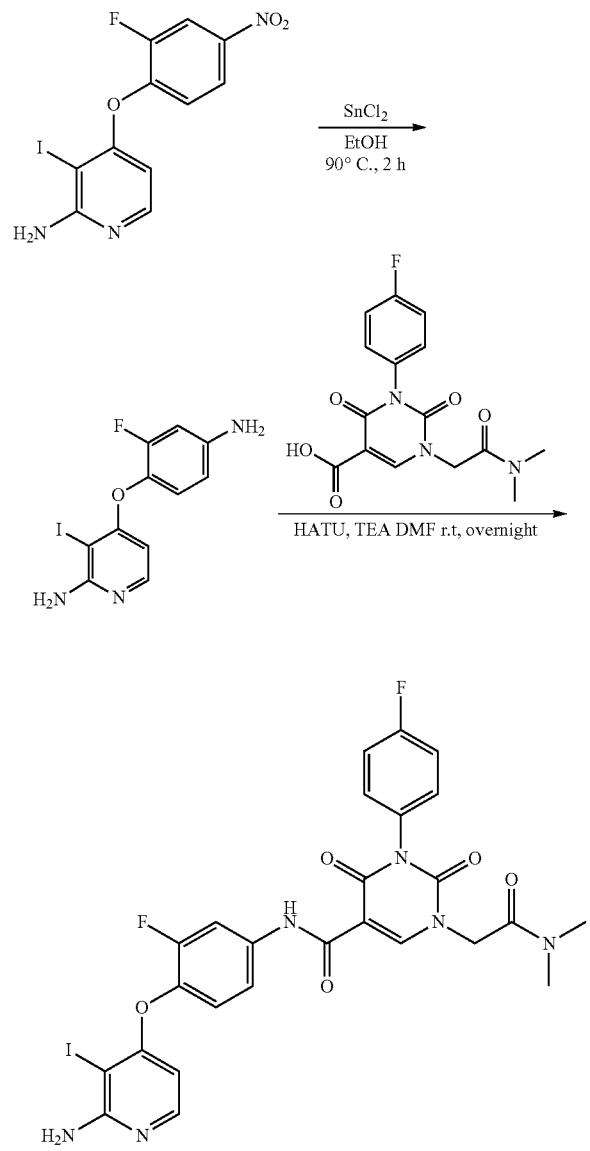

To a mixture of 1-(2-(dimethylamino)-2-oxoethyl)-3-(4-fluorophenyl)-2,4-dioxo-1,2,3,4-tetrahydropyrimidine-5-carboxylic acid (intermediate 15, 194 mg, 0.58 mmol), HATU (331 mg, 0.87 mmol), DIPEA (0.30 mL, 1.74 mmol) in DMF (5.8 mL) was added and stirred for 10 min at room temperature. To the reaction mixture was added 4-(4-amino-2-fluorophenoxy)-3-iodopyridin-2-amine (200 mg, 0.58 mmol) and was stirred for overnight at room temperature. The cold water was poured into the reaction mixture. The resulting solid was collected by filtration, washed with water, and ether, and dried under vacuum to afford the N-(4-((2-amino-3-iodopyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (375 mg, 98%) as a beige solid, which was used for the next step without further purification. $^1$H-NMR (DMSO-d$_6$, Varian, 400 MHz): δ 2.85 (3H, s), 3.00 (3H, s), 4.93 (2H, s), 5.79 (1H, d, J=5.6 Hz), 6.23 (2H, s), 7.28-7.23 (1H, m), 7.36-7.23 (4H, m), 7.46-7.44 (1H, m), 7.71 (1H, d, J=5.6 Hz), 7.92-7.89 (1H, m), 8.75 (1H, s), 10.89 (1H, s).

Intermediate Example 17

This example describes the synthesis of 3-(4-fluorophenyl)-1-((2-methylthiazol-4-yl)methyl)-2,4-dioxo-1,2,3,4-tetrahydropyrimidine-5-carboxylic acid (Intermediate 17).

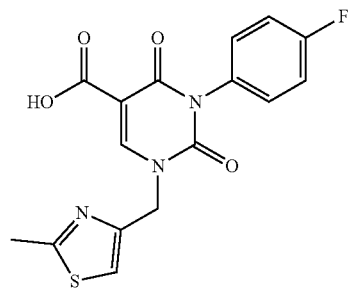 [SMILES: Cc1nc(Cn2cc(C(=O)O)c(=O)n(-c3ccc(F)cc3)c2=O)cs1]

Step A: Diethyl 2-((3-(4-fluorophenyl)ureido)methylene)malonate

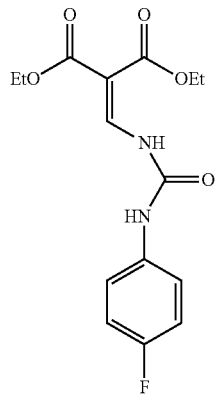

To a solution of diethyl 2-(aminoethylene)malonate (3.0 g, 16.03 mmol) in dichloroethane (4.5 mL) was added 1-fluro-4-isocyanatobenzene (1.9 mL, 16.83 mmol), followed by DIPEA (3.08 mL, 17.63 mmol) at room temperature. The reaction mixture was stirred for 6 h at 100° C. After being cooled to room temperature and the solvent was removed in vacuo. The resulting precipitate was collected by filtration, washed with Et$_2$O, and dried under vacuum to afford the diethyl 2-((3-(4-fluorophenyl)ureido)methylene)malonate (1.79 g, 34%) as a brown solid. $^1$H-NMR (DMSO-d$_6$, Varian, 400 MHz): δ 1.22-1.29 (6H, m), 4.15 (2H, q, J=7.2 Hz), 4.24 (2H, q, J=7.2 Hz), 7.17-7.21 (2H, m), 7.49-7.53 (2H, m), 8.46 (1H, d, J=12.8 Hz), 10.41 (1H, s), 10.58 (1H, d, J=12.4 Hz).

Step B: Ethyl 3-(4-fluorophenyl)-2,4-dioxo-1,2,3,4-tetrahydropyrimidine-5-carboxylate

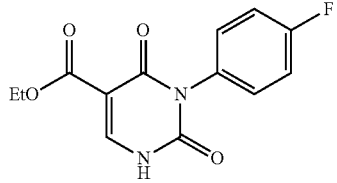

To a solution of diethyl 2-((3-(4-fluorophenyl)ureido)methylene)malonate (1.79 g, 5.54 mmol) in EtOH (14 mL) was added NaOEt (604 mg, 8.87 mmol) at 0° C. The reaction mixture was stirred for 2 h at room temperature, and concentrated in vacuo. The residue was partitioned with EtOAc and 1M citric acid (aq.), extracted with EtOAc. The combined organic layers were washed with brine, dried over Na$_2$SO$_4$, and concentrated in vacuo. The residue was triturated with diethylether and hexane to afford the ethyl 3-(4-fluorophenyl)-2,4-dioxo-1,2,3,4-tetrahydropyrimidine-5-carboxylate (1.4 g, 91%) as a yellow solid. $^1$H-NMR (DMSO-d$_6$, Varian, 400 MHz): δ 1.23 (3H, t, J=7.2 Hz), 4.18 (2H, q, J=7.2 Hz), 7.29-7.31 (4H, m), 8.25 (1H, s). * NH peak was not observed.

Step C: Ethyl 3-(4-fluorophenyl)-1-((2-methylthiazol-4-yl)methyl-2,4-dioxo-1,2,3,4-tetrahydropyrimidine-5-carboxylate

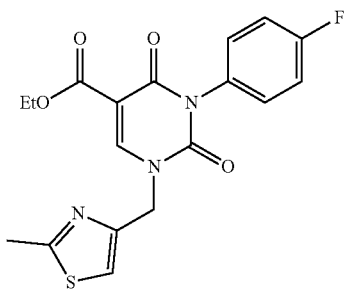

To a solution of ethyl 3-(4-fluorophenyl)-2,4-dioxo-1,2,3,4-tetrahydropyrimidine-5-carboxylate (600 mg, 2.15 mmol) in DMF (6 mL) was added K$_2$CO$_3$ (596 mg, 4.31 mmol), followed by 24-(chloromethyl)-2-methylthiazole (0.5 mL, 4.31 mmol) at room temperature. The reaction mixture was heated at 70° C. for overnight in a sealed tube. The reaction mixture was diluted with EtOAc and then filtered through Celite pad. The filtrate was extracted with EtOAc, washed with brine, dried over Na$_2$SO$_4$, filtered and concentrated in vacuo. The residue was purified by column chromatography on SiO$_2$ (EtOAc Hexane=1/1 to EtOAc only) to afford the Ethyl 3-(4-fluorophenyl)-1-((2-methylthiazol-4-yl)methyl)-2,4-dioxo-1,2,3,4-tetrahydropyrimidine-5-carboxylate (608 mg, 72%) as a yellow solid. $^1$H-NMR (CDCl$_3$, Varian, 400 MHz): δ 1.24-1.20 (3H, m), 2.62 (3H, s), 4.16-4.21 (2H, m), 5.10 (2H, s), 7.26-7.28 (4H, m), 7.46 (1H, s), 8.73 (1H, s).

Step D: 3-(4-fluorophenyl)-1-((2-methylthiazol-4-yl)methyl-2,4-dioxo-1,2,3,4-tetrahydropyrimidine-5-carboxylic acid

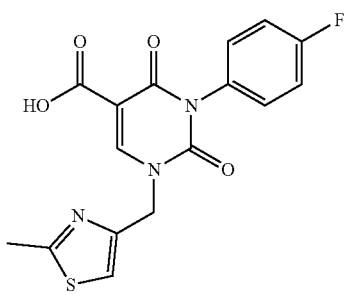

A mixture of Ethyl 3-(4-fluorophenyl)-1-((2-methylthiazol-4-yl)methyl)-2,4-dioxo-1,2,3,4-tetrahydropyrimidine-5-carboxylate (608 mg, 1.56 mmol) and HCl (4 M in dioxane, 2.0 mL, 7.82 mmol) in water (0.5 mL) was stirred overnight at 70° C. After cooling at room temperature, the reaction mixture was added water. The reaction mixture was extracted with DCM, washed with brine, dried over Na$_2$SO$_4$, filtered and concentrated in vacuo. The resulting residue was triturated with hexane to afford the 3-(4-fluorophenyl)-1-((2-methylthiazol-4-yl)methyl)-2,4-dioxo-1,2,3,4-tetrahydropyrimidine-5-carboxylic acid (565 mg, quant.) as a white solid. $^1$H-NMR (DMSO-d$_6$, Varian, 400 MHz): δ 2.62 (3H, s), 5.12 (2H, s), 7.27-7.35 (4H, m), 7.47 (1H, s), 8.83 (1H, s), 12.63 (1H, brs).

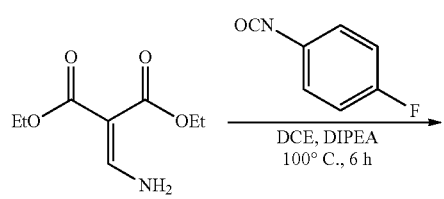
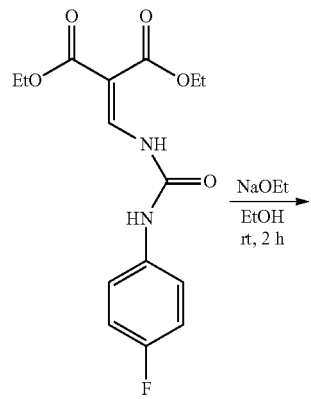

Intermediate Example 18

This example describes the synthesis of N-(4-((2-amino-3-iodopyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (Intermediate 18).

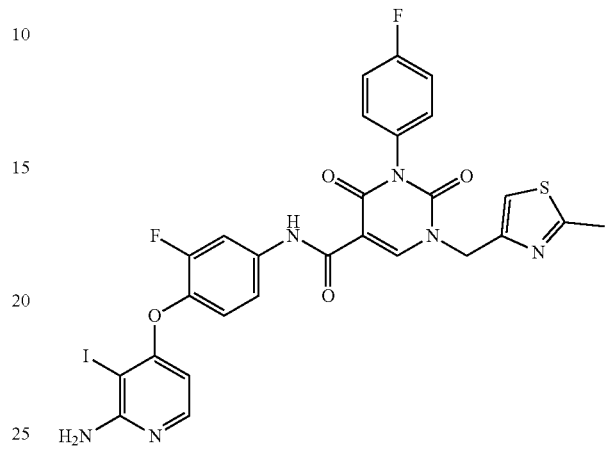

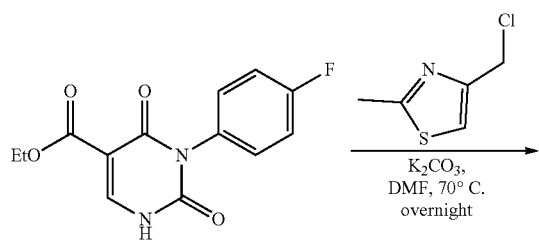

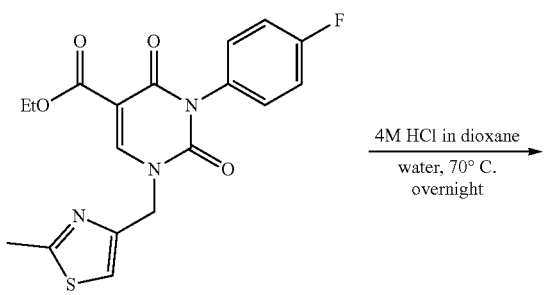

To a mixture of 3-(4-fluorophenyl)-1-((2-methylthiazol-4-yl)methyl)-2,4-dioxo-1,2,3,4-tetrahydropyrimidine-5-carboxylic acid (intermediate 17, 209 mg, 0.58 mmol), HATU (331 mg, 0.87 mmol), DIPEA (0.30 mL, 1.74 mmol) in DMF (2 mL) was added and stirred for 10 min at room temperature. To the reaction mixture was added 4-(4-amino-2-fluorophenoxy)-3-iodopyridin-2-amine (200 mg, 0.58 mmol) and was stirred for overnight at room temperature. The cold water was poured into the reaction mixture. The resulting solid was collected by filtration, washed with water and ether, and dried under vacuum to afford the N-(4-((2-amino-3-iodopyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (318 mg, 80%) as a beige solid, which was used to next step without further purification. $^1$H-NMR (DMSO-$d_6$, Varian, 400 MHz): δ 2.66 (3H, s), 5.20 (2H, s), 5.78 (1H, d, J=5.6 Hz), 6.19 (2H, s), 7.45-7.22 (7H, m), 7.71 (1H, d, J=6 Hz), 7.93-7.89 (1H, m), 8.83 (1H, s), 10.94 (1H, s).

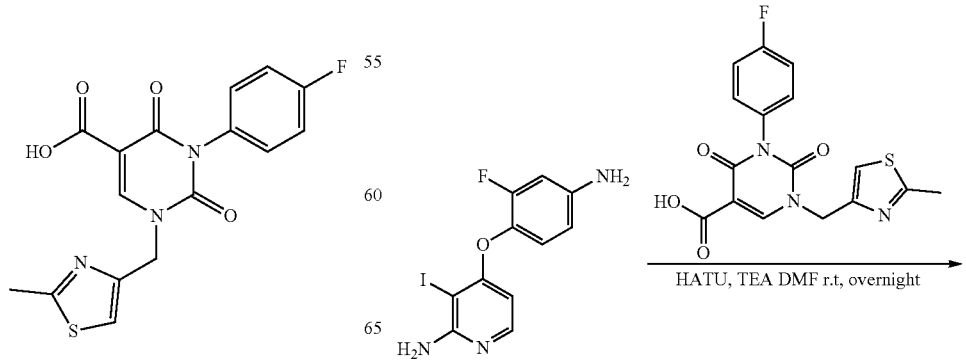

115

-continued

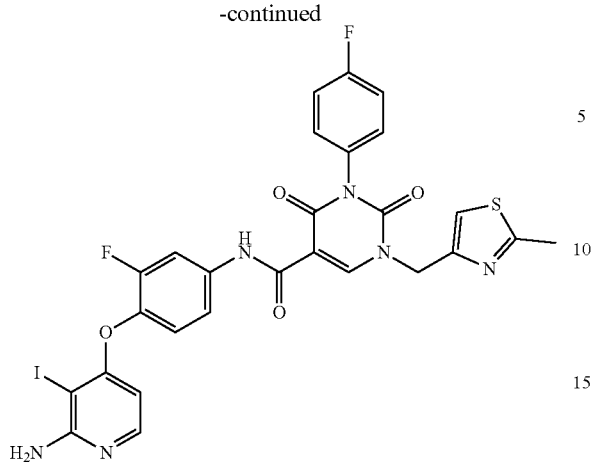

Intermediate Example 19

This example describes the synthesis of 4-(4-fluorophenyl)-2-methyl-3,5-dioxo-2,3,4,5-tetrahydro-1,2,4-triazine-6-carboxylic acid (Intermediate 19).

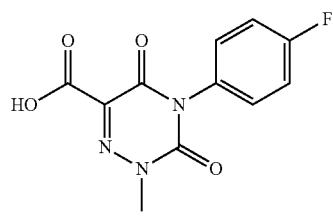

Step A: Ethyl 4-(4-fluorophenyl)-5-oxo-3-thioxo-2,3,4,5-tetrahydro-1,2,4-triazine-6-carboxylate

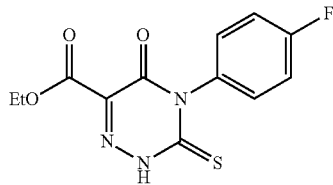

A mixture of diethyl 2-oxomalonate (2.5 mL, 16.20 mmol) and N-(4-fluorophenyl)hydrazinecarbothioamide (3.0 g, 16.20 mmol) in EtOH (60 mL) was heated at reflux for 3 days (72 hrs). The mixture was cooled to room temperature and the resulting precipitate was collected by filtration, dried under vacuum to afford ethyl 4-(4-fluorophenyl)-5-oxo-3-thioxo-2,3,4,5-tetrahydro-1,2,4-triazine-6-carboxylate (2.88 g, 60%) as a white solid. $^1$H-NMR (DMSO-d$_6$, Varian, 400 MHz): δ 1.25 (3H, t, J=7.2 Hz), 4.27 (2H, q, J=7.2 Hz), 7.31 (4H, d, J=7.2 Hz)

116

Step B: Ethyl 4-(4-fluorophenyl)-3,5-dioxo-2,3,4,5-tetrahydro-1,2,4-triazine-6-carboxylate

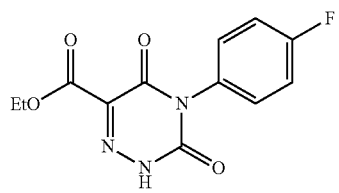

To a solution of ethyl 4-(4-fluorophenyl)-5-oxo-3-thioxo-2,3,4,5-tetrahydro-1,2,4-triazine-6-carboxylate (2.88 g, 9.78 mmol) in DMF (25 mL) and AcOH (10.64 mL, 186 mmol) was added H$_2$O$_2$ (35% in water, 5.14 mL, 58.7 mmol). The mixture was stirred at room temperature for 2 days (48 hrs). The reaction mixture was extracted with EtOAc, water and washed with brine. The organic layer was dried over Na$_2$SO$_4$, filtered and concentrated in vacuo. The crude was triturated with DCM and hexane to afford the ethyl 4-(4-fluorophenyl)-3,5-dioxo-2,3,4,5-tetrahydro-1,2,4-triazine-6-carboxylate (2.40 g, 88%) as a white solid. $^1$H-NMR (DMSO-d$_6$, Varian, 400 MHz): δ 1.24 (3H, t, J=7.2 Hz), 4.26 (2H, q, J=7.2 Hz), 7.29-7.38 (4H, m), 13.15 (s, 1H).

Step C: Ethyl 4-(4-fluorophenyl)-2-methyl-3,5-dioxo-2,3,4,5-tetrahydro-1,2,4-triazine-6-carboxylate

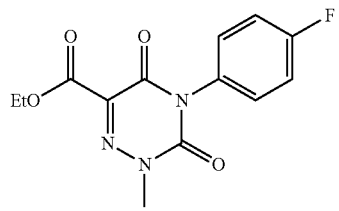

To a solution of ethyl 4-(4-fluorophenyl)-3,5-dioxo-2,3,4,5-tetrahydro-1,2,4-triazine-6-carboxylate (2.40 g, 8.61 mmol) in DMF (20 mL) was added K$_2$CO$_3$ (3.93 g, 28.4 mmol) and MeI (4.85 mL, 77.0 mmol). The mixture was stirred at 60° C. for overnight. The residue was dilute with EtOAc, and then filtered through a Celite pad and washed with EtOAc. The filtrate was washed with water and brine, dried over Na$_2$SO$_4$, filtered and concentrated in vacuo. The residue was purified by column chromatography on SiO$_2$ (Hexane/EtOAc=2/1) to give the ethyl 4-(4-fluorophenyl)-2-methyl-3,5-dioxo-2,3,4,5-tetrahydro-1,2,4-triazine-6-carboxylate (1.84 g, 73%) as a yellow solid. $^1$H-NMR (DMSO-d$_6$, Varian, 400 MHz): δ 1.25 (3H, t, J=7.2 Hz), 3.57 (3H, s), 4.28 (2H, q, J=6.8 Hz), 7.33 (4H, d, J=6.4 Hz).

Step D: 4-(4-fluorophenyl)-2-methyl-3,5-dioxo-2,3,4,5-tetrahydro-1,2,4-triazine-6-carboxylic acid

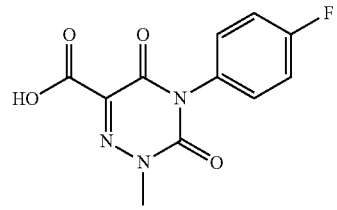 [SMILES: Cn1nc(C(=O)O)c(=O)n(-c2ccc(F)cc2)c1=O]

A mixture of ethyl 4-(4-fluorophenyl)-2-methyl-3,5-dioxo-2,3,4,5-tetrahydro-1,2,4-triazine-6-carboxylate (1.74 g, 5.94 mmol) and HCl (4 M in dioxane, 7.43 mL, 29.7 mmol) in water (2 mL) was stirred at 70° C. for 2 days (48 hrs). After cooling at room temperature, the reaction mixture was added water. The resulting precipitate was collected by filtration, washed with water and hexane, dried under vacuum to afford the 4-(4-fluorophenyl)-2-methyl-3,5-dioxo-2,3,4,5-tetrahydro-1,2,4-triazine-6-carboxylic acid (1.57 g, quant.) as a white solid. $^1$H-NMR (DMSO-$d_6$, Varian, 400 MHz): δ 3.55 (3H, s), 7.32-7.34 (4H, m).

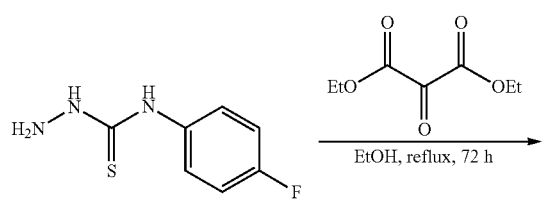

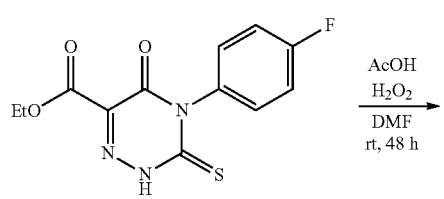

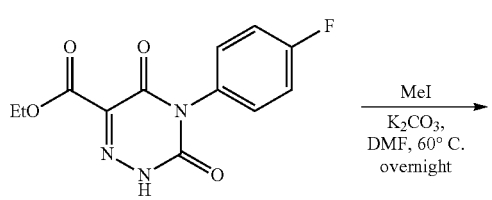

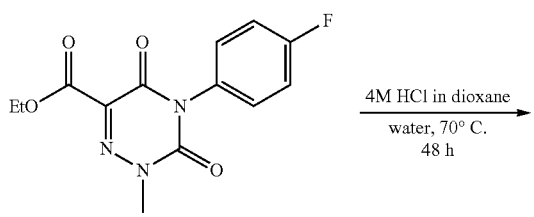

Intermediate Example 20

This example describes the synthesis of N-(4-((2-amino-3-iodopyridin-4-yl)oxy)-3-fluorophenyl)-4-(4-fluorophenyl)-2-methyl-3,5-dioxo-2,3,4,5-tetrahydro-1,2,4-triazine-6-carboxamide (Intermediate 20).

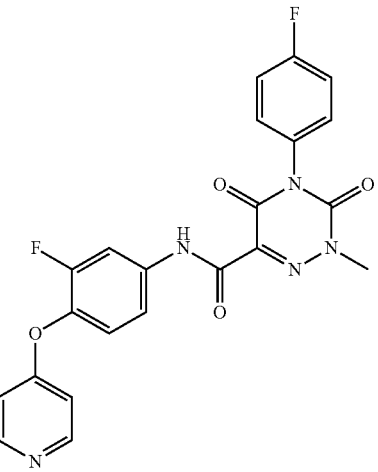

To a mixture of 4-(4-fluorophenyl)-2-methyl-3,5-dioxo-2,3,4,5-tetrahydro-1,2,4-triazine-6-carboxylic acid (intermediate 19, 660 mg, 2.51 mmol), HATU (1.43 g, 3.76 mmol), DIPEA (1.31 mL, 7.53 mmol) in DMF (13 mL) was added and stirred for 10 min at room temperature. To the reaction mixture was added 4-(4-amino-2-fluorophenoxy)-3-iodopyridin-2-amine (860 mg, 2.51 mmol) and was stirred for overnight at room temperature. The cold water was poured into the reaction mixture. The resulting solid was collected by filtration, washed with water and ether, and dried under vacuum to afford the N-(4-((2-amino-3-iodopyridin-4-yl)oxy)-3-fluorophenyl)-4-(4-fluorophenyl)-2-methyl-3,5-dioxo-2,3,4,5-tetrahydro-1,2,4-triazine-6-carboxamide (1.3 g, 88%) as a beige solid which was used for the next step without further purification. $^1$H-NMR (DMSO-$d_6$, Varian, 400 MHz): δ 3.65 (3H, s), 5.79 (1H, d, J=5.6 Hz), 6.25 (2H, brs), 7.28-7.38 (5H, m), 7.49-7.52 (1H, m), 7.71 (1H, d, J=5.6 Hz), 7.88 (1H, d, J=12.4 Hz), 10.87 (1H, s).

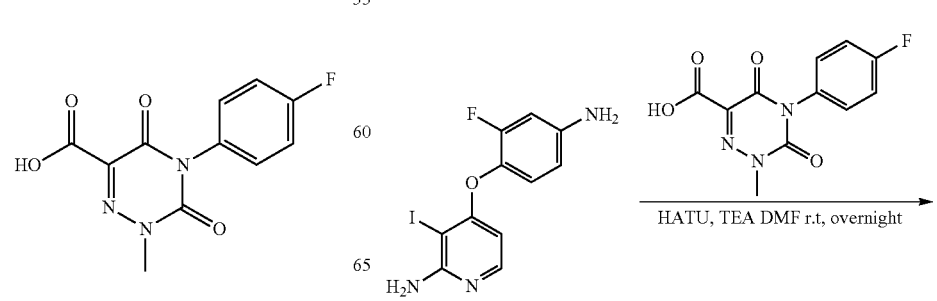

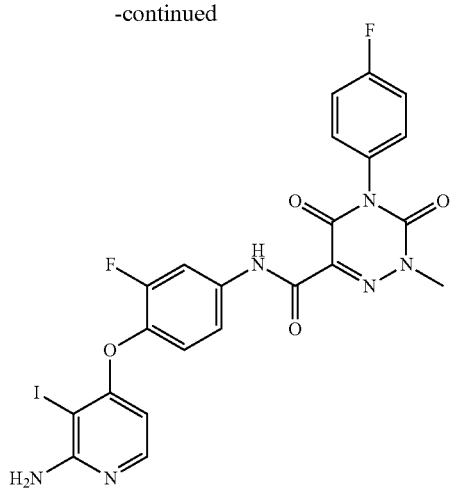

Intermediate Example 21

This example describes the synthesis of 3-(4-fluorophenyl)-2,4-dioxo-1,2,3,4-tetrahydropyrimidine-5-carboxylic acid (Intermediate 21).

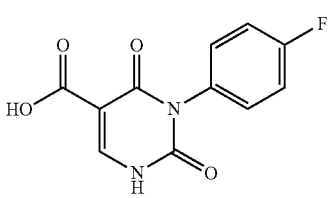

A mixture of ethyl 3-(4-fluorophenyl)-2,4-dioxo-1,2,3,4-tetrahydropyrimidine-5-carboxylate (1.0 g, 3.59 mmol) and HCl (4 M in dioxane, 4.49 mL, 17.97 mmol) in water (1.2 mL) was stirred overnight at 70° C. After cooling at room temperature, the reaction mixture was added water. The resulting precipitate was collected by filtration, washed with water and hexane, dried under vacuum to afford the 3-(4-fluorophenyl)-2,4-dioxo-1,2,3,4-tetrahydropyrimidine-5-carboxylic acid (776 mg, 86%) as a beige solid. $^1$H-NMR (DMSO-d$_6$, Varian, 400 MHz): δ 7.27-7.36 (4H, m), 8.35 (1H, s), 12.30 (1H, brs), 12.54 (1H, brs).

Intermediate Example 22

This example describes the synthesis N-(4-(2-amino-3-iodopyridin-4-yloxy)-3-fluorophenyl)-3-(4-fluorophenyl)-2,4-dioxo-1,2,3,4-tetrahydropyrimidine-5-carboxamide (Intermediate 22).

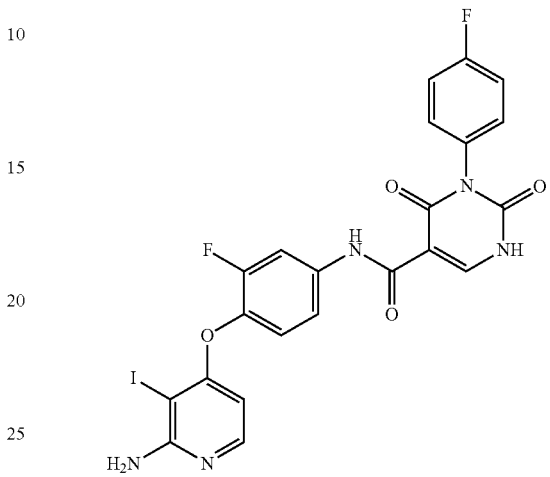

To a mixture of 3-(4-fluorophenyl)-2,4-dioxo-1,2,3,4-tetrahydropyrimidine-5-carboxylic acid (intermediate 21, 636 mg, 2.54 mmol), HATU (1.45 g, 3.82 mmol), DIPEA (1.33 mL, 7.63 mmol) in DMF (11 mL) was added and stirred for 10 min at room temperature. The reaction mixture was added 4-(4-amino-2-fluorophenoxy)-3-iodopyridin-2-amine (877 mg, 2.54 mmol) and was stirred for overnight at room temperature. The water was poured into the reaction mixture. The resulting solid was collected by filtration, washed with water, and ether, and dried under vacuum to afford the N-(4-(2-amino-3-iodopyridin-4-yloxy)-3-fluorophenyl)-3-(4-fluorophenyl)-2,4-dioxo-1,2,3,4-tetrahydropyrimidine-5-carboxamide (1.31 g, 89%) as a yellow solid which was used to next step without further purification. $^1$H-NMR (DMSO-d$_6$, Varian, 400 MHz): δ 5.80 (1H, d, J=5.6 Hz), 6.21 (2H, s), 7.28-7.23 (1H, t, J=8.8 Hz), 7.45-7.32 (5H, m), 7.73 (1H, d, J=5.2 Hz), 7.92-7.89 (1H, m), 8.44 (1H, s), 10.96 (1H, s).
* NH peak was not observed.

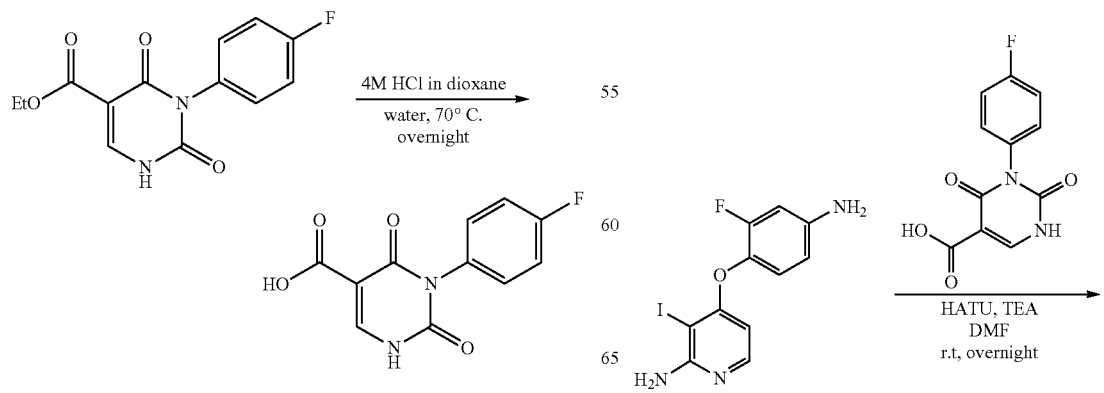

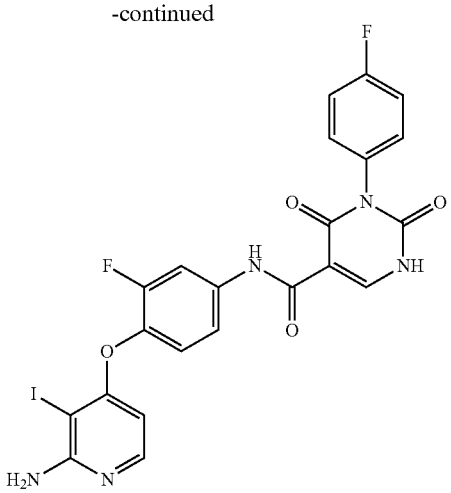

Intermediate Example 23

This example describes the synthesis of 3-(4-fluorophenyl)-2,4-dioxo-1,2,3,4-tetrahydropyrimidine-5-carboxylic acid (Intermediate 23).

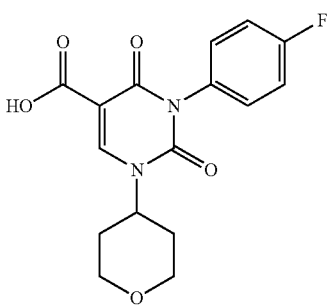

Step A: ethyl 3-(4-fluorophenyl)-2,4-dioxo-1-(tetrahydro-2H-pyran-4-yl)-1,2,3,4-tetrahydropyrimidine-5-carboxylate

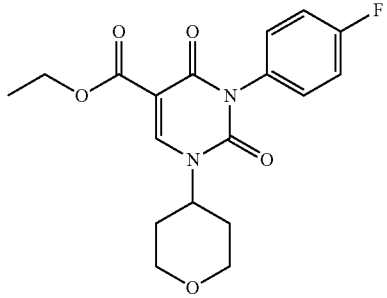

A mixture of ethyl 3-(4-fluorophenyl)-2,4-dioxo-1,2,3,4-tetrahydropyrimidine-5-carboxylate (1.0 g, 3.59 mmol), $K_2CO_3$ (993 mg, 7.19 mmol) in DMF (10 mL) was added 4-bromotetrahydro-2H-pyran (809 μL, 7.19 mmol). The mixture was heated in a sealed tube at 100° C. overnight. After being cooled to room temperature, the reaction mixture was diluted with EtOAc, filtered through a Celite pad The filtrate was washed with water and brine, dried over $Na_2SO_4$, filtered and concentrated in vacuo. The residue was purified by column chromatography on NH—$SiO_2$ (Hexane/EtOAc=1/1) to afford the Ethyl 3-(4-fluorophenyl)-2,4-dioxo-1-(tetrahydro-2H-pyran-4-yl)-1,2,3,4-tetrahydropyrimidine-5-carboxylate (457 mg, 35%) as a white solid. $^1$H-NMR (CDCl$_3$, Varian, 400 MHz): δ 1.36 (3H, t, J=6.8 Hz), 1.93-1.98 (4H, m), 3.50-3.58 (2H, m), 4.13-4.16 (2H, m), 4.35 (2H, q, J=6.8 Hz), 4.75-4.83 (1H, m), 7.17-7.19 (4H, m), 8.36 (1H, s)

Step B: 3-(4-fluorophenyl)-2,4-dioxo-1,2,3,4-tetrahydropyrimidine-5-carboxylic acid

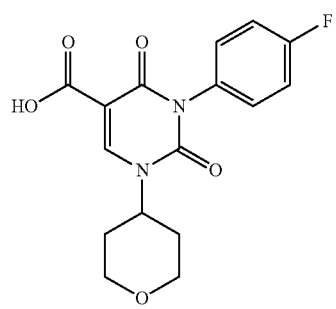 [SMILES: O=C(O)c1cn(C2CCOCC2)c(=O)n(-c2ccc(F)cc2)c1=O]

A mixture of ethyl 3-(4-fluorophenyl)-2,4-dioxo-1-(tetrahydro-2H-pyran-4-yl)-1,2,3,4-tetrahydropyrimidine-5-carboxylate (457 mg, 1.26 mmol) and HCl (4 M in dioxane, 1.58 mL, 6.32 mmol) in water (1 mL) was stirred overnight at 70° C. After cooling at room temperature, the reaction mixture was added water. The reaction mixture was extracted with DCM, washed with brine, dried over $Na_2SO_4$, filtered and concentrated in vacuo. The resulting residue was triturated with hexane to afford the 3-(4-fluorophenyl)-2,4-dioxo-1,2,3,4-tetrahydropyrimidine-5-carboxylic acid (282 mg, 67%) as a beige solid. $^1$H-NMR (CDCl$_3$, Varian, 400 MHz): δ 1.94-1.99 (4H, m), 3.49-3.56 (2H, m), 4.13-4.16 (2H, m), 4.75-4.83 (1H, m), 7.22-7.26 (4H, m), 8.58 (1H, s), 12.28 (1H, brs).

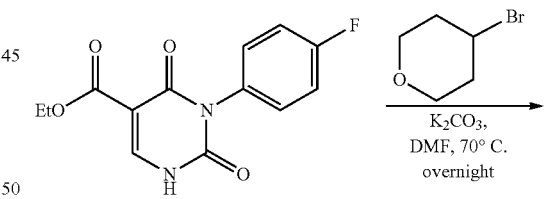

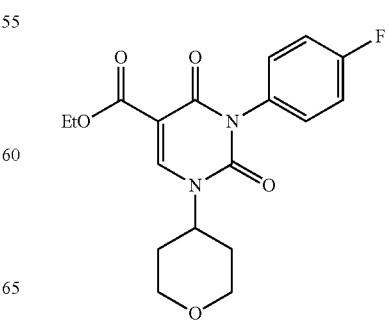

123

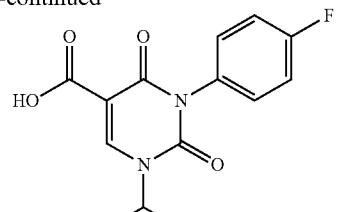

Intermediate Example 24

This example describes the synthesis of N-(4-(2-amino-3-iodopyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (Intermediate 24).

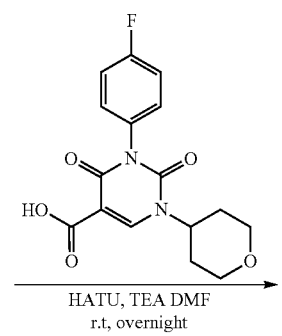

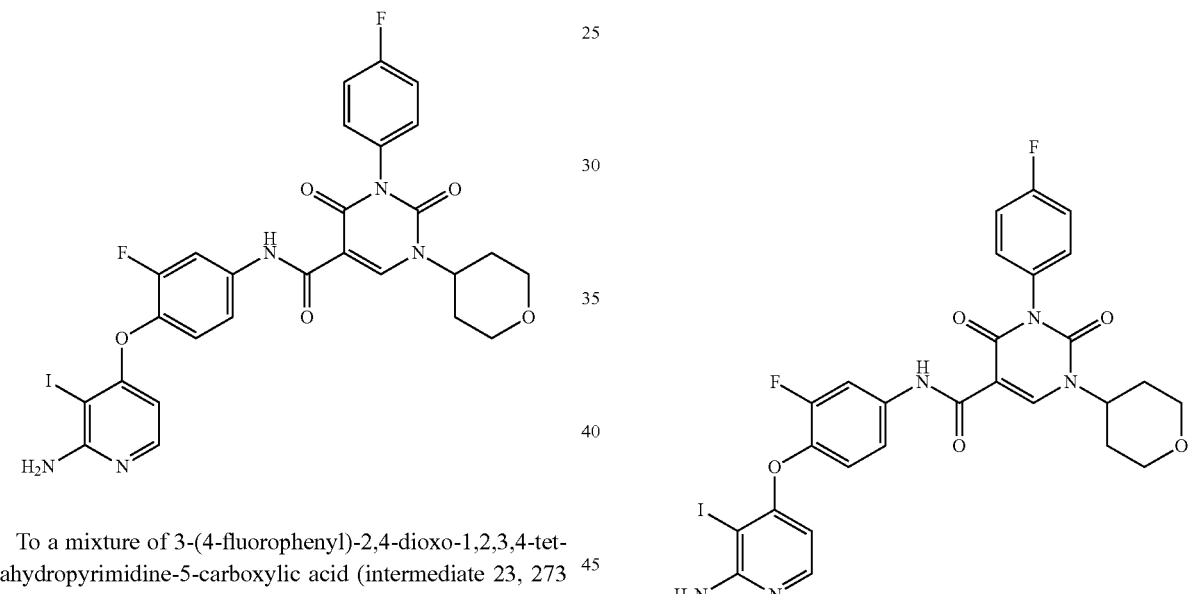

To a mixture of 3-(4-fluorophenyl)-2,4-dioxo-1,2,3,4-tetrahydropyrimidine-5-carboxylic acid (intermediate 23, 273 mg, 0.82 mmol), HATU (466 mg, 1.23 mmol), DIPEA (0.43 mL, 2.45 mmol) in DMF (8 mL) was added and stirred for 10 min at room temperature. The reaction mixture was added 4-(4-amino-2-fluorophenoxy)-3-iodopyridin-2-amine (282 mg, 0.82 mmol) and was stirred for overnight at room temperature. The water was poured into the reaction mixture. The resulting solid was collected by filtration, washed with water, and ether, and dried under vacuum to afford the N-(4-(2-amino-3-iodopyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (490 mg, 91%) as an ivory solid which was used for next step without further purification. $^1$H-NMR (DMSO-$d_6$, Varian, 400 MHz): δ 1.83-1.88 (2H, m), 1.96-2.03 (2H, m), 3.35-3.45 (2H, m), 3.96-3.98 (2H, m), 4.60-4.64 (1H, m), 5.78 (1H, d, J=6.0 Hz), 6.19 (2H, s), 7.24 (1H, t, J=8.8 Hz), 7.31-7.35 (2H, m), 7.38-7.45 (3H, m), 7.71 (1H, d, J=5.6 Hz), 7.90-7.94 (1H, m), 8.61 (1H, s), 10.94 (1H, s).

124

Intermediate Example 25

This example describes the synthesis of 3-cyclohexyl-1-ethyl-2,4-dioxo-1,2,3,4-tetrahydropyrimidine-5-carboxylic acid (Intermediate 25).

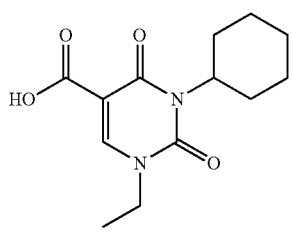

Step A: Diethyl 2-((3-cyclohexylureido)methylene)malonate

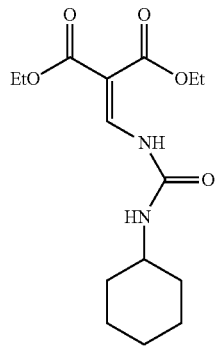

A mixture of diethyl 2-(aminomethylene)malonate (3.0 g, 16.03 mmol), DIPEA (3.36 mL, 19.23 mmol), isocyanatocyclohexane (2.25 mL, 17.63 mmol) in DCE (160 mL) was refluxed for 48 hours. The reaction mixture was cooled to room temperature, diluted with EtOAc, washed with brine. The combined organic layer was dried over $Na_2SO_4$, filtered and concentrated in vacuo. The residue was purified by column chromatography on (EtOAc/Hexanes=1/1) to give a diethyl 2-((3-cyclohexylureido)methylene)malonate (4.00 g, 80%) as a yellow oil. $^1$H-NMR (DMSO-$d_6$, Varian, 400 MHz): δ 1.10-1.24 (11H, m), 1.49-1.52 (1H, m), 1.60-1.70 (2H, m), 1.71-1.80 (2H, m), 3.47 (1H, brs) 4.09 (2H, q, J=7.0 Hz), 4.17 (2H, q, J=6.9 Hz), 8.04 (1H, d, J=7.6 Hz), 8.40 (1H, d, J=13.2 Hz), 10.28 (1H, d, J=12.8 Hz).

Step B: Ethyl 3-cyclohexyl-2,4-dioxo-1,2,3,4-tetrahydropyrimidine-5-carboxylate

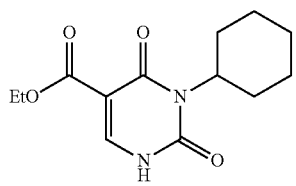

A mixture of diethyl 2-((3-cyclohexylureido)methylene)malonate (1.10 g, 3.52 mmol) and NaOEt (359 mg, 5.28 mmol) in EtOH (35.2 mL) was refluxed for 18 hours. The reaction mixture was cooled to room temperature and concentrated in vacuo. The residue was diluted with EtOAc, washed with brine. The combined organic layer was dried over $Na_2SO_4$, filtered and concentrated in vacuo. The residue was purified by column chromatography on (EtOAc/Hexanes=1/1) to give a ethyl 3-cyclohexyl-2,4-dioxo-1,2,3,4-tetrahydropyrimidine-5-carboxylate (320 mg, 34%) as a white solid. $^1$H-NMR (DMSO-$d_6$, Varian, 400 MHz): δ 1.07-1.26 (6H, m), 1.47-1.50 (2H, m), 1.54-1.61 (1H, m), 1.70-1.80 (2H, m), 2.20-2.30 (2H, m), 4.08 (2H, q, J=7.2 Hz), 4.51-4.60 (1H, m), 8.05 (1H, s).

Step C: Ethyl 3-cyclohexyl-1-ethyl-2,4-dioxo-1,2,3,4-tetrahydropyrimidine-5-carboxylate

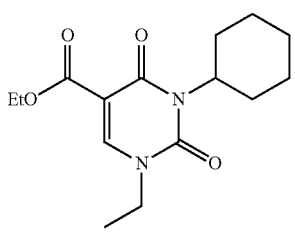

A mixture of ethyl 3-cyclohexyl-2,4-dioxo-1,2,3,4-tetrahydropyrimidine-5-carboxylate (220 mg, 0.83 mmol), $K_2CO$ (171 mg, 1.24 mmol) and iodoethane (80.0 μL, 0.99 mmol) in DMF (8.26 mL) was stirred at 70° C. for 6 hours. The reaction mixture was cooled to room temperature, diluted with EtOAc, washed with brine. The combined organic layer was dried over $Na_2SO_4$, filtered and concentrated in vacuo. The residue was purified by column chromatography on (EtOAc/Hexanes=1/1) to give a ethyl 3-cyclohexyl-1-ethyl-2,4-dioxo-1,2,3,4-tetrahydropyrimidine-5-carboxylate (130 mg, 53%) as a yellow solid. $^1$H-NMR (DMSO-$d_6$, Varian, 400 MHz): δ 1.16-1.30 (9H, m), 1.45-1.50 (2H, m), 1.55-1.64 (1H, m), 1.70-1.80 (2H, m), 2.22-2.31 (2H, m), 3.82 (2H, q, J=7.1 Hz), 4.16 (2H, q, J=7.1 Hz), 4.60-4.66 (1H, m), 8.46 (1H, s).

Step D: Ethyl 3-cyclohexyl-1-ethyl-2,4-dioxo-1,2,3,4-tetrahydropyrimidine-5-carboxylic acid

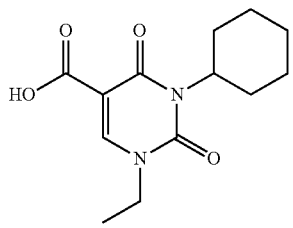 [SMILES: CCn1cc(C(=O)O)c(=O)n(C2CCCCC2)c1=O]

A mixture of ethyl 3-cyclohexyl-1-ethyl-2,4-dioxo-1,2,3,4-tetrahydropyrimidine-5-carboxylate (130 mg, 0.44 mmol) and LiOH (106 mg, 4.42 mmol) in EtOH (3.68 mL) and Water (0.74 mL) was stirred at room temperature for 6 hours. The reaction mixture was concentrated in vacuo, acidified with aq. 1N HCl solution. The precipitated solid was collected by filtration and dried in vacuo to give 3-cyclohexyl-1-ethyl-2,4-dioxo-1,2,3,4-tetrahydropyrimidine-5-carboxylic acid (110 mg, 94%) as a white solid, which was used for the next step without further purification. $^1$H-NMR (DMSO-$d_6$, Varian, 400 MHz): δ 1.08-1.31 (7H, m), 1.56-1.62 (2H, m), 1.75-1.78 (2H, m), 2.21-2.30 (2H, m), 3.87 (2H, q, J=7.1 Hz), 4.62-4.68 (1H, m), 8.67 (1H, s), 12.95 (1H, brs).

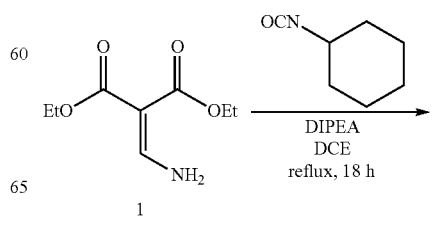

-continued

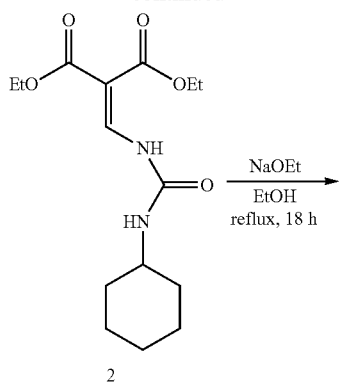

2

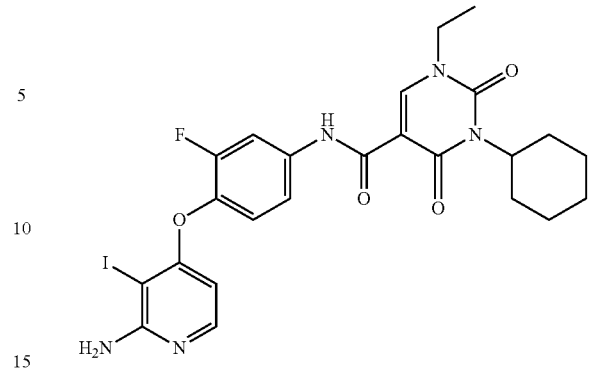

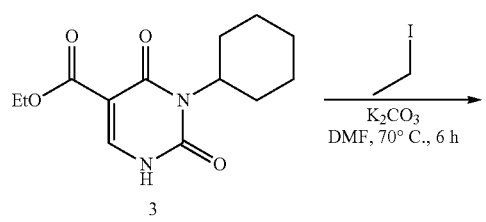

3

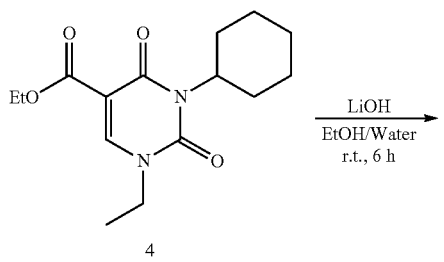

4

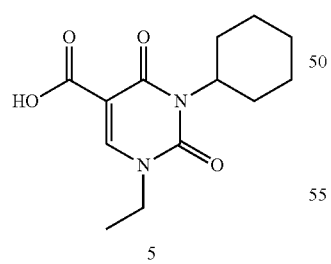

5

Intermediate Example 26

This example describes the synthesis of N-(4-(2-amino-3-iodopyridin-4-yloxy)-3-fluorophenyl)-3-cyclohexyl-1-ethyl-2,4-dioxo-1,2,3,4-tetrahydropyrimidine-5-carboxamide (Intermediate 26).

A mixture of 3-cyclohexyl-1-ethyl-2,4-dioxo-1,2,3,4-tetrahydropyrimidine-5-carboxylic acid (Intermediate 26, 110 mg, 0.41 mmol), HATU (236 mg, 0.62 mmol), DIPEA (0.22 mL, 1.24 mmol) and 4-(4-amino-2-fluorophenoxy)-3-iodopyridin-2-amine (143 mg, 0.41 mmol) in DMF (4.13 mL) was stirred at room temperature for 4 hours. The reaction mixture was diluted with EtOAc, washed with brine. The combined organic layer was dried over $Na_2SO_4$, filtered and concentrated in vacuo. The residue was purified by column chromatography on (EtOAc/Hexanes=1/1) to give a N-(4-(2-amino-3-iodopyridin-4-yloxy)-3-fluorophenyl)-3-cyclohexyl-1-ethyl-2,4-dioxo-1,2,3,4-tetrahydropyrimidine-5-carboxamide (180 mg, 73%) as a yellow solid. $^1$H-NMR (DMSO-$d_6$, Varian, 400 MHz): δ 1.17-1.34 (6H, m), 1.55-1.61 (3H, m), 1.78-1.80 (2H, m), 2.30-2.33 (2H, m), 3.91-3.99 (2H, m), 4.47-4.74 (1H, m), 5.79 (1H, d, J=5.6 Hz), 6.20 (2H, s), 7.26 (1H, t, J=8.8 Hz), 7.45 (1H, d, J=8.0 Hz), 7.72 (1H, d, J=5.6 Hz), 7.92 (1H, d, J=14.8 Hz), 8.69 (1H, s), 11.15 (1H, s).

Intermediate Example 27

This example describes the synthesis of 1,3-diallyl-2,4-dioxo-1,2,3,4-tetrahydropyrimidine-5-carboxylic acid (Intermediate 27)

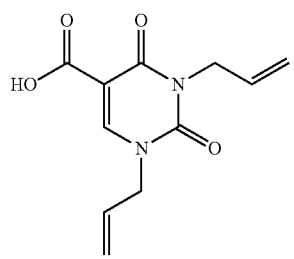

Step A: Ethyl 1,3-diallyl-2,4-dioxo-1,2,3,4-tetrahydropyrimidine-5-carboxylate

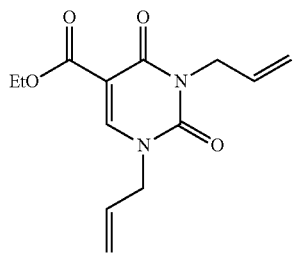

A mixture of ethyl 2,4-dioxo-1,2,3,4-tetrahydropyrimidine-5-carboxylate (1.0 g, 5.43 mmol), K$_2$CO$_3$ (1.87 g, 13.6 mmol) and 3-iodoprop-1-ene (1.24 mL, 13.6 mmol) in DMF (54.3 mL) 80° C. for 6 hour. The reaction mixture was cooled to room temperature, diluted with EtOAc, washed with brine. The combined organic layer was dried over Na$_2$SO$_4$, filtered and concentrated in vacuo. The residue was purified by column chromatography on (EtOAc/Hexanes=1/1) to give a ethyl 1,3-diallyl-2,4-dioxo-1,2,3,4-tetrahydropyrimidine-5-carboxylate (1.1 g, 77%) as a yellow oil. $^1$H-NMR (DMSO-d$_6$, Varian, 400 MHz): δ 1.22 (3H, t, J=7.0 Hz), 4.18 (2H, q, J=7.6 Hz), 4.38 (2H, d, J=5.2 Hz), 4.47 (2H, d, J=5.6 Hz), 5.07-5.09 (2H, m), 5.16-5.21 (2H, m), 5.73-5.83 (1H, m), 5.86-5.95 (1H, m), 8.48 (1H, s)

Step B: 1,3-diallyl-2,4-dioxo-1,2,3,4-tetrahydropyrimidine-5-carboxylic acid

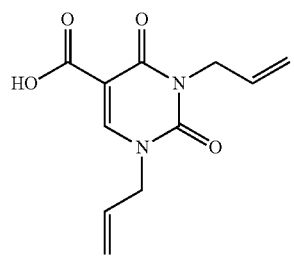 [SMILES: C=CCn1cc(C(=O)O)c(=O)n(CC=C)c1=O]

A mixture of ethyl 1,3-diallyl-2,4-dioxo-1,2,3,4-tetrahydropyrimidine-5-carboxylate (1.1 g, 4.16 mmol) and LiOH (997 mg, 41.6 mmol) in EtOH (41.6 mL) was stirred at room temperature for 18 hours. The reaction mixture was acidified with aq. 1N HCl solution and extracted with EtOAc. The separated organic layer was dried over Na$_2$SO$_4$, filtered and concentrated in vacuo to give a 1,3-diallyl-2,4-dioxo-1,2,3,4-tetrahydropyrimidine-5-carboxylic acid (810 mg, 82%) as a yellow solid. $^1$H-NMR (DMSO-d$_6$, Varian, 400 MHz): δ 4.41 (2H, d, J=5.2 Hz), 4.50 (2H, d, J=4.8 Hz), 5.07-5.11 (2H, m), 5.19-5.24 (2H, m), 5.76-5.94 (2H, m), 8.61 (1H, s) * A proton from OH was not observed.

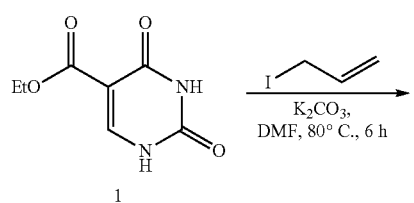

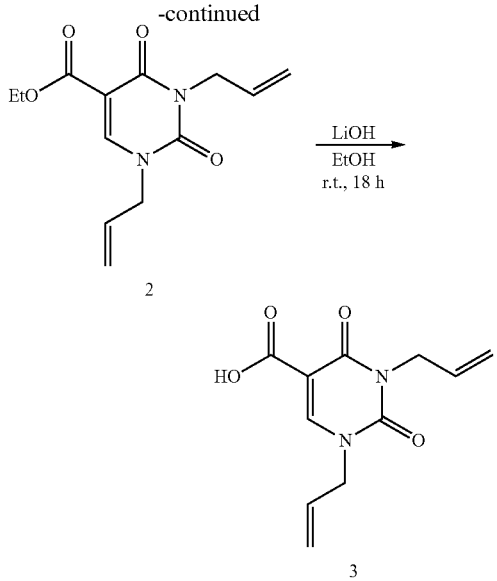

Intermediate Example 28

This example describes the synthesis of 1,3-diallyl-N-(4-(2-amino-3-iodopyridin-4-yloxy)-3-fluorophenyl)-2,4-dioxo-1,2,3,4-tetrahydropyrimidine-5-carboxamide (Intermediate 28).

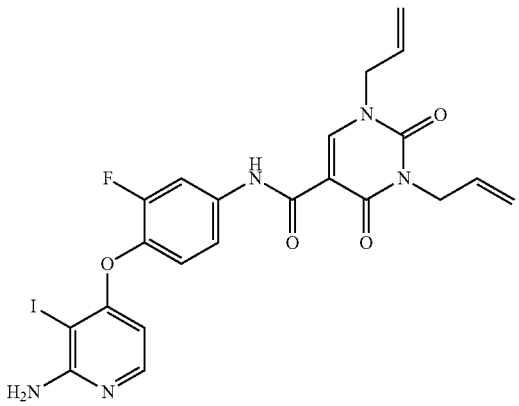 [SMILES: C=CCn1cc(C(=O)Nc2ccc(Oc3ccnc(N)c3I)c(F)c2)c(=O)n(CC=C)c1=O]

A mixture of 1,3-diallyl-2,4-dioxo-1,2,3,4-tetrahydropyrimidine-5-carboxylic acid (810 mg, 3.43 mmol), HATU (1.96 g, 5.14 mmol), DIPEA (1.78 mL, 10.29 mmol) and 4-(4-amino-2-fluorophenoxy)-3-iodopyridin-2-amine (1.18 g, 3.43 mmol) in DMF (34.3 mL) was stirred at room temperature for 4 hours. The reaction mixture was diluted with EtOAc, washed with brine. The combined organic layer was dried over Na$_2$SO$_4$, filtered and concentrated in vacuo. The residue was purified by column chromatography on (EtOAc/Hexanes=1/1) to give a of 1,3-diallyl-N-(4-(2-amino-3-iodopyridin-4-yloxy)-3-fluorophenyl)-2,4-dioxo-1,2,3,4-tetrahydropyrimidine-5-carboxamide (1.5 g, 78%) as a yellow solid. $^1$H-NMR (DMSO-d$_6$, Varian, 400 MHz): δ 4.48-4.52 (2H, m), 4.57 (2H, d, J=5.6 Hz), 5.12-5.15 (2H, m), 5.22-5.27 (2H, m), 5.79 (1H, d, J=5.2 Hz), 5.81-5.92 (2H, m) 6.19 (2H, s), 7.27 (1H, t, J=9.0 Hz), 7.45 (1H, d, J=9.2 Hz), 7.72 (1H, d, J=5.2 Hz), 7.92 (1H, d, J=15.2 Hz), 8.68 (1H, s), 11.05 (1H, s).

Example 1

Figure 1:
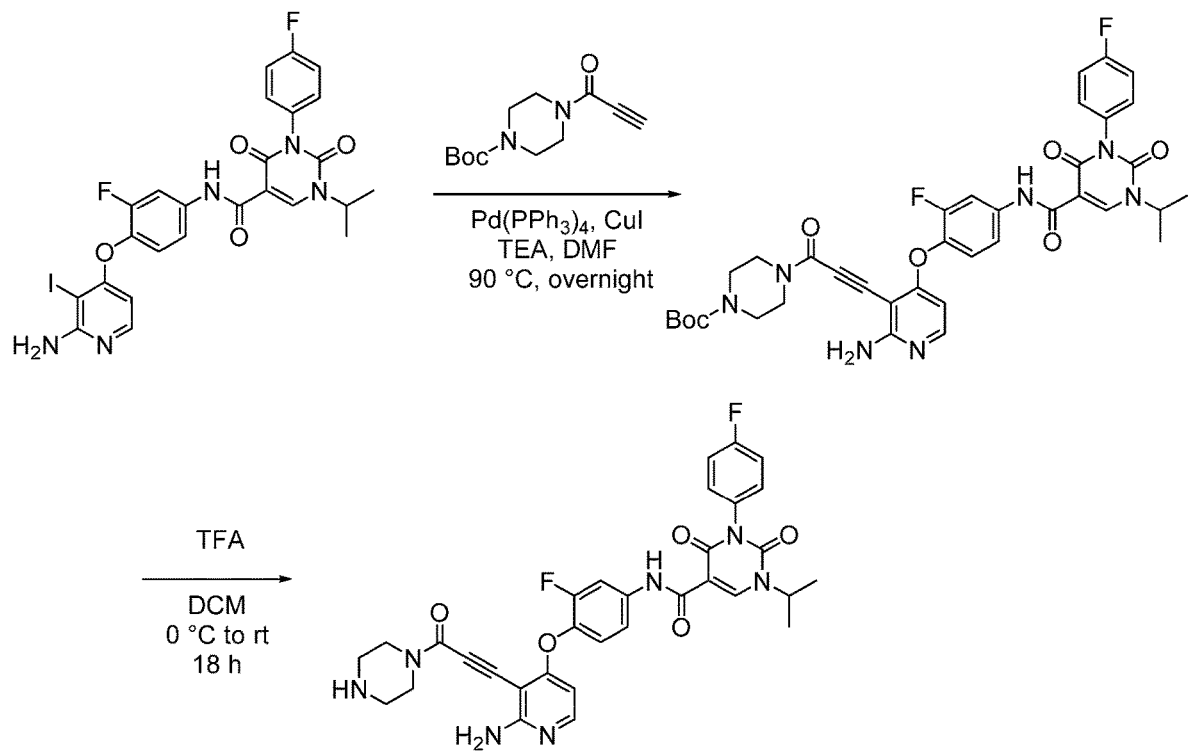
FIG. 1 is a chemical synthesis of N-(4-(2-amino-3-(3-oxo-3-(piperazin-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-oxo-3-(piperazin-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 1.

Step A: tert-butyl 4-(3-(2-amino-4-(2-fluoro-4-(3-(4-fluorophehynl)-1-isopropyl-2,4-dioxo-1,2,3,4-tetrahydropyrimidine-5-carboxamido)phenoxy)pyridin-3-yl)propioloyl)piperazine-1-carboxylate

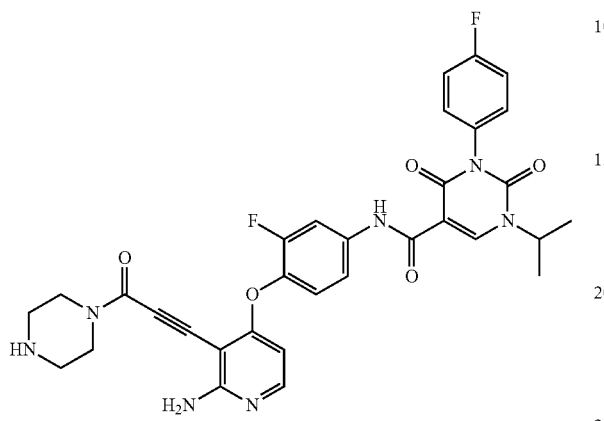

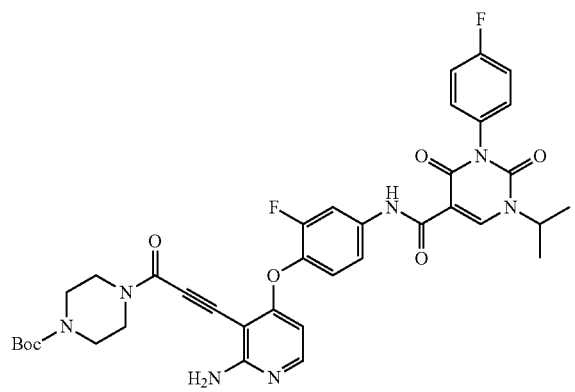

To a degassed solution of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 8.40 g, 13.6 mmol), tert-butyl 4-propioloylpiperazine-1-carboxylate (intermediate 4, 6.46 g, 27.1 mmol), copper(I) iodide (0.52 g, 2.71 mmol), and TEA (7.52 mL, 54.2 mmol) in DMF (45 mL) was added Pd(PPh$_3$)$_4$ (1.57 g, 1.36 mmol) under argon atmosphere. The reaction mixture was stirred overnight at 90° C. After being cooled to room temperature, EtOAc and saturated NH$_4$Cl solution (aq.) were added the mixture, and the separated aqueous layer was extracted with EtOAc. The combined organic layers were dried over Na$_2$SO$_4$, filtered, and concentrated in vacuo. The residue was purified by column chromatography on SiO$_2$ (EtOAc/MeOH=97/3) to afford the tert-butyl 4-(3-(2-amino-4-(2-fluoro-4-(3-(4-fluorophenyl)-1-isopropyl-2,4-dioxo-1,2,3,4-tetrahydropyrimidine-5-carboxamido)phenoxy)pyridin-3-yl)propioloyl)piperazine-1-carboxylate (5.20 g, 53%) as a dark brown form. $^1$H-NMR (CDCl$_3$, Varian, 400 MHz): δ 1.46 (9H, s), 1.51 (6H, d, J=6.8 Hz), 3.45 (4H, brs), 3.65 (2H, brs), 3.82 (2H, brs), 4.96-4.99 (1H, m), 5.32 (2H, brs), 5.97 (1H, d, J=6.0 Hz), 7.11 (1H, t, J=8.0 Hz), 7.23-7.27 (5H, m), 7.85 (1H, d, J=7.6 Hz), 7.91 (1H, d, J=5.6 Hz), 8.69 (1H, s), 10.95 (1H, s).

Step B: N-(4-(2-amino-3-(3-oxo-3-(piperazin-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide

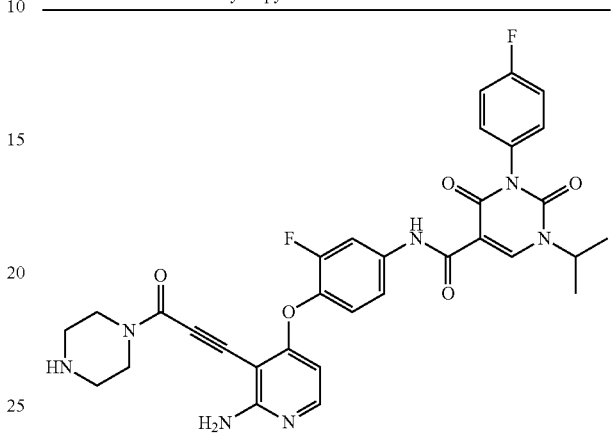

To a solution of tert-butyl 4-(3-(2-amino-4-(2-fluoro-4-(3-(4-fluorophenyl)-1-isopropyl-2,4-dioxo-1,2,3,4-tetrahydropyrimidine-5-carboxamido)phenoxy)pyridin-3-yl)propioloyl)piperazine-1-carboxylate (300 mg, 0.41 mmol) in DCM (8 mL) was added TFA (0.32 mL, 4.11 mmol) at 0° C. The mixture was stirred for 18 h at room temperature. The excess TFA was removed by evaporation, and DCM was poured into the residue. The mixture was neutralized with saturated NaHCO$_3$ solution (aq.). The separated aqueous layer was extracted with DCM, and the combined organic layers were dried over Na$_2$SO$_4$, filtered, and concentrated in vacuo. The residue was purified by column chromatography on SiO$_2$ (EtOAc/MeOH=95/5) to afford the N-(4-(2-amino-3-(3-oxo-3-(piperazin-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (230 mg, 90%) as a white solid. $^1$H-NMR (CDCl$_3$, Varian, 400 MHz): δ 1.50 (6H, d, J=6.8 Hz), 2.86 (4H, brs), 3.65 (2H, brs), 3.81 (2H, brs), 4.96-4.99 (1H, m), 5.32 (2H, brs), 5.98 (1H, d, J=6.4 Hz), 7.10 (1H, t, J=8.8 Hz), 7.21-7.26 (5H, m), 7.84 (1H, d, J=11.6 Hz), 7.91 (1H, d, J=4.8 Hz), 8.68 (1H, s), 10.95 (1H, s). * NH peak was not observed.

Example 2

Figure 2:
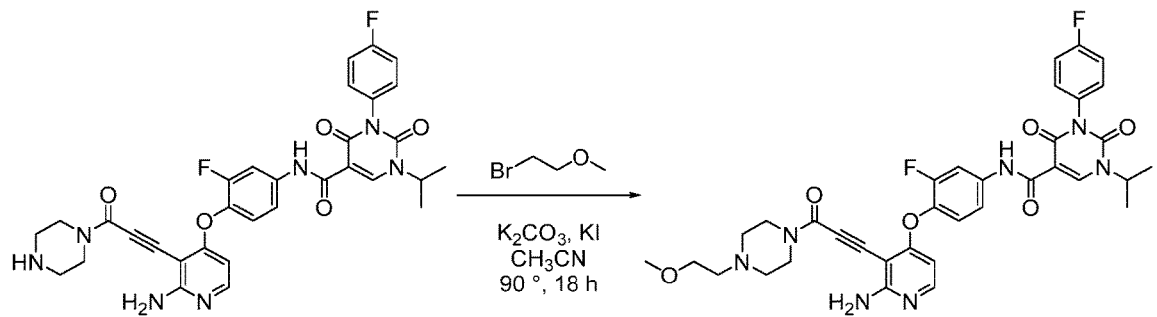
FIG. 2 is a chemical synthesis of N-(4-(2-amino-3-(3-(4-(2-methoxyethyl)piperazin-1-yl)-3-oxoprop-1-ynyl)pyridin-4-yloxy)-3-fluorophenyl)-3-(4-fluorophenyl)-1-isopropyl-2,4-dioxo-1,2,3,4-teterahydropyrimidine-5-carboxamide in an aspect of the invention.

This example describes the synthesis of N-(4-(2-amino-3-(3-(4-(2-methoxyethyl)piperazin-1-yl)-3-oxoprop-1-ynyl)pyridin-4-yloxy)-3-fluorophenyl)-3-(4-fluorophenyl)-1-isopropyl-2,4-dioxo-1,2,3,4-teterahydropyrimidine-5-carboxamide in an aspect of the invention. See FIG. 2.

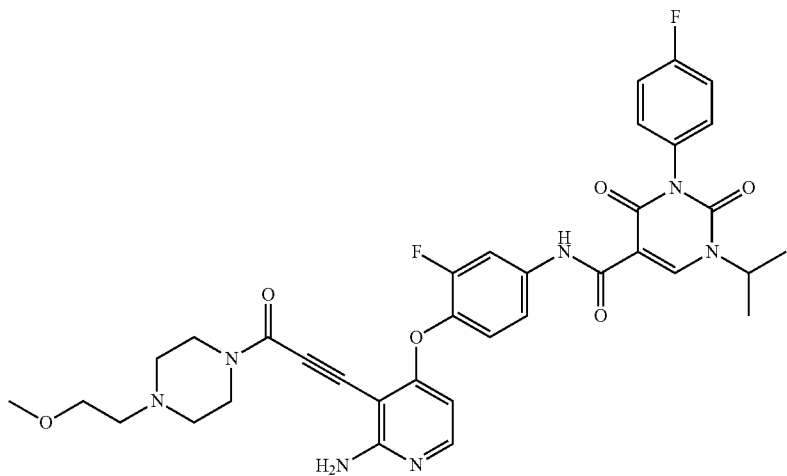 [SMILES: COCCN1CCN(C(=O)C#Cc2c(Oc3ccc(NC(=O)c4cn(C(C)C)c(=O)n(-c5ccc(F)cc5)c4=O)cc3F)ccnc2N)CC1]

A mixture of N-(4-(2-amino-3-(3-oxo-3-(piperazin-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (Example 1, 30 mg, 0.05 mmol), 1-bromo-2-methoxyethane (5.37 μL, 0.06 mmol), potassium iodide (7.90 mg, 0.05 mmol) and K$_2$CO$_3$ (6.59 mg, 0.09 mmol) in CH$_3$CN (1.0 mL) was heated at for 18 h 90° C. After being cooled to room temperature, the reaction mixture was washed with saturated NaHCO$_3$ (aq.) and extracted with EtOAc. The organic layer was dried over Na$_2$SO$_4$, filtered and concentrated in vacuo. The residue was purified by column chromatography on NH—SiO$_2$ (EtOAc/MeOH=99/1) to afford the N-(4-(2-amino-3-(3-(4-(2-methoxyethyl)piperazin-1-yl)-3-oxoprop-1-ynyl)pyridin-4-yloxy)-3-fluorophenyl)-3-(4-fluorophenyl)-1-isopropyl-2,4-dioxo-1,2,3,4-teterahydropyrimidine-5-carboxamide (28 mg, 85%) as a yellow solid. $^1$H-NMR (CDCl$_3$, Varian, 400 MHz): δ 1.51 (6H, d, J=6.4 Hz), 2.50 (4H, brs), 2.59 (2H, t, J=5.2 Hz), 3.34 (3H, s), 3.50 (2H, t, J=5.2 Hz), 3.71 (2H, brs), 3.86 (2H, brs), 4.94-5.01 (1H, m), 5.28 (2H, brs), 5.97 (1H, d, J=6.0 Hz), 7.11 (1H, t, J=8.4 Hz), 7.22-7.26 (5H, m), 7.84 (1H, d, J=10.0 Hz), 7.90 (1H, d, J=5.6 Hz), 8.68 (1H, s), 10.94 (1H, s).

Example 3

Figure 3:
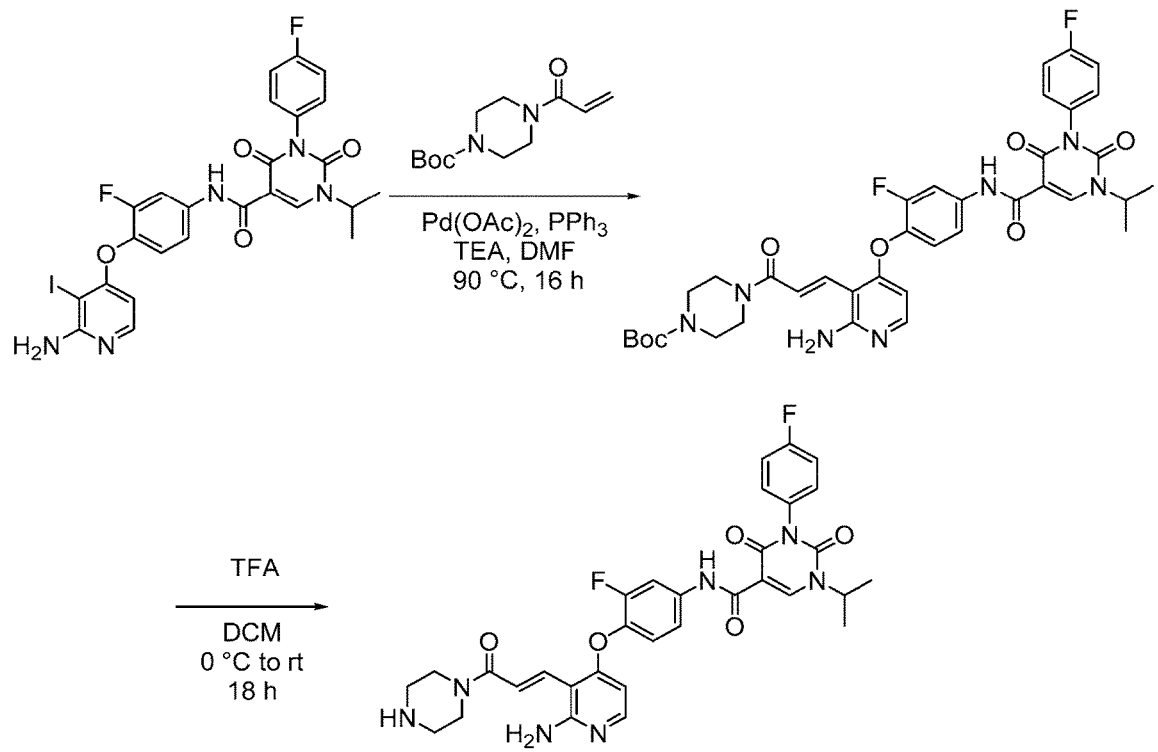
FIG. 3 is a chemical synthesis of (E)-N-(4-(2-amino-3-(3-oxo-3-(piperazin-1-yl)prop-1-enyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of (E)-N-(4-(2-amino-3-(3-oxo-3-(piperazin-1-yl)prop-1-enyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 3.

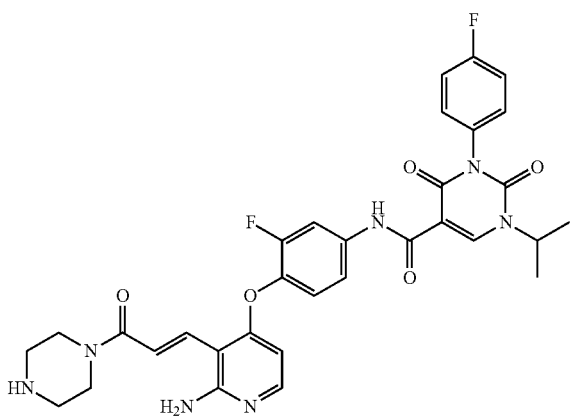

Step A: (E)-tert-butyl 4-(3-(2-amino-4-(2-fluoro-4-(3fluorophenyl)-1-isopropyl-2,4-dioxo-1,2,3,4-tetrahydropyrimidine-5-carboxamido)phenoxy)pyridin-3-yl)acryloyl)piperazine-1-carboxylate

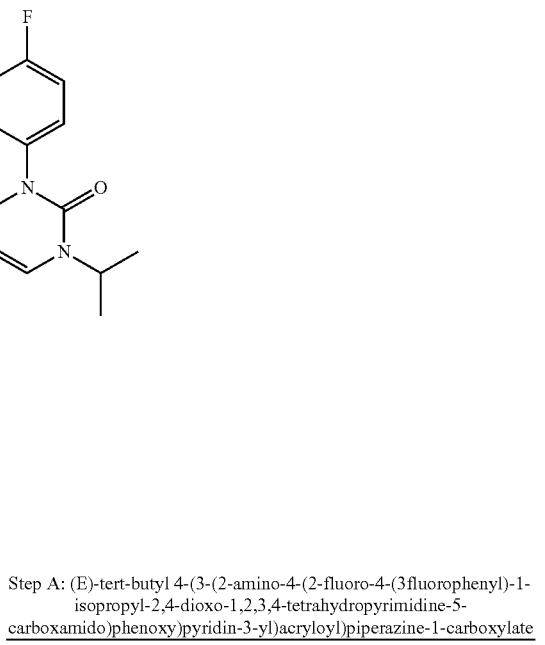

A mixture of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 200 mg, 0.32 mmol), tert-butyl 4-acryloylpiperazine-1-carboxylate (intermediate 5, 116 mg, 0.48 mmol), PPh$_3$ (3.62 mg, 0.02 mmol), TEA (90 μL, 0.70 mmol) and Pd(OAc)$_2$ (3.62 mg, 0.02 mmol) in DMF (3.0 mL) was stirred for 16 h at 90° C. After being cooled to room temperature, the reaction mixture was concentrated in vacuo. The residue was diluted EtOAc, washed with saturated NH$_4$Cl solution (aq.). The organic layer was dried over Na$_2$SO$_4$, filtered, and concentrated in vacuo. The residue was purified by column chromatography on SiO$_2$ (EtOAc/MeOH=9/1) to afford the (E)-tert-butyl 4-(3-(2-amino-4-(2-fluoro-4-(3-fluorophenyl)-1-isopropyl-2,4-dioxo-1,2,3,4-tetrahydropyrimidine-5-carboxamido)phenoxy)pyridin-3-yl)acryloyl)piperazine-1-carboxylate (140 mg, 59%) as a yellow solid. $^1$H-NMR (CDCl$_3$, Varian, 400 MHz): δ 1.47 (9H, s), 1.50 (6H, d, J=6.4 Hz), 3.45 (4H, d, J=4.4 Hz), 3.55 (2H, s), 3.70 (2H, s), 4.97-5.01 (1H, m), 6.04 (1H, d, J=5.6 Hz), 7.07 (1H, t, J=8.00 Hz), 7.15 (2H, d, J=6.8 Hz), 7.18-7.27 (5H, m), 7.71 (1H, d, J=15.6 Hz), 7.82-7.85 (2H, m), 8.68 (1H, s), 10.9 (1H, s). * NH peak was not observed.

Step B: (E)-N-(4-(2-amino-3-(3-oxo-3-(piperazin-1-yl)prop-1-enyl)pyridin-4-yloxy)-3-fluorophenyl)-3-(4-fluorophenyl)-1-isopropyl-2,4-dioxo-1,2,3,4-tetrahydropyrimidine-5-carboxamide

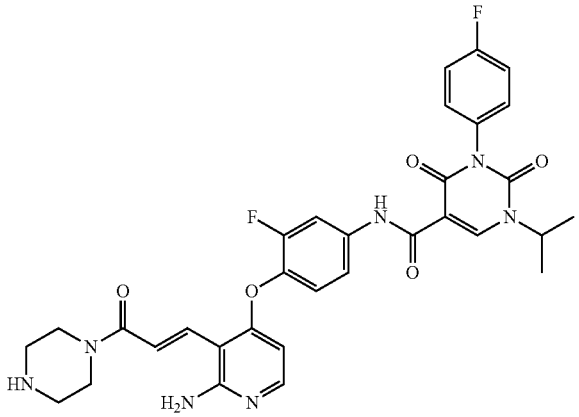 [SMILES: CC(C)n1cc(C(=O)Nc2ccc(Oc3ccnc(N)c3/C=C/C(=O)N3CCNCC3)c(F)c2)c(=O)n(-c2ccc(F)cc2)c1=O]

To a solution of (E)-tert-butyl 4-(3-(2-amino-4-(2-fluoro-4-(3-fluorophenyl)-1-isopropyl-2,4-dioxo-1,2,3,4-tetrahydropyrimidine-5-carboxamido)phenoxy)pyridin-3-yl)acryloyl)piperazine-1-carboxylate (140 mg, 0.19 mmol) in DCM (2.2 ml) was added TFA (0.15 mL, 1.90 mmol) at room temperature. The reaction mixture was stirred for 18 h at room temperature. The reaction mixture was concentrated in vacuo. The residue was diluted with DCM, and then neutralized with TEA. The mixture was stirred for 10 min at room temperature and concentrated in vacuo. The residue was purified by column chromatography on NH—SiO$_2$ (DCM/EtOAc=10/1) to afford the (E)-N-(4-(2-amino-3-(3-oxo-3-(piperazin-1-yl)prop-1-enyl)pyridin-4-yloxy)-3-fluorophenyl)-3-(4-fluorophenyl)-1-isopropyl-2,4-dioxo-1,2,3,4-tetrahydropyrimidine-5-carboxamide (104 mg, 87%) as a yellow solid. $^1$H-NMR (CDCl$_3$, Varian, 400 MHz): δ 1.50 (6H, d, J=6.4 Hz), 2.89 (4H, brs), 3.55 (2H, brs), 3.71 (2H, brs), 4.96-5.01 (1H, m), 6.04 (1H, d, J=6.0 Hz), 7.07 (1H, t, J=8.8 Hz), 7.17 (2H, d, J=16.0 Hz), 7.25-7.26 (6H, m), 7.70 (1H, d, J=15.6 Hz), 7.82-7.86 (2H, m), 8.68 (1H, s), 11.3 (1H, s). * NH peak was not observed.

Example 4

Figure 4:
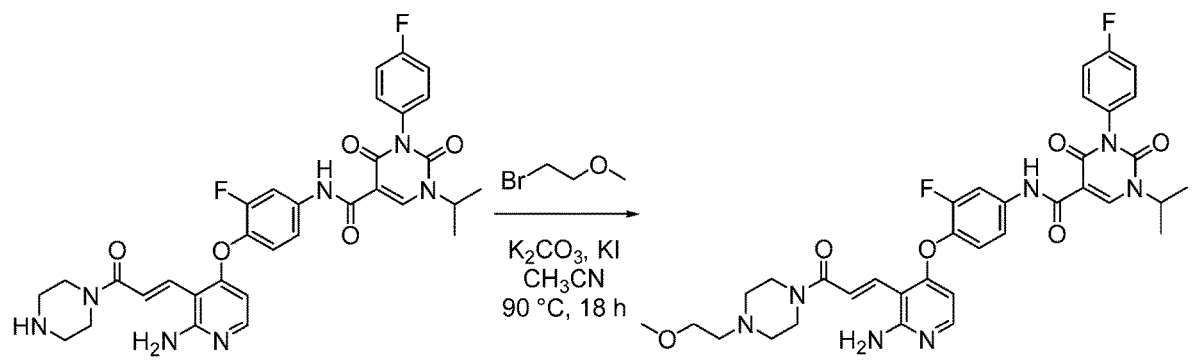
FIG. 4 is a chemical synthesis of (E)-N-(4-(2-amino-3-(3-(4-(2-methoxyethyl)piperazin-1-yl)-3-oxoprop-1-enyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of (E)-N-(4-(2-amino-3-(3-(4-(2-methoxyethyl)piperazin-1-yl)-3-oxoprop-1-enyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 4.

To a solution of (E)-N-(4-(2-amino-3-(3-oxo-3-(piperazin-1-yl)prop-1-enyl)pyridin-4-yloxy)-3-fluorophenyl)-3-(4-fluorophenyl)-1-isopropyl-2,4-dioxo-1,2,3,4-tetrahydropyrimidine-5-carboxamide (Example 3, 90 mg, 0.14 mmol), 1-bromo-2-methoxyethane (14 μL, 0.14 mmol), potassium iodide (24 mg, 0.14 mmol) and K$_2$CO$_3$ (20 mg, 0.14 mmol) in CH$_3$CN (2 mL) was heated for 18 h to 90° C. After being cooled to room temperature, the reaction mixture was washed with saturated NaHCO$_3$ (aq.) and extracted with EtOAc. The organic layer was dried over Na$_2$SO$_4$, filtered and concentrated in vacuo. The residue was purified by column chromatography on NH—SiO$_2$ (EtOAc/MeOH=97/3) to afford the N-(4-(2-amino-3-(3-(4-(2-methoxyethyl)piperazin-1-yl)-3-oxoprop-1-ynyl)pyridin-4-yloxy)-3-fluorophenyl)-3-(4-fluorophenyl)-1-isopropyl-2,4-dioxo-1,2,3,4-teterahydropyrimidine-5-carboxamide (52 mg, 53%) as a yellow solid. $^1$H-NMR (CDCl$_3$, Varian, 400 MHz): δ 1.50 (6H, d, J=6.8 Hz), 2.52 (4H, brs), 2.60 (2H, t, J=5.6 Hz), 3.36 (3H, s), 3.51 (2H, t, J=5.6 Hz), 3.62 (2H, brs), 3.78 (2H, brs), 4.96-4.99 (1H, m), 6.03 (1H, d, J=5.2 Hz), 7.07 (1H, t, J=8.8 Hz), 7.17 (2H, d, J=15.6 Hz), 7.25-7.26 (5H, m), 7.70 (1H, d, J=15.6 Hz), 7.82-7.85 (2H, m), 8.68 (1H, s), 10.9 (1H, s). * NH peak was not observed.

Example 5

Figure 5:
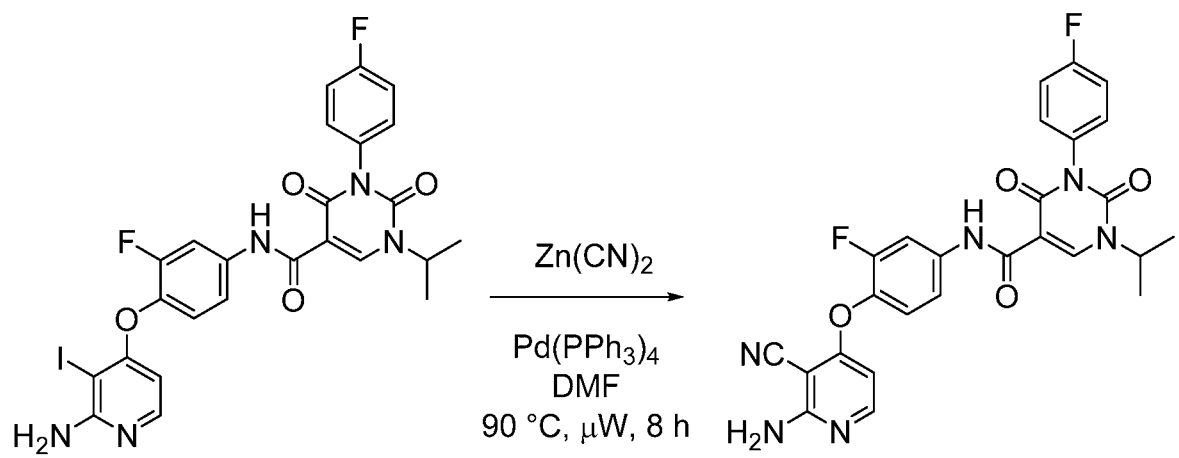
FIG. 5 is a chemical synthesis of N-(4-(2-amino-3-cyanopyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-cyanopyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 5.

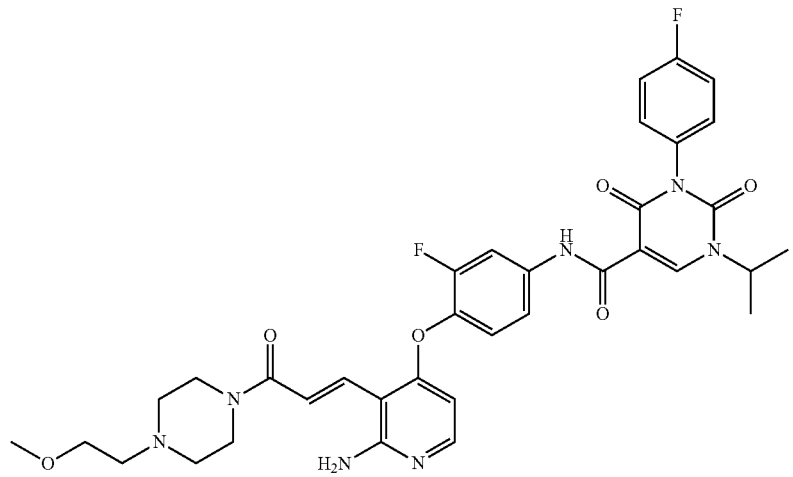 [SMILES: COCCN1CCN(C(=O)/C=C/c2c(Oc3ccc(NC(=O)c4cn(C(C)C)c(=O)n(-c5ccc(F)cc5)c4=O)cc3F)ccnc2N)CC1]

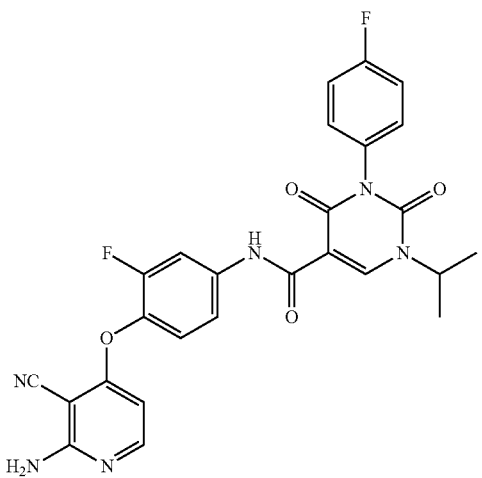 [SMILES: CC(C)n1cc(C(=O)Nc2ccc(Oc3ccnc(N)c3C#N)c(F)c2)c(=O)n(-c2ccc(F)cc2)c1=O]

To a solution of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 200 mg, 0.32 mmol) in DMF (4.0 mL) was added dicyanozinc (76.0 mg, 0.65 mmol) and Pd(PPh$_3$)$_4$ (37.3 mg, 0.03 mmol). The reaction mixture was sealed and submitted to microwave irradiation for 8 h at 90° C. The mixture was filtered through a CELITE™ pad (Sigma-Aldrich, St. Louis, MO), and the filtrate was concentrated in vacuo. The residue was purified by column chromatography on SiO$_2$ (EtOAc/MeOH=10/1). The product was purified by prep-LC to afford the N-(4-(2-amino-3-cyanopyridin-4-yloxy)-3-fluorophenyl)-3-(4-fluorophenyl)-1-isopropyl-2,4-dioxo-1,2,3,4-tetrahydropyrimidine-5-carboxamide (50.0 mg, 30%) as a white solid. $^1$H-NMR (CDCl$_3$, Varian, 400 MHz): δ 1.50 (6H, d, J=6.4 Hz), 4.94-5.00 (1H, m), 5.28 (2H, s), 5.96 (1H, d, J=6.0 Hz), 7.14 (1H, t, J=8.8 Hz), 7.24-7.26 (4H, m), 7.86 (1H, dd, J=2.4 Hz, 12.0 Hz), 8.01 (1H, d, J=6.0 Hz), 8.68 (1H, s), 10.9 (1H, s). * NH peak was not observed.

Example 6

Figure 6:
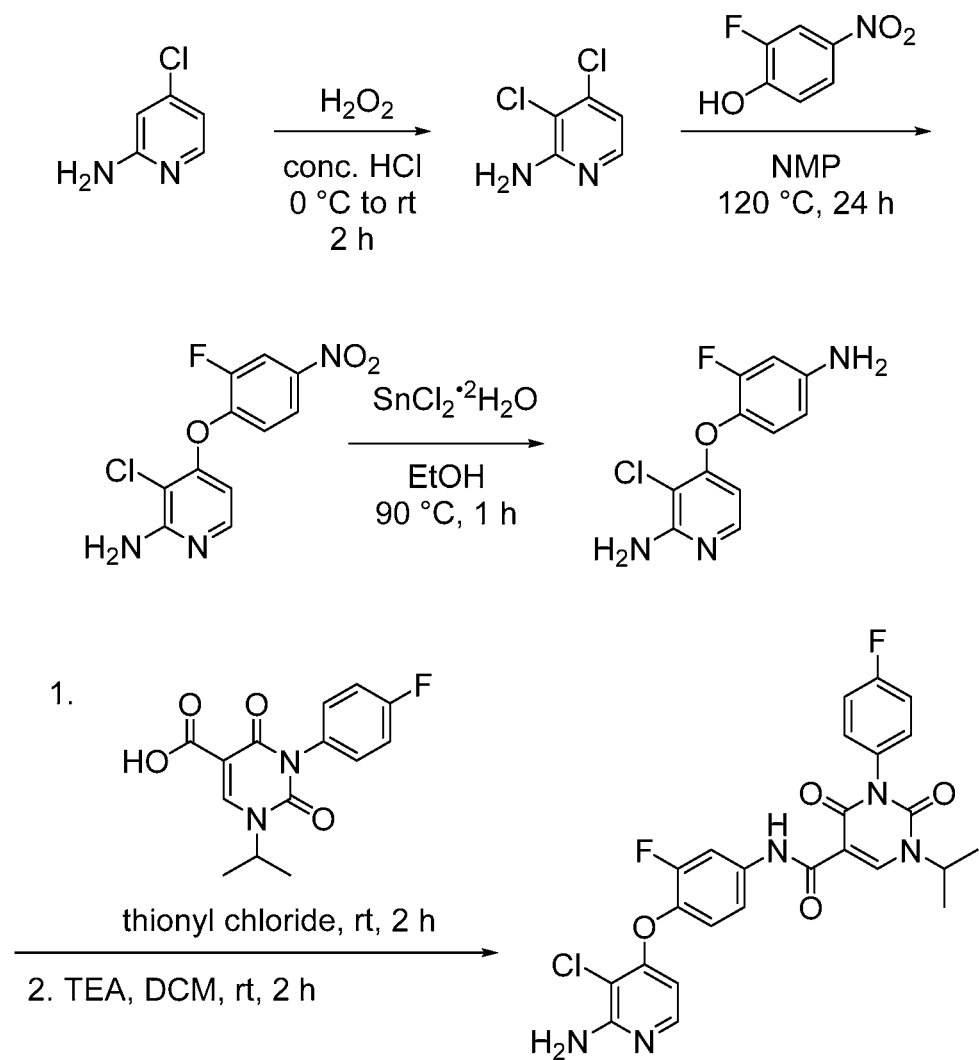
FIG. 6 is a chemical synthesis of N-(4-(2-amino-3-chloropyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-chloropyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 6.

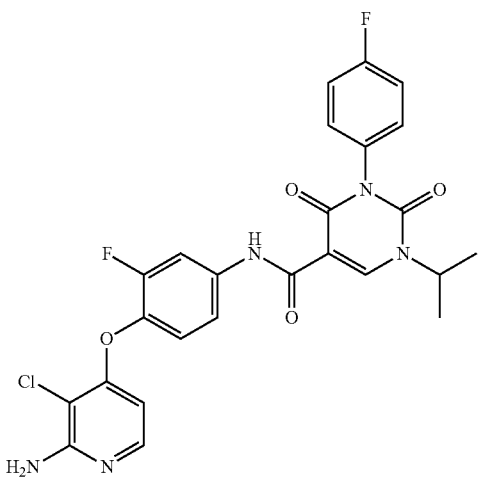

Step A: 3,4-dichloropyridin-2-amine

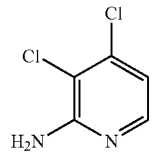

Hydrogen peroxide (1.49 mL, 15.6 mmol) was added to a solution of 4-chloropyridin-2-amine (2.00 g, 15.6 mmol) in conc. HCl (11 mL) at 0° C. The reaction mixture was stirred for 2 h at room temperature. The reaction mixture was poured into water, and made basic by the addition of Na$_2$CO$_3$ until pH 10, then extracted with EtOAc. The organic layers were dried over Na$_2$SO$_4$, filtered, and concentrated in vacuo. The residue was purified by column chromatography on SiO$_2$ (Hexanes/EtOAc=2/1) to afford the 3,4-dichloropyridin-2-amine (594 mg, 23%) as a yellow solid. $^1$H-NMR (CDCl$_3$, Varian, 400 MHz): δ 5.24 (2H, s), 6.75 (1H, d, J=5.6 Hz), 7.85 (1H, d, J=5.2 Hz).

Step B: 3-chloro-4-(2-fluoro-4-nitrophenoxy)pyridin-2-amine

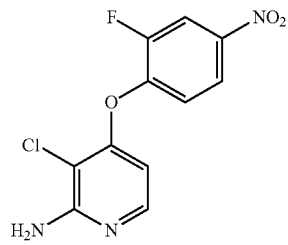

To a solution of 3,4-dichloropyridin-2-amine (200 mg, 1.23 mmol) and 2-fluoro-4-nitrophenol (771 mg, 4.91 mmol) in NMP (3.0 mL) was stirred for 24 h at 120° C. in a sealed tube. After being cooled at room temperature, the reaction mixture was dissolved with EtOAc and washed with water. The organic layer was dried over Na$_2$SO$_4$, filtered, and concentrated in vacuo. The residue was purified by column chromatography on SiO$_2$ (Hexanes/EtOAc=1/1) to afford the 3-chloro-4-(2-fluoro-4-nitrophenoxy)pyridin-2-amine (58 mg, 17%) as a yellow solid. $^1$H-NMR (CDCl$_3$, Varian, 400 MHz): δ 5.19 (2H, s), 5.31 (1H, s), 6.23 (1H, d, J=5.2 Hz), 7.19 (1H, t, J=8.4 Hz), 7.92 (1H, d, J=5.6 Hz), 8.11 (1H, dd, J=9.2, 20.0 Hz).

Step C: 4-(4-amino-2-fluorophenoxy)-3-chloropyridin-2-amine

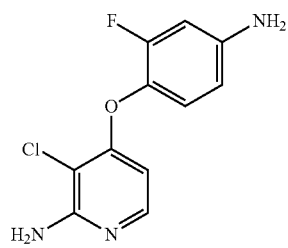

To a solution of 3-chloro-4-(2-fluoro-4-nitrophenoxy)pyridin-2-amine (58.0 mg, 0.20 mmol) in EtOH (2.0 mL) was added Tin (II) chloride dihydrate (185 mg, 0.82 mmol) at room temperature. The reaction mixture was stirred for 1 h at 90° C. After being cooled at room temperature, the solvent was removed in vacuo. The residue was dissolved with EtOAc and neutralized with 2N NaOH until pH 9, and filtered through a CELITE™ pad (Sigma-Aldrich, St. Louis, MO). The filtrate was extracted with EtOAc and dried over $Na_2SO_4$, filtered and concentrated in vacuo to afford the 4-(4-amino-2-fluorophenoxy)-3-chloropyridin-2-amine (26.0 mg, 50%) as a brown solid, which was used for the next step without further purification. $^1$H-NMR (CDCl$_3$, Varian, 400 MHz): δ 4.95 (2H, s), 6.01 (1H, d, J=6.00 Hz), 6.44 (1H, d, J=8.8 Hz), 6.50 (1H, dd, J=2.4, 11.8 Hz), 6.95 (1H, t, J=8.8 Hz), 7.77 (1H, d, J=6.0 Hz). * $NH_2$ peak was not observed.

Step D: N-(4-(2-amino-3-chloropyridin-4-yloxy)-3-fluorophenyl)-3-(4-fluorophenyl)-1-isopropyl-2,4-dioxo-1,2,3,4-tetrahydropyrimidine-5-carboxamide

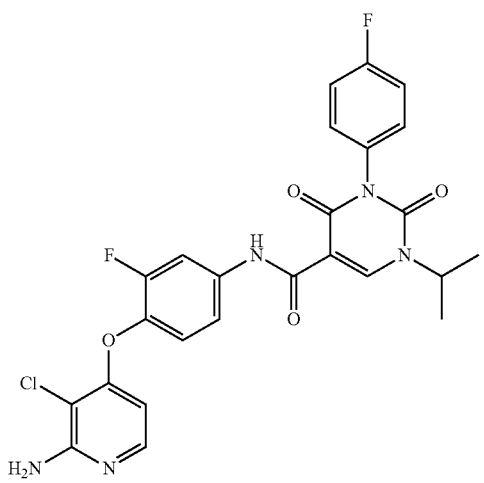 [SMILES: CC(C)n1cc(C(=O)Nc2ccc(Oc3ccnc(N)c3Cl)c(F)c2)c(=O)n(-c2ccc(F)cc2)c1=O]

To a solution of 3-(4-fluorophenyl)-1-isopropyl-2,4-dioxo-1,2,3,4-tetrahydropyrimidine-5-carboxylic acid (intermediate 10, 40.0 mg, 0.14 mmol) in thionyl chloride (3.0 mL) was stirred for 2 h at room temperature. The reaction mixture was concentrated in vacuo to give corresponding acyl chloride which was used to the next reaction without further purification.

The above obtained acyl chloride was re-dissolved in DCM (2.0 mL), and a solution was added 4-(4-amino-2-fluorophenoxy)-3-chloropyridin-2-amine (20.0 mg, 0.08 mmol), and TEA (22.0 μL, 0.16 mmol). The reaction mixture was stirred for 2 h at room temperature. The mixture was washed with water and extracted with DCM. The organic layer was dried over $Na_2SO_4$, filtered and concentrated in vacuo. The residue was purified by column chromatography on $SiO_2$ (EtOAc/MeOH=10/1) to afford the N-(4-(2-amino-3-chloropyridin-4-yloxy)-3-fluorophenyl)-3-(4-fluorophenyl)-1-isopropyl-2,4-dioxo-1,2,3,4-tetrahydropyrimidine-5-carboxamide (18 mg, 42%) as a pale-yellow solid. $^1$H-NMR (CDCl$_3$, Varian, 400 MHz): δ 1.50 (6H, d, J=6.4 Hz), 4.91-4.99 (1H, m), 6.03 (1H, d, J=5.2 Hz), 7.11 (2H, t, J=8.4 Hz), 7.20-7.26 (5H, m), 7.79 (1H, brs), 7.84 (1H, dd, J=2.0 Hz, 12.4 Hz), 8.68 (1H, s), 10.9 (1H, s). * NH peak was not observed.

Example 7

Figure 7:
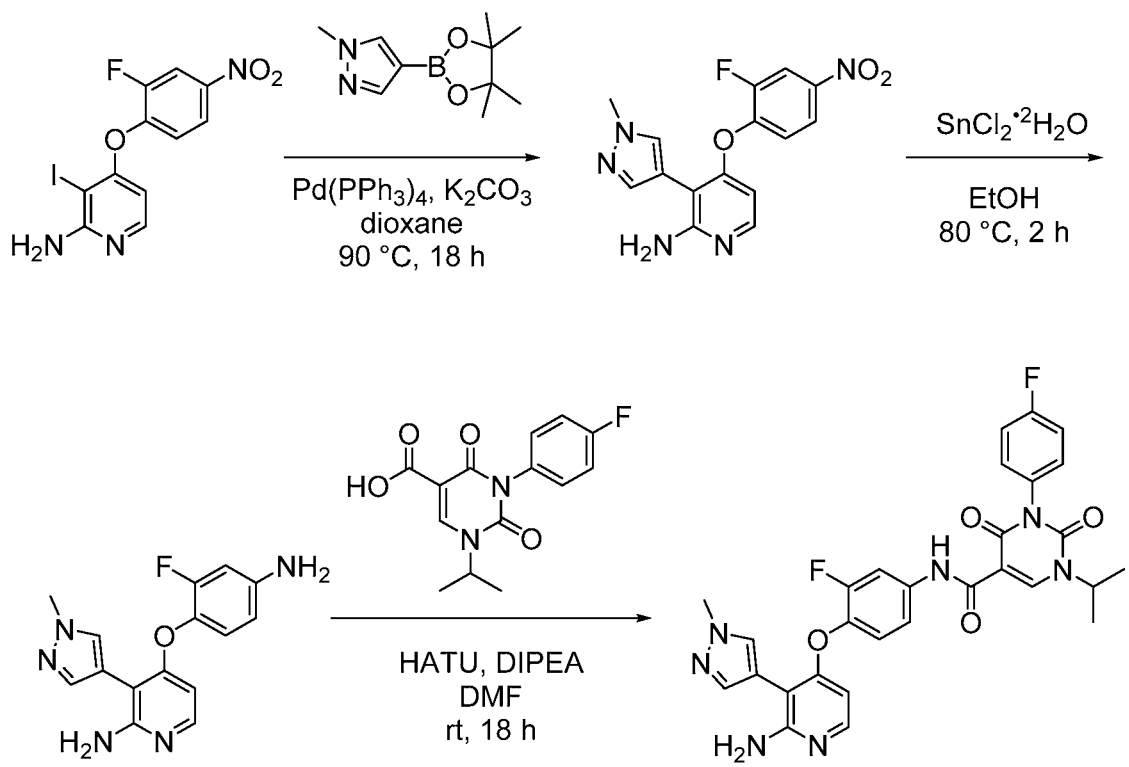
FIG. 7 is a chemical synthesis of N-(4-(2-amino-3-(1-methyl-1H-pyrazol-4-yl)pyridin-4-yloxy)-3-fluorophenyl)-1-isopropyl-2,4-dioxo-1,2,3,4-tetrahydropyrimidine-5-carboxamide in an aspect of the invention.

This example describes the synthesis of N-(4-(2-amino-3-(1-methyl-1H-pyrazol-4-yl)pyridin-4-yloxy)-3-fluorophenyl)-1-isopropyl-2,4-dioxo-1,2,3,4-tetrahydropyrimidine-5-carboxamide in an aspect of the invention. See FIG. 7.

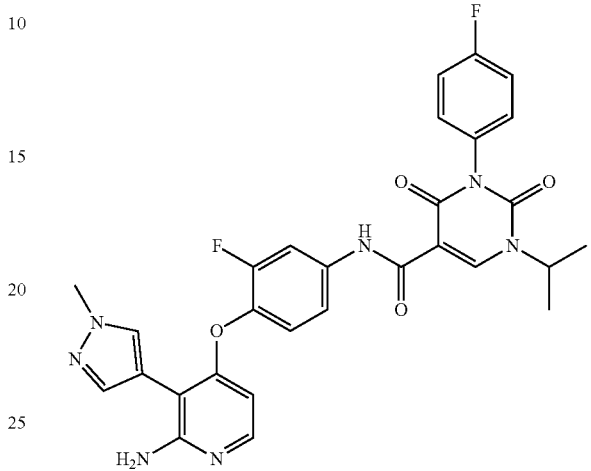

Step A: 4-(2-fluoro-4-nitrophenoxy)-3-(1-methyl-1H-pyrazol-4-yl)pyridine-2-amine

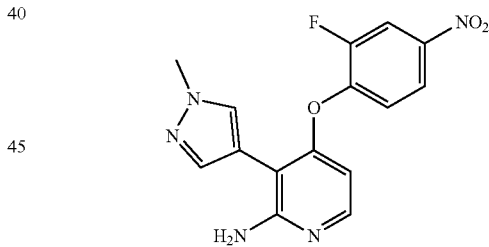

A mixture of 4-(2-fluoro-4-nitrophenoxy)-3-iodopyridin-2-amine (step D of intermediate 11, 0.20 g, 0.53 mmol), 1-methyl-4-(4,4,5,5-tetramethyl-1,3,2-dioxaborolan-2-yl)-1H-pyrazole (0.17 g, 0.80 mmol) and $K_2CO_3$ (0.22 g, 1.60 mmol) and Pd(PPh$_3$)$_4$ (62 mg, 0.05 mmol) in 1,4-dioxane/$H_2O$ (v/v=2:1, 6.0 mL) was refluxed for 18 h at 90° C. under argon atmosphere. The mixture was poured into saturated NaHCO$_3$ (aq.), then extracted with EtOAc. The combined organic layers were dried over $Na_2SO_4$, filtered and concentrated in vacuo. The residue was purified by column chromatography on $SiO_2$ (DCM/MeOH=9/1) to afford the 4-(2-fluoro-4-nitrophenoxy)-3-(1-methyl-1H-pyrazol-4-yl)pyridine-2-amine (0.14 g, 80%) as a yellow solid. $^1$H-NMR (CDCl$_3$, Varian, 400 MHz): δ 3.91 (3H, s), 4.90 (2H, s), 6.22 (1H, d, J=5.6 Hz), 7.05 (1H, t, J=8.6 Hz), 7.56 (1H, s), 7.64 (1H, s), 7.93 (1H, d, J=5.6 Hz), 7.95-8.03 (2H, m).

Step B: 4-(4-amino-2-fluorophenoxy)-3-(1-methyl-1H-pyrazol-4-yl)pyridine-2-amine

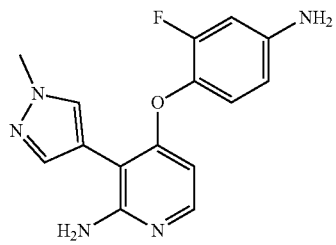

To a solution of 4-(2-fluoro-4-nitrophenoxy)-3-(1-methyl-1H-pyrazol-4-yl)pyridine-2-amine (0.14 g, 0.42 mmol) in EtOH (5.0 mL) was added tin (II) chloride dihydrate (0.38 g, 1.70 mmol) at room temperature. The reaction mixture was stirred for 1 h at 90° C. After being cooled at room temperature, the solvent was removed in vacuo, EtOAC was poured in the residue. The mixture was neutralized with saturated NaHCO₃ (aq.) and 2N NaOH (aq.) until pH 9.0, filtered through a CELITE™ pad (Sigma-Aldrich, St. Louis, MO). The filtrate was extracted with EtOAc and combined organic layers were dried over Na₂SO₄, filtered and concentrated in vacuo to afford the 4-(4-amino-2-fluorophenoxy)-3-(1-methyl-1H-pyrazol-4-yl)pyridine-2-amine (0.11 g, 86%) as a yellow form, which was used for the next step without further purification. $^1$H-NMR (CDCl₃, Varian, 400 MHz): δ 3.96 (3H, s), 4.73 (2H, brs), 6.05 (1H, d, J=6.0 Hz), 6.04-6.42 (1H, m), 6.46-6.50 (1H, m), 6.87 (1H, t, J=8.4 Hz), 7.66 (1H, s), 7.73 (1H, s), 7.80 (1H, d, J=6.4 Hz). * NH₂ peak was not observed.

Step C: N-(4-(2-amino-3-(1-methyl-1H-pyrazol-4-yl)pyridin-4-yloxy)-3-fluoropehynl)-1-isopropyl-2,4-dioxo-1,2,3,4-tetrahydropyrimidine-5-carboxamide

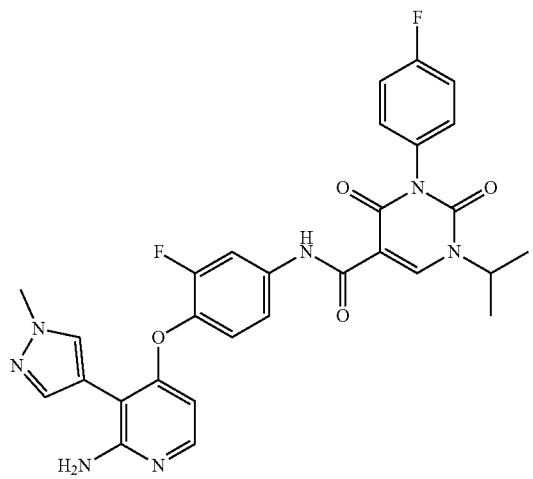 [SMILES: CC(C)n1cc(C(=O)Nc2ccc(Oc3ccnc(N)c3-c3cnn(C)c3)c(F)c2)c(=O)n(-c2ccc(F)cc2)c1=O]

A mixture of 3-(4-fluorophenyl)-1-isopropyl-2,4-dioxo-1,2,3,4-tetrahydropyrimidine-5-carboxylic acid (intermediate 10, 0.10 g, 0.36 mmol), HATU (0.15 g, 0.40 mmol) and DIPEA (0.16 mL, 0.91 mmol) in DMF (3.0 mL) was stirred for 30 mins at room temperature. The reaction mixture was added 4-(4-amino-2-fluorophenoxy)-3-(1-methyl-1H-pyrazol-4-yl)pyridine-2-amine (0.11 g, 0.36 mmol) and stirred for 18 h at room temperature. The reaction mixture was quenched with water and extracted with EtOAc. The combined organic layers were dried over Na₂SO₄, filtered and concentrated in vacuo. The residue was purified by column chromatography on SiO₂ (EtOAc/MeOH=9/1) to afford the N-(4-(2-amino-3-(1-methyl-1H-pyrazol-4-yl)pyridin-4-yloxy)-3-fluorophenyl)-1-isopropyl-2,4-dioxo-1,2,3,4-tetrahydropyrimidine-5-carboxamide (0.14 g, 66%) as a white solid. $^1$H-NMR (CDCl₃, Varian, 400 MHz): δ 1.49 (6H, d, J=6.8 Hz), 3.96 (3H, s), 4.93-5.00 (1H, m), 6.07 (1H, d, J=5.6 Hz), 7.02 (1H, t, J=8.4 Hz), 7.18 (1H d, J=8.8 Hz), 7.24-7.25 (4H, m), 7.64 (1H, s), 7.75-7.84 (3H, m), 8.67 (1H, s), 10.87 (1H, s). * NH₂ peak was not observed.

Example 8

Figure 8:
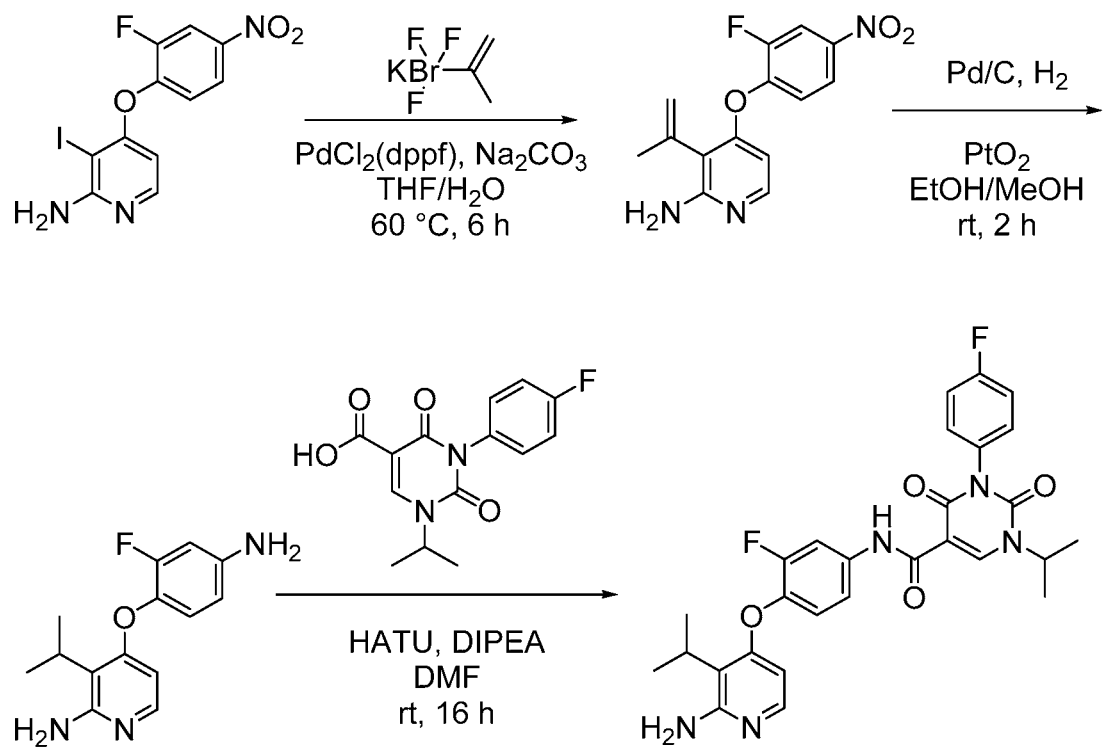
FIG. 8 is a chemical synthesis of N-(4-(2-amino-3-(1-methyl-1H-pyrazol-4-yl)pyridine-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(1-methyl-1H-pyrazol-4-yl)pyridine-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 8.

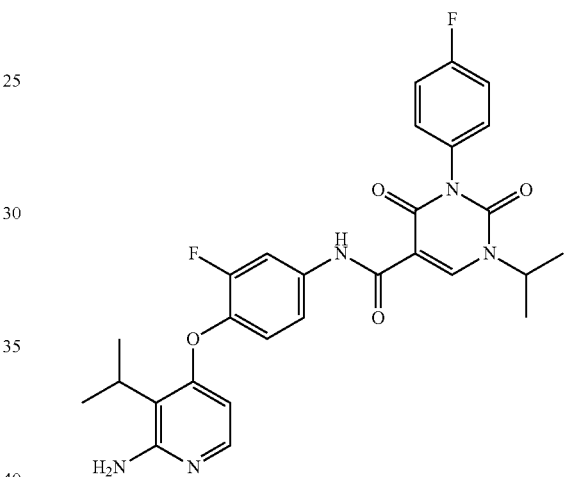

Step A: 4-(2-fluoro-4-nitrophenoxy)-3-(prop-1-en-2-yl)pyridin-2-amine

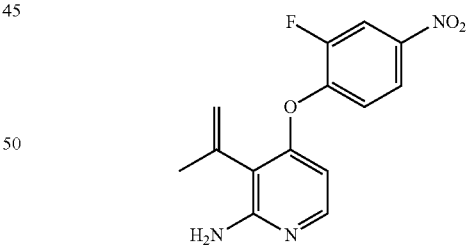

A mixture of 4-(2-fluoro-4-nitrophenoxy)-3-iodopyridin-2-amine (step D of intermediate 11, 0.20 g, 0.53 mmol), potassium isopropenyltrifluoroborate (0.12 g, 0.80 mmol), Na₂CO₃ (0.40 g, 3.73 mmol) and PdCl₂(dppf) (dppf: 1,1'-bis(diphenylphosphino)ferrocene) (44 mg, 0.05 mmol) in THF/H₂O (v/v=1:1, 6.0 mL) was refluxed for 16 h at 60° C. under argon atmosphere. The mixture was poured into saturated NaHCO₃, (aq.) then extracted with EtOAc. The combined organic layers were dried over Na₂SO₄, filtered and concentrated in vacuo. The residue was purified by column chromatography on SiO₂ (Hexanes/EtOAc=1/4) to afford the 4-(2-fluoro-4-nitrophenoxy)-3-(prop-1-en-2-yl)

pyridin-2-amine (0.15 g, 71%) as a yellow oil. ¹H-NMR (CDCl₃, Varian, 400 MHz): δ 2.05 (3H, s), 4.80 (2H, s), 5.08 (1H, s), 5.38 (1H, s), 6.16 (1H, d, J=5.2 Hz), 7.12 (1H, t, J=8.8 Hz), 7.91 (1H, d, J=6.0 Hz), 8.01-8.05 (1H, m), 8.07-8.10 (1H, m).

Step B: 4-(4-amino-2-fluorophenoxy)-3-iospropylpyridin-2-amine

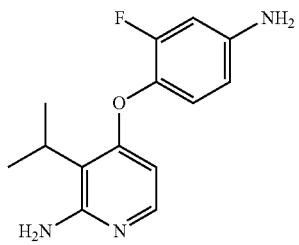

A mixture of 4-(2-fluoro-4-nitrophenoxy)-3-(prop-1-en-2-yl)pyridin-2-amine (110 mg, 0.38 mmol), platinum (IV) oxide (25 mg, 0.11 mmol) and 10% palladium on carbon (40 mg, 0.038 mmol) in EtOH/MeOH (v/v=1:2, 8.0 mL) was stirred for 2 h at room temperature under a H₂ atmosphere. The mixture was filtered through a CELITE™ pad (Sigma-Aldrich, St. Louis, MO), the filter cake washed with MeOH and the filtrate concentrated in vacuo to afford the 4-(4-amino-2-fluorophenoxy)-3-iospropylpyridin-2-amine (63 mg, 63%) as a yellow solid. ¹H-NMR (CDCl₃, Varian, 400 MHz): δ 1.38 (6H, d, J=4.0 Hz), 3.18-3.30 (1H, m), 3.78 (2H, s), 4.51 (2H, s), 5.97 (1H, d, J=5.2 Hz), 6.40 (1H, dd, J=2.4 Hz, 8.4 Hz), 6.47 (1H, dd, J=2.4 Hz, 11.8 Hz), 6.86 (1H, t, J=8.8 Hz), 7.69 (1H, d, J=6.0 Hz).

Step C: N-(4-(2-amino-3-(1-methyl-1H-pyrazol-4-yl)pyridine-4-yloxy-3-fluorophenyl)-3-(4-fluorophenyl)-1-isopropyl-2,4-dioxo-1,2,3,4-tetrahydropyrimidine-5-carboxamide

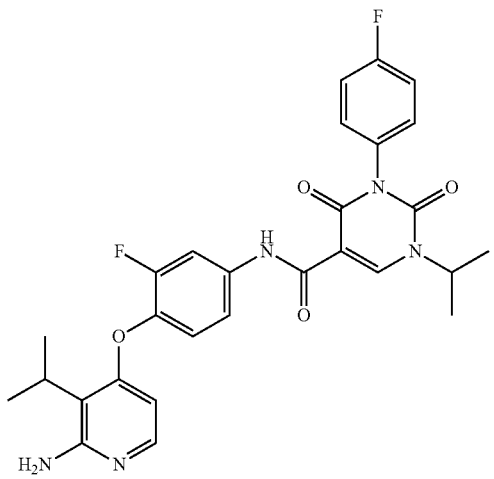 [SMILES: CC(C)c1c(Oc2ccc(NC(=O)c3cn(C(C)C)c(=O)n(-c4ccc(F)cc4)c3=O)cc2F)ccnc1N]

A mixture of 3-(4-fluorophenyl)-1-isopropyl-2,4-dioxo-1,2,3,4-tetrahydropyrimidine-5-carboxylic acid (intermediate 10, 70 mg, 0.24 mmol), HATU (0.10 g, 0.26 mmol) and DIPEA (0.10 mL, 0.60 mmol) in DMF (2.0 mL) was stirred at room temperature for 30 mins. The reaction mixture was added 4-(4-amino-2-fluorophenoxy)-3-iospropylpyridin-2-amine (63 mg, 0.36 mmol) and stirred for 16 h at room temperature. The reaction mixture was quenched with water and extracted with EtOAc. The combined organic layers were dried over Na₂SO₄, filtered and concentrated in vacuo. The residue was purified by column chromatography on SiO₂ (EtOAc/MeOH=9/1) to afford the N-(4-(2-amino-3-(1-methyl-1H-pyrazol-4-yl)pyridine-4-yloxy)-3-fluorophenyl)-3-(4-fluorophenyl)-1-isopropyl-2,4-dioxo-1,2,3,4-tetrahydropyrimidine-5-carboxamide (47 mg, 36%) as a white solid. ¹H-NMR (CDCl₃, Varian, 400 MHz): δ 1.40 (6H, d, J=7.2 Hz), 1.50 (6H, d, J=6.8 Hz), 4.47-4.52 (1H, m), 4.93-5.00 (1H, m), 6.00 (1H, d, J=5.6 Hz), 7.03 (1H, t, J=8.4 Hz), 7.20 (1H, d, J=8.0 Hz), 7.25 (5H, d, J=6.0 Hz), 7.75 (1H, d, J=6.0 Hz), 7.79 (1H, dd, J=2.4 Hz, 12.6 Hz), 8.68 (1H, s), 10.87 (1H, s). * NH peak was not observed.

Example 9

Figure 9:
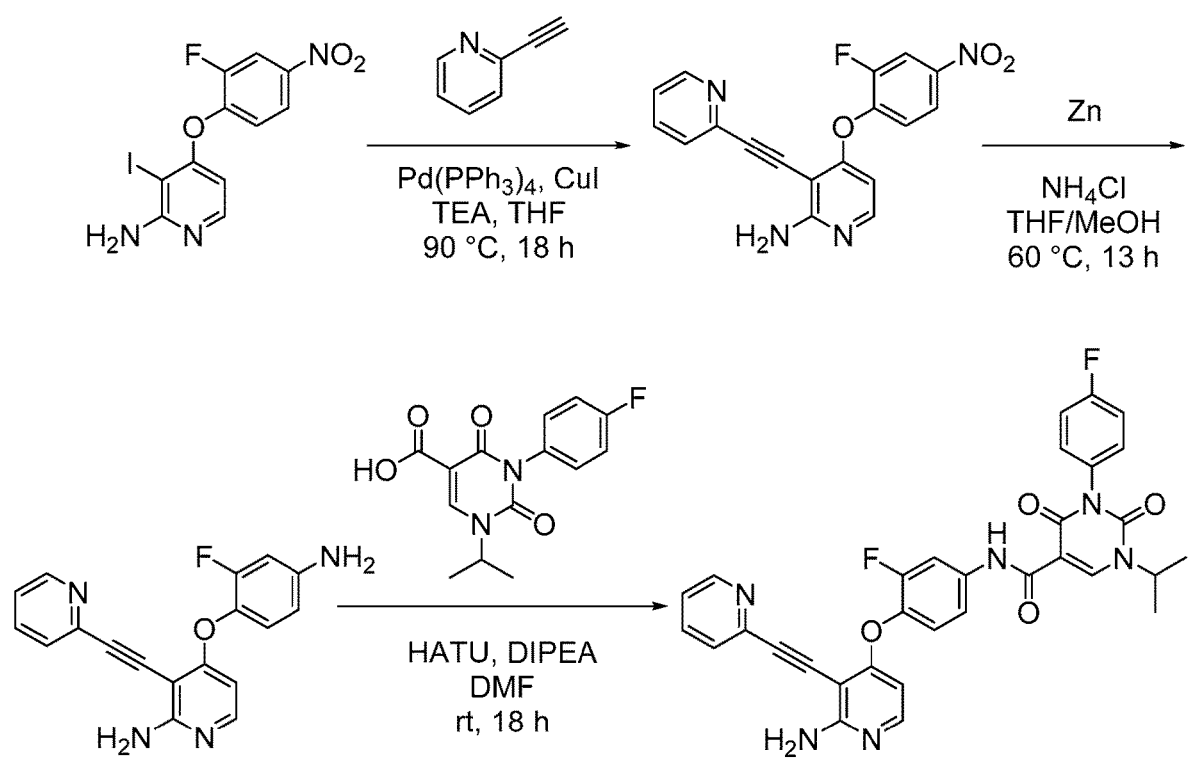
FIG. 9 is a chemical synthesis of N-(4-(2-amino-3-(pyridin-2-ylethnyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(pyridin-2-ylethnyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 9.

Step A: 4-(2-fluoro-4-nitrophenoxy)-3-(pyridine-2-ylethynyl)pyridin-2-amine

To a degassed solution of 4-(2-fluoro-4-nitrophenoxy)-3-iodopyridin-2-amine (step D of intermediate 11, 0.20 g, 0.53 mmol), 2-ethynylpyridine (0.10 mL, 1.06 mmol), CuI (20 mg, 0.10 mmol) and TEA (0.70 mL, 5.33 mmol) in THF (2.0 mL) was added Pd(PPh₃)₄ (20 mg, 0.1 mmol) under argon atmosphere and stirred 18 h at 90° C. for. After being cooled at room temperature, the mixture was poured into water and extracted with EtOAc. The combined organic layers were dried over Na₂SO₄, filtered and concentrated in vacuo. The residue was purified by column chromatography on SiO₂ (DCM/MeOH=9/1) to afford the 4-(2-fluoro-4-nitrophenoxy)-3-(pyridine-2-ylethynyl)pyridin-2-amine (0.12 g, 64%) as a yellow solid. ¹H-NMR (CDCl₃, Varian, 400 MHz): δ 5.46 (2H, s), 6.16 (1H, d, J=5.2 Hz), 7.24-7.27 (2H, m), 7.39 (1H, d, J=7.6H), 7.65-7.69 (1H, m), 7.99 (1H, d, J=5.2 Hz), 8.07-8.13 (2H, m), 8.59 (1H, d, J=5.2H).

Step B: 4-(4-amino-2-fluorophenoxy)-3-(pyridin-2-ylethynyl)-pyridin-2-amine

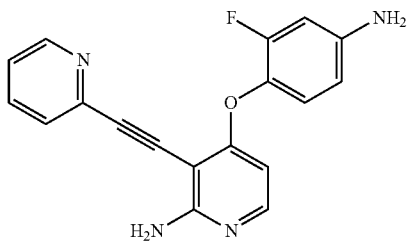

A mixture of 4-(2-fluoro-4-nitrophenoxy)-3-(pyridine-2-ylethynyl)pyridin-2-amine (0.12 g, 0.34 mmol), zinc (0.22 g, 3.43 mmol) and ammonium chloride (0.18 g, 3.43 mmol) in MeOH (2.0 mL) was stirred for 18 h at 60° C. The reaction mixture was filtered and the residue was partitioned between EtOAc and saturated NaHCO₃ (aq.). The aqueous was extracted with EtOAc. The combined layers were dried over Na₂SO₄, filtered and concentrated in vacuo. The residue was purified by column chromatography on SiO₂ (EtOAc/MeOH=95/5) to afford the 4-(4-amino-2-fluorophenoxy)-3-(pyridin-2-ylethynyl)-pyridin-2-amine (23 mg, 20%) as a yellow solid. ¹H-NMR (CDCl₃, Varian, 400 MHz): δ 5.42 (2H, s), 5.97 (1H, dd, J=1.2 Hz, 6.0 Hz), 6.42-6.52 (2H, m), 6.97 (1H, t, J=8.4 Hz), 7.22-7.26 (1H, m), 7.55 (1H, d, J=8.0 Hz), 7.65-7.69 (1H, m), 7.84 (1H, d, J=6.0. Hz), 8.60 (1H, d, J=5.2 Hz). * NH₂ peak was not observed.

Step C: N-(4-(2-amino-3-(pyridin-2-ylethnyl)pyridin-4-yloxy)-3-fluorophenyl)-3-(4-fluorophenyl)-1-isopropyl-2,4-dioxo-1,2,3,4-tetrahydropyrimidine-5-carboxamide

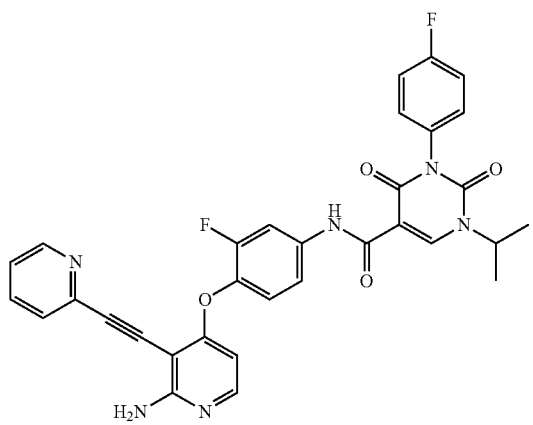 [SMILES: CC(C)n1cc(C(=O)Nc2ccc(Oc3ccnc(N)c3C#Cc3ccccn3)c(F)c2)c(=O)n(-c2ccc(F)cc2)c1=O]

A mixture of 3-(4-fluorophenyl)-1-isopropyl-2,4-dioxo-1,2,3,4-tetrahydropyrimidine-5-carboxylic acid (intermediate 10.18 mg, 0.06 mmol), HATU (0.26 g, 0.07 mmol) and DIPEA (0.3 mL, 0.15 mmol) in DMF (1.0 mL) was stirred for 30 mins at room temperature. The reaction mixture was added 4-(4-amino-2-fluorophenoxy)-3-(pyridin-2-ylethynyl)-pyridin-2-amine (20 mg, 0.06 mmol) and stirred for 18 h at room temperature. The reaction mixture was quenched with water and extracted with EtOAc. The combined organic layers were dried over Na₂SO₄, filtered and concentrated in vacuo. The residue was purified by column chromatography on SiO₂ (EtOAc/MeOH=9/1) to afford the N-(4-(2-amino-3-(pyridin-2-ylethnyl)pyridin-4-yloxy)-3-fluorophenyl)-3-(4-fluorophenyl)-1-isopropyl-2,4-dioxo-1,2,3,4-tetrahydropyrimidine-5-carboxamide (16 mg, 43%) as a white solid. ¹H-NMR (CDCl₃, Varian, 400 MHz): δ 1.49 (6H, d, J=6.8 Hz), 4.93-5.01 (1H, m), 5.99 (1H, d, J=5.6 Hz), 7.12-7.18 (2H, m), 7.21-7.24 (7H, m), 7.52 (1H, d, J=7.6 Hz), 7.64-7.68 (1H, m), 7.81-7.88 (2H, m), 8.60 (1H, d, J=4.4 Hz), 8.68 (1H, s), 10.9 (1H, s).

Example 10

Figure 10:
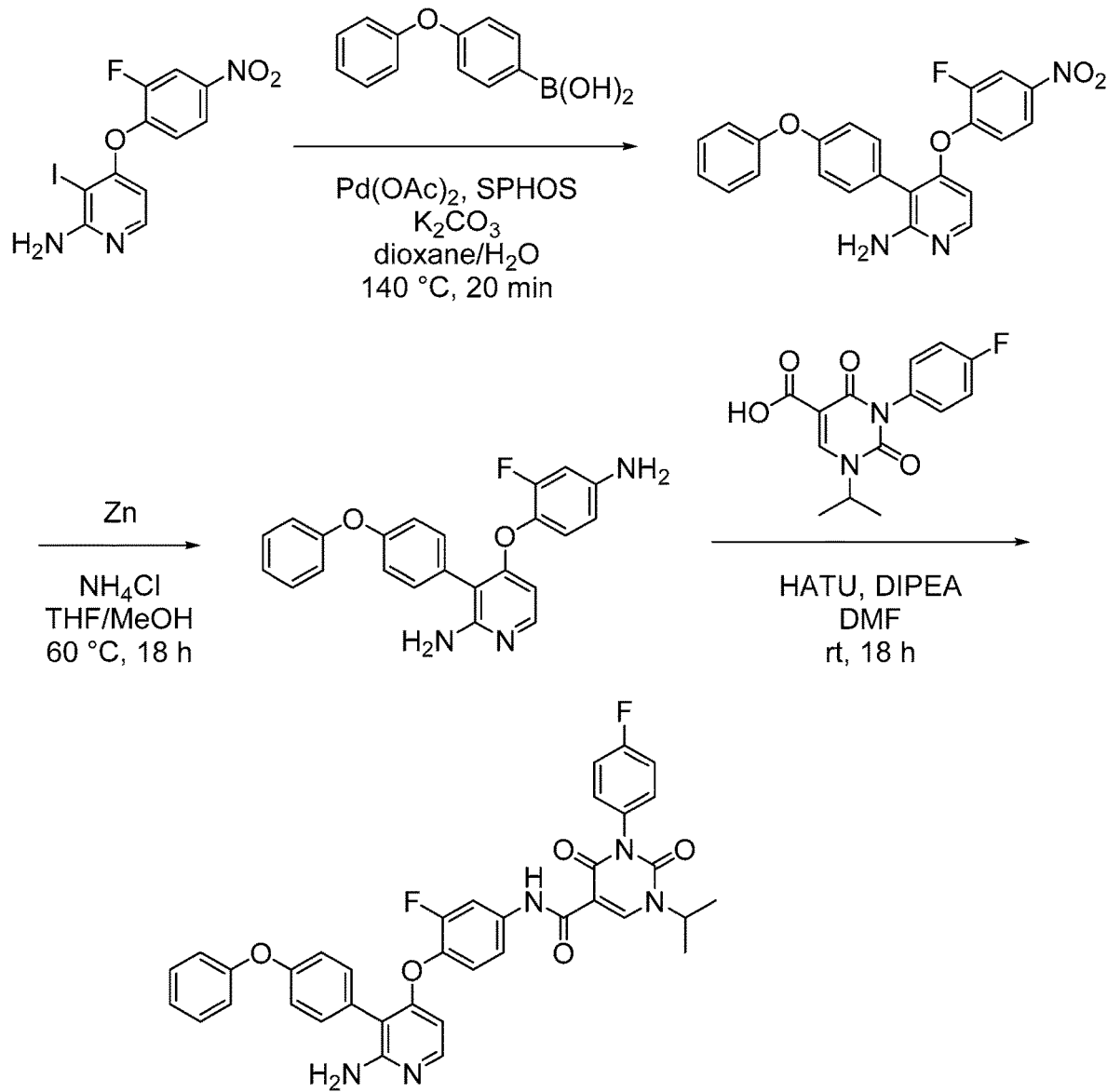
FIG. 10 is a chemical synthesis of N-(4-(2-amino-3-(4-phenoxyphenyl)pyridin-4-yloxy)-3-fluorophenyl)-1-isopropyl-2,4-dioxo-1,2,3,4-tetrahydropyrimidine-5-carboxamide in an aspect of the invention.

This example describes the synthesis of N-(4-(2-amino-3-(4-phenoxyphenyl)pyridin-4-yloxy)-3-fluorophenyl)-1-iosopropyl-2,4-dioxo-1,2,3,4-tetrahydropyrimidine-5-carboxamide in an aspect of the invention. See FIG. 10.

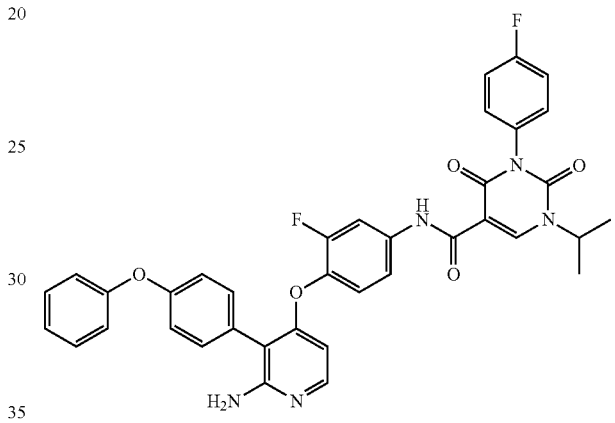

Step A: 4-(2-fluoro-4-nitrophenoxy)-3-(4-phenoxyphenyl)pyridin-2-amine

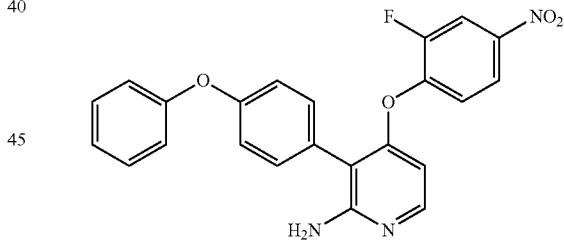

To a solution of 4-(2-fluoro-4-nitrophenoxy)-3-iodopyridin-2-amine (step D of intermediate 11, 0.30 g, 0.80 mmol) in dioxane/H₂O (v/v=10/1, 1.0 mL) was added 4-phenoxyphenylboronic acid (0.25 g, 1.20 mmol), Pd(OAc)₂ (8.9 mg, 0.04 mmol), SPHOS (32 mg, 0.08 mmol) and K₂CO₃ (0.33 g, 2.40 mmol) under N₂ at room temperature. The reaction mixture was subjected to microwave irradiation for 20 mins at 90° C. After being cooled at room temperature, Na₂SO₄ was added to the mixture which was subsequently filtered through a CELITE™ pad (Sigma-Aldrich, St. Louis, MO) and filtrate was concentrated in vacuo. The residue was purified by MPLC (EtOAc/Hex=1/4 to MeOH) to afford the 4-(2-fluoro-4-nitrophenoxy)-3-(4-phenoxyphenyl)pyridin-2-amine (0.29 g, 88%) as a yellow solid. ¹H-NMR (CDCl₃, Varian, 400 MHz): δ 4.82 (2H, s), 6.27 (1H, d, J=6.0 Hz), 6.98-7.09 (4H, m), 7.11-7.16 (2H, m), 7.29-7.37 (4H, m), 7.88-8.05 (3H, m).

Step B: 4-(4-amino-2-fluorophenoxy)-3-(4-phenoxyphenyl)pyridine-2-amine

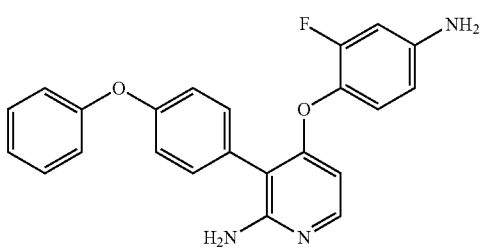

A mixture of 4-(2-fluoro-4-nitrophenoxy)-3-(4-phenoxyphenyl)pyridin-2-amine (0.29 g, 0.69 mmol), zinc (0.45 g, 6.95 mmol) and ammonium chloride (0.37 g, 6.95 mmol) in THF/MeOH (v/v=1/1, 8.0 mL) was stirred for 18 h at 60° C. The reaction mixture was filtered and the residue was partitioned between EtOAc and saturated NaHCO$_3$ (aq.). The aqueous was extracted with EtOAc. The combined organic layers were dried over Na$_2$SO$_4$, filtered and concentrated in vacuo. The residue was purified by column chromatography on SiO$_2$ (EtOAc/MeOH=95/5) to afford the 4-(4-amino-2-fluorophenoxy)-3-(4-phenoxyphenyl)pyridine-2-amine (0.26 g, 97%) as a yellow solid. $^1$H-NMR (CDCl$_3$, Varian, 400 MHz): δ 6.97-7.04 (6H, m), 7.08-7.14 (2H, m), 7.31-7.37 (6H, m). * NH$_2$ peak was not observed.

Step C: N-(4-(2-amino-3-(4-phenoxyphenyl)pyridin-4-yloxy)-3-fluorophenyl)-1-isopropyl-2,4-dioxo-1,2,3,4-tetrahydropyrimidine-5-carboxamide

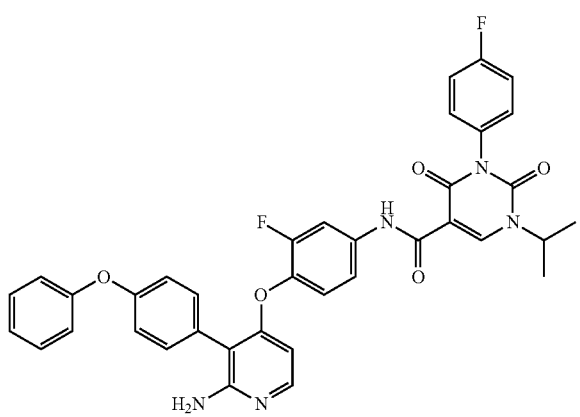 [SMILES: CC(C)n1cc(C(=O)Nc2ccc(Oc3ccnc(N)c3-c3ccc(Oc4ccccc4)cc3)c(F)c2)c(=O)n(-c2ccc(F)cc2)c1=O]

A mixture of 3-(4-fluorophenyl)-1-isopropyl-2,4-dioxo-1,2,3,4-tetrahydropyrimidine-5-carboxylic acid (intermediate 10, 0.26 g, 0.67 mmol), HATU (0.28 g, 0.76 mmol), DIPEA (0.30 mL, 1.67 mmol) in DMF (5.0 mL) was stirred for 30 mins at room temperature. The reaction mixture was added 4-(4-amino-2-fluorophenoxy)-3-(4-phenoxyphenyl)pyridine-2-amine (0.26 g, 0.67 mmol) and stirred for 18 h at room temperature. The reaction mixture was quenched with water and extracted with EtOAc. The combined organic layers were dried over Na$_2$SO$_4$, filtered and concentrated in vacuo. The residue was purified by column chromatography on SiO$_2$ (EtOAc/MeOH=9/1) to afford the N-(4-(2-amino-3-(4-phenoxyphenyl)pyridin-4-yloxy)-3-fluorophenyl)-1-isopropyl-2,4-dioxo-1,2,3,4-tetrahydropyrimidine-5-carboxamide (0.25 g, 56%) as a white solid. $^1$H-NMR (DMSO-d$_6$, Varian, 400 MHz): δ 1.50 (6H, d, J=6.4 Hz), 4.93-5.0 (1H, m), 6.26 (1H, d, J=6.8 Hz), 7.04-7.14 (5H, m), 7.20-7.26 (8H, m), 7.35-7.41 (4H, m), 7.72 (1H, d, J=6.8 Hz), 7.87-7.87 (1H, m), 8.67 (1H, s), 10.99 (1H, s).

Example 11

Figure 11:
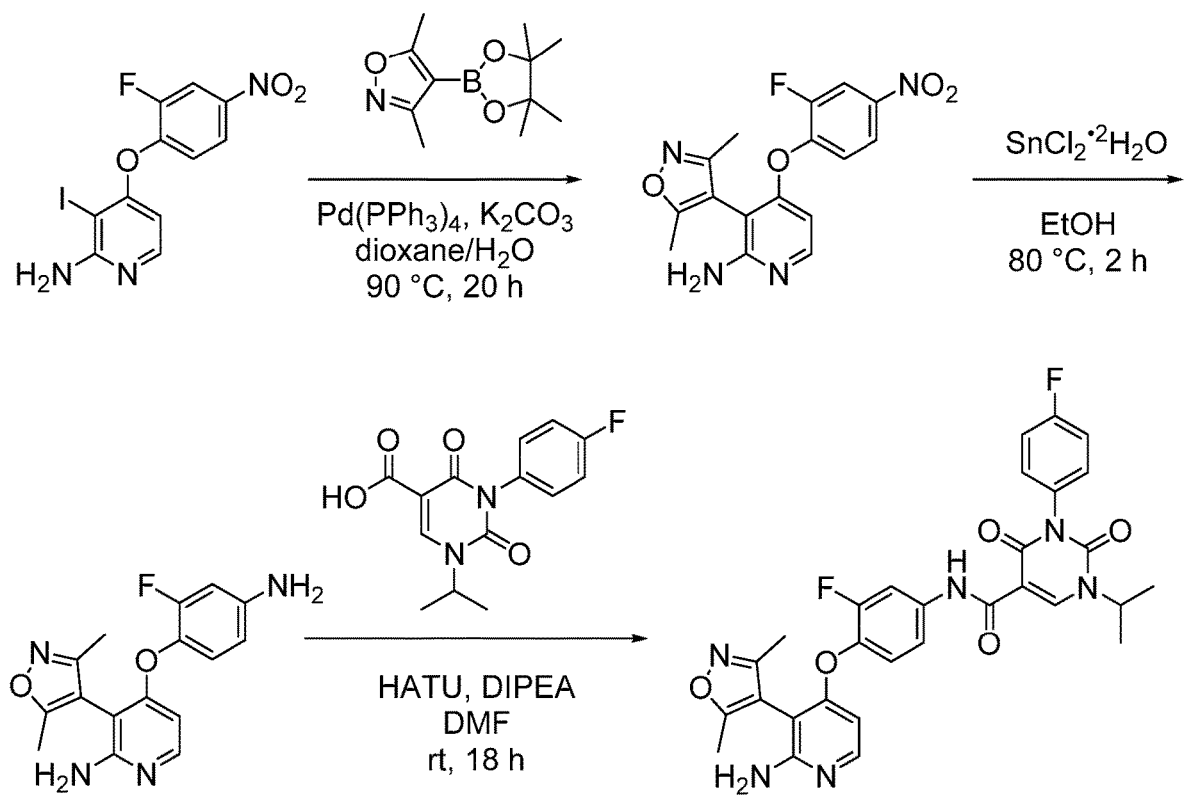
FIG. 11 is a chemical synthesis of N-(4-(2-amino-3-(3,5-dimethylisoxazol-4-yl)-3-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3,5-dimethylisoxazol-4-yl)-3-fluorophenyl)-1-isopropyl-2,4-dioxo-1,2,3,4-tetrahydropyrimidine-5-carboxamide in an aspect of the invention. See FIG. 11.

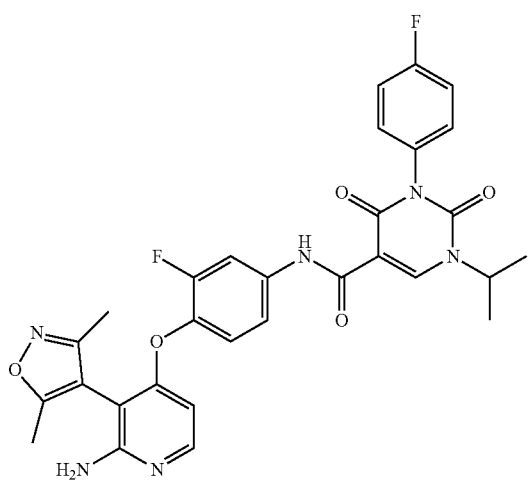

Step A: 3-(3,5-dimethylisoxazol-4-yl)-4-(2-fluoro-4-nitrophenoxy)pyridine-2-amine

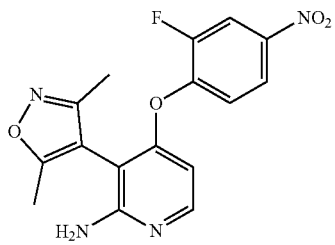

To a solution of 4-(2-fluoro-4-nitrophenoxy)-3-iodopyridin-2-amine (step D of intermediate 11, 0.20 g, 0.53 mmol) in dioxane/H$_2$O (v/v=2/1, 6.0 mL) was added 3,5-dimethyl-4-(4,4,5,5-tetramethyl-1,3,2-dioxaborolan-2-yl)isoxazole (0.17 g, 0.80 mmol) and K$_2$CO$_3$ (0.22 g, 1.60 mmol). The mixture was degassed with argon and added Pd(PPh$_3$)$_4$ (61 mg, 0.05 mmol). The reaction mixture was stirred for 20 h at 90° C. After being cooled at room temperature, the mixture was quenched with water and extracted with EtOAc. The combined organic layers were dried over Na$_2$SO$_4$, filtered and concentrated in vacuo. The residue was purified by column chromatography on SiO$_2$ (Hexanes/EtOAc=1/4) to afford the 3-(3,5-dimethylisoxazol-4-yl)-4-(2-fluoro-4-nitrophenoxy)pyridine-2-amine (0.13 g, 74%) as a yellow solid. $^1$H-NMR (CDCl$_3$, Varian, 400 MHz): δ 2.19 (3H, s), 2.32 (3H, s), 4.70 (2H, s), 6.18 (1H, d, J=4.4 Hz), 7.14-7.16 (1H, m), 7.18-7.33 (2H, m), 8.05 (1H, brs).

Step B: 4-(4-amino-2-fluorophenoxy)-3-(3,5-dimethylisoxazol-4-yl)pyridin-2-amine

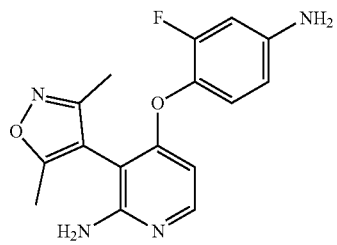

To a solution of 3-(3,5-dimethylisoxazol-4-yl)-4-(2-fluoro-4-nitrophenoxy)pyridine-2-amine (0.13 g, 0.39 mmol) in EtOH (4.0 mL) was added tin (II) chloride dihydrate (0.09 g, 0.39 mmol). The reaction mixture was stirred for 2 h at 80° C. After being cooled at room temperature, the solvent was concentrated in vacuo and dissolved with EtOAc. The organic layer was washed with water and dried over Na$_2$SO$_4$, filtered and concentrated in vacuo to afford the 4-(4-amino-2-fluorophenoxy)-3-(3,5-dimethylisoxazol-4-yl)pyridin-2-amine (90 mg, 72%) as a brown solid, which was used for the next step without further purification. $^1$H-NMR (CDCl$_3$, Varian, 400 MHz): δ 2.24 (3H, s), 2.36 (3H, s), 4.57 (2H, s), 5.94 (1H, d, J=8.4 Hz), 6.34-6.41 (2H, m), 6.80-6.84 (1H, m), 7.96 (1H, d, J=4.8 Hz). * NH$_2$ peak was not observed.

Step C: N-(4-(2-amino-3-(3,5-dimethylisoxazol-4-yl)-3-fluorophenyl)-1-isopropyl-2,4-dioxo-1,2,3,4-tetrahydropyrimidine-5-carboxamide

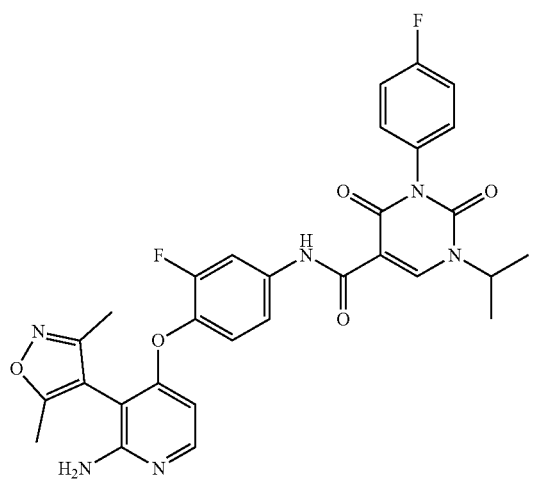 [SMILES: Cc1noc(C)c1-c1c(Oc2ccc(NC(=O)c3cn(C(C)C)c(=O)n(-c4ccc(F)cc4)c3=O)cc2F)ccnc1N]

A mixture of 3-(4-fluorophenyl)-1-isopropyl-2,4-dioxo-1,2,3,4-tetrahydropyrimidine-5-carboxylic acid (intermediate 10, 84 mg, 0.28 mmol), HATU (120 mg, 0.31 mmol) and DIPEA (125 µL, 0.71 mmol) in DMF (3.0 mL) was stirred for 1 h at room temperature. The reaction mixture was added 4-(4-amino-2-fluorophenoxy)-3-(3,5-dimethylisoxazol-4-yl)pyridin-2-amine (90 mg, 0.28 mmol) and stirred for 3 h at room temperature. The reaction mixture was quenched with water and extracted with EtOAc. The organic layers were dried over Na$_2$SO$_4$, filtered and concentrated in vacuo. The residue was purified by column chromatography on SiO$_2$ (EtOAc/MeOH=9/1) to afford the N-(4-(2-amino-3-(3,5-dimethylisoxazol-4-yl)-3-fluorophenyl)-1-isopropyl-2,4-dioxo-1,2,3,4-tetrahydropyrimidine-5-carboxamide (52 mg, 30%) as a white solid. $^1$H-NMR (CDCl$_3$, Varian, 400 MHz): δ 1.49 (6H, d, J=6.8 Hz), 2.22 (3H, s), 2.57 (3H, s), 4.45 (2H, s), 4.96-4.98 (1H, m), 6.05 (1H, d, J=6.4 Hz), 7.00 (1H, t, J=6.4 Hz), 7.20 (1H, d, J=9.6 Hz), 7.24-7.26 (4H, m), 7.79 (1H, dd, J=2.4 Hz, 12.0 Hz), 7.94 (1H, d, J=5.6 Hz), 8.67 (1H, s), 10.8 (s, 1H).

Example 12

Figure 12:
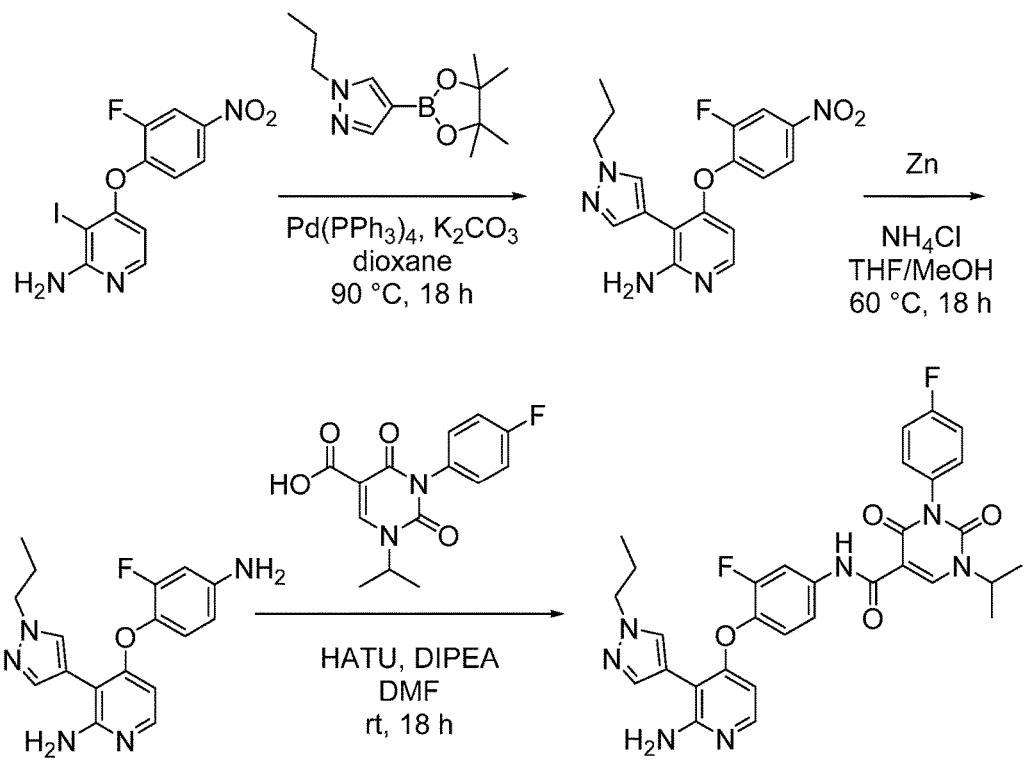
FIG. 12 is a chemical synthesis of N-(4-(2-amino-3-(1-propyl-1H-pyrazol-4-yl)pyridine-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(1-propyl-1H-pyrazol-4-yl)pyridine-4-yloxy)-3-fluoro-phenyl)-3-(4-fluorophenyl)-1-isopropyl-2,4-dioxo-1,2,3,4-tetrahydropyrimidine-5-carboxamide in an aspect of the invention. See FIG. 12.

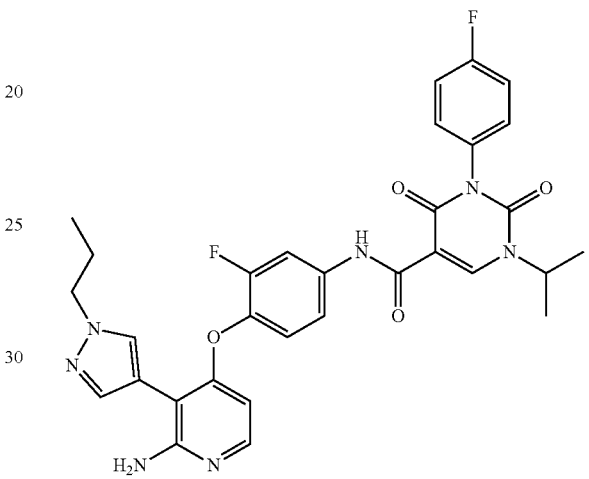

Step A: 4-(2-fluoro-4-nitrophenoxy)-3-(1-propyl-1H-pyrazol-4-yl)pyridine-2-amine

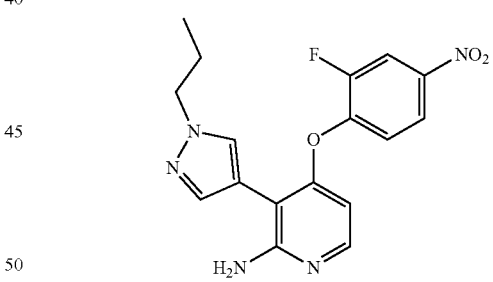

To a degassed solution of 4-(2-fluoro-4-nitrophenoxy)-3-iodopyridin-2-amine (step D of intermediate 11, 200 mg, 0.533 mmol), 1-methyl-4-(4,4,5,5-tetramethyl-1,3,2-dixaborolan-yl)-1H-pyrazole (189 mg, 0.800 mmol) in 1,4-dioxane (4.0 mL) were added a degassed solution of K$_2$CO$_3$ (221 mg, 1.60 mmol) in H$_2$O (2.0 mL) and Pd(PPh$_3$)$_4$ (61 mg, 0.05 mmol). The reaction mixture was stirred for 18 h at 90° C. After being cooled at room temperature, to the mixture was added saturated NaHCO$_3$ (aq.) and extracted with EtOAc. The combined organic layer was dried over Na$_2$SO$_4$, filtered concentrated in vacuo. The residue was purified by column chromatography on SiO$_2$ (DCM/MeOH=9/1) to afford the 4-(2-fluoro-4-nitrophenoxy)-3-(1-propyl-1H-pyrazol-4-yl)pyridine-2-amine (156 mg, 82%) as a yellow solid. $^1$H-NMR (CDCl$_3$, Varian, 400 MHz): δ 0.86

(3H, t, J=7.6 Hz), 1.82-1.91 (2H, m), 4.08 (2H, t, J=7.2 Hz), 4.84 (2H, s), 6.30 (1H, d, J=5.2 Hz), 7.02 (1H, t, J=8.0 Hz), 7.58 (1H, s), 7.66 (1H, s), 7.96-8.04 (3H, m).

Step B: 4-(4-Amino-2-fluorophenoxy)-3-(1-propyl-1H-pyrazol-4-yl)pyridin-2-amine

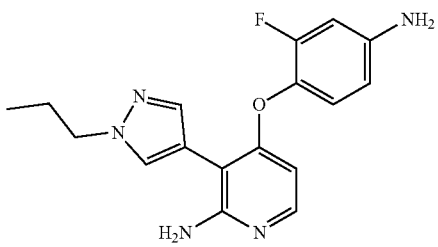

A mixture of 4-(2-fluoro-4-nitrophenoxy)-3-(1-propyl-1H-pyrazol-4-yl)pyridine-2-amine (156 mg, 0.43 mmol), zinc (285 mg, 4.37 mmol), and ammonium chloride (234 mg, 4.37 mmol) in THF/MeOH (v/v=1/1, 4.0 mL) was stirred for 18 h at 60° C. After being cooled to room temperature, the mixture was filtered and the filtrate was partitioned between EtOAc and saturated NaHCO₃ (aq.). The aqueous layer was extracted with EtOAc. The combined organic layer was washed with brine, dried over $Na_2SO_4$, filtered and concentrated in vacuo. The residue was purified by column chromatography on $SiO_2$ (EtOAc/MeOH=95/5) to afford the 4-(4-amino-2-fluorophenoxy)-3-(1-propyl-1H-pyrazol-4-yl)pyridin-2-amine (140 mg, 98%) as a yellow solid. ¹H-NMR (CD₃OD, Varian, 400 MHz): δ 0.93 (3H, t, J=7.6 Hz), 1.88-1.97 (2H, m), 4.17 (2H, t, J=7.2 Hz), 6.08 (1H, d, J=6.4 Hz), 6.49-6.55 (2H, m), 6.85-6.89 (1H, m), 7.54-7.57 (1H, m), 7.61-7.68 (1H, m), 7.70 (1H, s), 7.80 (1H, d, J=6.0 Hz), 7.87 (1H, s). * NH₂ peak was not observed.

Step C: N-(4-(2-amino-3-(1-propyl-1H-pyrazol-4-yl)pyridine-4-yloxy)-3-fluorophenyl)-3-(4-fluorophenyl-1-isopropyl-2,4-dioxo-1,2,3,4-tetrahydropyrimidine-5-carboxamide

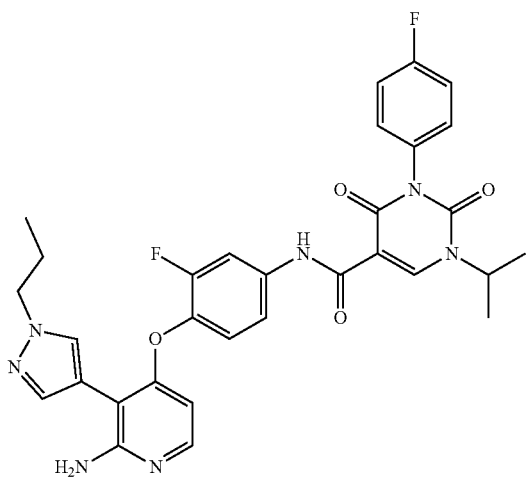 [SMILES: CCCn1cc(-c2c(Oc3ccc(NC(=O)c4cn(C(C)C)c(=O)n(-c5ccc(F)cc5)c4=O)cc3F)ccnc2N)cn1]

A mixture of 4-(4-amino-2-fluorophenoxy)-3-(1-propyl-1H-pyrazol-4-yl)pyridin-2-amine (65 mg, 0.20 mmol), 3-(4-fluorophenyl)-1-isopropyl-2,4-dioxo-1,2,3,4-tetrahydropyrimidine-5-carboxylic acid (intermediate 10, 58 mg, 0.20 mmol), HATU (83 mg, 0.22 mmol) and DIPEA (0.09 mL, 0.50 mmol) in DMF (2.0 mL) was stirred for 18 h at room temperature. The reaction was quenched by water and extracted with EtOAc. The organic layer was dried over $Na_2SO_4$, filtered and concentrated in vacuo. The residue was purified by column chromatography on $SiO_2$ (EtOAc/MeOH=9/1) to afford the N-(4-(2-amino-3-(1-propyl-1H-pyrazol-4-yl)pyridine-4-yloxy)-3-fluorophenyl)-3-(4-fluorophenyl)-1-isopropyl-2,4-dioxo-1,2,3,4-tetrahydropyrimidine-5-carboxamide (25 mg, 21%) as a white solid. ¹H-NMR (CDCl₃, Varian, 400 MHz): δ 0.94 (3H, t, J=13.2 Hz), 1.50 (6H, d, J=6.4 Hz), 1.88-1.97 (2H, m), 4.13 (2H, t, J=7.2 Hz), 4.93-5.0 (1H, m), 6.11 (1H, d, J=6.0 Hz), 7.02 (1H, t, J=8.4 Hz), 7.18 (1H, d, J=8.4 Hz), 7.24-7.26 (6H, m), 7.67 (1H, s), 7.76-7.82 (3H, m), 8.67 (1H, s), 10.8 (1H, s).

Example 13

Figure 13:
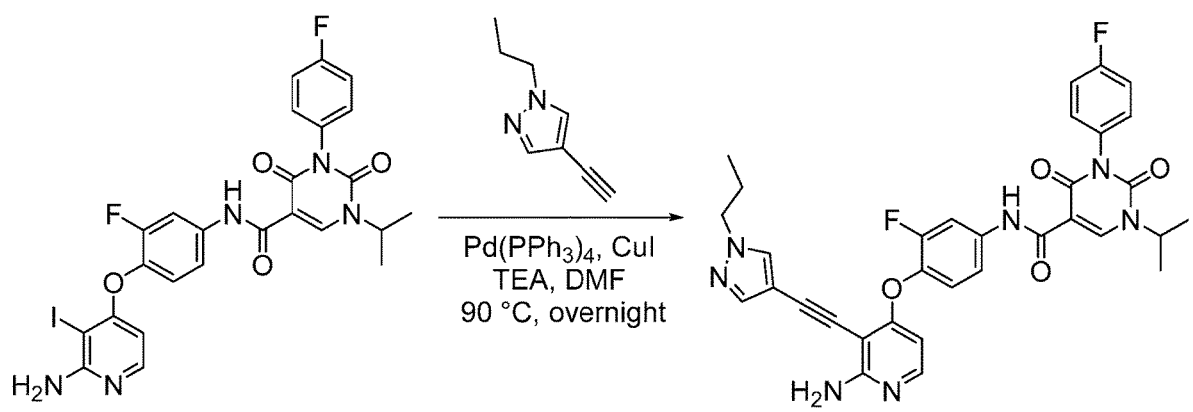
FIG. 13 is a chemical synthesis of N-(4-(2-amino-3-((1-propyl-1H-pyrazol-4-yl)ethynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-((1-propyl-1H-pyrazol-4-yl)ethynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 13.

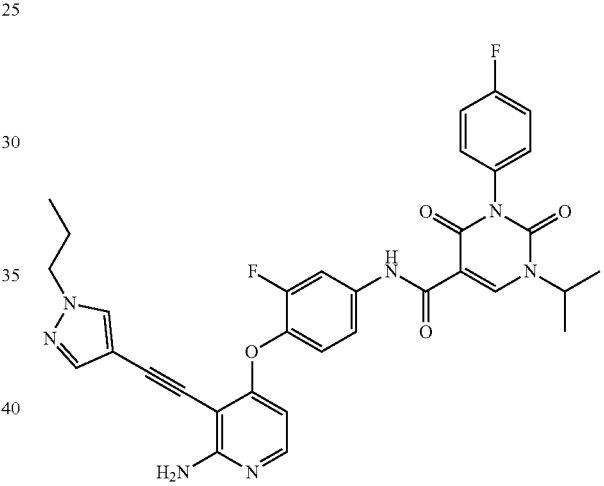

A mixture of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 290 mg, 0.47 mmol), 4-ethynyl-1-propyl-1H-pyrazole (intermediate 9, 94 mg, 0.70 mmol), Pd(PPh₃)₄ (54 mg, 0.05 mmol), copper(I) iodide (18 mg, 0.09 mmol), and TEA (0.26 mL, 1.87 mmol) in DMF (3.0 mL) was purged with N₂. The reaction mixture was stirred overnight at 90° C. After cooled at room temperature, EtOAc and saturated NH₄Cl solution (aq.) were added the mixture, and the separated aqueous layer was extracted with EtOAc. The combined organic layers were dried over Na₂SO₄, filtered, and concentrated in vacuo. The residue was purified by prep-LC to afford the N-(4-(2-amino-3-((1-propyl-1H-pyrazol-4-yl)ethynyl)pyridin-4-yloxy)-3-fluorophenyl)-3-(4-fluorophenyl)-1-isopropyl-2,4-dioxo-1,2,3,4-tetrahydropyrimidine-5-carboxamide (35 mg, 12%) as a white solid. ¹H-NMR (CDCl₃, Varian, 400 MHz): δ 0.91 (3H, t, J=7.2 Hz), 1.49 (6H, d, J=7.2 Hz), 1.87 (2H, t, J=7.2 Hz), 4.06 (2H, t, J=6.8 Hz), 4.93-5.00 (1H, m), 5.20 (2H, s), 5.99 (1H, d, J=5.6 Hz), 7.08-7.15 (1H, m), 7.21 (1H, d, J=8.4 Hz), 7.25-7.27 (2H, m), 7.53-7.56 (3H, m), 7.59 (1H, s), 7.79-7.84 (2H, m), 8.06 (1H, s), 10.91 (1H, s).

Example 14

Figure 14:
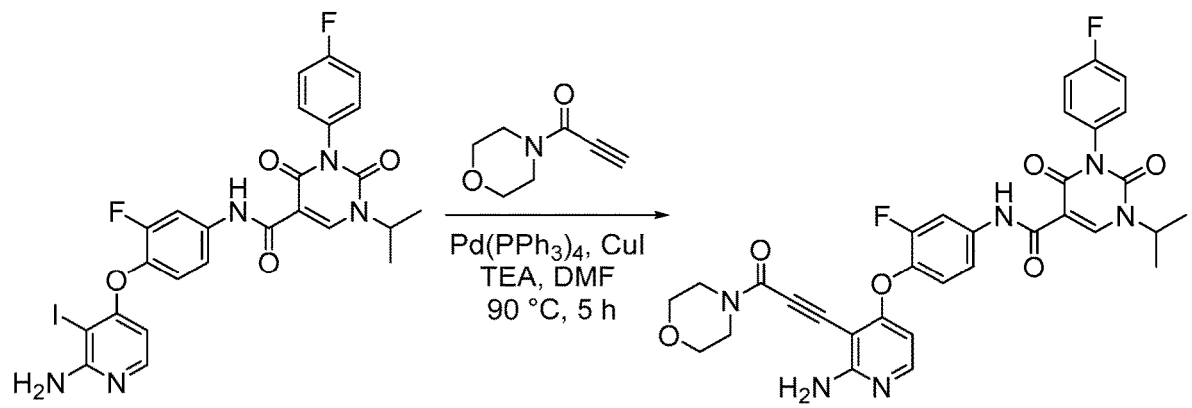
FIG. 14 is a chemical synthesis of N-(4-(2-amino-3-(3-morpholino-3-oxoprop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-morpholino-3-oxoprop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 14.

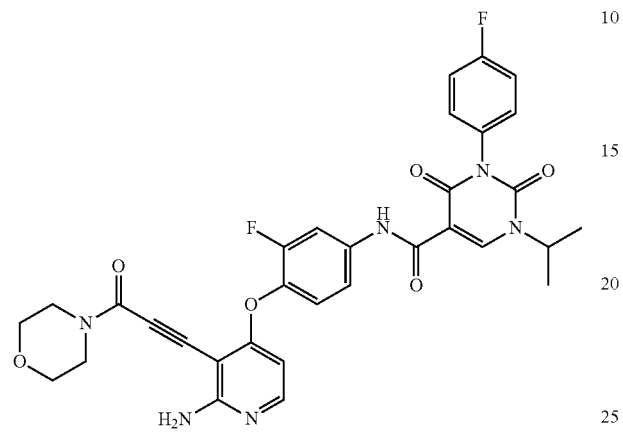

A mixture of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 100 mg, 0.16 mmol), 1-Morpholinoprop-2-yn-1-one (intermediate 1, 22 mg, 0.16 mmol), Pd(PPh$_3$)$_4$ (19 mg, 0.02 mmol), copper(I) iodide (6 mg, 0.03 mmol), and TEA (0.09 mL, 0.64 mmol) in DMF (1.0 mL) was purged with N$_2$. The reaction mixture was stirred for 5 h at 90° C. After cooled at room temperature, EtOAc and saturated NH$_4$Cl solution (aq.) were added the mixture, and the separated aqueous layer was extracted with EtOAc. The combined organic layers were dried over Na$_2$SO$_4$, filtered, and concentrated in vacuo. The residue was purified by column chromatography on SiO$_2$ (Hexanes/EtOAc=1/9 to EtOAc) to afford the N-(4-(2-amino-3-(3-morpholino-3-oxoprop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (10 mg, 10%) as a beige solid. $^1$H-NMR (CDCl$_3$, Varian, 400 MHz): δ 1.50 (6H, d, J=6.4 Hz), 1.63 (2H, brs), 3.67-3.68 (6H, m), 4.94-5.01 (1H, m), 5.25 (2H, s), 5.98 (1H, d, J=6.0 Hz), 7.21-7.26 (4H, m), 7.85 (1H, dd, J=2.0 Hz, 12.2 Hz), 7.91 (1H, d, J=5.6 Hz), 8.68 (1H, s), 10.9 (1H, s). * NH$_2$ peak was not observed.

Example 15

Figure 15:
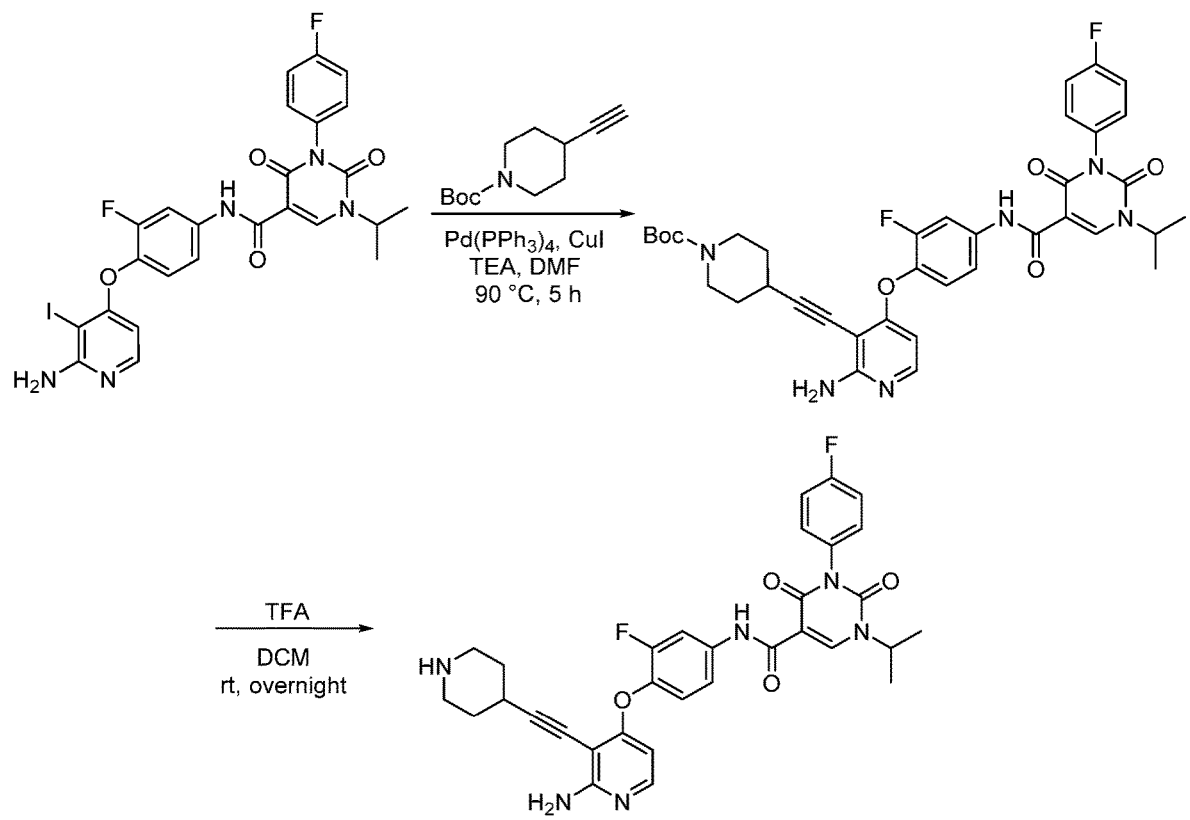
FIG. 15 is a chemical synthesis of N-(4-(2-amino-3-(piperidin-4-ylethynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(piperidin-4-ylethynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 15.

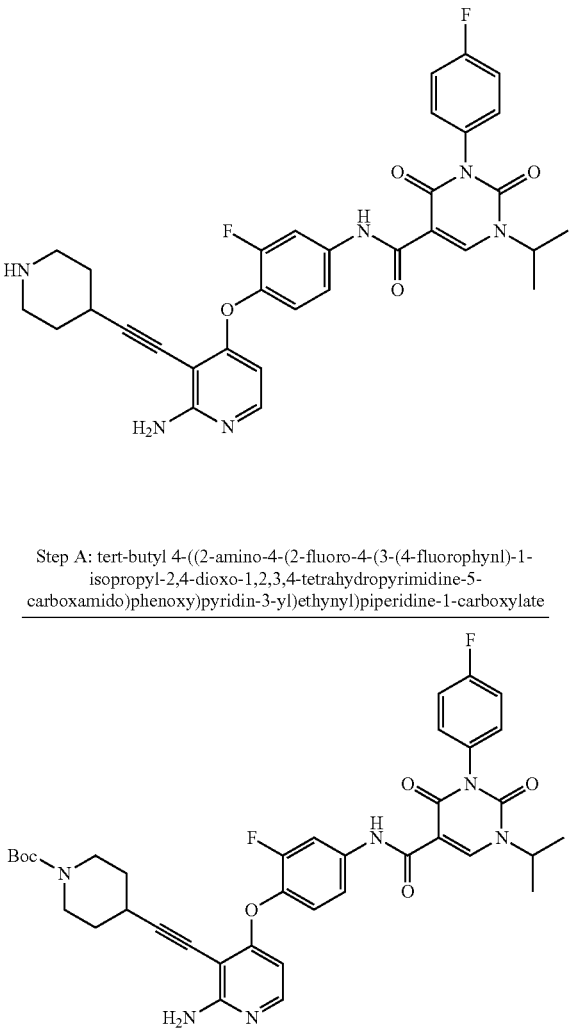

Step A: tert-butyl 4-((2-amino-4-(2-fluoro-4-(3-(4-fluorophynl)-1-isopropyl-2,4-dioxo-1,2,3,4-tetrahydropyrimidine-5-carboxamido)phenoxy)pyridin-3-yl)ethynyl)piperidine-1-carboxylate A mixture of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 200 mg, 0.32 mmol), tert-butyl 4-ethynylpiperidine-1-carboxylate (100 mg, 0.48 mmol), Pd(PPh$_3$)$_4$ (37 mg, 0.03 mmol), copper(I) iodide (12 mg, 0.06 mmol), and TEA (0.18 mL, 1.3 mmol) in DMF (2 mL) was purged with N$_2$. The reaction mixture was stirred for 5 h at 90° C. After cooled at room temperature, EtOAc and saturated NH$_4$Cl solution (aq.) were added the mixture, and the separated aqueous layer was extracted with EtOAc. The combined organic layers were dried over Na$_2$SO$_4$, filtered, and concentrated in vacuo. The residue was purified by column chromatography on SiO$_2$ (EtOAc/Hex=9/1 to EtOAc) to afford the tert-butyl 4-((2-amino-4-(2-fluoro-4-(3-(4-fluorophenyl)-1-isopropyl-2,4-dioxo-1,2,3,4-tetrahydropyrimidine-5-carboxamido)phenoxy)pyridin-3-yl)ethynyl)piperidine-1-carboxylate (150 mg, 66%) as a gray solid. $^1$H-NMR (CDCl$_3$, Varian, 400 MHz): δ 1.45 (9H, s), 1.50 (6H, d, J=6.8 Hz), 1.65-1.72 (3H, m). 1.85-1.89 (2H, m), 3.20-3.27 (2H, m), 3.71-3.74 (2H, m), 4.95-4.98 (1H, m), 5.01 (2H, s), 5.99 (1H, d, J=5.6 Hz), 7.08 (1H, t, J=8.8 Hz), 7.21 (1H, d, J=8.8 Hz), 7.24-7.26 (4H, m), 7.80-7.83 (2H, m), 8.68 (1H, s), 10.8 (1H, s).

Step B: N-(4-(2-amino-3-(piperidin-4-yethynyl)pyridin-4-yloxy)-3-fluorophenyl)-3-(4-fluorophenyl)-1-isopropyl-2,4-dioxo-1,2,3,4-tetrahydropyrimidine-5-carboxamide

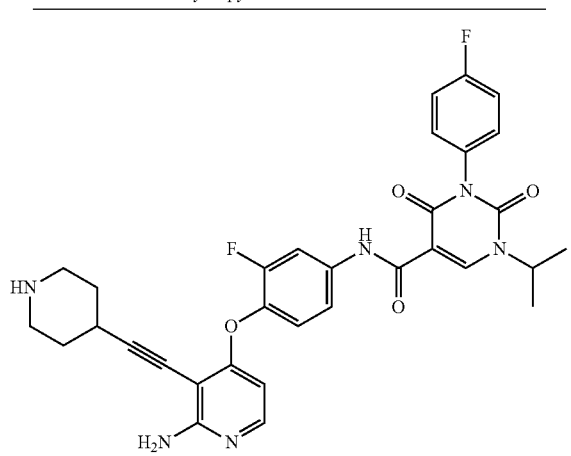

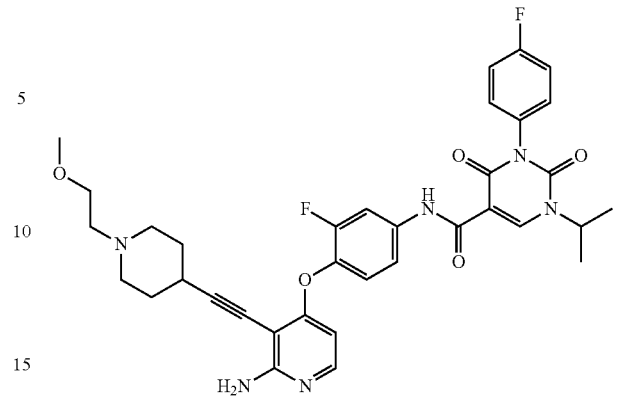

To a solution of tert-butyl 4-((2-amino-4-(2-fluoro-4-(3-(4-fluorophynl)-1-isopropyl-2,4-dioxo-1,2,3,4-tetrahydropyrimidine-5-carboxamido)phenoxy)pyridin-3-yl)ethynyl)piperidine-1-carboxylate (150 mg, 0.21 mmol) in DCM (5.0 ml) was added TFA (0.16 mL, 2.14 mmol) at room temperature. The reaction mixture was stirred overnight at room temperature. The reaction mixture was concentrated in vacuo. The residue was diluted with DCM, and then neutralized with TEA. The mixture was stirred for 10 min at room temperature and concentrated in vacuo. The residue was purified by column chromatography on $SiO_2$ (EtOAc/MeOH=95/5) to afford the N-(4-(2-amino-3-(piperidin-4-ylethynyl)pyridin-4-yloxy)-3-fluorophenyl)-3-(4-fluorophenyl)-1-isopropyl-2,4-dioxo-1,2,3,4-tetrahydropyrimidine-5-carboxamide (74 mg, 57%) as a white solid. $^1$H-NMR (CDCl$_3$, Varian, 400 MHz): δ 1.50 (6H, d, J=6.8 Hz), 1.90-1.92 (2H, m), 2.67-2.73 (2H, m), 2.81-2.83 (1H, m), 3.04-3.10 (2H, m), 4.74 (4H, s), 4.93-5.00 (1H, m), 5.03 (1H, s), 6.00 (1H, d, J=6.0 Hz), 7.08 (1H, t, J=8.8 Hz), 7.20 (1H, d, J=8.8 Hz), 7.24-7.26 (4H, m), 7.79-7.82 (1H, m), 8.68 (1H, s), 10.8 (1H, s). * NH peak was not observed.

Example 16

Figure 16:
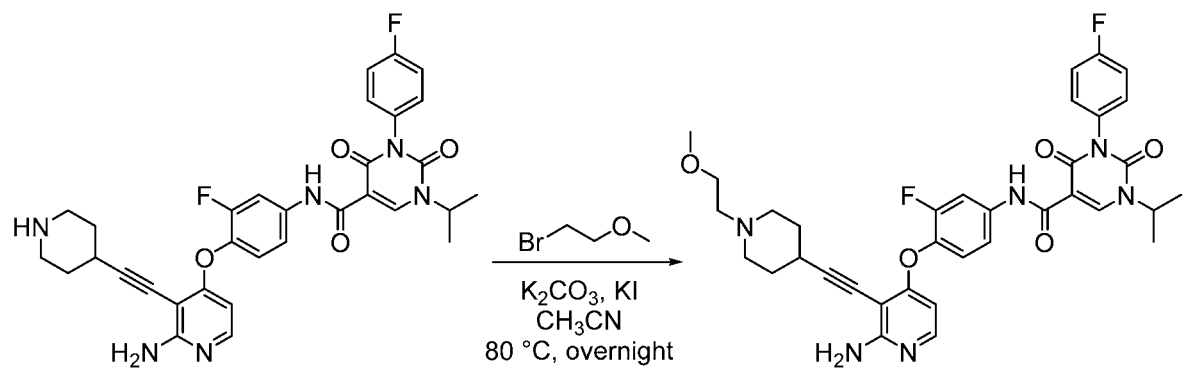
FIG. 16 is a chemical synthesis of N-(4-(2-amino-3-((1-(2-methoxyethyl)piperidin-4-yl)ethynyl)pyridin-4-yloxy)-3-fluorophenyl)-1-isopropyl-2,4-dioxo-1,2,3,4-tetrahydropyrimidine-5-carboxamide in an aspect of the invention.

This example describes the synthesis of N-(4-(2-amino-3-((1-(2-methoxyethyl)piperidin-4-yl)ethynyl)pyridin-4-yloxy)-3-fluorophenyl)-1-isopropyl-2,4-dioxo-1,2,3,4-tetrahydropyrimidine-5-carboxamide in an aspect of the invention. See FIG. 16.

A mixture of N-(4-(2-amino-3-(piperidin-4-ylethynyl)pyridin-4-yloxy)-3-fluorophenyl)-3-(4-fluorophenyl)-1-isopropyl-2,4-dioxo-1,2,3,4-tetrahydropyrimidine-5-carboxamide (Example 15, 30.0 mg, 0.05 mmol), 1-bromo-2-methoxyethane (5.6 µL, 0.06 mmol), potassium iodide (8.30 mg, 0.05 mmol) and K$_2$CO$_3$ (6.90 mg, 0.05 mmol) in CH$_3$CN (2 mL) was heated overnight at 80° C. in a sealed vessel. After being cooled at room temperature, EtOAc and water were poured into the reaction mixture and the separated aqueous layer was extracted with EtOAc. The combined organic layer was dried over Na$_2$SO$_4$, filtered, and concentrated in vacuo. The residue was purified by column chromatography on SiO$_2$ (EtOAc/MeOH=95/5) to afford the N-(4-(2-amino-3-((1-(2-methoxyethyl)piperidin-4-yl)ethynyl)pyridin-4-yloxy)-3-fluorophenyl)-1-isopropyl-2,4-dioxo-1,2,3,4-tetrahydropyrimidine-5-carboxamide (18.0 mg, 55%) as a white solid. $^1$H-NMR (CDCl$_3$, Varian, 400 MHz): δ 1.49 (6H, d, J=6.8 Hz), 1.78-1.84 (2H, m), 1.95-1.99 (2H, m), 2.02 (1H, s), 2.29 (2H, brs), 2.55 (2H, t, J=5.6 Hz), 2.76 (2H, brs), 3.34 (3H, s), 3.49 (2H, t, J=5.2 Hz), 4.93-5.00 (1H, m), 5.04 (2H, s), 5.98 (1H, d, J=6.0 Hz), 7.09 (1H, t, J=8.8 Hz), 7.20 (1H, d, J=8.4 Hz), 7.24-7.26 (3H, m), 7.79-7.83 (2H, m), 8.68 (1H, s), 10.8 (1H, s). * NH peak was not observed.

Example 17

Figure 17:
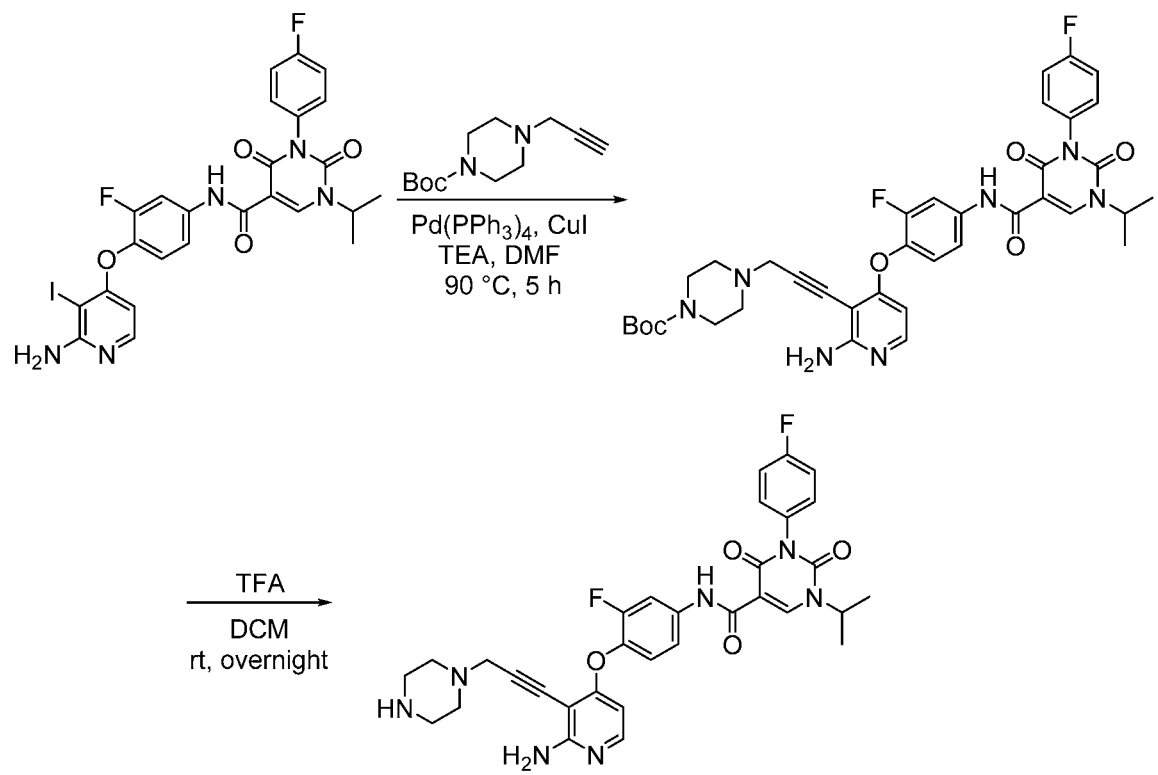
FIG. 17 is a chemical synthesis of N-(4-(2-amino-3-(3-piperzain-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-piperzain-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 17.

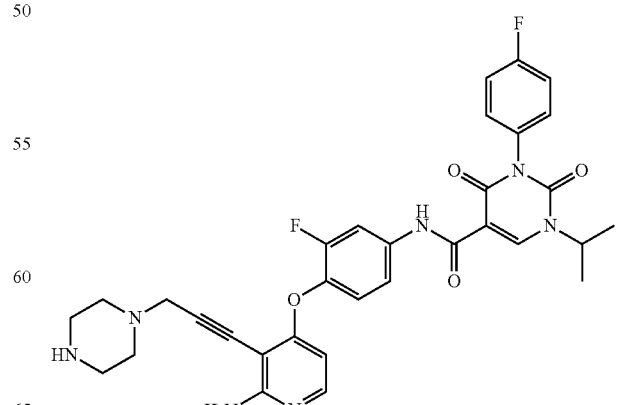

Step A: tert-butyl 4-(3-(2-amino-4-(2-fluoro-4-(3-(4-fluorophenyl)-1-isopropyl-2,4-dioxo-1,2,3,4-tetrahydropyrimidine-5-carboxamido)phenoxy)ypridin-3-yl)prop-2-ynyl)piperazine-1-carboxylate

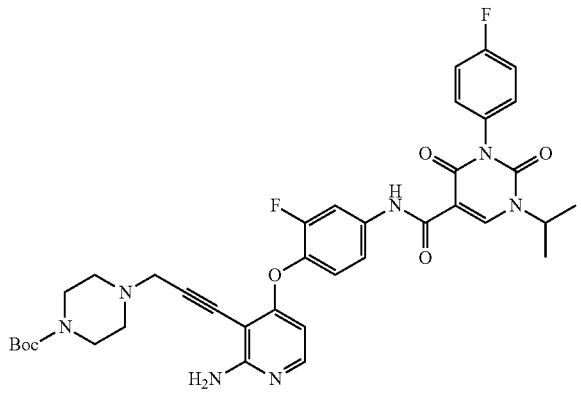

A mixture of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 200 mg, 0.32 mmol), tert-Butyl 4-(prop-2-ynyl)pipearazine-1-carboxylate (intermediate 3, 110 mg, 0.48 mmol), Pd(PPh$_3$)$_4$ (37 mg, 0.03 mmol), copper(I) iodide (12 mg, 0.06 mmol), and TEA (0.18 mL, 1.3 mmol) in DMF (2 mL) was purged with N$_2$. The reaction mixture was stirred for 5 h at 90° C. After cooled at room temperature, EtOAc and saturated NH$_4$Cl solution (aq.) were added the mixture, and the separated aqueous layer was extracted with EtOAc. The combined organic layers were dried over Na$_2$SO$_4$, filtered, and concentrated in vacuo. The residue was purified by column chromatography on SiO$_2$ (EtOAc/MeOH=95/5) to afford the tert-butyl 4-(3-(2-amino-4-(2-fluoro-4-(3-(4-fluorophenyl)-1-isopropyl-2,4-dioxo-1,2,3,4-tetrahydropyrimidine-5-carboxamido)phenoxy)ypridin-3-yl)prop-2-ynyl) piperazine-1-carboxylate (92 mg, 39%) as a white solid. $^1$H-NMR (CDCl$_3$, Varian, 400 MHz): δ 1.44 (9H, s), 1.49 (6H, d, J=6.4 Hz), 2.56-2.58 (4H, m), 3.40-3.62 (4H, m), 3.71 (2H, s), 4.95-4.98 (1H, m), 5.11 (2H, s), 5.97 (1H, d, J=6.0 Hz), 7.07-7.12 (1H, m), 7.21 (1H, d, J=8.8 Hz), 7.24-7.27 (3H, m), 7.81-7.84 (2H, m), 8.68 (1H, s), 10.9 (1H, s). * NH peak was not observed.

Step B: N-(4-(2-amino-3-(3-piperzain-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide

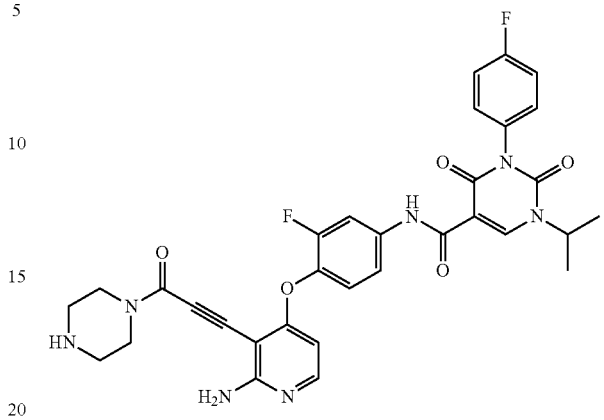

To a solution of tert-butyl 4-(3-(2-amino-4-(2-fluoro-4-(3-(4-fluorophenyl)-1-isopropyl-2,4-dioxo-1,2,3,4-tetrahydropyrimidine-5-carboxamido)phenoxy)ypridin-3-yl)prop-2-ynyl)piperazine-1-carboxylate (90 mg, 0.13 mmol) in DCM (5.0 ml) was added TFA (96 μL, 1.26 mmol) at room temperature. The reaction mixture was stirred overnight at room temperature. The reaction mixture was concentrated in vacuo. The residue was diluted with DCM, and then neutralized with TEA. The mixture was stirred for 10 min at room temperature and concentrated in vacuo. The residue was purified by column chromatography on SiO$_2$ (EtOAc/MeOH=95/5) to afford the N-(4-(2-amino-3-(3-piperzain-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (37 mg, 48%) as a white solid. $^1$H-NMR (CDCl$_3$, Varian, 400 MHz): δ 1.50 (6H, d, J=6.4 Hz), 2.58 (4H, brs), 2.92 (3H, t, J=4.8 Hz), 3.59 (2H, s), 4.93-5.00 (1H, m), 5.07 (2H, s), 5.99 (1H, d, J=5.6 Hz), 7.09 (1H, t, J=8.4 Hz), 7.19-7.26 (5H, m), 7.80-7.83 (2H, m), 8.67 (1H, s), 10.9 (1H, s). * NH peak was not observed.

Example 18

Figure 18:
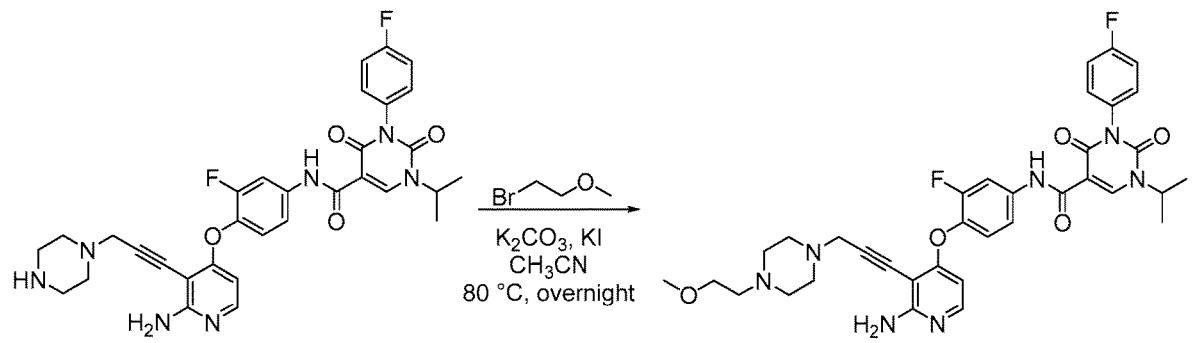
FIG. 18 is a chemical synthesis of N-(4-(2-amino-3-(3-(4-(2-methoxyethyl)piperazin-1-yl)prop-1-ylny)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-(4-(2-methoxyethyl)piperazin-1-yl)prop-1-ylny)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 18.

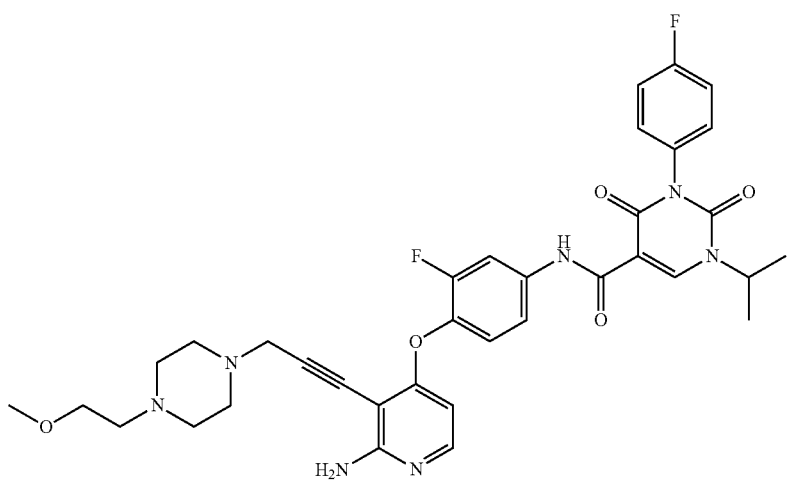 [SMILES: COCCN1CCN(CC#Cc2c(Oc3ccc(NC(=O)c4cn(C(C)C)c(=O)n(-c5ccc(F)cc5)c4=O)cc3F)ccnc2N)CC1]

A mixture of the N-(4-(2-amino-3-(3-piperzain-1-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (Example 17, 27.0 mg, 0.04 mmol), 1-bromo-2-methoxyethane (4.91 μL, 0.05 mmol), potassium iodide (7.28 mg, 0.04 mmol) and K$_2$CO$_3$ (6.06 mg, 0.04 mmol) in CH$_3$CN (1 mL) was heated overnight at 80° C. in a sealed vessel. After being cooled at room temperature, EtOAc and water were poured into the reaction mixture and the separated aqueous layer was extracted with EtOAc. The combined organic layer was dried over Na$_2$SO$_4$, filtered, and concentrated in vacuo. The residue was purified by column chromatography on SiO$_2$ (EtOAc/MeOH=95/5) to afford the N-(4-(2-amino-3-(3-(4-(2-methoxyethyl)piperazin-1-yl)prop-1-ylny)pyridin-4-yloxy)-3-fluorophenyl)-3-(4-fluorophenyl)-1-isopropyl-2,4-dioxo-1,2,3,4-tetrahydropyrimidine-5-carboxamide (5.7 mg, 19%) as a white solid. $^1$H-NMR (CDCl$_3$, Varian, 400 MHz): δ 1.49-1.60 (8H, m), 2.63-2.74 (8H, m), 3.34 (3H, s), 3.54 (2H, brs), 3.60 (2H, s), 4.95-4.99 (1H, m), 5.09 (2H, s), 5.96 (1H, d$_0$, J=6.0 Hz), 7.10 (1H, t, J=8.4 Hz), 7.24-7.26 (3H, m), 7.79-7.83 (2H, m), 8.68 (1H, s), 10.9 (1H, s). * NH$_2$ peak was not observed.

Example 19

Figure 19:
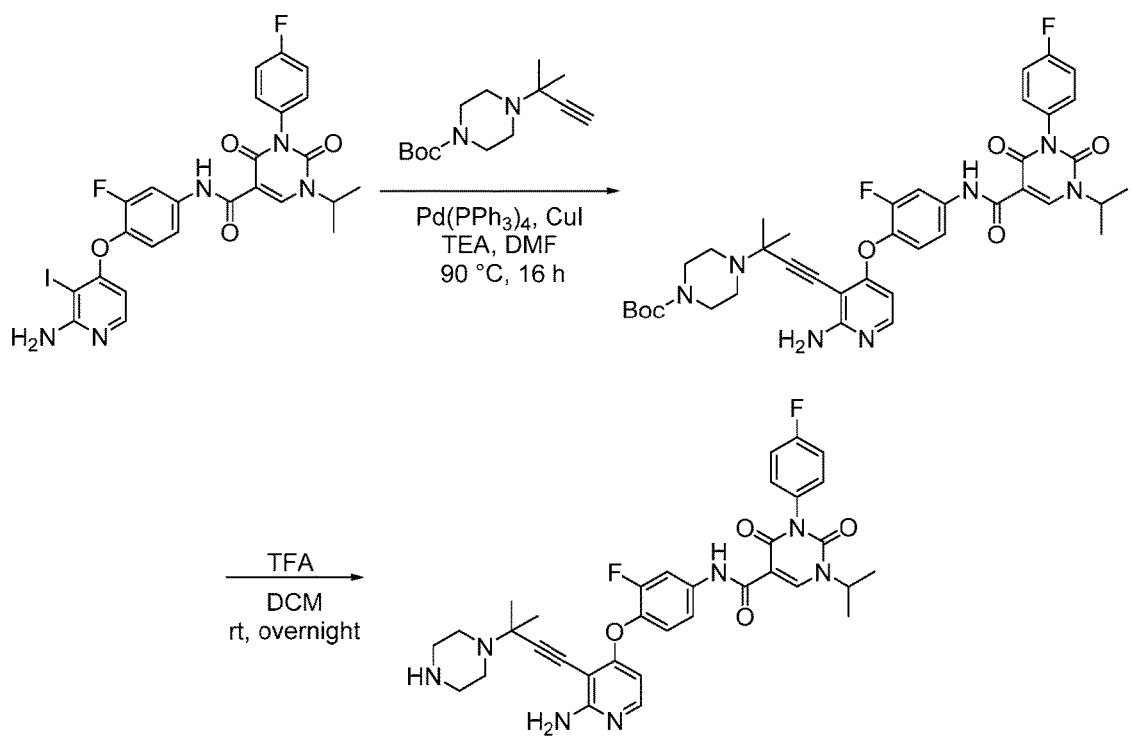
FIG. 19 is a chemical synthesis of N-(4-(2-amino-3-(3-methyl-3-(piperazin-1-yl)but-1-ynyl)pyridin-4-yloxy)-3-fluorophenyl)-3-(4-fluorophenyl)-1-isopropyl-2,4-dioxo-1,2,3,4-tetrahydropyridmidine-5-carboxamide in an aspect of the invention.

This example describes the synthesis of N-(4-(2-amino-3-(3-methyl-3-(piperazin-1-yl)but-1-ynyl)pyridin-4-yloxy)-3-fluorophenyl)-3-(4-fluorophenyl)-1-isopropyl-2,4-dioxo-1,2,3,4-tetrahydropyridmidine-5-carboxamide in an aspect of the invention. See FIG. 19.

A mixture of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 200 mg, 0.32 mmol), tert-Butyl 4-(2-methylbut-3-yn-2-yl)piperazine-1-carboxylate (intermediate 6, 122 mg, 0.48 mmol), Pd(PPh$_3$)$_4$ (37 mg, 0.03 mmol), copper(I) iodide (12 mg, 0.06 mmol), and TEA (0.18 mL, 1.3 mmol) in DMF (2 mL) was purged with N$_2$. The reaction mixture was stirred for 16 h at 90° C. After being cooled at room temperature, EtOAc and saturated NH$_4$Cl solution (aq.) were added the mixture, and the separated aqueous layer was extracted with EtOAc. The combined organic layers were dried over Na$_2$SO$_4$, filtered, and concentrated in vacuo. The residue was purified by MPLC (EtOAc to EtOAc/MeOH) to afford the tert-butyl 4-(4-(2-amino-4-(2-fluoro-4-(3-(4-fluorophenyl)-1-isopropyl-2,4-dioxo-1,2,3,4-tetrahydropyrimidine-5-carboxamido)phenoxy)pyridin-3-yl)-2-methylbut-3-yn-2-yl)piperazine-1-carboxylate (110 mg, 46%) as an ivory solid. $^1$H-NMR (CDCl$_3$, Varian, 400 MHz): δ 1.43 (9H, s), 1.47-1.59 (12H, m), 2.62-2.64 (4H, m), 3.43-3.46 (4H, m), 4.93-5.00 (1H, m), 5.42 (2H, brs), 6.01 (1H, d, J=6.0 Hz), 7.07 (1H, t, J=8.8 Hz), 7.19 (1H, d, J=1.2 Hz), 7.21-7.27 (4H, m), 7.71-7.87 (2H, m), 8.68 (1H, s), 10.9 (1H, s).

Step B: N-(4-(2-amino-3-(3-methyl-3-(piperazin-1-yl)but-1-ynyl)pyridin-4-yloxy)-3-fluorophenyl)-3-(4-fluorophenyl)-1-isopropyl-2,4-dioxo-1,2,3,4-tetrahydropyridmidine-5-carboxamide

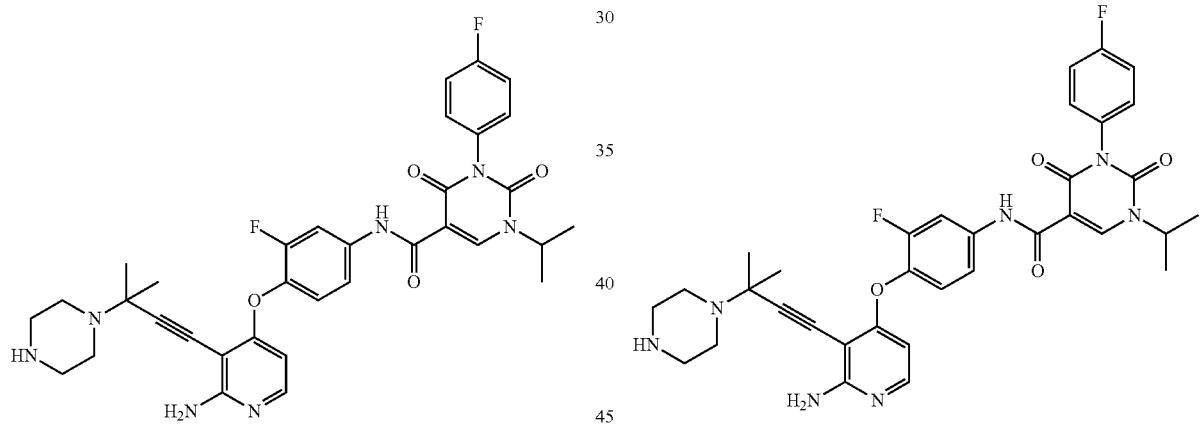

To a solution of tert-butyl 4-(4-(2-amino-4-(2-fluoro-4-(3-(4-fluorophenyl)-1-isopropyl-2,4-dioxo-1,2,3,4-tetrahydropyrimidine-5-carboxamido)phenoxy)pyridin-3-yl)-2-methylbut-3-yn-2-yl)piperazine-1-carboxylate (110 mg, 0.15 mmol) in DCM (5.0 ml) was added TFA (0.11 mL, 1.48 mmol) at room temperature. The reaction mixture was stirred overnight at room temperature. The reaction mixture was concentrated in vacuo. The residue was diluted with DCM, and then neutralized with TEA. The mixture was stirred at room temperature for 10 min and concentrated in vacuo. The residue was purified by column chromatography on SiO$_2$ (EtOAc/MeOH=95/5) to afford the N-(4-(2-amino-3-(3-methyl-3-(piperazin-1-yl)but-1-ynyl)pyridin-4-yloxy)-3-fluorophenyl)-3-(4-fluorophenyl)-1-isopropyl-2,4-dioxo-1,2,3,4-tetrahydropyridmidine-5-carboxamide (32 mg, 33%) as a pale yellow solid. $^1$H-NMR (CDCl$_3$, Varian, 400 MHz): δ 1.44 (6H, s), 1.48 (6H, d, J=6.4 Hz), 2.63 (4H, brs), 2.92 (4H, brs), 4.93-4.97 (1H, m), 5.05 (2H, s), 6.04 (1H, d, J=6.0 Hz), 7.04 (1H, t, J=8.4 Hz), 7.18 (1H, d, J=8.4 Hz), 7.23-7.25 (3H, m), 7.78-7.83 (2H, m), 8.67 (1H, s), 10.8 (1H, s). * NH$_2$ peak was not observed.

Step A: tert-butyl 4-(4-(2-amino-4-(2-fluoro-4-(3-(4-fluorophenyl)-1-isopropyl-2,4-dioxo-1,2,3,4-tetrahydropyrimidine-5-carboxamido)phenoxy)pyridin-3-yl)-2-methylbut-3-yn-2-yl)piperazine-1-carboxylate

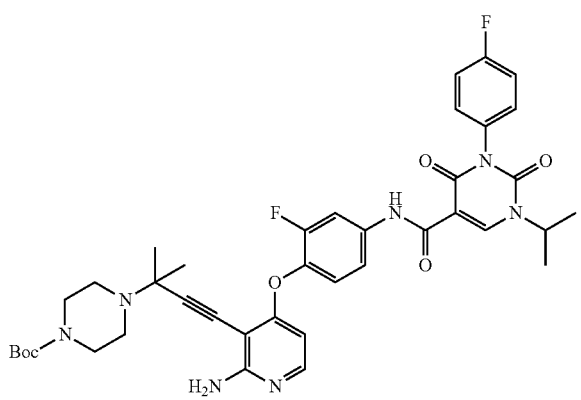

Example 20

Figure 20:
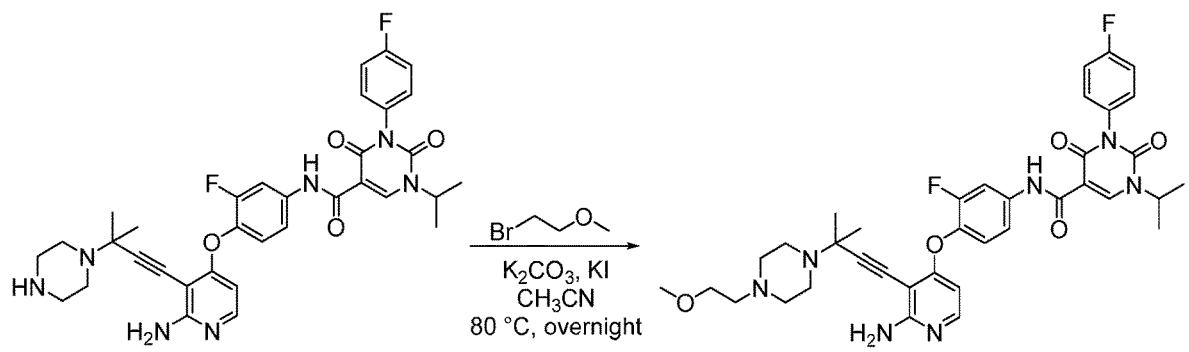
FIG. 20 is a chemical synthesis of N-(4-(2-amino-3-(3-(4-(2-methoxyethyl)piperazin-1-yl)-3-methylbut-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-(4-(2-methoxyethyl)piperazin-1-yl)-3-methylbut-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 20.

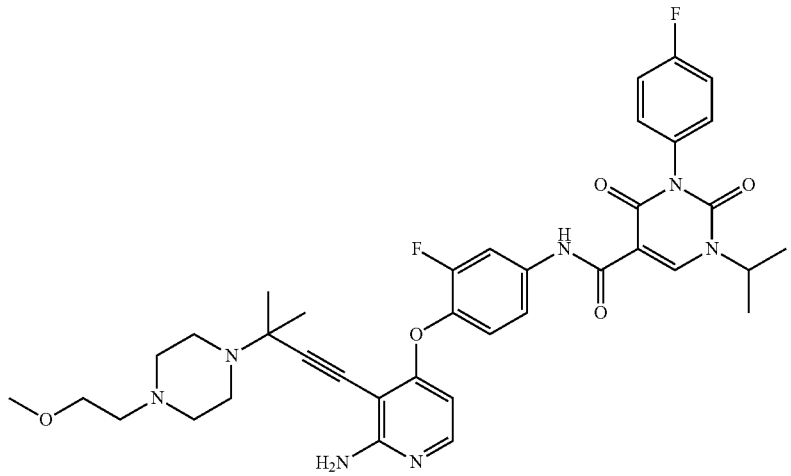 [SMILES: COCCN1CCN(C(C)(C)C#Cc2c(Oc3ccc(NC(=O)c4cn(C(C)C)c(=O)n(-c5ccc(F)cc5)c4=O)cc3F)ccnc2N)CC1]

A mixture of the N-(4-(2-amino-3-(3-methyl-3-(piperazin-1-yl)but-1-ynyl)pyridin-4-yloxy)-3-fluorophenyl)-3-(4-fluorophenyl)-1-isopropyl-2,4-dioxo-1,2,3,4-tetrahydropyridmidine-5-carboxamide (Example 19, 27.0 mg, 0.04 mmol), 1-bromo-2-methoxyethane (4.70 μL, 0.05 mmol), potassium iodide (7.00 mg, 0.04 mmol) and $K_2CO_3$ (5.80 mg, 0.04 mmol) in $CH_3CN$ (1 mL) was heated overnight at 80° C. in a sealed vessel. After being cooled at room temperature, EtOAc and water were poured into the reaction mixture and the separated aqueous layer was extracted with EtOAc. The combined organic layer was dried over $Na_2SO_4$, filtered, and concentrated in vacuo. The residue was purified by column chromatography on $NH—SiO_2$ (EtOAc/MeOH=95/5) to afford the N-(4-(2-amino-3-(3-(4-(2-methoxyethyl)piperazin-1-yl)-3-methylbut-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (10 mg, 34%) as a white solid. $^1$H-NMR ($CDCl_3$, Varian, 400 MHz): δ 0.84-0.86 (2H, m), 1.46 (6H, s), 1.50 (6H, d, J=6.8 Hz), 2.57-2.60 (4H, m), 2.77 (4H, brs), 3.33 (3H, s), 3.48-3.51 (2H, m), 4.93-5.00 (1H, m), 5.06 (2H, s), 6.02 (1H, d, J=6.0 Hz), 7.07 (1H, t, J=8.8 Hz), 7.19 (1H, d, J=8.0 Hz), 7.20-7.24 (3H, m), 7.79-7.82 (2H, m), 8.68 (1H, s), 10.8 (1H, s). * NH peak was not observed.

Example 21

Figure 21:
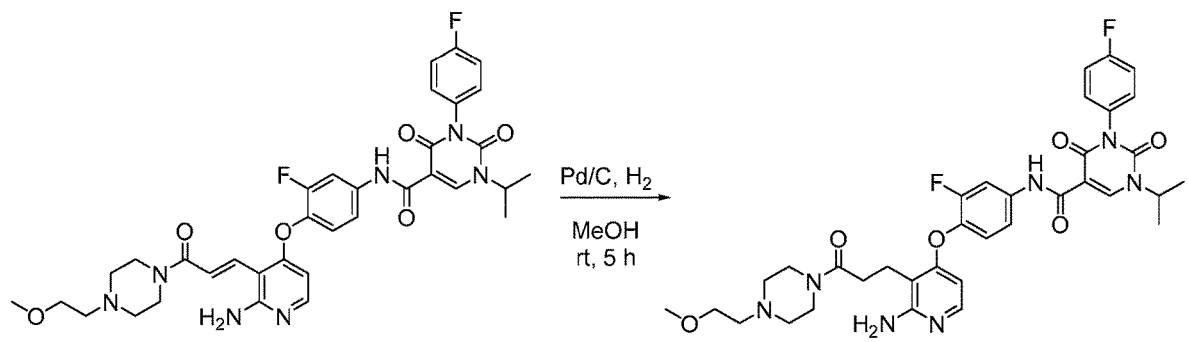
FIG. 21 is a chemical synthesis of N-(4-(2-amino-3-(3-(4-(2-methoxyethyl)piperazin-1-yl)-3-oxopropyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-(4-(2-methoxyethyl)piperazin-1-yl)-3-oxopropyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 21.

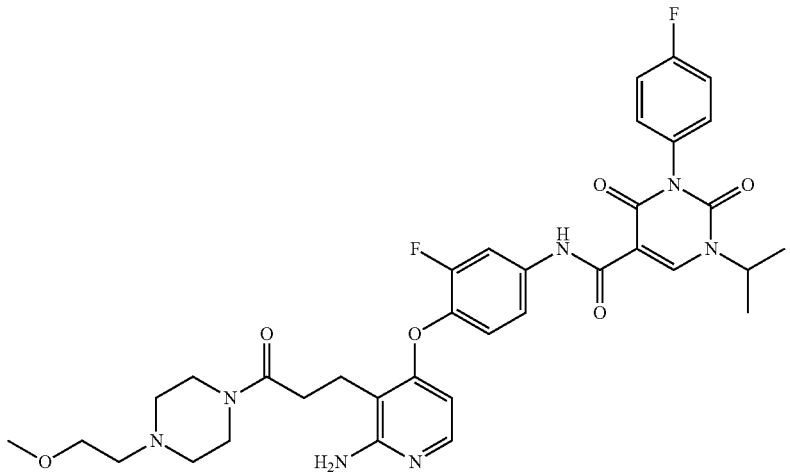 [SMILES: COCCN1CCN(C(=O)CCc2c(Oc3ccc(NC(=O)c4cn(C(C)C)c(=O)n(-c5ccc(F)cc5)c4=O)cc3F)ccnc2N)CC1]

To a solution of the N-(4-(2-amino-3-(3-(4-(2-methoxyethyl)piperazin-1-yl)-3-oxoprop-1-ynyl)pyridin-4-yloxy)-3-fluorophenyl)-3-(4-fluorophenyl)-1-isopropyl-2,4-dioxo-1,2,3,4-teterahydropyrimidine-5-carboxamide (Example 4, 100.0 mg, 0.15 mmol) in methanol (3.0 mL) was added 10% palladium on carbon (11 mg, 10.2 μmol) at room temperature. The reaction mixture was stirred for 5 h at room temperature under H$_2$ atmosphere. The mixture was filtered through a CELITE™ pad (Sigma-Aldrich, St. Louis, MO), the filtrate was concentrated in vacuo. The residue was purified by column chromatography on SiO$_2$ (EtOAc/MeOH=97/3) to afford the N-(4-(2-amino-3-(3-(4-(2-methoxyethyl)piperazin-1-yl)-3-oxopropyl)pyridin-4-yloxy)-3-fluorophenyl)-3-(4-fluorophenyl)-1-isopropyl-2,4-dioxo-1,2,3,4-tetrahydropyrimidine-5-carboxamide (10 mg, 10%) as a white solid. $^1$H-NMR (CDCl$_3$, Varian, 400 MHz): δ 1.50 (6H, d, J=6.8 Hz), 2.35 (2H, t, J=4.8 Hz), 2.42 (2H, d, J=4.8 Hz), 2.54 (2H, t, J=5.2 Hz), 2.72 (2H, t, J=6.4 Hz), 3.01 (2H, t, J=6.4 Hz), 3.34 (3H, s), 3.45-3.51 (4H, m), 3.64 (2H, t, J=4.8 Hz), 4.93-5.00 (1H, m), 5.29 (2H, s), 5.94 (1H, d, J=5.6 Hz), 7.06 (1H, t, J=8.4 Hz), 7.20-7.26 (4H, m), 7.76 (1H, d, J=6.0 Hz), 7.82 (1H, dd, J=2.0 Hz, 12.2 Hz), 8.68 (1H, s), 10.9 (1H, s). * NH peak was not observed.

Example 22

Figure 22:
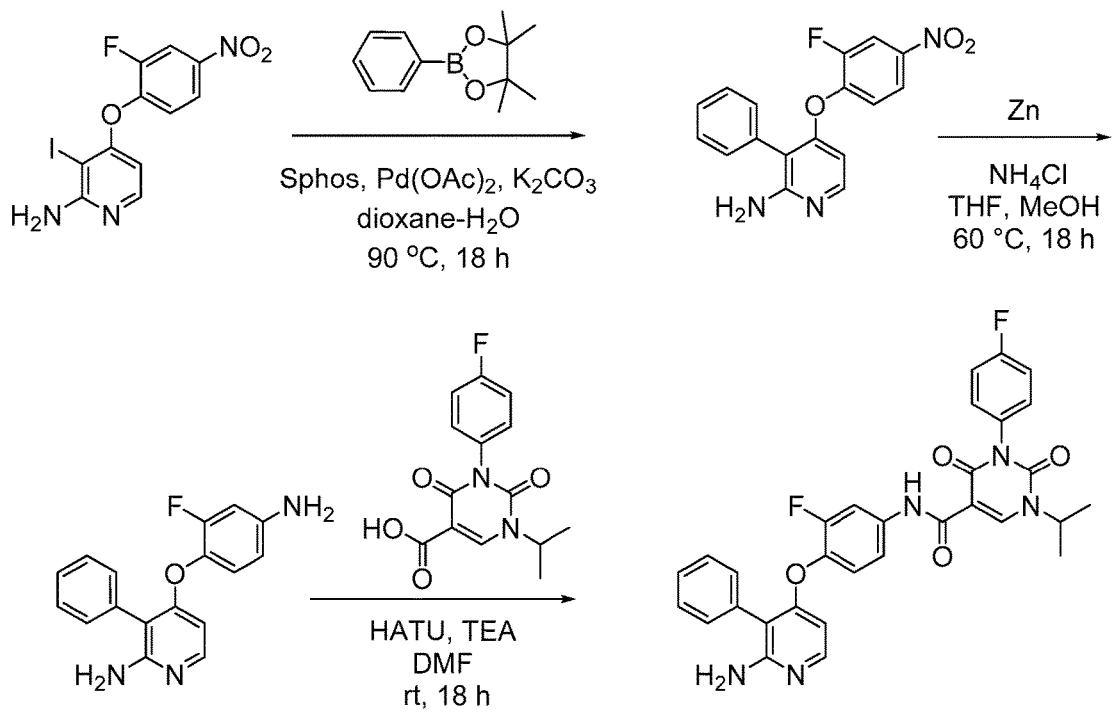
FIG. 22 is a chemical synthesis of N-(4-(2-amino-3-phenylpyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-phenylpyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 22.

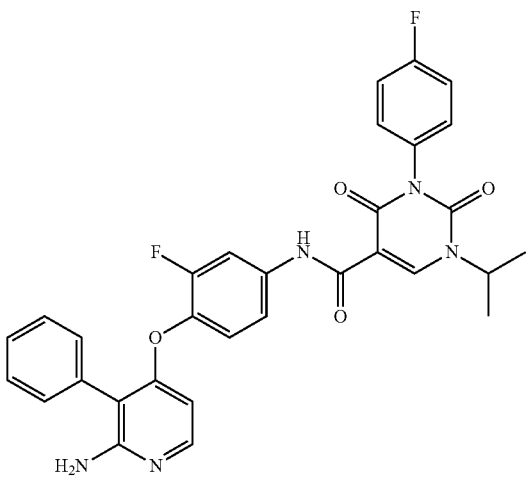

Step A: 4-(2-fluoro-4-nitrophenoxy)-3-phenylpyridin-2-amine

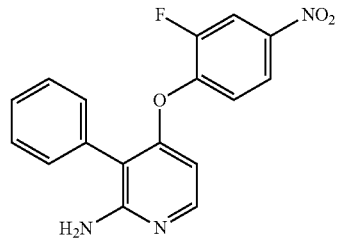

To a solution of 4-(2-fluoro-4-nitrophenoxy)-3-iodopyridin-2-amine (step D of intermediate 11, 0.20 g, 0.53 mmol) in 1,4-dioxane/water (v/v=2/1, 6.0 mL) was added 4,4,5,5-tetramethyl-2-phenyl-1,3,2-dioxaborolane (163 mg, 0.80 mmol), and K$_2$CO$_3$ (221 mg, 1.60 mmol). The reaction mixture was degassed with argon and added Pd(PPh$_3$)$_4$ (62 mg, 0.05 mmol) and stirred for 18 h at 90° C. After being cooled at room temperature, the mixture was quenched with water and extracted with EtOAc. The combined organic layers were dried over Na$_2$SO$_4$, filtered and concentrated in vacuo. The residue was purified by MPLC (EtOAc/Hexanes=2/3) to afford the 4-(2-fluoro-4-nitrophenoxy)-3-phenylpyridin-2-amine (147 mg, 85%) as a pale-yellow solid. $^1$H-NMR (CDCl$_3$, Varian, 400 MHz): δ 4.65 (2H, s), 6.27 (1H, d, J=6.0 Hz), 7.08 (1H, t, J=8.4 Hz), 7.33-7.44 (5H, m), 7.98 (2H, d, J=9.2 Hz), 8.02 (1H, d, J=6.0 Hz).

Step B: 4-(4-amino-2-fluorophenoxy)-3-phenylpyridin-2-amine

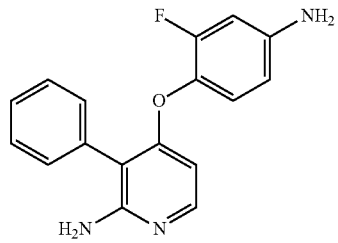

A mixture of 4-(2-fluoro-4-nitrophenoxy)-3-phenylpyridin-2-amine (140 mg, 0.43 mmol), zinc (280 mg, 4.30 mmol), and NH$_4$Cl (230 mg, 4.30 mmol) in THF/MeOH (v/v=1/1, 5.0 mL) was stirred for 18 h at 60° C. The reaction mixture was filtered and the residue was partitioned between EtOAc and saturated NaHCO$_3$ solution (aq.). The aqueous was extracted with EtOAc. The combined organic layers were dried over Na$_2$SO$_4$, filtered and concentrated in vacuo. The residue was purified by column chromatography on SiO$_2$ (EtOAc/MeOH=95/5) to afford the 4-(4-amino-2-fluorophenoxy)-3-phenylpyridin-2-amine (110 mg, 87%) as a yellow solid. $^1$H-NMR (CDCl$_3$, Varian, 400 MHz): δ 3.76 (2H, s), 5.86 (2H, s), 6.12-6.15 (1H, m), 6.38-6.47 (2H, m), 6.83 (1H, t, J=9.2 Hz), 7.41 (3H, d, J=8.4 Hz), 7.49 (2H, d, J=7.2 Hz), 8.00 (1H, d, J=6.4 Hz).

Step C: N-(4-(2-amino-3-phenylpyridin-4-yloxy)-3-fluorophenyl)-3-(4-fluorophenyl)-1-isopropyl-2,4-dioxo-1,2,3,4-tetrahydropyrimidine-5-carboxamide

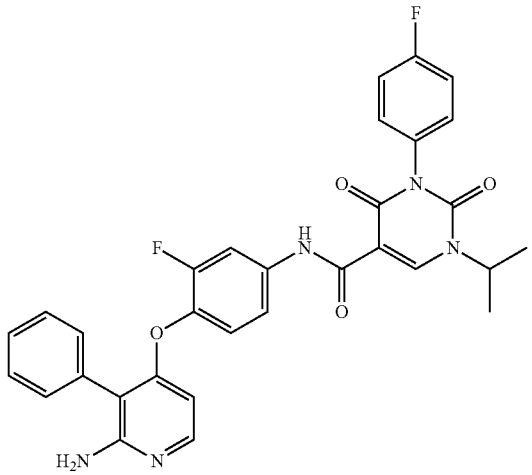 [SMILES: CC(C)n1cc(C(=O)Nc2ccc(Oc3ccnc(N)c3-c3ccccc3)c(F)c2)c(=O)n(-c2ccc(F)cc2)c1=O]

A mixture of 3-(4-fluorophenyl)-1-isopropyl-2,4-dioxo-1,2,3,4-tetrahydropyrimidine-5-carboxylic acid (intermediate 10, 50 mg, 0.17 mmol), HATU (71 mg, 0.19 mmol), and DIPEA (74 µL, 0.42 mmol) was stirred for 1 h at room temperature. The reaction mixture was added 4-(4-amino-2-fluorophenoxy)-3-phenylpyridin-2-amine (50.0 mg, 0.17 mmol) and stirred for 18 h at room temperature. The reaction was quenched by water and extracted with EtOAc. The combined organic layers were dried over Na₂SO₄, filtered and concentrated in vacuo. The residue was purified by column chromatography on SiO₂ (EtOAc/MeOH=95/5) to afford the N-(4-(2-amino-3-phenylpyridin-4-yloxy)-3-fluorophenyl)-3-(4-fluorophenyl)-1-isopropyl-2,4-dioxo-1,2,3,4-tetrahydropyrimidine-5-carboxamide (15 mg, 16%) as a white solid. $^1$H-NMR (CDCl₃, Varian, 400 MHz): δ 1.48 (6H, d, J=6.8 Hz), 4.53 (2H, s), 4.92-4.99 (1H, m), 6.09 (1H, d, J=6.0 Hz), 7.01 (1H, t, J=8.8 Hz), 7.16 (1H, d, J=8.8 Hz), 7.23-7.26 (4H, m), 7.33-7.40 (1H, m), 7.45-7.49 (4H, m), 7.73-7.76 (1H, m), 7.89 (1H, d, J=4.0 Hz), 8.66 (1H, s), 10.8 (1H, s).

Example 23

Figure 23:
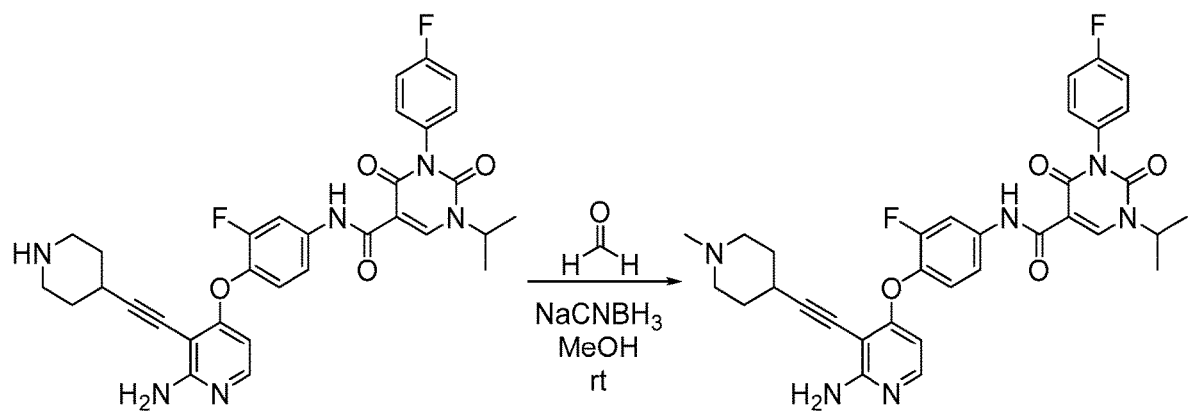
FIG. 23 is a chemical synthesis of N-(4-(2-amino-3-((1-methylpiperidin-4-yl)ethynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-((1-methylpiperidin-4-yl)ethynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 23.

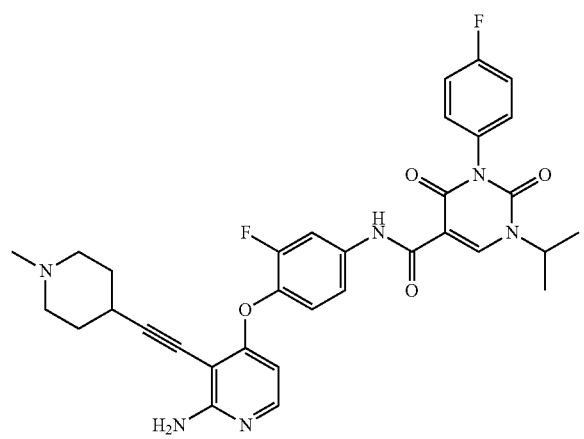 [SMILES: CC(C)n1cc(C(=O)Nc2ccc(Oc3ccnc(N)c3C#CC3CCN(C)CC3)c(F)c2)c(=O)n(-c2ccc(F)cc2)c1=O]

A mixture of N-(4-(2-amino-3-(piperidin-4-ylethynyl)pyridin-4-yloxy)-3-fluorophenyl)-3-(4-fluorophenyl)-1-isopropyl-2,4-dioxo-1,2,3,4-tetrahydropyrimidine-5-carboxamide (Example 15, 20 mg, 0.03 mmol), and formaldehyde (37%, 12.4 µL, 0.17 mmol) in MeOH (2.0 mL) was stirred for 30 min at room temperature. The reaction mixture was added NaCNBH3 (21 mg, 0.33 mmol) and stirred for 18 h at room temperature. The mixture was quenched with saturated NaHCO₃ solution (aq.) and dilute with DCM. The separated aqueous layer was extracted with DCM, the combined organic layers were dried over Na₂SO₄, filtered and concentrated in vacuo. The residue was purified by column chromatography on SiO₂ (EtOAc/MeOH=20/1) to afford the N-(4-(2-amino-3-((1-methylpiperidin-4-yl)ethynyl)pyridin-4-yloxy)-3-fluorophenyl)-3-(4-fluorophenyl)-1-isopropyl-2,4-dioxo-1,2,3,4-tetrahydropyrimidine-5-carboxamide (7.0 mg, 34%) as a white solid. $^1$H-NMR (CDCl₃, Varian, 400 MHz): δ 1.50 (6H, d, J=6.4 Hz), 1.61 (2H, s), 1.74 (2H, m), 1.88-1.96 (2H, m), 2.25 (3H, s), 2.68 (3H, brs), 4.93-4.98 (1H, m), 5.99 (1H, d, J=5.6 Hz), 7.08 (1H, t, J=8.8 Hz), 7.20 (1H, d, J=8.4 Hz), 7.24-7.26 (5H, m), 7.79-7.82 (2H, m), 8.68 (1H, s), 10.8 (1H, s).

Example 24

Figure 24:
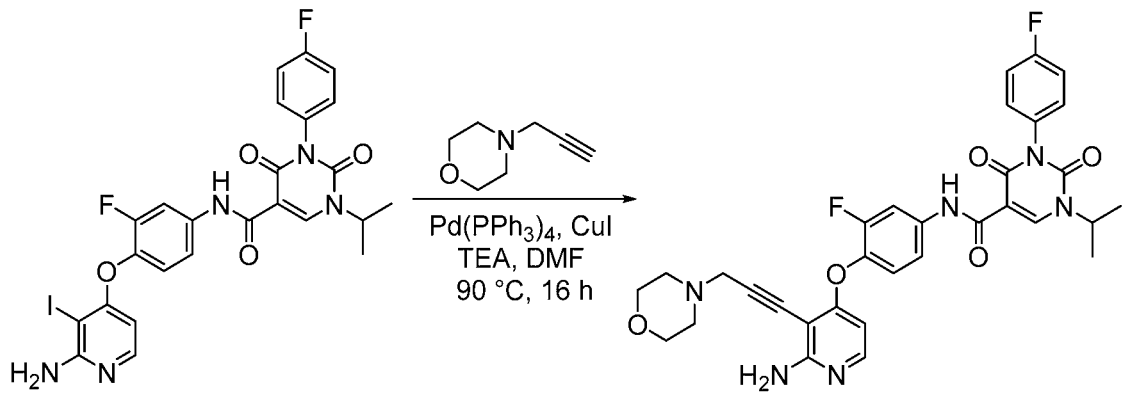
FIG. 24 is a chemical synthesis of N-(4-(2-amino-3-(3-morpholinoprop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-morpholinoprop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 24.

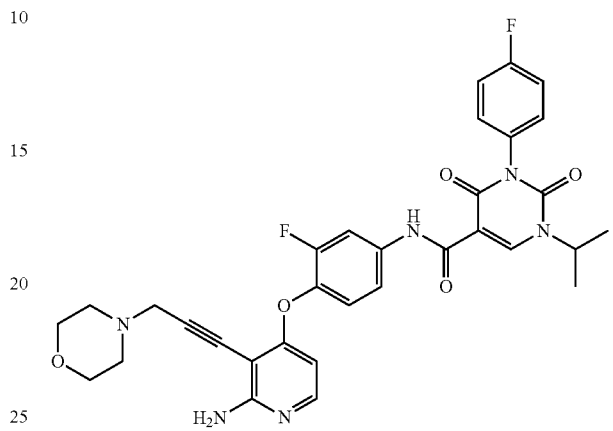

A mixture of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 100 mg, 0.16 mmol), 4-(prop-2-ynyl)morpholine (intermediate 2, 30 mg, 0.24 mmol), Pd(PPh₃)₄ (19 mg, 0.016 mmol), copper(I) iodide (6.2 mg, 0.03 mmol), and TEA (0.09 mL, 0.65 mmol) in DMF (1.0 mL) was purged with N₂. The reaction mixture was stirred for 16 h at 90° C. After cooled at room temperature, EtOAc and saturated NH₄Cl solution (aq.) were added the mixture, and the separated aqueous layer was extracted with EtOAc. The combined organic layers were dried over Na₂SO₄, filtered, and concentrated in vacuo. The residue was purified by MPLC (EtOAc to EtOAc/MeOH) to afford the N-(4-(2-amino-3-(3-morpholinoprop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (46 mg, 46%) as an ivory solid. $^1$H-NMR (CDCl₃, Varian, 400 MHz): δ $^1$H-NMR (CDCl₃, Varian, 400 MHz): δ 1.49 (6H, d, J=6.8 Hz), 2.61-2.63 (4H, m), 5.39 (2H, s), 3.73-3.75 (4H, m), 4.93-5.00 (1H, m), 5.11 (2H, s), 5.98 (1H, d, J=5.6 Hz), 7.09 (1H, t, J=8.8 Hz), 7.02-7.26 (5H, m), 7.80-7.83 (2H, m), 8.68 (1H, s), 10.9 (1H, s).

Example 25

Figure 25:
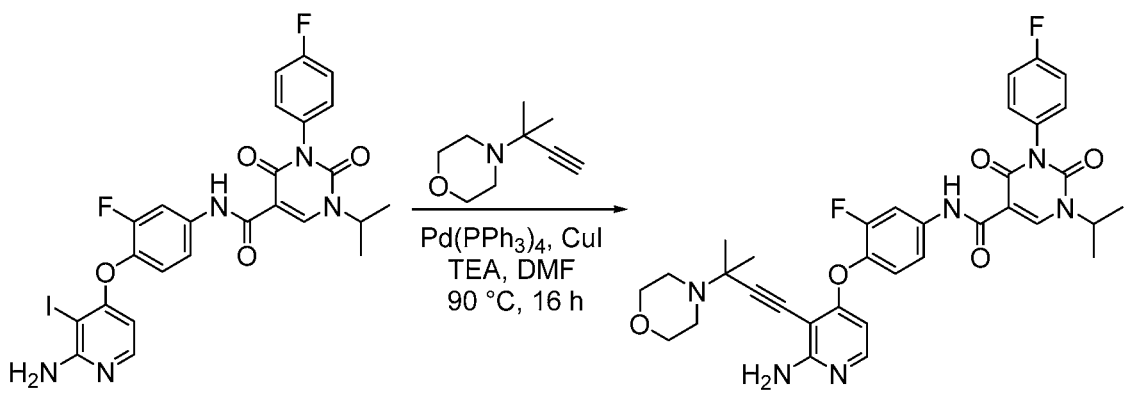
FIG. 25 is a chemical synthesis of N-(4-(2-amino-3-(3-methyl-3-morpholinobut-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-methyl-3-morpholinobut-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide. See FIG. 25.

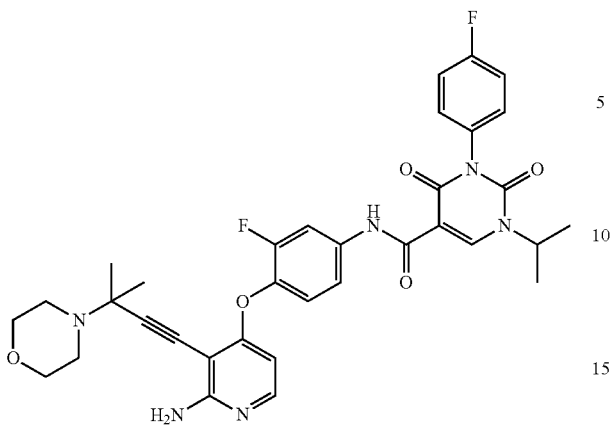

A mixture of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 50 mg, 0.08 mmol), 4-(2-methylbut-3-yn-2-yl)morpholine (intermediate 7, 13 mg, 0.08 mmol), Pd(PPh₃)₄ (9.3 mg, 0.008 mmol), copper(I) iodide (3.1 mg, 0.016 mmol), and TEA (45 μL, 0.32 mmol) in DMF (1.0 mL) was purged with N₂. The reaction mixture was stirred for 16 h at 90° C. After cooled at room temperature, EtOAc and saturated NH₄Cl solution (aq.) were added the mixture, and the separated aqueous layer was extracted with EtOAc. The combined organic layers were dried over Na₂SO₄, filtered, and concentrated in vacuo. The residue was purified by MPLC (EtOA/Hexane=9/1) to afford the N-(4-(2-amino-3-(3-methyl-3-morpholinobut-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (18 mg, 35%) as a yellow solid. ¹H-NMR (CDCl₃, Varian, 400 MHz): δ ¹H-NMR (CDCl₃, Varian, 400 MHz): δ 1.46 (6H, s), 1.50 (6H, d, J=6.8 Hz), 2.66-2.69 (4H, m), 3.72-3.75 (4H, m), 4.96-5.00 (3H, m), 6.05 (1H, d, J=5.6 Hz), 7.07 (1H, t, J=8.4 Hz), 7.20 (1H, d, J=8.8 Hz), 7.25-7.26 (4H, m), 7.79-7.85 (2H, m), 8.68 (1H, s), 10.9 (1H, s).

Example 26

Figure 26:
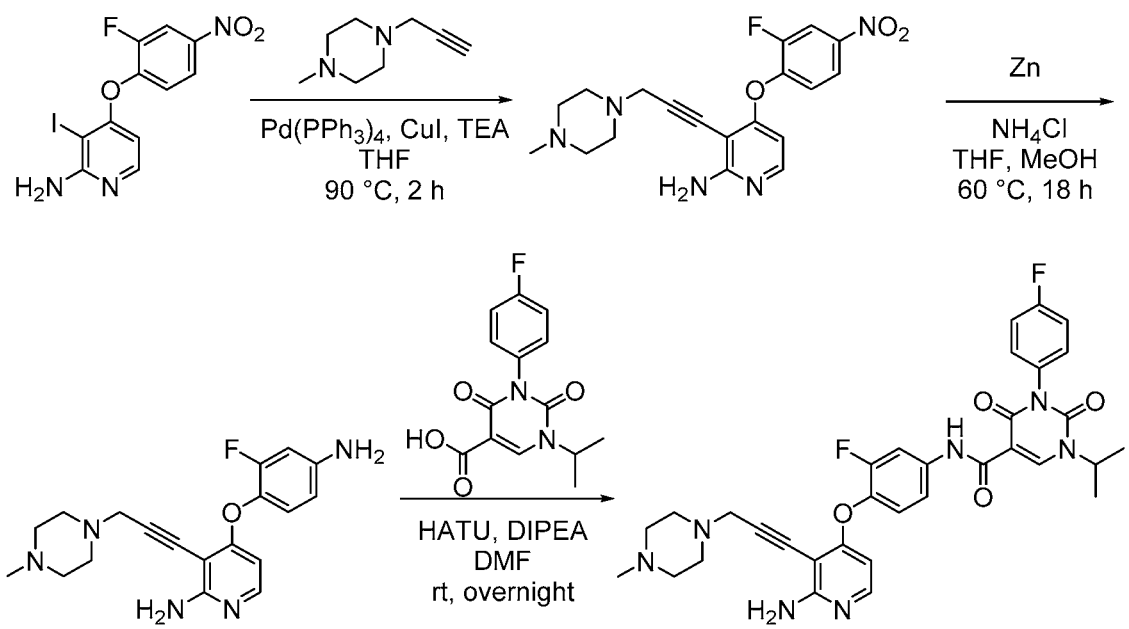
FIG. 26 is a chemical synthesis of N-(4-(2-amino-3-(3-(4-methylpiperazin-1-yl)prop-1-ynyl)pyridine-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-(4-methylpiperazin-1-yl)prop-1-ynyl)pyridine-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 26.

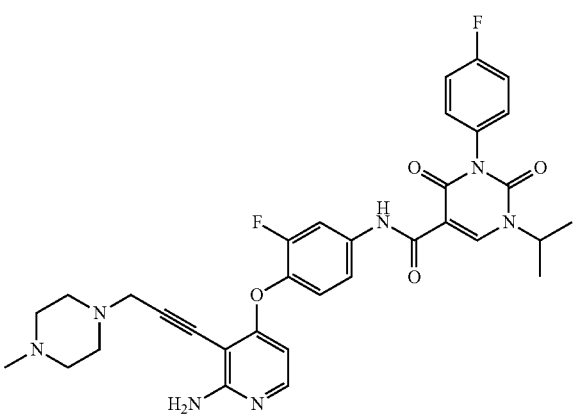 [SMILES: CC(C)n1cc(C(=O)Nc2ccc(Oc3ccnc(N)c3C#CCN3CCN(C)CC3)c(F)c2)c(=O)n(-c2ccc(F)cc2)c1=O]

Step A: 4-(2-Fluoro-4-nitrophenoxy)-3-(3-(4-methylpiperazin-1-yl)prop-1-ynyl)pyridin-2-amine

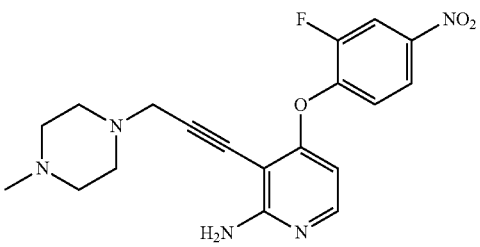

A mixture of 4-(2-fluoro-4-nitrophenoxy)-3-iodopyridin-2-amine (step D of intermediate 11, 200 mg, 0.53 mmol), 1-methyl-4-(prop-2-ynyl)piperazine (intermediate 8, 110 mL, 0.80 mmol), Pd(PPh₃)₄ (62 mg, 53.0 μmol) and copper (I) iodide (20.0 mg, 0.10 mmol) in DMF (2.0 mL) was purged with N₂. The reaction mixture was stirred for 2 h at 90° C. After cooled at room temperature, EtOAc and saturated NH₄Cl (aq.) were poured into the residue, and the separated aqueous layer was extracted with EtOAc. The combined organic layer was dried over Na₂SO₄, filtered, and concentrated in vacuo. The residue was purified by MPLC (EtOAc/MeOH) to afford the 4-(2-fluoro-4-nitrophenoxy)-3-(3-(4-methypiperazin-1-yl)prop-1-ynyl)pyridin-2-amine (139 mg, 67%) as a yellow solid. ¹H-NMR (CDCl₃, Varian, 400 MHz): δ 2.68 (3H, s), 2.29-2.53 (8H, m), 3.51 (2H, s), 5.28 (2H, s), 6.20 (1H, d, J=6.0 Hz), 7.37 (1H, t, J=8.0 Hz), 8.04 (1H, d, J=3.6 Hz), 8.05-8.06 (1H, m), 8.10 (1H, d, J=11.6 Hz).

Step B: 4-(4-Amino-2-fluorophenyl)-3-(3-(4-methylpiperazin-1-yl)prop-1-ynyl)pyridin-2-amine

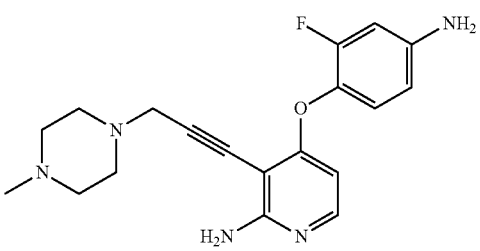

A mixture of 4-(2-fluoro-4-nitrophenoxy)-3-(3-(4-methylpiperazin-1-yl)prop-1-ynyl)pyridin-2-amine (130 mg, 0.36 mmol), zinc (236 mg, 3.61 mmol), and NH₄Cl (193 mg, 3.61 mmol) in THF-MeOH (v/v=1/1, 6 mL) was stirred for 18 h at 60° C. After being cooled at room temperature, the solvent was evaporated in vacuo and the residue was dissolved with EtOAc. The organic layer was washed with saturated NaHCO₃ (aq.) and dried over Na₂SO₄, filtered and concentrated in vacuo. The residue was purified by MPLC (DCM/MeOH) to afford the 4-(4-Amino-2-fluorophenyl)-3-(3-(4-methylpiperazin-1-yl)prop-1-ynyl)pyridin-2-amine (49.0 mg, 39%) as a yellow solid. ¹H-NMR (CDCl₃, Varian, 400 MHz): δ 2.29 (3H, s), 2.52 (4H, brs), 2.70 (4H, brs), 3.62 (2H, s), 5.09 (2H, s), 5.94 (1H, d, J=6.0 Hz), 6.41-6.44 (1H, m), 6.49 (1H, dd, J=11.8 Hz), 6.94 (1H, t, J=8.4 Hz), 7.78 (1H, d, J=5.6 Hz). * NH₂ peak was not observed.

Step C: *N*-(4-(2-amino-3-(3-(4-methylpiperazin-1-yl)prop-1-ynyl)pyridine-4-yloxy)-3-fluorophenyl)-3-(4-fluorophenyl)-1-isopropyl-2,4-dioxo-1,2,3,4-tetrahydropyrimidine-5-carboxamide

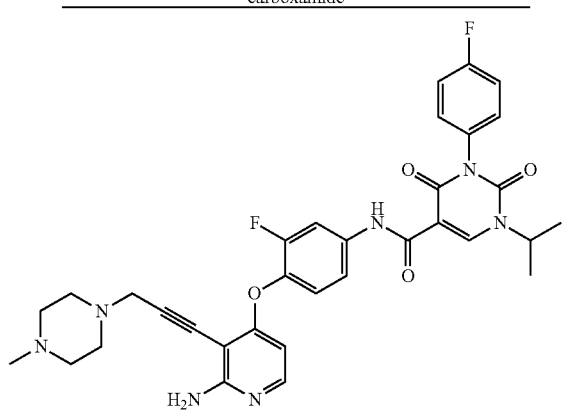

A mixture of 4-(4-amino-2-fluorophenoxy)-3-(3-(4-methylpiperazin-1-yl)prop-1-ynyl)pyridine-2-amine (42 mg, 0.12 mmol), 3-(4-fluorophenyl)-1-isopropyl-2,4-dioxo-1,2,3,4-tetrahydropyrimidine-5-carboxylic acid (intermediate 10, 35 mg, 0.12 mmol), HATU (49.4 mg, 0.13 mmol) and DIPEA (52.0 µL, 0.30 mmol) in DMF (3.0 mL) was stirred for 1 h at 50° C. After cooled at room temperature, EtOAc and saturated NH₄Cl (aq.) were poured into the residue, and the separated aqueous layer was extracted with EtOAc. The combined organic layer was dried over Na₂SO₄, filtered, and concentrated in vacuo. The residue was purified by column chromatography on NH—SiO₂ (DCM/MeOH=100/1) to afford the N-(4-(2-amino-3-(3-(4-methylpiperazin-1-yl)prop-1-ynyl)pyridine-4-yloxy)-3-fluorophenyl)-3-(4-fluorophenyl)-1-isopropyl-2,4-dioxo-1,2,3,4-tetrahydropyrimidine-5-carboxamide (32 mg, 43%) as a white solid. ¹H-NMR (DMSO-d₆, Varian, 400 MHz): δ 1.42 (6H, d, J=6.4 Hz), 2.12 (3H, s), 3.32 (8H, s), 3.53 (2H, s), 4.75-4.78 (1H, m), 5.89 (1H, d, J=6.4 Hz), 6.23 (2H, s), 7.25 (1H, t, J=8.8 Hz), 7.35-7.37 (2H, m), 7.40-7.45 (3H, m), 7.78 (1H, d, J=6.0 Hz), 7.92-7.95 (1H, m), 8.67 (1H, s). 10.98 (1H, s).

Example 27

Figure 27:
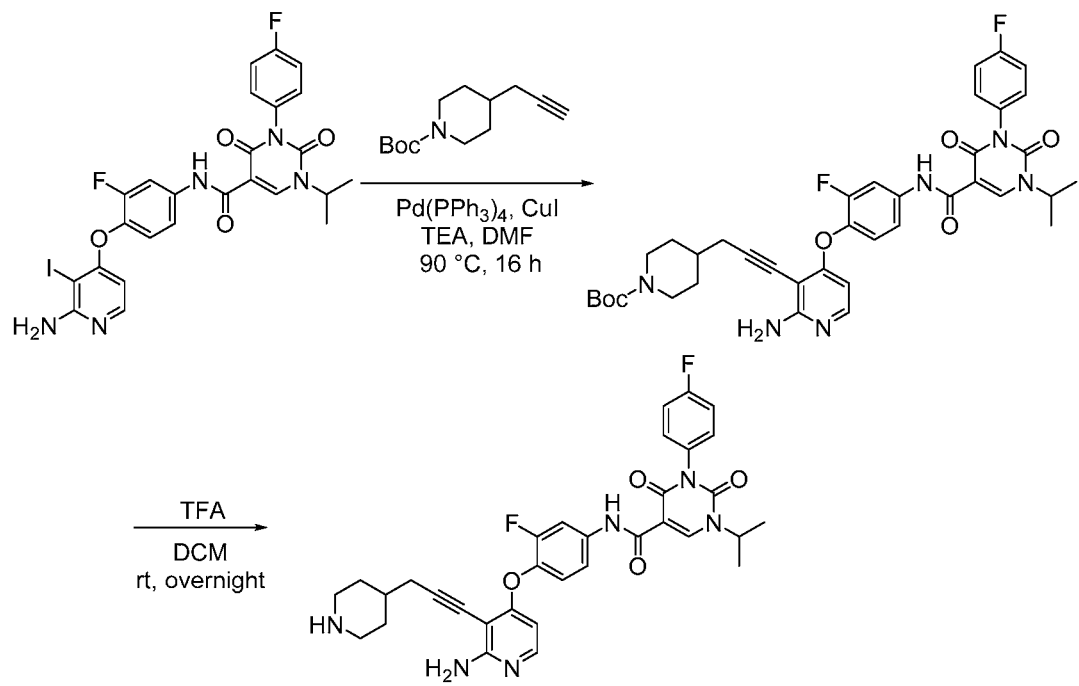
FIG. 27 is a chemical synthesis of N-(4-(2-amino-3-(3-(piperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-(piperidin-4-yl)prop-1-ynyl)pyrid-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 27.

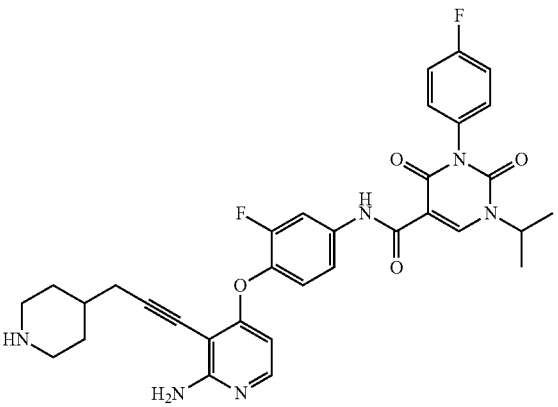

Step A: *tert*-butyl 4-(3-(2-amino-4-(2-fluoro-4-(3-(4-fluorophenyl)-1-isopropyl-2,4-dioxo-1,2,3,4-tetrahydropyrimidine-5-carboxamido)phenoxy)pyridin-3-yl)prop-2-ynyl)piperadine-1-carboxylate

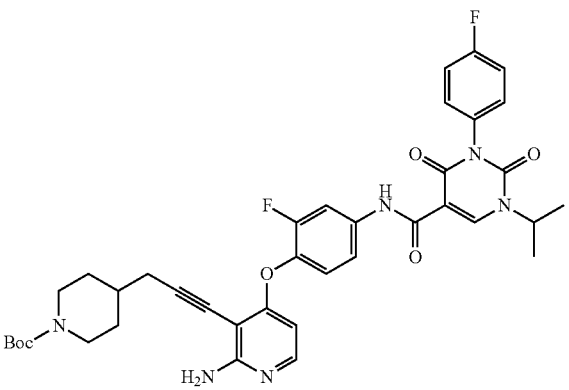

To a solution of N-(4-(2-amino-3-iodopyridin-4-yloxy)-3-fluorophenyl)-3-(4-fluorophenyl)-1-isopropyl-2,4-dioxo-1,2,3,4-tetrahydropyrimidine-5-carboxamide (intermediate 11, 250 mg, 0.40 mmol), tert-butyl 4-(prop-2-ynyl)piperidine-1-carboxylate (135 mg, 0.61 mmol), TEA (0.23 mL, 1.62 mmol), and copper(I) iodide (15 mg, 0.08 mmol) in DMF (2.0 mL) was degassed with argon. The reaction mixture was added Pd(PPh₃)₄ (47 mg, 0.04 mmol) and stirred for 5 h at 90° C. After being cooled at room temperature, the mixture was dissolved with EtOAc and washed with saturated NH₄Cl solution (aq.). The organic layer was dried over Na₂SO₄, filtered and concentrated in vacuo. The residue was purified by MPLC (Hexanes/EtOAc=1/9) to afford the tert-butyl 4-(3-(2-amino-4-(2-fluoro-4-(3-(4-fluorophenyl)-1-isopropyl-2,4-dioxo-1,2,3,4-tetrahydropyrimidine-5-carboxamido)phenoxy)pyridin-3-yl)prop-2-ynyl)piperidine-1-carboxylate (180 mg, 62%) as a brown solid. ¹H-NMR (CDCl₃, Varian, 400 MHz): δ 1.44 (9H, s), 1.50 (6H, d, J=6.4 Hz), 1.72-1.73 (3H, m), 1.81 (2H, d, J=13.2 Hz), 2.45 (2H, d, J=6.4 Hz), 2.69 (2H, brs), 4.11 (2H, s), 4.93-5.00 (1H, m), 5.06 (2H, s), 5.99 (1H, s), 7.08 (1H, t, J=8.4 Hz), 7.23 (1H, d, J=8.0 Hz), 7.44 (4H, s), 7.80-7.83 (2H, m), 8.67 (1H, s), 10.9 (1H, s).

Step B: *N*-(4-(2-amino-3-(3-piperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide

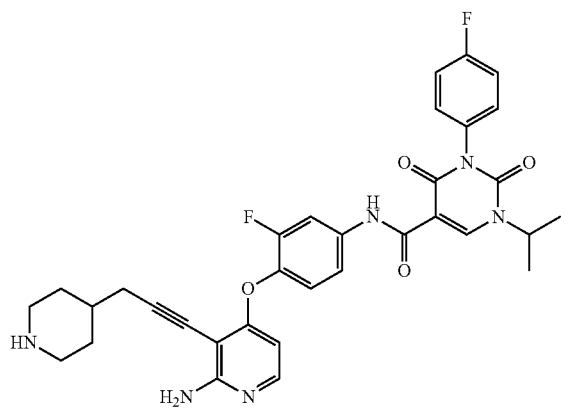

To a solution of tert-butyl 4-(3-(2-amino-4-(2-fluoro-4-(3-(4-fluorophenyl)-1-isopropyl-2,4-dioxo-1,2,3,4-tetrahydropyrimidine-5-carboxamido)phenoxy)pyridin-3-yl)prop-2-ynyl)piperidine-1-carboxylate (180 mg, 0.25 mmol) in DCM (5.0 ml) was added TFA (0.19 mL, 2.52 mmol) at room temperature and stirred overnight at room temperature. The reaction mixture was concentrated in vacuo. The residue was diluted with DCM, and then neutralized with saturated NaHCO₃ solution (aq.). The organic layer was dried over Na₂SO₄, filtered and concentrated in vacuo. The residue was purified by column chromatography on NH—SiO₂ (DCM/MeOH=98/2) to afford the N-(4-(2-amino-3-(3-(piperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (136 mg, 88%) as a white solid. ¹H-NMR (CDCl₃, Varian, 400 MHz): δ 1.49 (6H, d, J=6.4 Hz), 1.64-1.74 (1H, m), 1.81 (3H, d, J=13.2 Hz), 2.43 (2H, d, J=6.8 Hz), 2.56-2.63 (2H, m), 3.08 (2H, d, J=12.4 Hz), 4.93-5.00 (1H, m), 5.05 (2H, s), 5.99 (1H, d, J=5.6 Hz), 7.08 (1H, t, J=8.4 Hz), 7.20 (1H, d, J=5.6 Hz), 7.25 (4H, d, J=6.4 Hz), 7.79-7.83 (2H, m), 8.67 (1H, s), 10.89 (1H, s). * NH₂ peak was not observed.

Example 28

Figure 28:
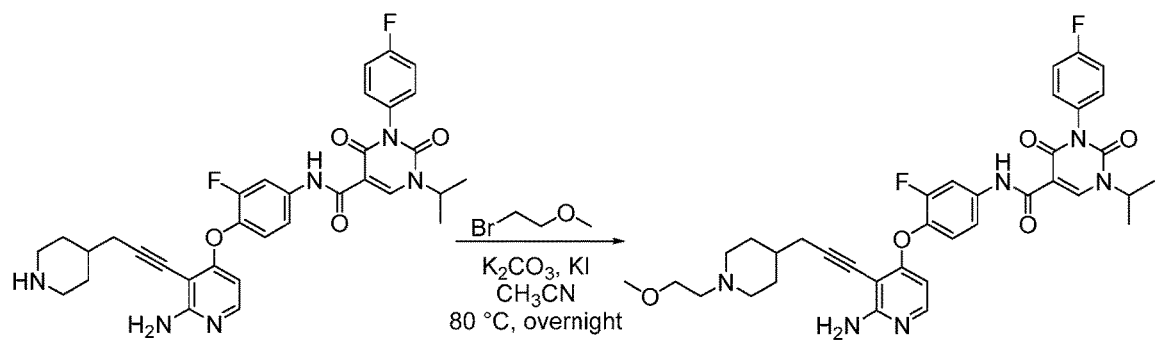
FIG. 28 is a chemical synthesis of N-(4-(2-amino-3-(3-(1-(2-methoxyethyl)piperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention.

This example describes the synthesis of N-(4-(2-amino-3-(3-(1-(2-methoxyethyl)piperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide in an aspect of the invention. See FIG. 28.

A mixture of the N-(4-(2-amino-3-(3-(piperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (Example 27, 60 mg, 0.01 mmol), 1-bromo-2-methoxyethane (11.0 μL, 0.12 mmol), potassium iodide (13.0 mg, 0.01 mmol) and K₂CO₃ (16.0 mg, 0.01 mmol) in CH₃CN (2.0 mL) was heated overnight at 80° C. in a sealed vessel. After being cooled at room temperature, DCM and water were poured into the reaction mixture and the separated aqueous layer was extracted with DCM. The combined organic layer was dried over Na₂SO₄, filtered, and concentrated in vacuo. The residue was purified by column chromatography on NH—SiO₂ (EtOAc/MeOH=98/2) to afford the N-(4-(2-amino-3-(3-(1-(2-methoxyethyl)piperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (24 mg, 37%) as an ivory solid. ¹H-NMR (CDCl₃, Varian, 400 MHz): δ 1.49 (6H, d, J=6.8 Hz), 1.53-1.61 (1H, m), 1.86 (2H, d, J=16.0 Hz), 2.01 (2H, t, J=14.0 Hz), 2.42 (2H, d, J=6.8 Hz), 2.54 (2H, t, J=6.0 Hz), 2.95 (2H, d, J=11.6 Hz), 3.34 (3H, s), 3.49 (2H, t, J=5.6 Hz), 4.93-4.98 (1H, m), 5.01 (2H, s), 5.98 (1H, d, J=5.6 Hz), 7.08 (1H, t, J=8.4 Hz), 7.20 (1H, d, J=7.6 Hz), 7.25 (4H, d, J=6.8 Hz), 7.79-7.83 (2H, m), 8.67 (1H, s), 10.89 (1H, s). * NH₂ peak was not observed.

Example 29

Figure 29:
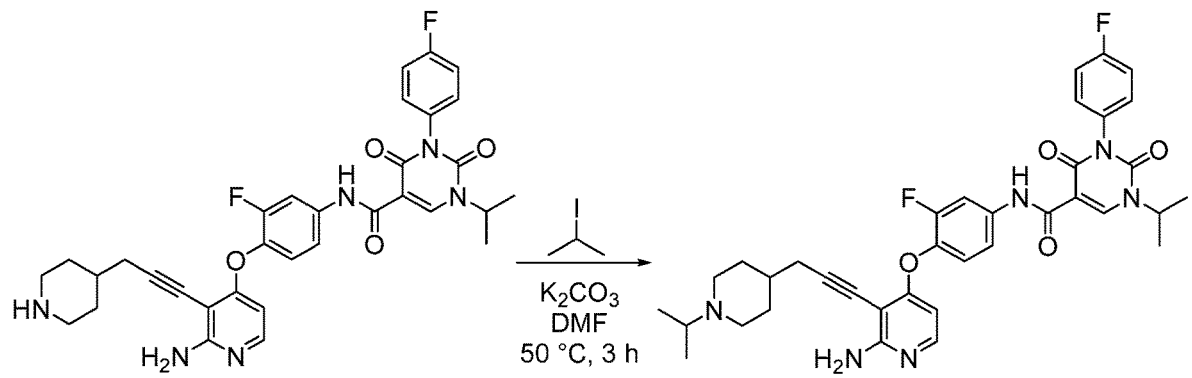
FIG. 29 is a chemical synthesis of N-(4-(2-amino-3-(3-(1-isopropylpiperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxmide in an aspect of the invention.

This example describes the synthesis of N-(4-(2-amino-3-(3-(1-isopropylpiperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxmide in an aspect of the invention. See FIG. 29.

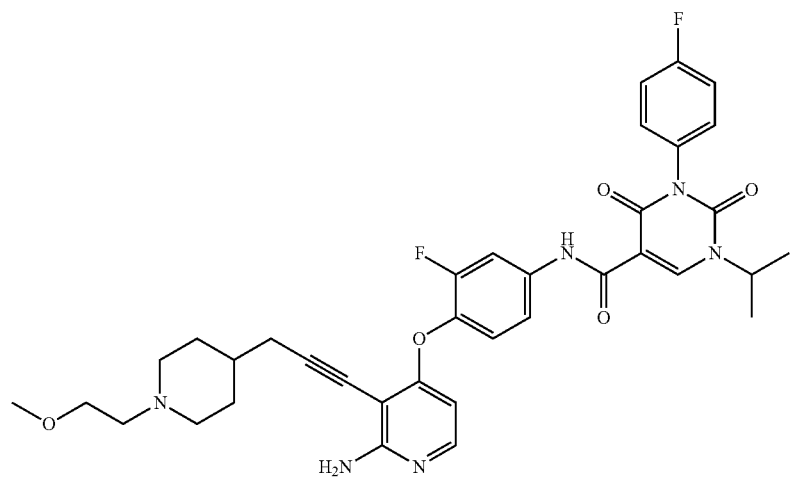

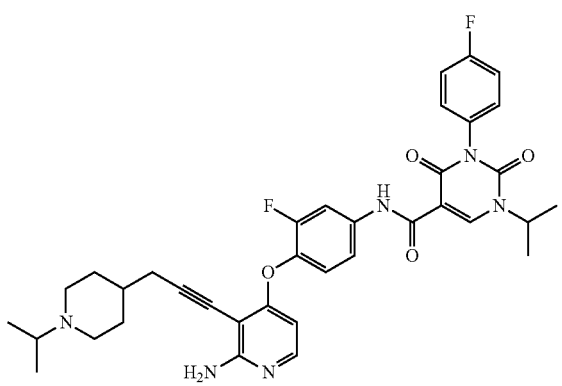 [SMILES: CC(C)N1CCC(CC#Cc2c(Oc3ccc(NC(=O)c4cn(C(C)C)c(=O)n(-c5ccc(F)cc5)c4=O)cc3F)ccnc2N)CC1]

A mixture of N-(4-(2-amino-3-(3-(piperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxamide (Example 27, 50.0 mg, 0.08 mmol), 2-iodopropane (16.0 μL, 0.16 mmol), and $K_2CO_3$ (22.0 mg, 0.16 mmol) was stirred for 3 h at 50° C. After cooled at room temperature, the reaction mixture was washed with water and extracted with EtOAc. The combined organic layers were dried over $Na_2SO_4$, filtered and concentrated in vacuo. The residue was purified by column chromatography on NH—$SiO_2$ (DCM/MeOH=97/3) to afford the N-(4-(2-amino-3-(3-(1-isopropylpiperidin-4-yl)prop-1-ynyl)pyridin-4-yloxy)-3-fluorophenyl)-3-(4-fluorophenyl)-1-isopropyl-2,4-dioxo-1,2,3,4-tetrahydropyrimidine-5-carboxmide (17.0 mg, 32%) as a white solid. $^1$H-NMR (MeOD, Varian, 400 MHz): δ 0.91 (6H, d, J=6.8 Hz), 1.17 (2H, d, J=8.4 Hz), 1.41 (6H, d, J=6.4 Hz), 1.67 (2H, d, J=12.4 Hz), 2.02 (2H, t, J=11.2 Hz), 2.38 (2H, d, J=6.0 Hz), 2.50-2.61 (1H, m), 2.71 (2H, d, J=10.0 Hz), 4.75-4.77 (1H, m), 5.93 (1H, d, J=5.6 Hz), 6.14 (1H, s), 7.19 (1H, t, J=8.4 Hz), 7.33-7.41 (5H, m), 7.76 (1H, d, J=6.0 Hz), 7.93 (1H, d, J=12.8 Hz), 8.66 (1H, s), 10.9 (1H, s). * NH peak was not observed.

Example 30

This example illustrates an enzymatic assay to determine the inhibitory activity of exemplary compounds of Formula (I) in an aspect of the invention.

All the kinase reactions were performed in 5 μL using tyrosine kinase buffer with 0.2 μg/μL poly (Glu4, Tyr1) substrate, 10 M ATP, serial dilution of the inhibitor, and incubated at room temperature for 60 min. After the indicated incubation times, 5 μL ADP-GLO™ reagent (Promega, Madison, WI) was added to the reactions and the plate was incubated at room temperature for 40 min. Then, 10 μL of kinase detection reagent was added and after an incubation time of 40 min, luminescence was recorded and $IC_{50}$ values were determined (Table 1). All 384-well assay plates were read using a GLOMAX™ Discover Microplate Luminometer from Promega (Madison, WI). To plot, analyze the data and calculate all kinase reaction biochemical values, both Microsoft Excel and Prism from GraphPad 7 Software (La Jolla, CA) were used.

TABLE 1

| | Enzymatic assay $IC_{50}$ (nM) | | |
|---|---|---|---|
| Ex. No | c-MET | AXL | MER |
| 1 | <10 | <10 | <10 |
| 2 | <10 | <10 | <10 |

TABLE 1-continued

| | Enzymatic assay $IC_{50}$ (nM) | | |
|---|---|---|---|
| Ex. No | c-MET | AXL | MER |
| 3 | <100 | <10 | <10 |
| 4 | <10 | <10 | <10 |
| 5 | <10 | <10 | <10 |
| 6 | <10 | <10 | <100 |
| 7 | <10 | <10 | <100 |
| 8 | <10 | <10 | <100 |
| 9 | <10 | <10 | <100 |
| 10 | <10000 | <100 | <10 |
| 11 | <10000 | <100 | <10 |
| 12 | <10000 | <1000 | <1000 |
| 13 | <1000 | <10 | <10 |
| 14 | <10 | <10 | <10 |
| 15 | <100 | <10 | <10 |
| 16 | <10 | <10 | <10 |
| 17 | <10 | <10 | <10 |
| 18 | <10 | <10 | <10 |
| 19 | <1000 | <10 | <10 |
| 20 | <10 | <10 | <10 |
| 21 | <10000 | <1000 | <1000 |
| 22 | <100 | <100 | <100 |
| 23 | <1000 | <10 | <10 |
| 24 | <10 | <10 | N.A |
| 25 | <10 | <10 | <10 |
| 26 | <10 | <10 | <10 |
| 27 | <10 | <10 | <10 |
| 28 | <10 | <10 | <10 |
| 29 | <10 | <10 | <10 |

Example 31

This example describes the preparation of epidermal growth factor receptor (EGFR) TKI-resistant cell lines in an aspect of the invention.

EGFR tyrosine kinase inhibitor (TKI) inhibit the EGFR and are used to treat non-small cell lung cancer (NSCLC) that have activating mutations in the EGFR gene. Most EGFR mutant NSCLCs respond to EGFR TKI, the majority of these tumors eventually become resistant to the drug treatment. In about 50% of these cases, resistance is due to the occurrence of a secondary mutation in $EGFR^{T790M}$, about 5% is due to amplification of c-MET, and about 20% is due to overexpression of AXL.

c-MET amplification contributes to the acquisition of resistance to EGFR TKIs because it is a redundant pathway for the activation of PI3K/AKT signaling that facilitates the survival of cancer cells, thus bypassing the inhibition of upstream EGFR signaling in the presence of EGFR TKIs.

AXL is a member of the TAM (TYRO3-AXL-MER) family of receptor tyrosine kinases when activated, can increase tumor cell survival, proliferation, migration and invasion, angiogenesis, and tumor-host interactions. Overexpression or abnormal activation of AXL has been described in a number of malignancies from epithelial and blood origin, and is often associated with poor prognosis, increased recurrence rates, reduced disease-free survival, and poor overall survival. Moreover, AXL expression is associated with epithelial mesenchymal transition (EMT), a common feature of metastatic tumors, often correlated with EGFR TKIs resistance. Therefore, AXL is an attractive molecular target for many solid tumors, including NSCLC.

To explore c-MET and AXL mechanisms of EGFR TKI resistance, resistant cells of the EGFR TKI hypersensitive EGFR exon 19 mutant NSCLC cell line, HCC827 and PC9 were generated by exposing these cells to increasing concentrations of EGFR TKI for over 3 months.

The human cell line HCC827 was purchased from the American Type Culture Collection (Manassas, VA), and the PC9 cell line was obtained from RIKEN Cell Bank (Ibaraki, Japan). The HCC827/ER, HCC827/GR, HCC827/OR, and PC9/ER cells, which contain deletions in the EGFR exon 19 and the c-MET and AXL overexpression, were developed from HCC827 or PC9 cells by stepwise exposure to gefitinib, erlotinib, and osimertinib. Gefitinib-resistant cells were referred to as HCC827/GR. Erlotinib-resistant cells were referred to as PC9/ER, HCC827/ER. Osimertinib-resistant cells were referred to as HCC827/OR.

All of these cell lines were maintained in Roswell Park Memorial Institute (RPMI) 1640 medium (GIBCO, Carlsbad, CA) containing 1 µM of gefitinib, erlotinib, and osimertinib with 10% fetal bovine serum (FBS), penicillin (100 U/mL), and streptomycin (50 g/mL) in a humidified $CO_2$ incubator at 37° C. All cell lines were authenticated by Sanger sequencing, Human phospho-RTK array kit (R&D systems), and western blot analysis.

All references, including publications, patent applications, and patents, cited herein are hereby incorporated by reference to the same extent as if each reference were individually and specifically indicated to be incorporated by reference and were set forth in its entirety herein.

Example 32

This example illustrates a cell viability assay of exemplary compounds of Formula (I) in an aspect of the invention.

Cell viability assays were carried out by plating 1,000 cells per well of HCC827 or PC9 resistant cells, respectively, into white transparent-bottom 384-well plates. The cells were treated with each TKI across a 10-dose range from 1 nM to 10,000 nM. After 72 h of drug treatment, cell viability was measured using the CellTiter-Glo 2.0 assay (Promega, Madison, WI). EGFR TKIs (gefitinib, erlotinib, and osimertinib)-resistant cell lines that was derived from the parental EGFR TKIs-sensitive HCC827 or PC9 cell line was established by continuous exposure of cells to EGFR TKIs more than a period of 3 months. The resistant cell lines were designated HCC827/ER, PC9/ER and exhibited a 1,000-fold higher resistance to erlotinib than the parental cells (erlotinib $IC_{50}$, <0.01 µM in HCC827 or PC9 cells and >10 µM in HCC827/ER or PC9/ER). HCC827/GR exhibited a 4,000-fold higher resistance to gefitinib than the parental cells (gefitinib $IC_{50}$, <0.002 µM in HCC827 cells and 8.9 µM in HCC827/GR cells). HCC827/OR exhibited a 3,000-fold higher resistance to osimertinib than the parental cells (osimertinib $IC_{50}$, <0.0003 µM in HCC827 cells and >1 µM in HCC827/OR cells). The combination of EGFR TKIs and inhibitor of Formula (I) overcame acquired resistance to EGFR TKIs. Table 2 shows the resistance overcoming of EGFR TKI resistant cells by representative compounds.

TABLE 2

| | Relative cell viability; $IC_{50}$ (nM) | | | |
|---|---|---|---|---|
| Ex. No | PC9ER | HCC827ER | HCC827GR | HCC827OR |
| 1 | <10 | <10 | <10 | <10 |
| 2 | <10 | <10 | <10 | <10 |
| 3 | <1000 | <100 | <100 | <100 |
| 4 | <1000 | <10 | <10 | <10 |
| 5 | <1000 | <10 | <100 | <100 |
| 6 | <1000 | <10 | <100 | <100 |
| 7 | <1000 | <10 | <10 | <10 |
| 8 | <10000 | <100 | <100 | <100 |
| 9 | >10000 | <100 | <100 | <100 |
| 10 | <100 | <1000 | <1000 | <1000 |
| 11 | <10000 | <10000 | <10000 | <10000 |
| 12 | <1000 | <100 | <100 | <10 |
| 13 | <10 | <10 | <10 | <10 |
| 14 | <10 | <10 | <100 | <10 |
| 15 | <10 | <100 | <100 | <10 |
| 16 | <10 | <10 | <10 | <10 |
| 17 | <100 | <100 | <100 | <100 |
| 18 | <100 | <10 | <100 | <10 |
| 19 | <100 | <10 | <100 | <100 |
| 20 | <10 | <10 | <10 | <10 |
| 21 | <1000 | <1000 | <100 | <1000 |
| 22 | <100 | <100 | <10 | <100 |
| 23 | <10 | <100 | <100 | <10 |
| 24 | <10 | <10 | <10 | <10 |
| 25 | <10 | <10 | <10 | <10 |
| 26 | <1000 | <10 | <100 | <10 |
| 27 | <10 | <10 | <10 | <10 |
| 28 | <10 | <10 | <10 | <10 |
| 29 | <10 | <10 | <10 | <10 |

Example 33

Figure 30:
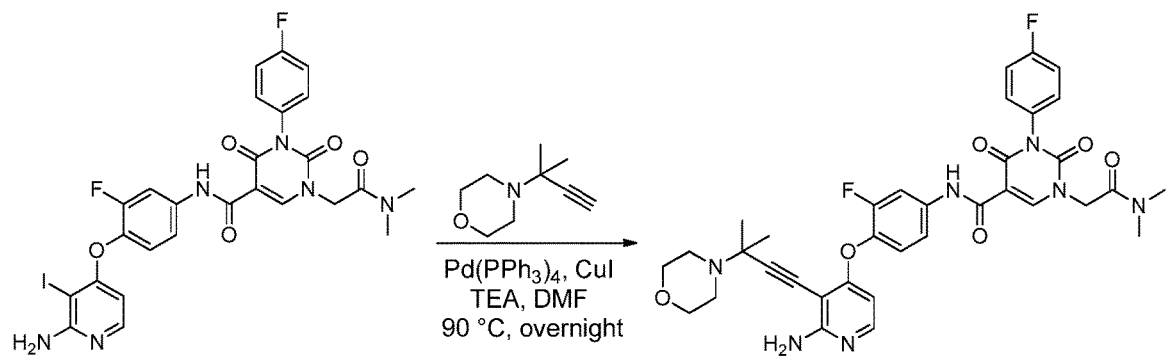
FIG. 30 is a chemical synthesis of N-(4-((2-amino-3-(3-methyl-3-morpholinobut-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention.

This example describes the synthesis of N-(4-((2-amino-3-(3-methyl-3-morpholinobut-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention. See FIG. 30.

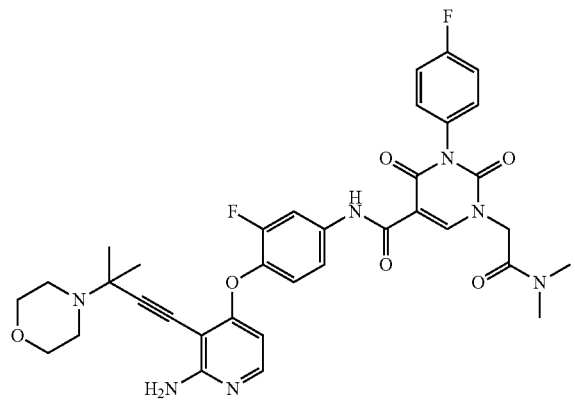 [SMILES: CN(C)C(=O)Cn1cc(C(=O)Nc2ccc(Oc3ccnc(N)c3C#CC(C)(C)N3CCOCC3)c(F)c2)c(=O)n(-c2ccc(F)cc2)c1=O]

A mixture of N-(4-((2-amino-3-iodopyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (intermediate 16, 50.0 mg, 0.08 mmol), 4-(2-methylbut-3-yn-2-yl)morpholine (17.0 mg, 0.11 mmol), copper(I) iodide (2.8 mg, 0.02 mmol), and TEA (41.0 µL, 0.30 mmol) in DMF (1 mL) was degassed with $N_2$. To reaction mixture was added Pd(PPh$_3$)$_4$ (8.7 mg, 7.55 µmol) and stirred for overnight at 90° C. After being cooled at room temperature, the reaction mixture was extracted with EtOAc, washed with brine, dried over $Na_2SO_4$, filtered and concentrated in vacuo. The residue was purified by MPLC (EtOAc/MeOH=9/1) to afford the N-(4-((2-amino-3-(3-methyl-3-morpholinobut-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5- carboxamide (8.0 mg, 15%) as an ivory solid. ¹H-NMR (CDCl₃, Varian, 400 MHz): δ 1.46 (6H, s), 2.69 (4H, m), 3.02 (3H, s), 3.10 (3H, s), 3.74 (4H, m), 4.74 (2H, s) 5.14 (2H, brs), 6.05 (1H, d, J=5.6 Hz), 7.07 (1H, t, J=8.4 Hz), 7.26-7.18 (5H, m), 7.78-7.82 (2H, m), 8.52 (1H, s), 10.79 (1H, s).

Example 34

Figure 31:
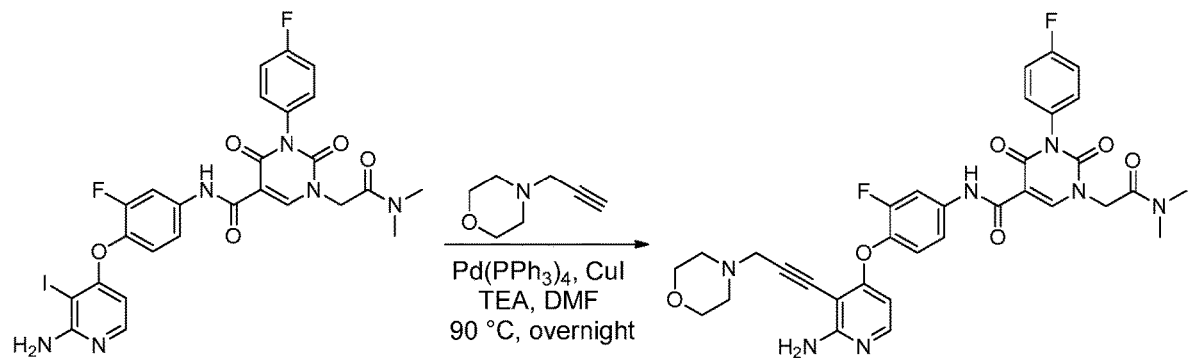
FIG. 31 is a chemical synthesis of N-(4-((2-amino-3-(3-morpholinoprop-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention.

This example describes the synthesis of N-(4-((2-amino-3-(3-morpholinoprop-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention. See FIG. 31.

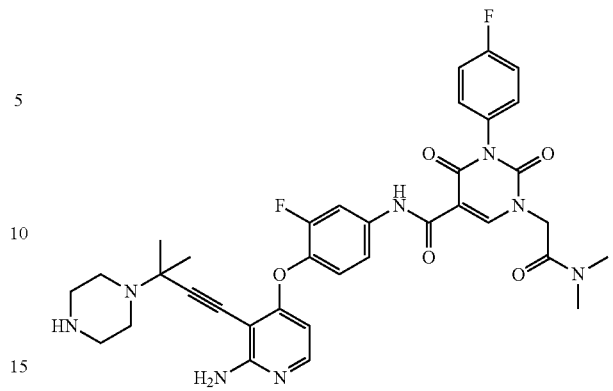

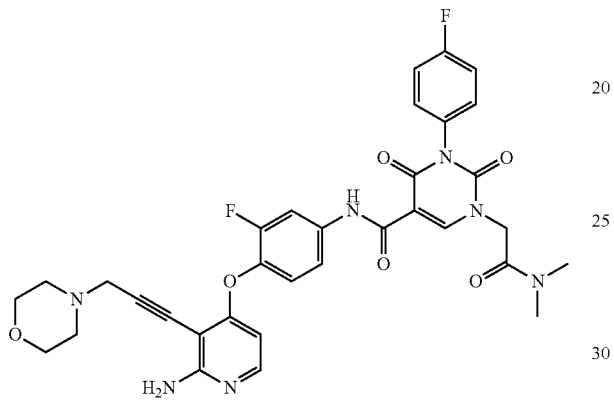

A mixture of N-(4-((2-amino-3-iodopyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (intermediate 16, 50.0 mg, 0.08 mmol), 4-(prop-2-yn-1-yl)morpholine (14.0 mg, 0.11 mmol), copper(I) iodide (2.8 mg, 0.02 mmol), and TEA (41.0 µL, 0.30 mmol) in DMF (1 mL) was degassed with N₂. To reaction mixture was added Pd(PPh₃)₄ (8.7 mg, 7.55 µmol) and stirred for overnight at 90° C. To a reaction mixture was added 4-(prop-2-yn-1-yl)morpholine (14.0 mg, 0.11 mmol), copper(I) iodide (2.8 mg, 0.02 mmol), TEA (41.0 µL, 0.30 mmol) and Pd(PPh₃)₄ (8.7 mg, 7.55 µmol) again. After degassing with N₂, stirred for 3 h at 90° C. After being cooled at room temperature, the reaction mixture was extracted with EtOAc, washed with brine, dried over Na₂SO₄, filtered and concentrated in vacuo. The residue was purified by MPLC (EtOAc/MeOH=9/1) to afford the N-(4-((2-amino-3-(3-morpholinoprop-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide. (6.0 mg, 11%) as an ivory solid. ¹H-NMR (CDCl₃, Varian, 400 MHz): δ 2.63-2.64 (4H, m), 3.02 (3H, s), 3.10 (3H, s), 3.60 (2H, s), 3.73-3.75 (4H, m), 4.73 (2H, s), 5.18 (2H, brs) 5.99 (1H, brs), 7.08 (1H, t, J=8.8 Hz), 7.19-7.26 (5H, m), 7.79-7.82 (2H, m), 8.52 (1H, s), 10.8 (1H, s).

Example 35

Figure 32:
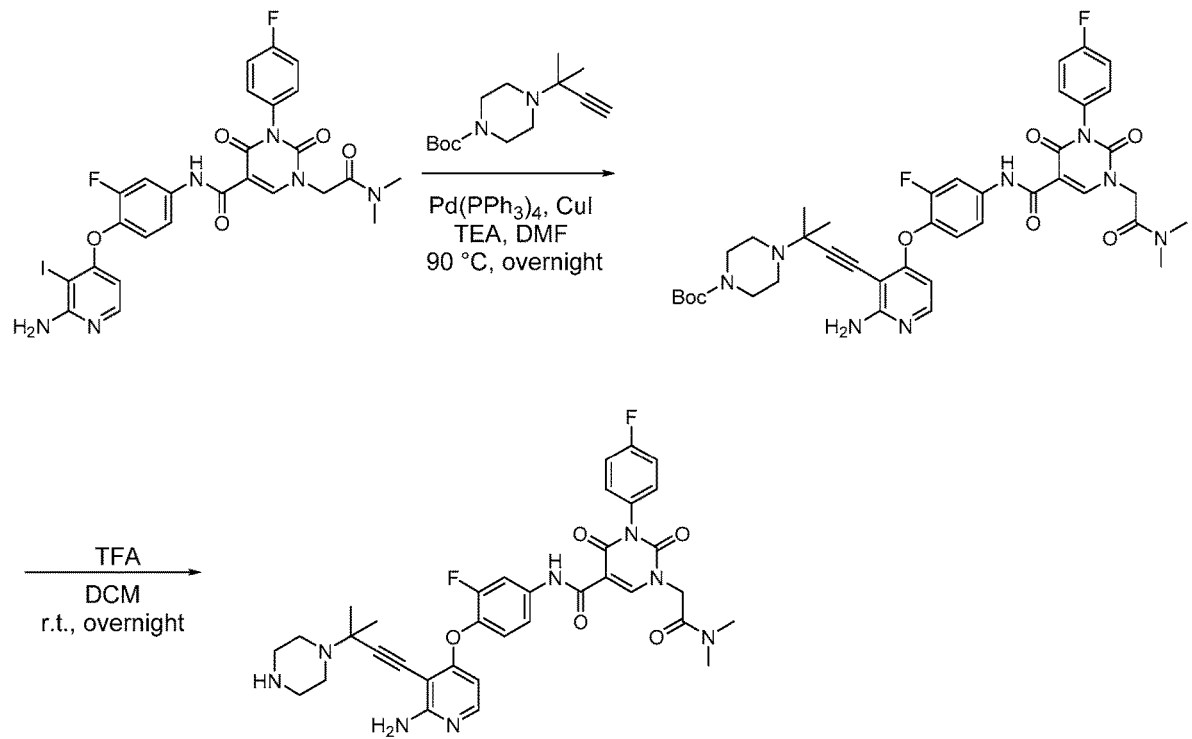
FIG. 32 is a chemical synthesis of N-(4-((2-amino-3-(3-methyl-3-(piperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention.

This example describes the synthesis of N-(4-((2-amino-3-(3-methyl-3-(piperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention. See FIG. 32.

Step A: tert-butyl 4-(4-(2-amino-4-(4-(1-(2-dimethylamino)-2-oxoethyl)-3-(4-fluorophenyl)-2,4-dioxo-1,2,3,4-tetrahydropyrimidine-5-carboxamido)-2-fluorophenoxy)pyridin-3-yl)-2-methylbut-3-yn-2-yl)piperazine-1-carboxylate

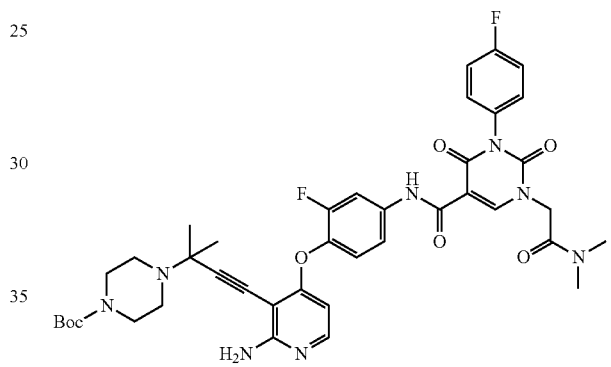

A mixture of N-(4-((2-amino-3-iodopyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (intermediate 16, 100 mg, 0.15 mmol), tert-butyl 4-(2-methylbut-3-yn-2-yl)piperazine-1-carboxylate (76.0 mg, 0.30 mmol), copper(I) iodide (5.75 mg, 0.03 mmol), and TEA (82.0 µL, 0.60 mmol) in DMF (1 mL) was degassed with N₂. To reaction mixture was added Pd(PPh₃)₄ (17.45 mg, 0.02 mmol) and stirred for overnight at 90° C. After being cooled at room temperature, the reaction mixture was extracted with EtOAc, washed with brine, dried over Na₂SO₄, filtered and concentrated in vacuo. The residue was purified by MPLC (EtOAc/MeOH=95/5 to EtOAc/MeOH=9/1) to afford the tert-butyl 4-(4-(2-amino-4-(4-(1-(2-(dimethylamino)-2-oxoethyl)-3-(4-fluorophenyl)-2,4-dioxo-1,2,3,4-tetrahydropyrimidine-5-carboxamido)-2-fluorophenoxy)pyridin-3-yl)-2-methylbut-3-yn-2-yl)piperazine-1-carboxylate (34 mg, 29%) as an orange solid. ¹H-NMR (CDCl₃, Varian, 400 MHz): δ 1.42 (9H, s), 1.46 (6H, s), 2.62 (4H, m), 3.02 (3H, s), 3.10 (3H, s), 3.44 (4H, m), 4.73 (2H, s), 5.03 (2H, s), 6.06 (1H, d, J=5.6 Hz), 7.03 (1H, t, J=8.8 Hz), 7.17-7.26 (5H, m), 7.79-7.81 (2H, m), 8.51 (1H, s), 10.79 (1H, s).

Step B: N-(4-((2-amino-3-(3-methyl-3-(piperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide

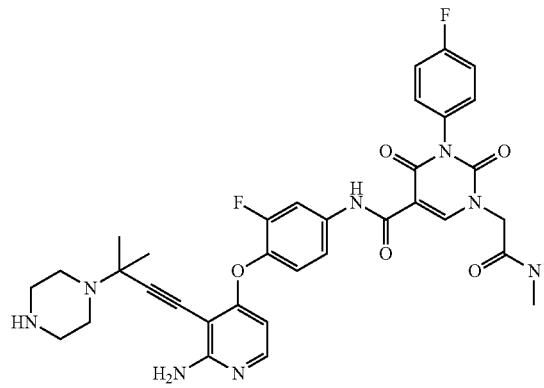

To a solution of tert-butyl 4-(4-(2-amino-4-(4-(1-(2-(dimethylamino)-2-oxoethyl)-3-(4-fluorophenyl)-2,4-dioxo-1,2,3,4-tetrahydropyrimidine-5-carboxamido)-2-fluorophenoxy)pyridin-3-yl)-2-methylbut-3-yn-2-yl)piperazine-1-carboxylate (34.0 mg, 0.04 mmol) in DCM (1 mL) was added TFA (33.0 µL, 0.43 mmol) at room temperature. The reaction mixture was stirred for overnight at room temperature. The reaction mixture was concentrated in vacuo. The residue was diluted with DCM, and then neutralized with TEA. The mixture was stirred for 10 min at room temperature and concentrated in vacuo. The residue was purified by column chromatography on NH—SiO$_2$ (EtOAc/MeOH=9/1) to afford the N-(4-((2-amino-3-(3-methyl-3-(piperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (32.0 mg, 98%) as a white solid. $^1$H-NMR (CDCl$_3$, Varian, 400 MHz): δ 1.44 (6H, s), 2.62 (4H, brs), 2.91 (4H, t, J=4.8 Hz), 3.02 (3H, s), 3.10 (3H, s), 4.74 (2H, s), 5.02 (2H, s), 6.06 (1H, d, J=5.6 Hz), 7.04 (1H, t, J=8.8 Hz), 7.17-7.26 (5H, m), 7.76-7.80 (1H, m), 7.83 (1H, d, J=6.0 Hz), 8.53 (1H, s), 10.78 (1H, s). * NH peak was not observed.

Example 36

Figure 33:
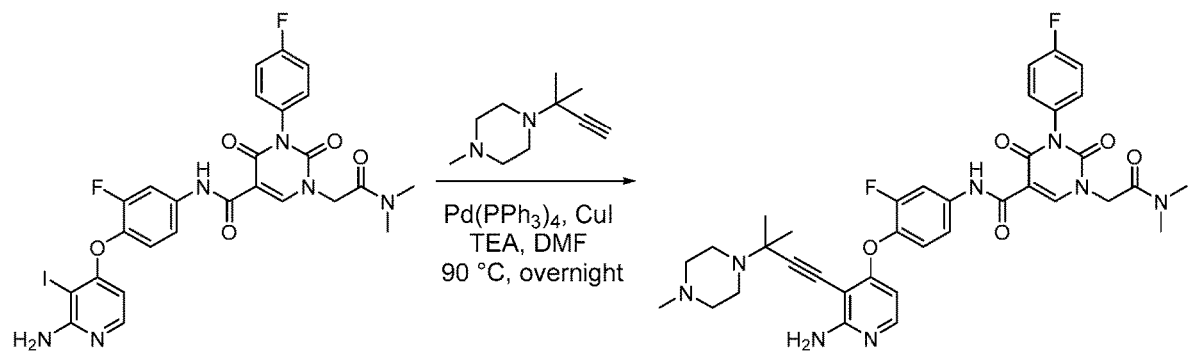
FIG. 33 is a chemical synthesis of N-(4-((2-amino-3-(3-methyl-3-(4-methylpiperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention.

This example describes the synthesis of N-(4-((2-amino-3-(3-methyl-3-(4-methylpiperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention. See FIG. 33.

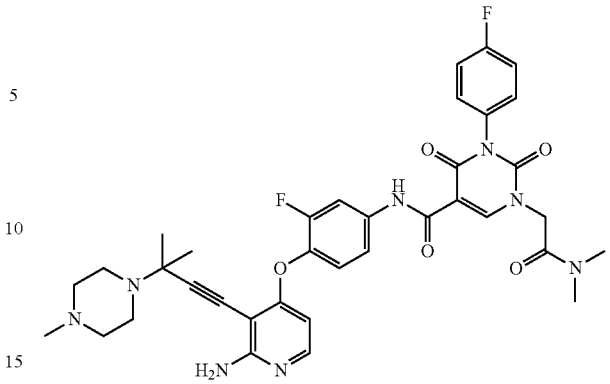

A mixture of N-(4-((2-amino-3-iodopyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (intermediate 16, 50.0 mg, 0.07 mmol), 1-methyl-4-(2-methylbut-3-yn-2-yl)piperazine (25.0 mg, 0.15 mmol), copper(I) iodide (2.88 mg, 0.02 mmol), and TEA (41.0 L, 0.30 mmol) in DMF (1 mL) was degassed with N$_2$. To reaction mixture was added Pd(PPh$_3$)$_4$ (8.7 mg, 7.55 µmol) and stirred for overnight at 90° C. After being cooled at room temperature, the reaction mixture was extracted with EtOAc, washed with brine, dried over Na$_2$SO$_4$, filtered and concentrated in vacuo. The residue was purified by column chromatography on NH—SiO$_2$ (EtOAc only to EtOAc/MeOH=97/3) to afford the N-(4-((2-amino-3-(3-methyl-3-(4-methylpiperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (9.7 mg, 15%) as an orange solid. $^1$H-NMR (CDCl$_3$, Varian, 400 MHz): δ 1.45 (6H, s), 2.26 (3H, s), 2.49 (4H, brs), 2.73 (4H, brs), 3.02 (3H, s), 3.10 (3H, s), 4.73 (2H, s), 5.02 (2H, s), 6.01 (1H, d, J=6.0 Hz), 7.06 (1H, t, J=8.8 Hz), 7.17-7.26 (5H, m), 7.77-7.81 (2H, m), 8.51 (1H, s). 10.78 (1H, s).

Example 37

Figure 34:
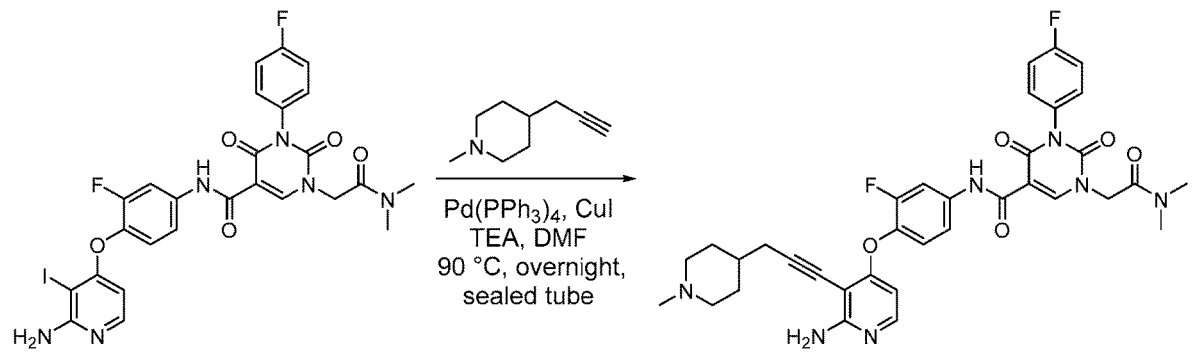
FIG. 34 is a chemical synthesis of N-(4-((2-amino-3-(3-(1-methylpiperidin-4-yl)prop-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention.

This example describes the synthesis of N-(4-((2-amino-3-(3-(1-methylpiperidin-4-yl)prop-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention. See FIG. 34.

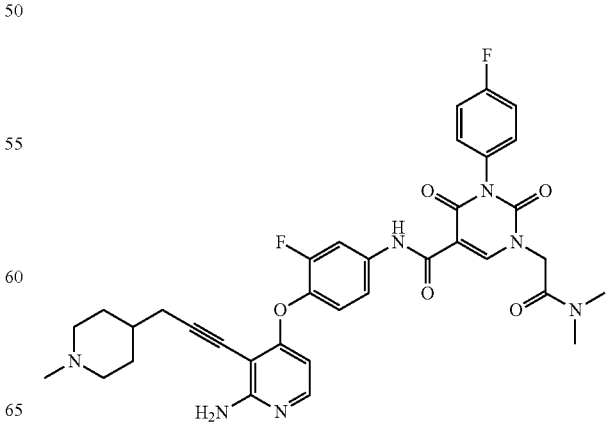

A mixture of N-(4-((2-amino-3-iodopyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (intermediate 16, 30.0 mg, 0.04 mmol), 1-methyl-4-(prop-2-yn-1-yl)piperidine hydrochloride (15.7 mg, 0.09 mmol), copper(I) iodide (1.7 mg, 9.06 μmol), and TEA (25.0 L, 0.18 mmol) in DMF (1 mL) was degassed with N₂. To reaction mixture was added Pd(PPh₃)₄ (5.23 mg, 4.53 μmol) and stirred for overnight at 90° C. in sealed tube. After being cooled at room temperature, the reaction mixture was extracted with EtOAc, washed with brine, dried over Na₂SO₄, filtered and concentrated in vacuo. The residue was purified by column chromatography on NH—SiO₂ (EtOAc only to EtOAc/MeOH=95/5) to afford the N-(4-((2-amino-3-(3-(1-methylpiperidin-4-yl)prop-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (1.5 mg, 4.5%) as an orange solid. ¹H-NMR (CDCl₃, Varian, 400 MHz): δ 1.40-1.45 (2H, m), 1.56 (1H, m), 1.84 (2H, d, J=12.8 Hz), 1.93-2.00 (2H, m), 2.27 (3H, s), 2.42 (2H, d, J=6.4 Hz), 2.89 (2H, d, J=11 Hz), 3.02 (3H, s), 3.10 (3H, s), 4.73 (2H, s), 5.06 (2H, brs), 5.97 (1H, d, J=6 Hz), 7.08 (1H, t, J=8.4 Hz), 7.17-7.26 (5H, m), 7.77-7.82 (2H, m), 8.52 (1H, s), 10.80 (1H, s).

Example 38

Figure 35:
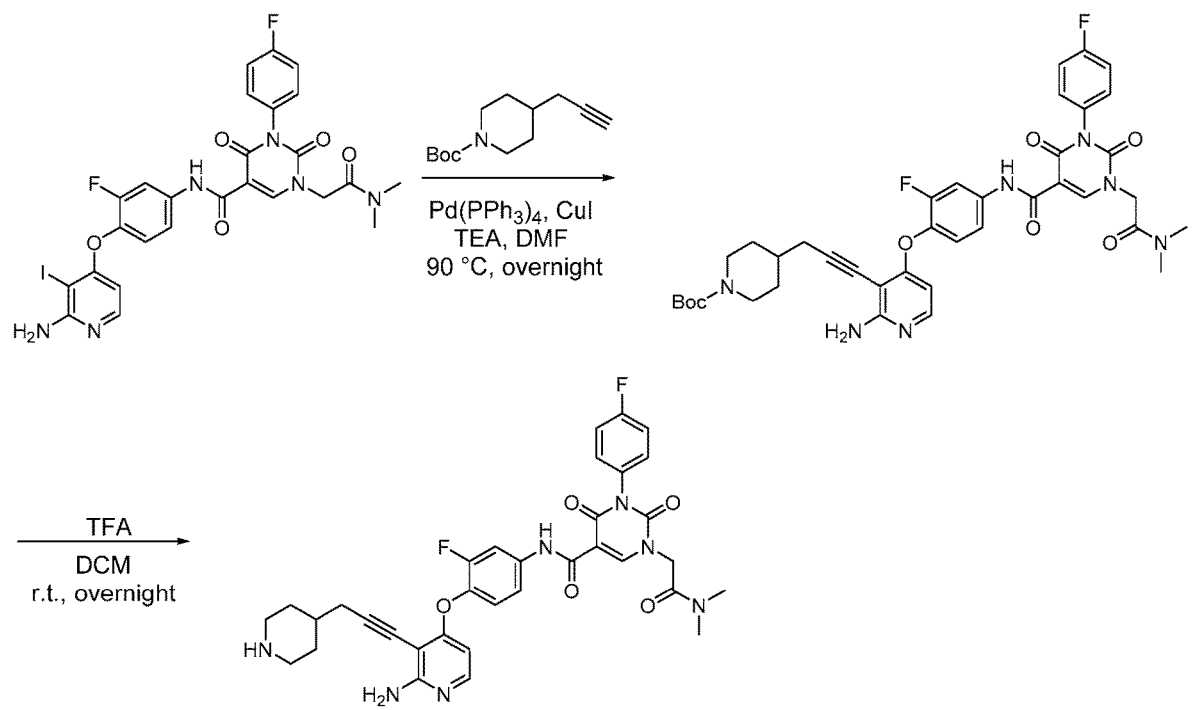
FIG. 35 is a chemical synthesis of N-(4-((2-amino-3-(3-(piperidin-4-yl)prop-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention.

This example describes the synthesis of N-(4-((2-amino-3-(3-(piperidin-4-yl)prop-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention. See FIG. 35.

A mixture of N-(4-((2-amino-3-iodopyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (intermediate 16, 75.0 mg, 0.11 mmol), tert-butyl 4-(prop-2-yn-1-yl)piperidine-1-carboxylate (50.0 mg, 0.22 mmol), copper(I) iodide (4.26 mg, 0.02 mmol), and TEA (61.0 L, 0.45 mmol) in DMF (1 mL) was degassed with N₂. To reaction mixture was added Pd(PPh₃)₄ (12.94 mg, 0.01 mmol) and stirred for overnight at 90° C. After being cooled at room temperature, the reaction mixture was extracted with EtOAc, washed with brine, dried over Na₂SO₄, filtered and concentrated in vacuo. The residue was purified by MPLC (EtOAc only to EtOAc/MeOH=97/3) to afford the tert-butyl 4-(3-(2-amino-4-(4-(1-(2-(dimethylamino)-2-oxoethyl)-3-(4-fluorophenyl)-2,4-dioxo-1,2,3,4-tetrahydropyrimidine-5-carboxamido)-2-fluorophenoxy)pyridin-3-yl)prop-2-yn-1-yl)piperidine-1-carboxylate (31.0 mg, 36%) as a yellow solid. ¹H-NMR (CDCl₃, Varian, 400 MHz): δ 1.44 (9H, s), 1.71 (3H, m), 1.81 (2H, d, J=8 Hz), 2.45 (2H, d, J=6.8 Hz), 2.69 (2H, brs), 3.02 (3H, s), 3.10 (3H, s), 4.12 (2H, brs), 4.73 (2H, s), 5.07 (2H, brs), 5.98 (1H, d, J=5.6 Hz), 7.08 (1H, t, J=8.4 Hz), 7.18-7.26 (5H, m), 7.77-7.79 (2H, m), 8.51 (1H, s), 10.80 (1H, s).

Step B: N-(4-((2-amino-3-(3-(piperidin-4-yl)prop-1-yn-1-yl)pyridin-4-yl)oxy)-3-fluorophenyl)-1-(2-(dimethylamino)-2-oxoethyl)-3-(4-fluorophenyl)-2,4-dioxo1,2,3,4-tetrahydropyrimidine-5-carboxamide

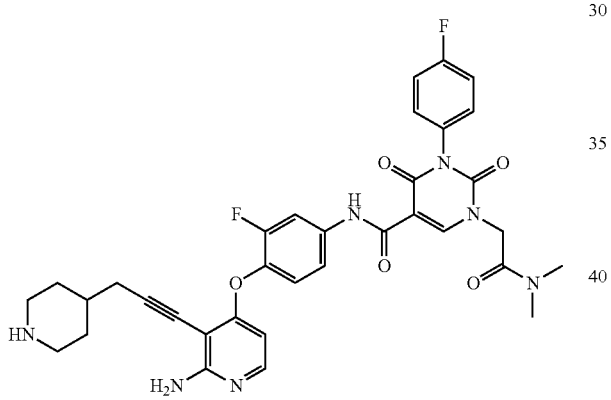

Step A: tert-butyl 4-(3-(2-amino-4-(4-(1-(2-dimethylamino-2-oxoethyl)-3-(4-fluorophenyl)-2,4-dioxo-1,2,3,4-tetrahydropyrimidine-5-carboxamido)-2-fluorophenoxy)pyridin-3-yl)prop-2-yn-1-yl)piperidine-1-carboxylate

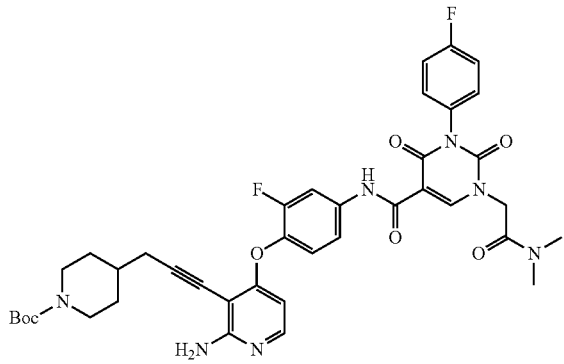

To a solution of tert-butyl 4-(3-(2-amino-4-(4-(1-(2-(dimethylamino)-2-oxoethyl)-3-(4-fluorophenyl)-2,4-dioxo-1,2,3,4-tetrahydropyrimidine-5-carboxamido)-2-fluorophenoxy)pyridin-3-yl)prop-2-yn-1-yl)piperidine-1-carboxylate (31.0 mg, 0.04 mmol) in DCM (1 mL) was added TFA (32.0 μL, 0.41 mmol) at room temperature. The reaction mixture was stirred for overnight at room temperature. To a reaction mixture was added TFA (32.0 μL, 0.41 mmol) again at room temperature. The reaction mixture was stirred for 2 h at room temperature. The reaction mixture was concentrated in vacuo. The residue was diluted with DCM, and then neutralized with TEA. The mixture was stirred for 10 min at room temperature and concentrated in vacuo. The residue was purified by column chromatography on NH—SiO₂ (EtOAc/MeOH=9/1) to afford the N-(4-((2-amino-3-(3-(piperidin-4-yl)prop-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide (14.0 mg, 44%) as a white solid. ¹H-NMR (CD₃OD, Varian, 400 MHz): δ 1.34-1.42 (3H, m), 1.75 (1H, m), 1.88-1.94 (2H, m), 2.49 (2H, d, J=6.4 Hz), 2.68-2.75 (2H, m), 2.99 (3H, s), 3.11 (3H, s), 3.11-3.16 (2H, m), 4.96 (2H, s), 6.00

(1H, d, J=6 Hz), 7.12-7.16 (1H, m), 7.23-7.30 (3H, m), 7.33-7.37 (2H, m), 7.71 (1H, d, J=6.4 Hz), 7.89 (1H, d, J=12.8 Hz), 8.67 (1H, s) * amide NH. NH₂ peak was not observed.

Example 39

Figure 36:
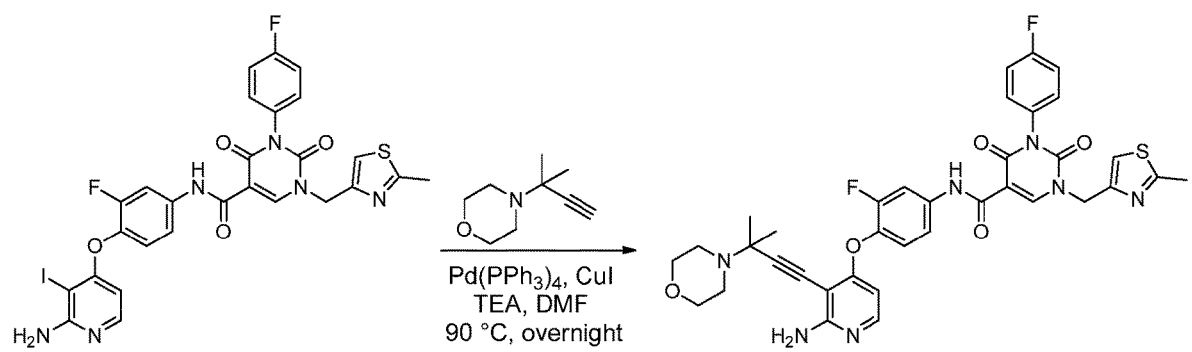
FIG. 36 is a chemical synthesis of N-(4-((2-amino-3-(3-methyl-3-morpholinobut-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention.

This example describes the synthesis of N-(4-((2-amino-3-(3-methyl-3-morpholinobut-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention. See FIG. 36.

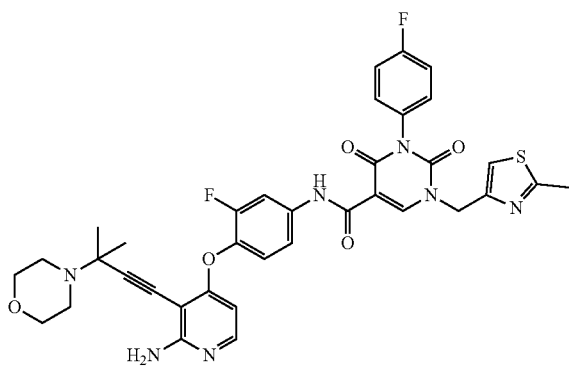 [SMILES: Cc1nc(Cn2cc(C(=O)Nc3ccc(Oc4ccnc(N)c4C#CC(C)(C)N4CCOCC4)c(F)c3)c(=O)n(-c3ccc(F)cc3)c2=O)cs1]

A mixture of N-(4-((2-amino-3-iodopyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (intermediate 18, 50.0 mg, 0.07 mmol), 4-(2-methylbut-3-yn-2-yl)morpholine (17.0 mg, 0.11 mmol), copper(I) iodide (2.8 mg, 0.01 mmol), and TEA (40.0 µL, 0.29 mmol) in DMF (1 mL) was degassed with N₂. To reaction mixture was added Pd(PPh₃)₄ (8.4 mg, 7.26 µmol) and stirred for overnight at 90° C. After being cooled at room temperature, the reaction mixture was extracted with EtOAc, washed with brine, dried over Na₂SO₄, filtered and concentrated in vacuo. The residue was purified by column chromatography on NH—SiO₂ (EtOAc/Hexane=4/1) to afford the N-(4-((2-amino-3-(3-methyl-3-morpholinobut-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (10 mg, 18%) as a white solid. ¹H-NMR (CDCl₃, Varian, 400 MHz): δ 1.45 (6H, s), 2.67 (4H, m), 2.71 (3H, s), 3.73 (4H, t, J=4.8 Hz), 5.03 (2H, brs), 5.12 (2H, s), 6.02 (1H, d, J=6.0 Hz), 7.06 (1H, t, J=8.4 Hz), 7.15-7.26 (6H, m), 7.79-7.83 (2H, m), 8.87 (1H, s), 10.82 (1H, s).

Example 40

Figure 37:
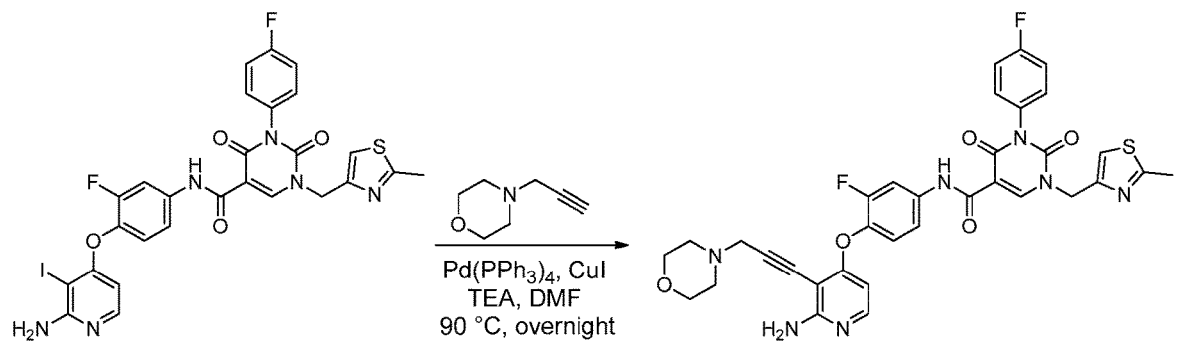
FIG. 37 is a chemical synthesis of N-(4-((2-amino-3-(3-morpholinoprop-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention.

This example describes the synthesis of N-(4-((2-amino-3-(3-morpholinoprop-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention. See FIG. 37.

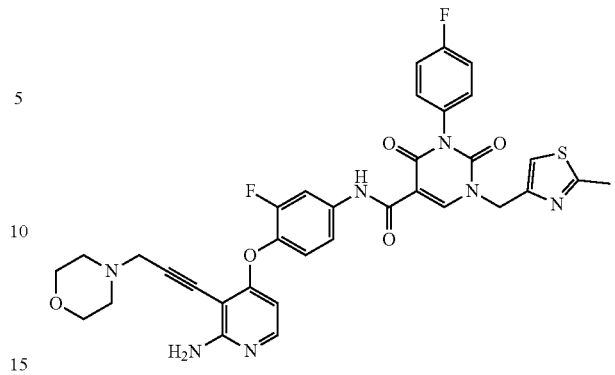

A mixture of N-(4-((2-amino-3-iodopyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (intermediate 18, 50.0 mg, 0.07 mmol), 4-(prop-2-yn-1-yl)morpholine (18.0 mg, 0.14 mmol), copper(I) iodide (2.8 mg, 0.02 mmol), and TEA (40.0 µL, 0.29 mmol) in DMF (1 mL) was degassed with N₂. To reaction mixture was added Pd(PPh₃)₄ (8.4 mg, 7.26 µmol) and stirred for overnight at 90° C. After being cooled at room temperature, the reaction mixture was extracted with EtOAc, washed with brine, dried over Na₂SO₄, filtered and concentrated in vacuo. The residue was purified by column chromatography on NH—SiO₂ (EtOAc only) to afford the N-(4-((2-amino-3-(3-morpholinoprop-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (7.4 mg, 13%) as an ivory solid. ¹H-NMR (CDCl₃, Varian, 400 MHz): δ 2.61-2.63 (4H, m), 2.71 (3H, s), 3.59 (2H, s), 3.73-3.75 (4H, m), 5.09 (2H, brs), 5.13 (2H, s), 5.97 (1H, d, J=6.0 Hz), 7.08 (1H, t, J=8.8 Hz), 7.17-7.26 (6H, m), 7.82-7.80 (2H, m), 8.87 (1H, s), 10.84 (1H, s).

Example 41

Figure 38:
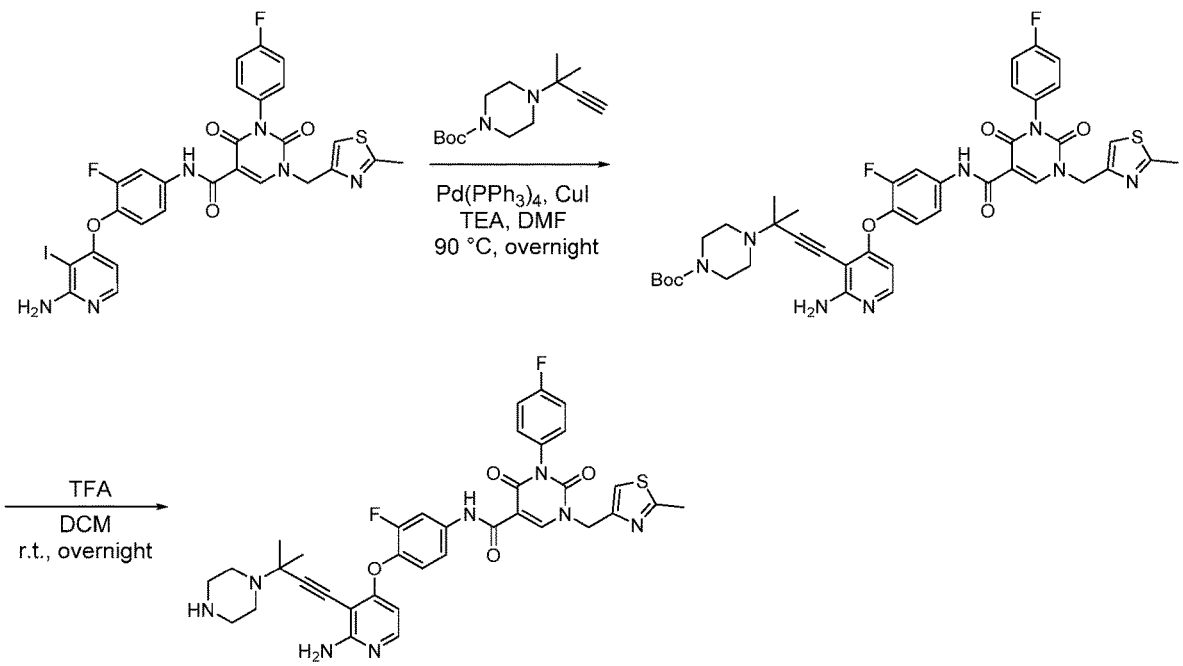
FIG. 38 is a chemical synthesis of N-(4-((2-amino-3-(3-methyl-3-(piperazin-1-yl)but-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention.

This example describes the synthesis of N-(4-((2-amino-3-(3-methyl-3-(piperazin-1-yl)but-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention. See FIG. 38.

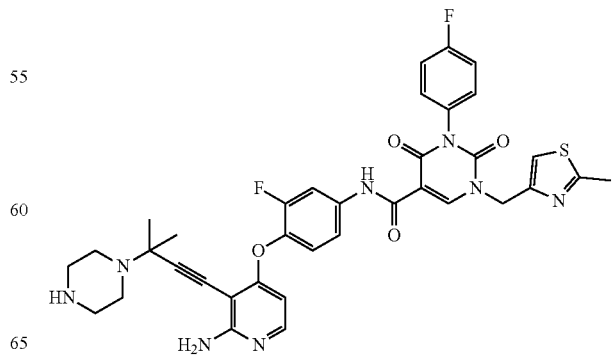

Step A: tert-butyl 4-(4-(2-amino-4-(2-fluoro-4-(3-(4-fluorophenyl)-1-((2-methylthiazol-4-yl)methyl)-2,4-dioxo-1,2,3,4-tetrahydropyrimidine-5-carboxamido)phenoxy)pyridin-3-yl)-2-methylbut-3-yn-2-yl)piperazine-1-carboxylate

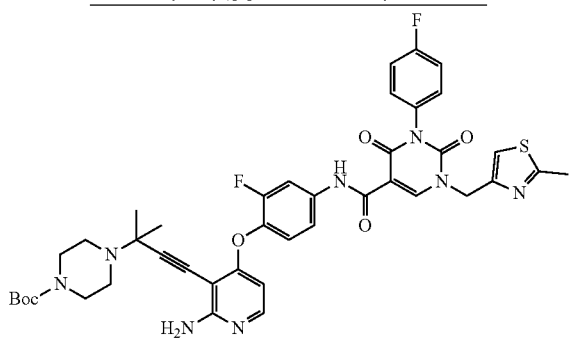

Step B: N-(4-((2-amino-3-(3-(methyl-3-(piperazin-1-yl)but-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide

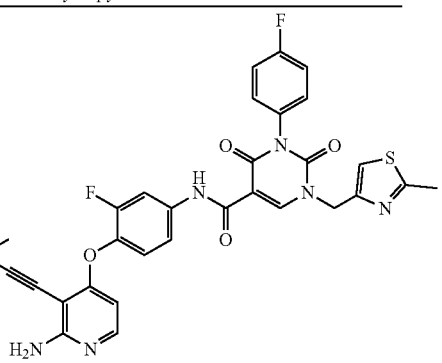

A mixture of N-(4-((2-amino-3-iodopyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (intermediate 18, 70.0 mg, 0.10 mmol), tert-butyl 4-(2-methylbut-3-yn-2-yl)piperazine-1-carboxylate (51.0 mg, 0.20 mmol), copper(I) iodide (3.87 mg, 0.02 mmol), and TEA (55.0 µL, 0.41 mmol) in DMF (1 mL) was degassed with $N_2$. To reaction mixture was added Pd(PPh$_3$)$_4$ (11.7 mg, 10.17 µmol) and stirred for overnight at 90° C. After being cooled at room temperature, the reaction mixture was extracted with EtOAc, washed with brine, dried over Na$_2$SO$_4$, filtered and concentrated in vacuo. The residue was purified by column chromatography on SiO$_2$ (EtOAc/MeOH=97/3) to afford the tert-butyl 4-(4-(2-amino-4-(2-fluoro-4-(3-(4-fluorophenyl)-1-((2-methylthiazol-4-yl)methyl)-2,4-dioxo-1,2,3,4-tetrahydropyrimidine-5-carboxamido)phenoxy)pyridin-3-yl)-2-methylbut-3-yn-2-yl)piperazine-1-carboxylate (36.0 mg, 44%) as a brown solid. $^1$H-NMR (CDCl$_3$, Varian, 400 MHz): δ 1.42 (6H, s), 1.44-1.46 (9H, m), 2.62 (4H, brs), 2.71 (3H, s), 3.44-3.45 (4H, m), 5.00 (2H, s), 5.13 (2H, brs), 5.99 (1H, m), 7.06 (1H, m), 6.99-7.25 (6H, m), 7.79-7.82 (2H, m), 8.87 (1H, s), 10.83 (1H, s).

To a solution of tert-butyl 4-(4-(2-amino-4-(2-fluoro-4-(3-(4-fluorophenyl)-1-((2-methylthiazol-4-yl)methyl)-2,4-dioxo-1,2,3,4-tetrahydropyrimidine-5-carboxamido)phenoxy)pyridin-3-yl)-2-methylbut-3-yn-2-yl)piperazine-1-carboxylate (36.0 mg, 0.04 mmol) in DCM (1 mL) was added TFA (35.0 µL, 0.45 mmol) at room temperature. The reaction mixture was stirred for overnight at room temperature. The reaction mixture was concentrated in vacuo. The residue was diluted with DCM, and then neutralized with TEA. The mixture was stirred for 10 min at room temperature and concentrated in vacuo. The residue was purified by column chromatography on NH—SiO$_2$ (EtOAc/MeOH=95/5) to afford the N-(4-((2-amino-3-(3-methyl-3-(piperazin-1-yl)but-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (5.4 mg, 10%) as a white solid. $^1$H-NMR (CDCl$_3$, Varian, 400 MHz): δ 1.44 (6H, s), 2.62 (4H, brs), 2.70 (3H, s), 2.90 (4H, brs), 5.01 (2H, brs), 5.12 (2H, s), 6.03 (1H, d, J=6 Hz), 7.05 (1H, t, J=8.4 Hz), 7.15-7.26 (6H, m), 7.79-7.83 (2H, m), 8.87 (1H, s), 10.83 (1H, s). * NH peak was not observed.

Example 42

Figure 39:
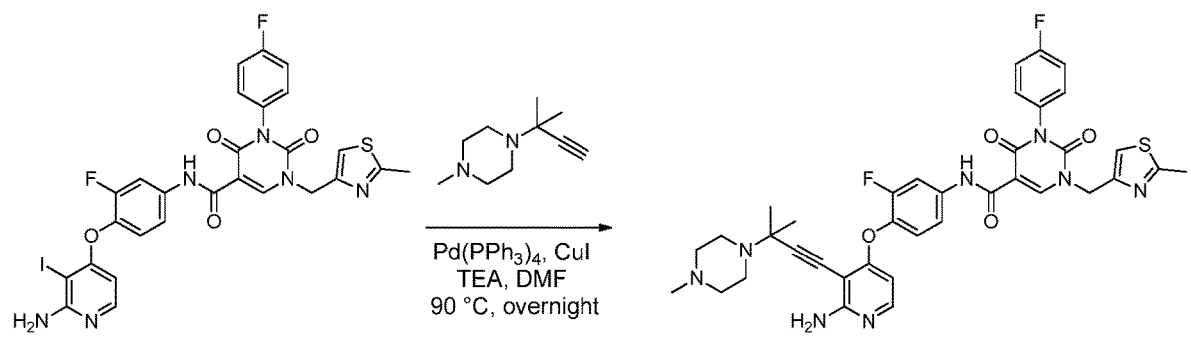
FIG. 39 is a chemical synthesis of N-(4-((2-amino-3-(3-methyl-3-(4-methylpiperazin-1-yl)but-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention.

This example describes the synthesis of N-(4-((2-amino-3-(3-methyl-3-(4-methylpiperazin-1-yl)but-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention. See FIG. 39.

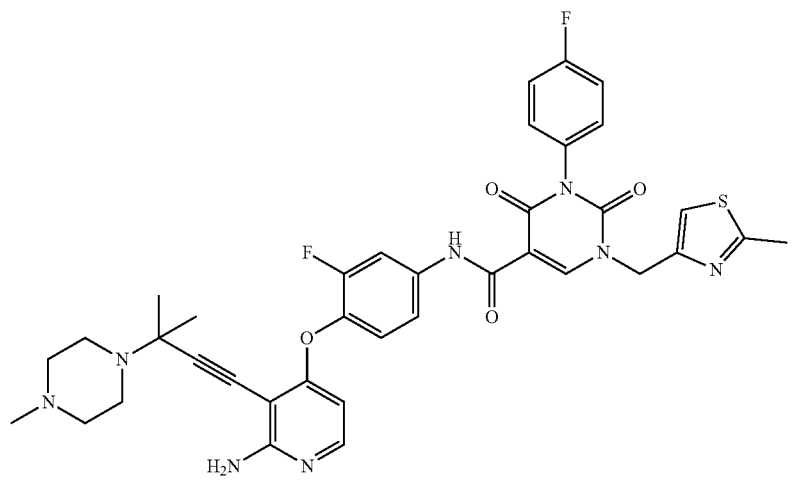

A mixture of N-(4-((2-amino-3-iodopyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (intermediate 18, 50.0 mg, 0.07 mmol), 1-methyl-4-(2-methylbut-3-yn-2-yl)piperazine (24.0 mg, 0.14 mmol), copper(I) iodide (2.8 mg, 0.02 mmol), and TEA (40.0 L, 0.29 mmol) in DMF (1 mL) was degassed with $N_2$. To reaction mixture was added Pd(PPh$_3$)$_4$ (8.4 mg, 7.26 µmol) and stirred for overnight at 90° C. After being cooled at room temperature, the reaction mixture was extracted with EtOAc, washed with brine, dried over Na$_2$SO$_4$, filtered and concentrated in vacuo. The residue was purified by column chromatography on NH—SiO$_2$ (EtOAc/MeOH=97/3) to afford the N-(4-((2-amino-3-(3-methyl-3-(4-methylpiperazin-1-yl)but-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (6.3 mg, 10%) as an ivory solid. $^1$H-NMR (CDCl$_3$, Varian, 400 MHz): δ 1.45 (6H, s), 2.26 (3H, s), 2.50 (4H, brs), 2.71 (4H, brs), 2.71 (3H, s), 5.04 (2H, brs), 5.12 (2H, s), 6.00 (1H, d, J=6.4 Hz), 7.06 (1H, t, J=8.4 Hz), 7.19-7.26 (6H, m), 7.78-7.81 (2H, m), 8.87 (1H, s), 10.82 (1H, s).

Example 43

Figure 40:
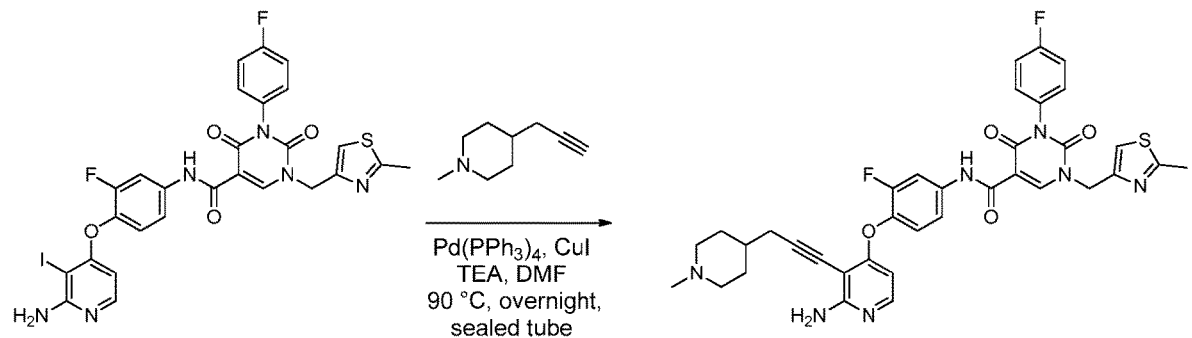
FIG. 40 is a chemical synthesis of N-(4-((2-amino-3-(3-(1-methylpiperidin-4-yl)prop-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention.

This example describes the synthesis of N-(4-((2-amino-3-(3-(1-methylpiperidin-4-yl)prop-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention. See FIG. 40.

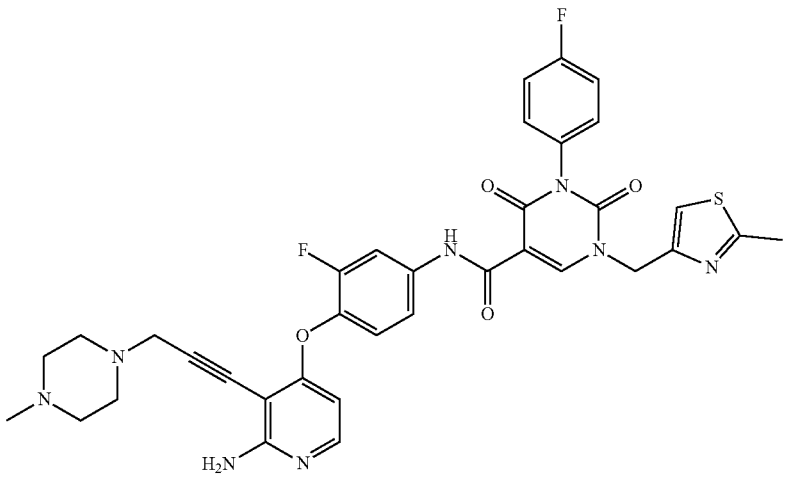

A mixture of N-(4-((2-amino-3-iodopyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (intermediate 18, 50.0 mg, 0.07 mmol), 1-methyl-4-(prop-2-yn-1-yl)piperidine hydrochloride (25.0 mg, 0.14 mmol), copper(I) iodide (2.8 mg, 0.02 mmol), and TEA (40.0 L, 0.29 mmol) in DMF (1 mL) was degassed with $N_2$. To reaction mixture was added Pd(PPh$_3$)$_4$ (8.4 mg, 7.26 µmol) and stirred for overnight at 90° C. in a sealed tube. After being cooled at room temperature, the reaction mixture was extracted with EtOAc, washed with brine, dried over Na$_2$SO$_4$, filtered and concentrated in vacuo. The residue was purified by column chromatography on NH—SiO₂ (EtOAc/MeOH=97/3) to afford the N-(4-((2-amino-3-(3-(1-methylpiperidin-4-yl)prop-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (3.5 mg, 5.8%) as a yellow solid. ¹H-NMR (CDCl₃, Varian, 400 MHz): δ 1.33-1.43 (2H, m), 1.55 (1H, m), 1.84 (2H, d, J=12 Hz), 2.00 (2H, t, J=17.4 Hz), 2.25 (3H, s), 2.43 (2H, d, J=6.8 Hz), 2.71 (3H, s), 2.85 (2H, d, J=12 Hz), 5.02 (2H, brs), 5.12 (2H, s), 5.96 (1H, d, J=6 Hz), 7.08 (1H, t, J=8.8 Hz), 7.17-7.20 (1H, m), 7.22-7.25 (5H, m), 7.77-7.82 (2H, m), 8.87 (1H, s), 10.84 (1H, s).

Example 44

Figure 41:
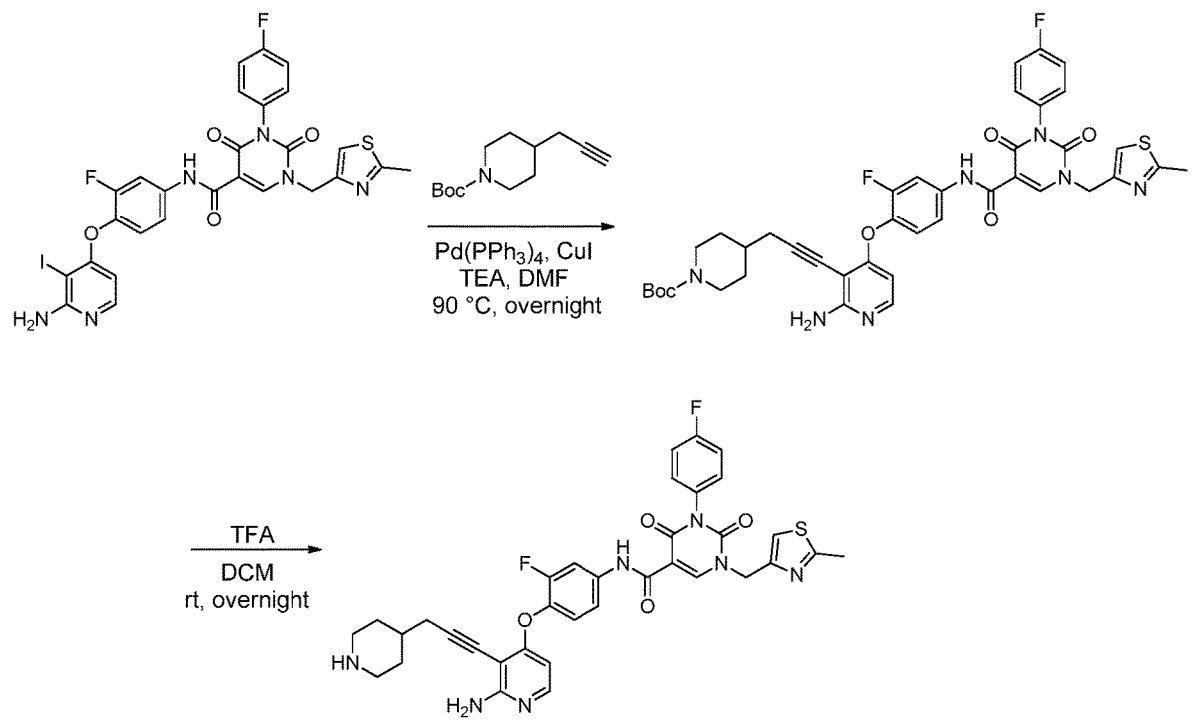
FIG. 41 is a chemical synthesis of N-(4-((2-amino-3-(3-(piperidin-4-yl)prop-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention.

This example describes the synthesis of N-(4-((2-amino-3-(3-(piperidin-4-yl)prop-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide in an aspect of the invention. See FIG. 41.

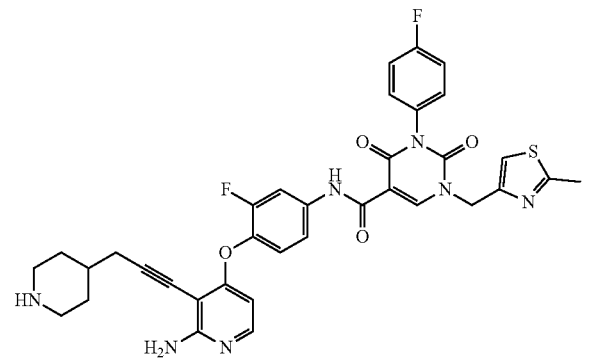 [SMILES: Cc1nc(Cn2cc(C(=O)Nc3ccc(Oc4ccnc(N)c4C#CCC4CCNCC4)c(F)c3)c(=O)n(-c3ccc(F)cc3)c2=O)cs1]

Step A: tert-butyl 4-(3-(2-amino-4-(2-fluoro-4-(3-(4-fluorophenyl)-1-((2-methylthiazol-4-yl)methyl)-2,4-dioxo-1,2,3,4-tetrahydropyrimidine-5-carboxamido)phenoxy)pyridin-3-yl)prop-2-yn-1-yl)piperdine-1-carboxylate

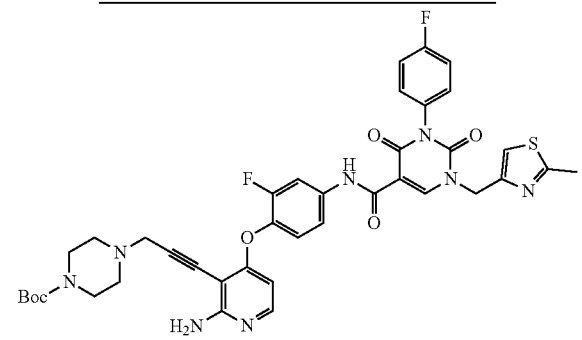

A mixture of N-(4-((2-amino-3-iodopyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (intermediate 18, 77.0 mg, 0.11 mmol), tert-butyl 4-(prop-2-yn-1-yl)piperidine-1-carboxylate (50.0 mg, 0.22 mmol), copper(I) iodide (4.26 mg, 0.02 mmol), and TEA (61.0 L, 0.45 mmol) in DMF (1 mL) was degassed with N₂. To reaction mixture was added Pd(PPh₃)₄ (12.9 mg, 0.01 mmol) and stirred for overnight at 90° C. After being cooled at room temperature, the reaction mixture was extracted with EtOAc, washed with brine, dried over Na₂SO₄, filtered and concentrated in vacuo. The residue was purified by MPLC (EtOAc only) to afford the tert-butyl 4-(3-(2-amino-4-(2-fluoro-4-(3-(4-fluorophenyl)-1-((2-methylthiazol-4-yl)methyl)-2,4-dioxo-1,2,3,4-tetrahydropyrimidine-5-carboxamido)phenoxy)pyridin-3-yl)prop-2-yn-1-yl)piperidine-1-carboxylate (27.0 mg, 30%) as an orange solid. ¹H-NMR (CDCl₃, Varian, 400 MHz): δ 1.44 (9H, s), 1.74-1.83 (3H, m), 2.45 (2H, d, J=6.8 Hz), 2.69 (2H, brs), 2.71 (3H, s), 4.10 (2H, brs), 5.13 (2H, s), 5.19 (2H, brs), 5.96 (1H, d, J=6.4 Hz), 7.08 (1H, t, J=8.4 Hz), 7.14-7.25 (6H, m), 7.77 (1H, d, J=6 Hz), 7.83-7.80 (1H, m), 8.87 (1H, s), 10.85 (1H, s). * NH₂ peak was not observed.

Step B: N-(4-((2-amino-3-(3-(piperidin-4-yl)prop-1-yn-1-yl)pyridin-4-yl)oxy)-3-fluorophenyl)-1-((2-methylthiazol-4-yl)methyl)-2,4-dioxo-1,2,3,4-tetrahydropyrimidine-5-carboxamide

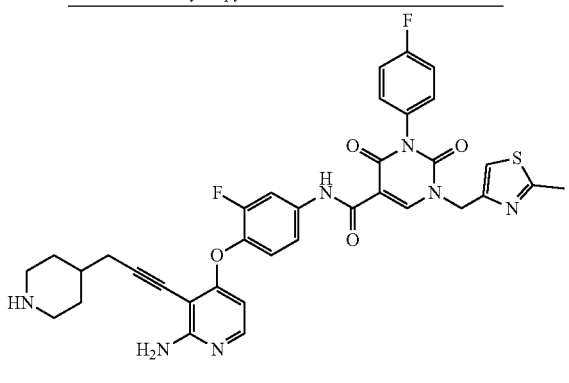

To a solution of tert-butyl 4-(3-(2-amino-4-(2-fluoro-4-(3-(4-fluorophenyl)-1-((2-methylthiazol-4-yl)methyl)-2,4-dioxo-1,2,3,4-tetrahydropyrimidine-5-carboxamido)phenoxy)pyridin-3-yl)prop-2-yn-1-yl)piperidine-1-carboxylate (27.0 mg, 0.03 mmol) in DCM (1 ml) was added TFA (26.0 µL, 0.34 mmol) at room temperature. The reaction mixture was stirred for overnight at room temperature. The reaction mixture was concentrated in vacuo. The residue was diluted with DCM, and then neutralized with TEA. The mixture was stirred for 10 min at room temperature and concentrated in vacuo. The residue was purified by column chromatography on NH—SiO₂ (EtOAc/MeOH=95/5) to afford the N-(4-((2-amino-3-(3-(piperidin-4-yl)prop-1-yn-1-yl)pyridin-4-yl)oxy)-3-fluorophenyl)-3-(4-fluorophenyl)-1-((2-methylthiazol-4-yl)methyl)-2,4-dioxo-1,2,3,4-tetrahydropyrimidine-5-carboxamide (7.1 mg, 27%) as a yellow solid. ¹H-NMR (CDCl₃, Varian, 400 MHz): δ 1.30-1.40 (3H, m), 1.61 (1H, m), 1.88 (2H, d, J=12 Hz), 2.45 (2H, d, J=6.8 Hz), 2.61-2.70 (2H, m), 2.71 (3H, s), 3.19 (2H, d, J=12 Hz), 5.02 (2H, brs), 5.13 (2H, s), 5.99 (1H, d, J=4 Hz), 7.03-7.08 (1H, m), 7.17-7.19 (1H, m), 7.22-7.24 (5H, m), 7.79-7.81 (2H, m), 8.87 (1H, s), 10.84 (1H, s).

Example 45

Figure 42:
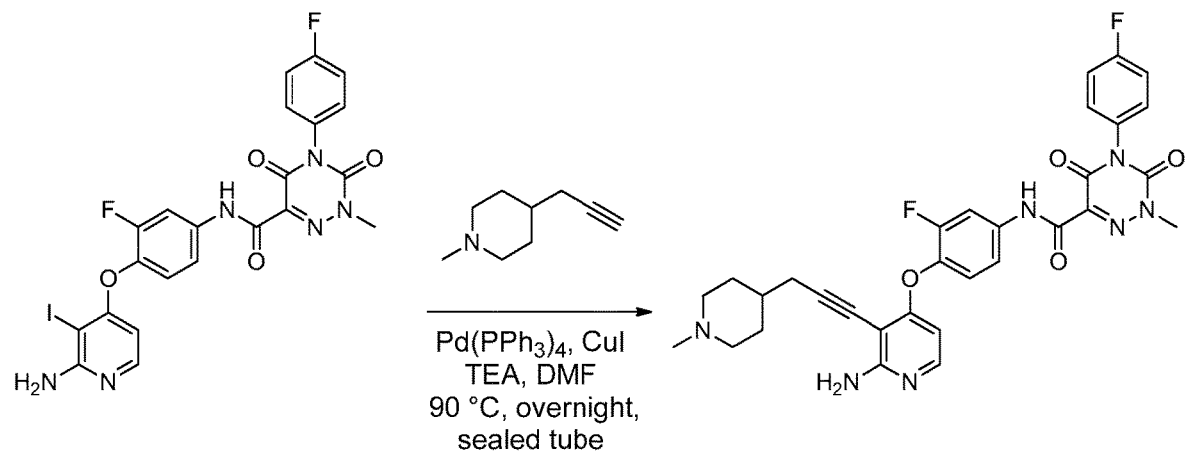
FIG. 42 is a chemical synthesis of N-(4-((2-amino-3-(3-(1-methylpiperidin-4-yl)prop-1-yn-1-yl)pyridin-4-yl)oxy)-3-fluorophenyl)-4-(4-fluorophenyl)-2-methyl-3,5-dioxo-2,3,4,5-tetrahydro-1,2,4-triazine-6-carboxamide in an aspect of the invention.

This example describes the synthesis of N-(4-((2-amino-3-(3-(1-methylpiperidin-4-yl)prop-1-yn-1-yl)pyridin-4-yl)oxy)-3-fluorophenyl)-4-(4-fluorophenyl)-2-methyl-3,5-dioxo-2,3,4,5-tetrahydro-1,2,4-triazine-6-carboxamide in an aspect of the invention. See FIG. 42.

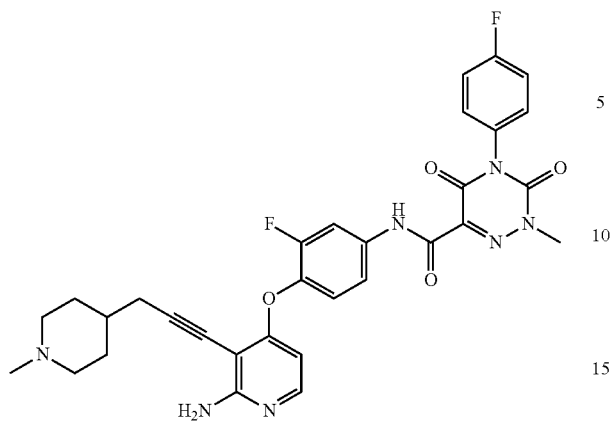

A mixture of N-(4-((2-amino-3-iodopyridin-4-yl)oxy)-3-fluorophenyl)-4-(4-fluorophenyl)-2-methyl-3,5-dioxo-2,3,4,5-tetrahydro-1,2,4-triazine-6-carboxamide (intermediate 20, 70.0 mg, 0.12 mmol), 1-methyl-4-(prop-2-yn-1-yl)piperidine hydrochloride (41.0 mg, 0.24 mmol), copper(I) iodide (4.5 mg, 0.02 mmol), and TEA (64.0 μL, 0.47 mmol) in DMF (1 mL) was degassed with $N_2$. To reaction mixture was added Pd(PPh$_3$)$_4$ (14.0 mg, 0.01 mmol) and stirred for overnight at 90° C. in a sealed tube. After being cooled at room temperature, the reaction mixture was extracted with EtOAc, washed with brine, dried over $Na_2SO_4$, filtered and concentrated in vacuo. The residue was purified by column chromatography on NH—SiO$_2$ (EtOAc/MeOH=97/3) to afford the N-(4-((2-amino-3-(3-(1-methylpiperidin-4-yl)prop-1-yn-1-yl)pyridin-4-yl)oxy)-3-fluorophenyl)-4-(4-fluorophenyl)-2-methyl-3,5-dioxo-2,3,4,5-tetrahydro-1,2,4-triazine-6-carboxamide (2.4 mg, 3%) as a yellow solid. $^1$H-NMR (CDCl$_3$, Varian, 400 MHz): δ 1.34-1.44 (3H, m), 1.81 (2H, m), 1.88-1.97 (2H, m), 2.26 (3H, s), 2.43 (2H, d, J=6.4 Hz), 2.83-2.89 (2H, brs), 3.93 (3H, s), 5.01 (2H, brs), 5.99 (1H, m), 7.14-7.10 (1H, m), 7.25-7.28 (5H, m), 7.82-7.85 (2H, m), 10.81 (1H, s).

Example 46

Figure 43:
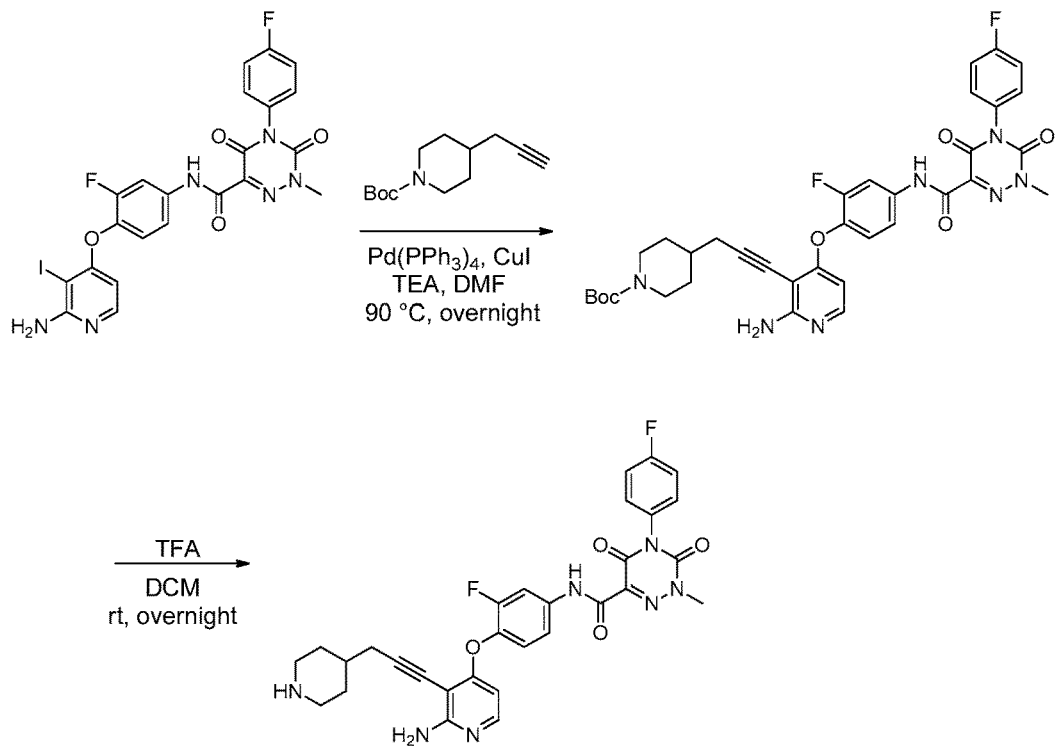
FIG. 43 is a chemical synthesis of N-(4-((2-amino-3-(3-(piperidin-4-yl)prop-1-yn-1-yl)pyridin-4-yl)oxy)-3-fluorophenyl)-4-(4-fluorophenyl)-2-methyl-3,5-dioxo-2,3,4,5-tetrahydro-1,2,4-triazine-6-carboxamide in an aspect of the invention.

This example describes the synthesis of N-(4-((2-amino-3-(3-(piperidin-4-yl)prop-1-yn-1-yl)pyridin-4-yl)oxy)-3-fluorophenyl)-4-(4-fluorophenyl)-2-methyl-3,5-dioxo-2,3,4,5-tetrahydro-1,2,4-triazine-6-carboxamide in an aspect of the invention. See FIG. 43.

Step A: tert-butyl 4-(3-(2-amino-4-(2-fluoro-4-(4-(4-fluorophenyl)-2-methyl-3,5-dioxo-2,3,4,5-tetrahydro-1,2,4-triazine-6-carboxamido)phenoxy)pyridin-3-yl)prop-2-yn-1-yl)piperidine-1-carboxylate

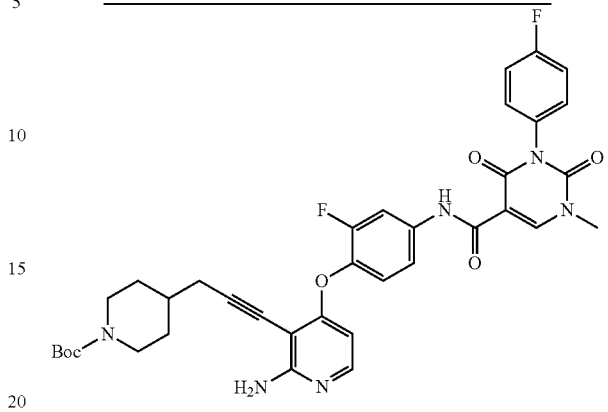

A mixture of N-(4-((2-amino-3-iodopyridin-4-yl)oxy)-3-fluorophenyl)-4-(4-fluorophenyl)-2-methyl-3,5-dioxo-2,3,4,5-tetrahydro-1,2,4-triazine-6-carboxamide (intermediate 20, 75.0 mg, 0.13 mmol), tert-butyl 4-(prop-2-yn-1-yl)piperidine-1-carboxylate (56.0 mg, 0.25 mmol), copper(I) iodide (4.82 mg, 0.02 mmol), and TEA (69.0 μL, 0.51 mmol) in DMF (1 mL) was degassed with $N_2$. To reaction mixture was added Pd(PPh$_3$)$_4$ (15.0 mg, 0.01 mmol) and stirred for overnight at 90° C. After being cooled at room temperature, the reaction mixture was extracted with EtOAc, washed with brine, dried over $Na_2SO_4$, filtered and concentrated in vacuo. The residue was purified by MPLC (EtOAc only) to afford the tert-butyl 4-(3-(2-amino-4-(2-fluoro-4-(4-(4-fluorophenyl)-2-methyl-3,5-dioxo-2,3,4,5-tetrahydro-1,2,4-triazine-6-carboxamido)phenoxy)pyridin-3-yl)prop-2-yn-1-yl)piperidine-1-carboxylate (17.0 mg, 19%) as a yellow solid. $^1$H-NMR (CDCl$_3$, Varian, 400 MHz): δ 1.43 (9H, s), 1.62 (3H, m), 1.78 (2H, d, J=12 Hz), 2.43 (2H, d, J=6 Hz), 2.69 (2H, brs), 3.92 (3H, s), 4.09 (2H, brs), 5.10 (2H, brs), 6.01 (1H, d, J=5.6 Hz), 7.08-7.12 (1H, m), 7.24-7.26 (1H, m), 7.26-7.28 (4H, m), 7.80 (1H, d, J=5.6 Hz), 7.86 (1H, dd, J=12, 2.8 Hz), 10.83 (1H, s).

Step B: N-(4-((2-amino-3-(3-(piperidin-4-yl)prop-1-yn-1-yl)pyridin-4-yl)oxy)-3-fluorophenyl)-1-(2-(dimethylamino)-2-oxoethyl)-3-(4-fluorophenyl)-2,4-dioxo1,2,3,4-tetrahydropyrimidine-5-carboxamide

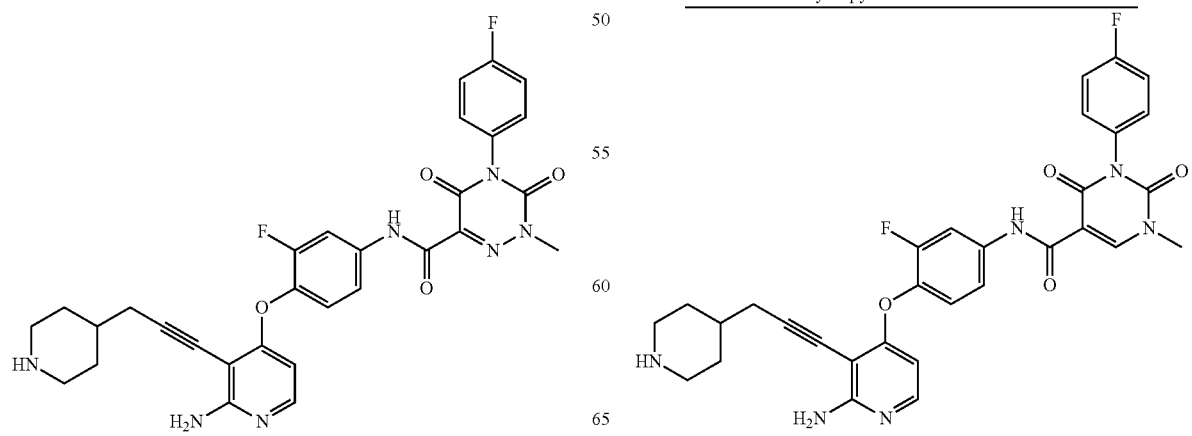

To a solution of tert-butyl 4-(3-(2-amino-4-(2-fluoro-4-(4-(4-fluorophenyl)-2-methyl-3,5-dioxo-2,3,4,5-tetrahydro-1,2,4-triazine-6-carboxamido)phenoxy)pyridin-3-yl)prop-2-yn-1-yl)piperidine-1-carboxylate (17.0 mg, 0.02 mmol) in DCM (1 mL) was added TFA (20.0 µL, 0.25 mmol) at room temperature. The reaction mixture was stirred for overnight at room temperature. The reaction mixture was concentrated in vacuo. The residue was diluted with DCM, and then neutralized with TEA. The mixture was stirred for 10 min at room temperature and concentrated in vacuo. The residue was purified by column chromatography on NH—SiO$_2$ (EtOAc/MeOH=9/1) to afford the N-(4-((2-amino-3-(3-(piperidin-4-yl)prop-1-yn-1-yl)pyridin-4-yl)oxy)-3-fluorophenyl)-4-(4-fluorophenyl)-2-methyl-3,5-dioxo-2,3,4,5-tetrahydro-1,2,4-triazine-6-carboxamide (5.9 mg, 38%) as a yellow solid. $^1$H-NMR (CD$_3$OD, Varian, 400 MHz): δ 1.29-1.38 (3H, m), 1.72 (1H, m), 1.84-1.91 (2H, m), 2.47 (2H, d, J=6.8 Hz), 2.62-2.69 (2H, m), 3.10 (2H, d, J=12 Hz), 3.79 (3H, s), 6.02 (1H, d, J=5.6 Hz), 7.16-7.20 (1H, m), 7.26-7.30 (2H, m), 7.35-7.41 (3H, m), 7.72 (1H, d, J=6 Hz), 7.90 (1H, dd, J=12.4, 2.4 Hz). * amide NH, NH$_2$ peak was not observed.

Example 47

Figure 44:
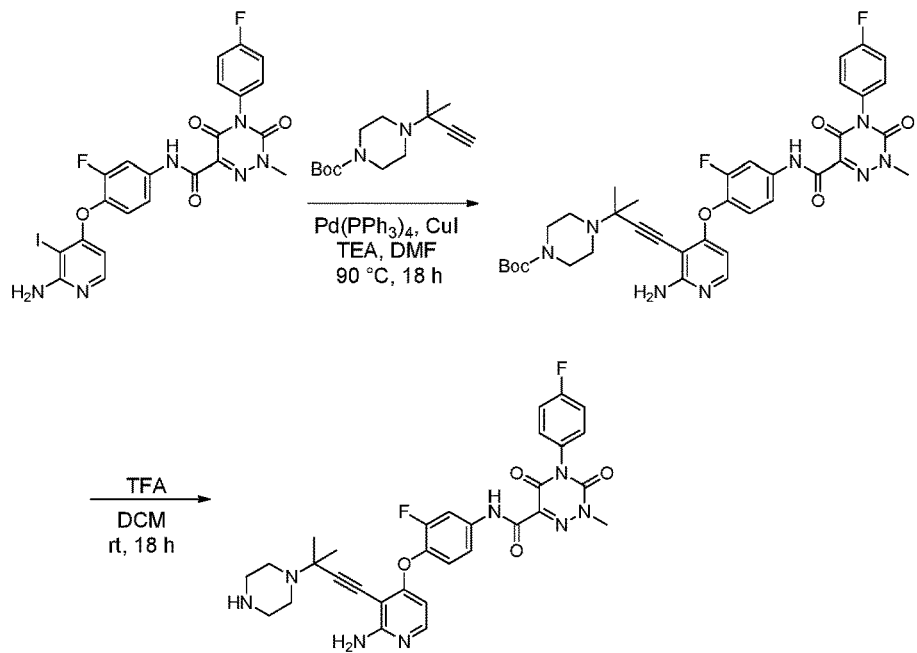
FIG. 44 is a chemical synthesis of N-(4-(2-amino-3-(3-methyl-3-(piperazin-1-yl)but-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide in an aspect of the invention.

This example describes the synthesis of N-(4-(2-amino-3-(3-methyl-3-(piperazin-1-yl)but-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide in an aspect of the invention. See FIG. 44.

Step A: tert-butyl 4-(4-(2-amino-4-(2-fluoro-4-(4-(4-fluorophenyl)-2-methyl-3,5-dioxo-2,3,4,5-tetrahydro-1,2,4-triazine-6-carboxamide)pyridin-3-yl)-2-methylbut-3-yn-2yl)piperazine-1-carboxylate

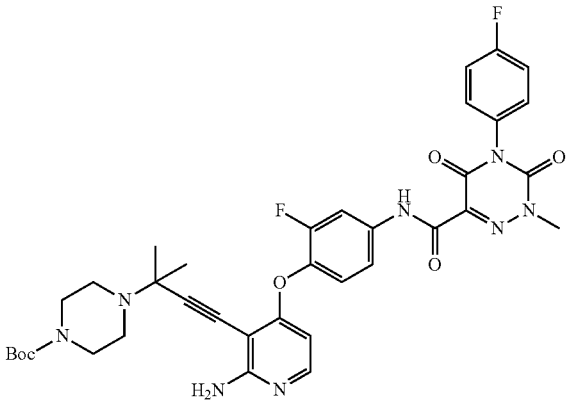

To a solution of N-(4-((2-amino-3-iodopyridin-4-yl)oxy)-3-fluorophenyl)-4-(4-fluorophenyl)-2-methyl-3,5-dioxo-2,3,4,5-tetrahydro-1,2,4-triazine-6-carboxamide (Intermediate 20, 100 mg, 0.17 mmol) in DMF (3.4 mL) were added tert-butyl 4-(2-methylbut-3-yn-2-yl)piperazine-1-carboxylate (43.0 mg, 0.17 mmol), copper(I) iodide (6.43 mg, 0.03 mmol) and TEA (92.0 µL, 0.68 mmol) at room temperature. The mixture was degassed by purging and re-filled with Ar in several times. After addition of Pd(PPh$_3$)$_4$ (20.0 mg, 0.02 mmol), the reaction mixture was heated at 90° C. for 18 hours. After cooled to room temperature, the reaction mixture was quenched with water and extracted with EtOAc. The organic layer was dried over Na$_2$SO$_4$, filtered, and concentrated in vacuo. The residue was purified by column chromatography on NH—SiO$_2$ (EtOAc only) to give the tert-butyl 4-(4-(2-amino-4-(2-fluoro-4-(4-(4-fluorophenyl)-2-methyl-3,5-dioxo-2,3,4,5-tetrahydro-1,2,4-triazine-6-carboxamide)pyridin-3-yl)-2-methylbut-3-yn-2yl)piperazine-1-carboxylate (30.0 mg, 25%) as a yellow solid. $^1$H-NMR (DMSO-d$_6$, Varian, 400 MHz): δ 1.31 (9H, s), 1.36 (6H, s), 2.44-2.50 (4H, m), 3.27 (4H, s), 3.67 (3H, s), 5.95 (1H, d, J=5.6 Hz), 6.13 (2H, s), 7.22 (1H, t, J=9.0 Hz), 7.35-7.39 (4H, s), 7.46 (1H, d, J=8.8 Hz), 7.79 (1H, d, J=6.0 Hz), 7.85 (1H, d, J=12.4 Hz), 10.8 (1H, s).

Step B: N-(4-(2-amino-3-(3-methyl-3-(piperazin-1-yl)but-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide

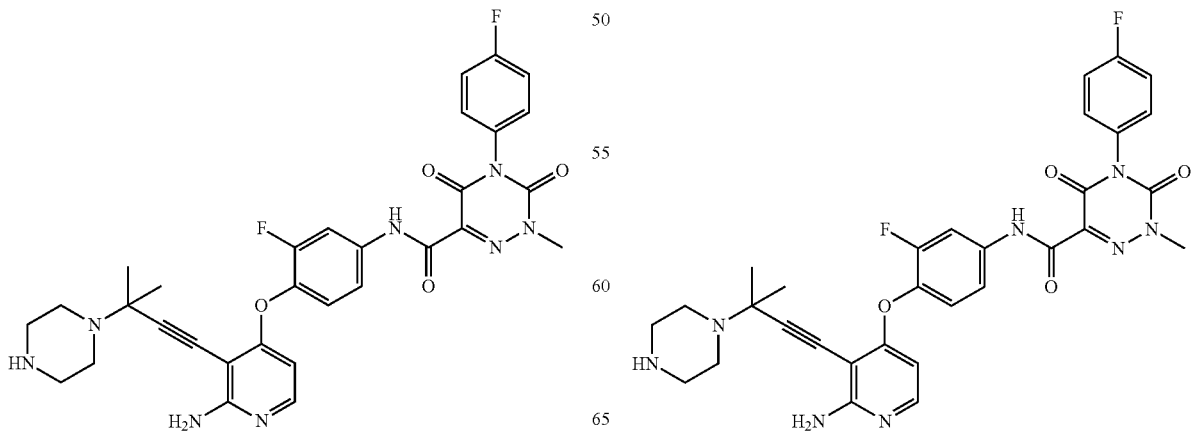

To a solution of tert-butyl 4-(4-(2-amino-4-(2-fluoro-4-(4-(4-fluorophenyl)-2-methyl-3,5-dioxo-2,3,4,5-tetrahydro-1,2,4-triazine-6-carboxamide)pyridin-3-yl)-2-methylbut-3-yn-2-yl)piperazine-1-carboxylate (30.0 mg, 0.04 mmol) in DCM (1 mL) was added TFA (32.0 µL, 0.42 mmol) at room temperature. The reaction mixture was stirred for 18 hours at room temperature. After cooled to 0° C., the reaction mixture was quenched with sat. NaHCO$_3$ solution and extracted with DCM. The organic layer was dried over Na$_2$SO$_4$, filtered and concentrated in vacuo. The residue was triturated with DCM and Hexanes. The resulted solid was collected by filtration and dried under vacuum afford the N-(4-(2-amino-3-(3-methyl-3-(piperazin-1-yl)but-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide (19.3 mg, 75%) as a yellow solid. $^1$H-NMR (DMSO-d$_6$, Varian, 400 MHz): δ 1.32 (6H, s), 2.42-2.48 (4H, m), 2.69 (4H, s), 3.67 (3H, s), 5.99 (1H, d, J=5.6 Hz), 6.11 (2H, s), 7.22 (1H, t, J=8.8 Hz), 7.39-7.34 (4H, m), 7.47 (1H, d, J=9.2 Hz), 7.80 (1H, d, J=5.6 Hz), 7.86 (1H, d, J=12.8 Hz), 10.8 (1H, s). * NH peak was not observed.

Example 48

Figure 45:
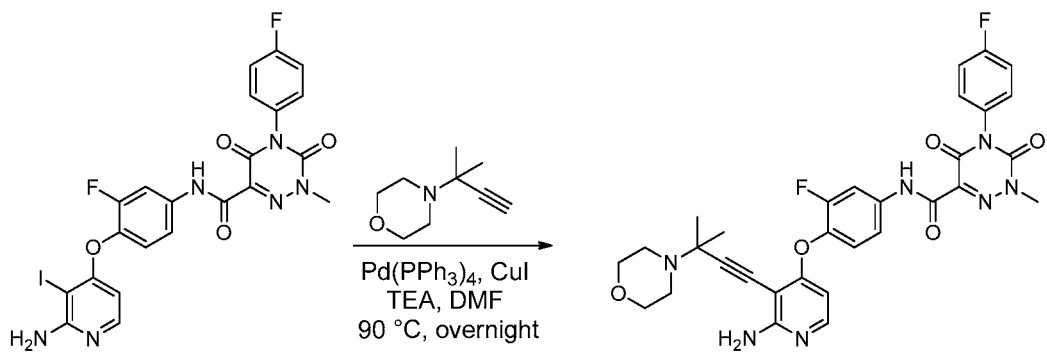
FIG. 45 is a chemical synthesis of N-(4-(2-amino-3-(3-methyl-3-morpholinobut-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide in an aspect of the invention.

This example describes the synthesis of N-(4-(2-amino-3-(3-methyl-3-morpholinobut-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide in an aspect of the invention. See FIG. 45.

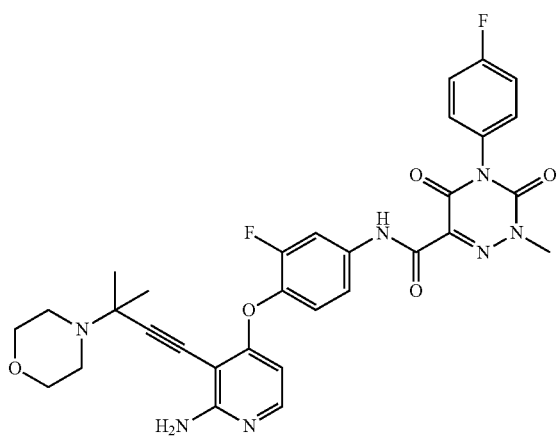 [SMILES: Cn1nc(C(=O)Nc2ccc(Oc3ccnc(N)c3C#CC(C)(C)N3CCOCC3)c(F)c2)c(=O)n(-c2ccc(F)cc2)c1=O]

A mixture of N-(4-((2-amino-3-iodopyridin-4-yl)oxy)-3-fluorophenyl)-4-(4-fluorophenyl)-2-methyl-3,5-dioxo-2,3,4,5-tetrahydro-1,2,4-triazine-6-carboxamide (intermediate 20, 50.0 mg, 0.08 mmol), 4-(2-methylbut-3-yn-2-yl)morpholine (19.43 mg, 0.13 mmol), copper(I) iodide (3.22 mg, 0.02 mmol), and TEA (46.0 µL, 0.34 mmol) in DMF (1 mL) was degassed with N$_2$. To reaction mixture was added Pd(PPh$_3$)$_4$ (9.77 mg, 8.46 mol) and stirred for overnight at 90° C. After being cooled at room temperature, the reaction mixture was extracted with EtOAc, washed with brine, dried over Na$_2$SO$_4$, filtered and concentrated in vacuo. The residue was purified by column chromatography on SiO$_2$ (EtOAc/MeOH=9/1) to afford the N-(4-(2-amino-3-(3-methyl-3-morpholinobut-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide (8.0 mg, 15%) as a brown solid. $^1$H-NMR (CDCl$_3$, Varian, 400 MHz): δ 1.45 (6H, s), 2.66 (4H, m), 3.71-3.74 (4H, m), 3.93 (3H, s), 5.05 (2H, s), 6.05 (1H, d, J=6.0 Hz), 7.10 (1H, t, J=8.4 Hz), 7.25-7.29 (5H, m), 7.83-7.85 (2H, m), 10.80 (1H, s).

Example 49

Figure 46:
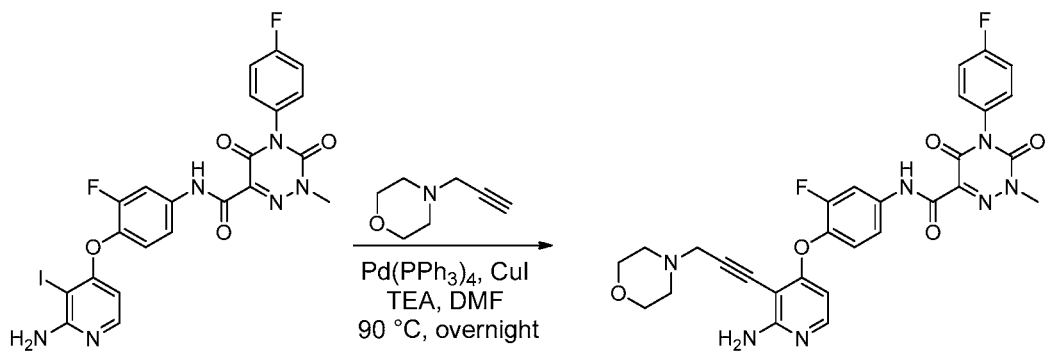
FIG. 46 is a chemical synthesis of N-(4-(2-amino-3-(3-morpholinoprop-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide in an aspect of the invention.

This example describes the synthesis of N-(4-(2-amino-3-(3-morpholinoprop-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide in an aspect of the invention. See FIG. 46.

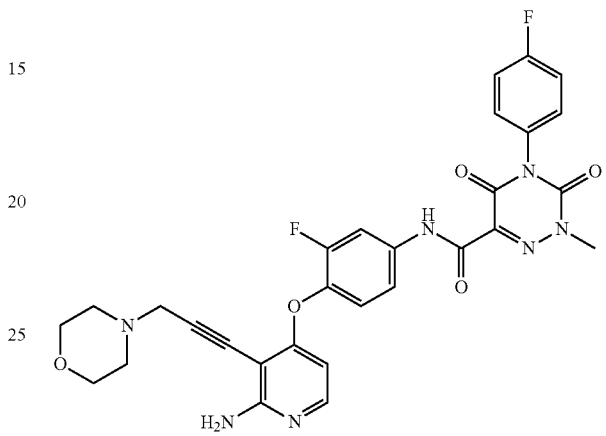

A mixture of N-(4-((2-amino-3-iodopyridin-4-yl)oxy)-3-fluorophenyl)-4-(4-fluorophenyl)-2-methyl-3,5-dioxo-2,3,4,5-tetrahydro-1,2,4-triazine-6-carboxamide (intermediate 20, 50.0 mg, 0.08 mmol), 4-(prop-2-yn-1-yl)morpholine (15.88 mg, 0.13 mmol), copper(I) iodide (3.22 mg, 0.02 mmol), and TEA (46.0 µL, 0.34 mmol) in DMF (1 mL) was degassed with N$_2$. To reaction mixture was added Pd(PPh$_3$)$_4$ (9.77 mg, 8.46 µmol) and stirred for overnight at 90° C. After being cooled at room temperature, the reaction mixture was extracted with EtOAc, washed with brine, dried over Na$_2$SO$_4$, filtered and concentrated in vacuo. The residue was purified by column chromatography on NH—SiO$_2$ (EA only to EA/MeOH=97/3) to afford the N-(4-(2-amino-3-(3-morpholinoprop-1-ynyl)pyridin-4-yloxy)-3-fluorophenyl)-4-(4-fluorophenyl)-2-methyl-3,5-dioxo-2,3,4,5-tetrahydro-1,2,4-triazine-6-carboxamide (4.9 mg, 10%) as a yellow solid. $^1$H-NMR (CDCl$_3$, Varian, 400 MHz): δ 2.62 (4H, m), 3.60 (2H, s), 3.75 (4H, m), 3.93 (3H, s), 5.07 (2H, s), 5.98 (1H, d, J=6.4 Hz), 7.13 (1H, t, J=8.6 Hz), 7.25-7.28 (5H, m), 7.83-7.86 (2H, m), 10.82 (1H, s).

Example 50

Figure 47:
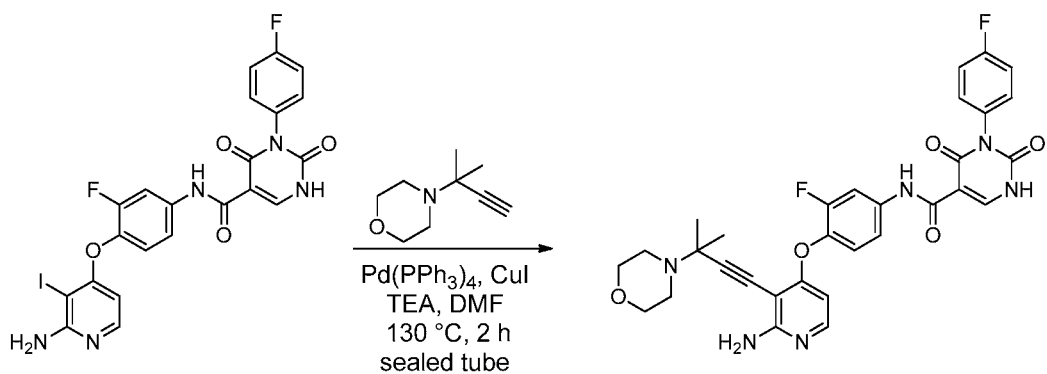
FIG. 47 is a chemical synthesis of N-(4-(2-amino-3-(3-methyl-3-morpholinobut-1-ynyl)pyridin-4-yloxy)-3-fluorophenyl)-3-(4-fluorophenyl)-2,4-dioxo-1,2,3,4-tetrahydropyrimidine-5-carboxamide in an aspect of the invention.

This example describes the synthesis of N-(4-(2-amino-3-(3-methyl-3-morpholinobut-1-ynyl)pyridin-4-yloxy)-3-fluorophenyl)-3-(4-fluorophenyl)-2,4-dioxo-1,2,3,4-tetrahydropyrimidine-5-carboxamide in an aspect of the invention. See FIG. 47.

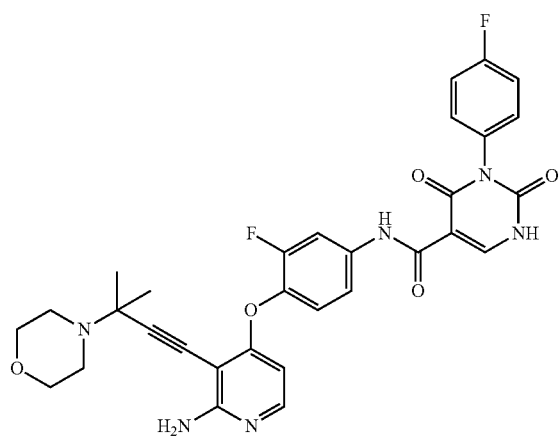 [SMILES: CC(C)(C#Cc1c(Oc2ccc(NC(=O)c3c[nH]c(=O)n(-c4ccc(F)cc4)c3=O)cc2F)ccnc1N)N1CCOCC1]

A mixture of N-(4-(2-amino-3-iodopyridin-4-yloxy)-3-fluorophenyl)-3-(4-fluorophenyl)-2,4-dioxo-1,2,3,4-tetrahydropyrimidine-5-carboxamide (intermediate 22, 100 mg, 0.17 mmol), 4-(2-methylbut-3-yn-2-yl)morpholine (39.8 mg, 0.26 mmol), copper(I) iodide (6.6 mg, 0.04 mmol) and TEA (94.0 µL, 0.69 mmol) in DMF (1 mL) was degassed with $N_2$. To reaction mixture was added $Pd(PPh_3)_4$ (20.0 mg, 0.02 mmol) and stirred for 2 h at 130° C. in sealed tube. After being cooled at room temperature, the reaction mixture was extracted with EtOAc, washed with brine, dried over $Na_2SO_4$, filtered and concentrated in vacuo. The residue was purified by column chromatography on $SiO_2$ (EtOAc/MeOH=9/1). The product was purified by prep-TLC on NH—$SiO_2$ (EtOAc/MeOH=9/1) to afford the N-(4-(2-amino-3-(3-methyl-3-morpholinobut-1-ynyl)pyridin-4-yloxy)-3-fluorophenyl)-3-(4-fluorophenyl)-2,4-dioxo-1,2,3,4-tetrahydropyrimidine-5-carboxamide (8.0 mg, 7.7%) as a yellow solid. $^1$H-NMR ($CD_3OD$, Varian, 400 MHz): δ 1.47 (6H, s), 2.72 (4H, m), 3.70 (4H, m), 6.03 (1H, d, J=6.4 Hz), 7.12 (1H, t, J=8.8 Hz), 7.20-7.29 (5H, m), 7.75 (1H, d, J=6.0 Hz), 7.85-7.88 (1H, m), 8.67 (1H, s). * Protons of amine and amides were not observed.

Example 51

Figure 48:
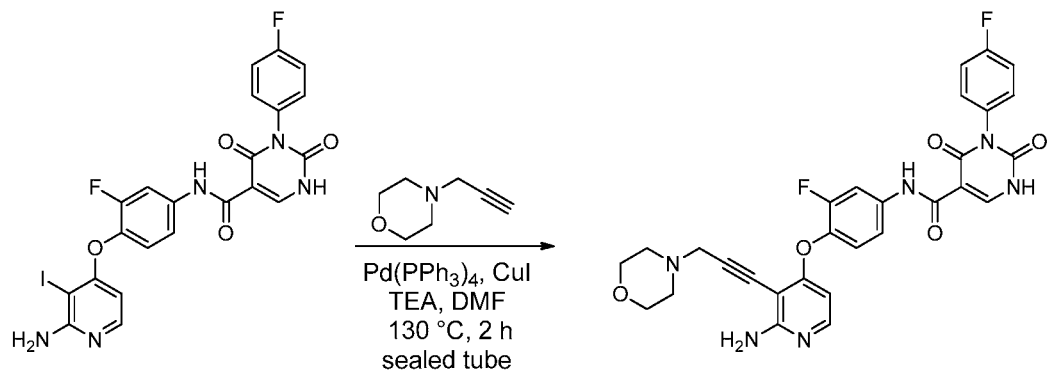
FIG. 48 is a chemical synthesis of N-(4-(2-amino-3-(3-morpholinoprop-1-ynyl)pyridin-4-yloxy)-3-fluorophenyl)-3-(4-fluorophenyl)-2,4-dioxo-1,2,3,4-tetrahydropyrimidine-5-carboxamide in an aspect of the invention.

This example describes the synthesis of N-(4-(2-amino-3-(3-morpholinoprop-1-ynyl)pyridin-4-yloxy)-3-fluorophenyl)-3-(4-fluorophenyl)-2,4-dioxo-1,2,3,4-tetrahydropyrimidine-5-carboxamide in an aspect of the invention. See FIG. 48.

A mixture of N-(4-(2-amino-3-iodopyridin-4-yloxy)-3-fluorophenyl)-3-(4-fluorophenyl)-2,4-dioxo-1,2,3,4-tetrahydropyrimidine-5-carboxamide (intermediate 22, 100 mg, 0.17 mmol), 4-(prop-2-yn-1-yl)morpholine (32.5 mg, 0.26 mmol), copper(I) iodide (6.6 mg, 0.04 mmol) and TEA (94.0 µL, 0.69 mmol) in DMF (1 mL) was degassed with $N_2$. To reaction mixture was added $Pd(PPh_3)_4$ (20.0 mg, 0.02 mmol) and stirred for 2 h at 130° C. in sealed tube. After being cooled at room temperature, the reaction mixture was extracted with EtOAc, washed with brine, dried over $Na_2SO_4$, filtered and concentrated in vacuo. The residue was purified by column chromatography on $SiO_2$ (EtOAc/MeOH=85/15). The product was purified by prep-TLC on NH—$SiO_2$ (EtOAc/MeOH=85/15) to afford the N-(4-(2-amino-3-(3-morpholinoprop-1-ynyl)pyridin-4-yloxy)-3-fluorophenyl)-3-(4-fluorophenyl)-2,4-dioxo-1,2,3,4-tetrahydropyrimidine-5-carboxamide (5.4 mg, 5.4%) as a yellow solid. $^1$H-NMR ($CD_3OD$, Varian, 400 MHz): δ 2.65 (4H, m), 3.59 (2H, s), 3.71 (4H, m), 5.97 (1H, d, J=6.0 Hz), 7.14 (1H, t, J=8.4 Hz), 7.20-7.29 (5H, m), 7.74 (1H, d, J=6.4 Hz), 7.85-7.89 (1H, m), 8.67 (1H, s). * Protons of amine and amides were not observed.

Example 52

Figure 49:
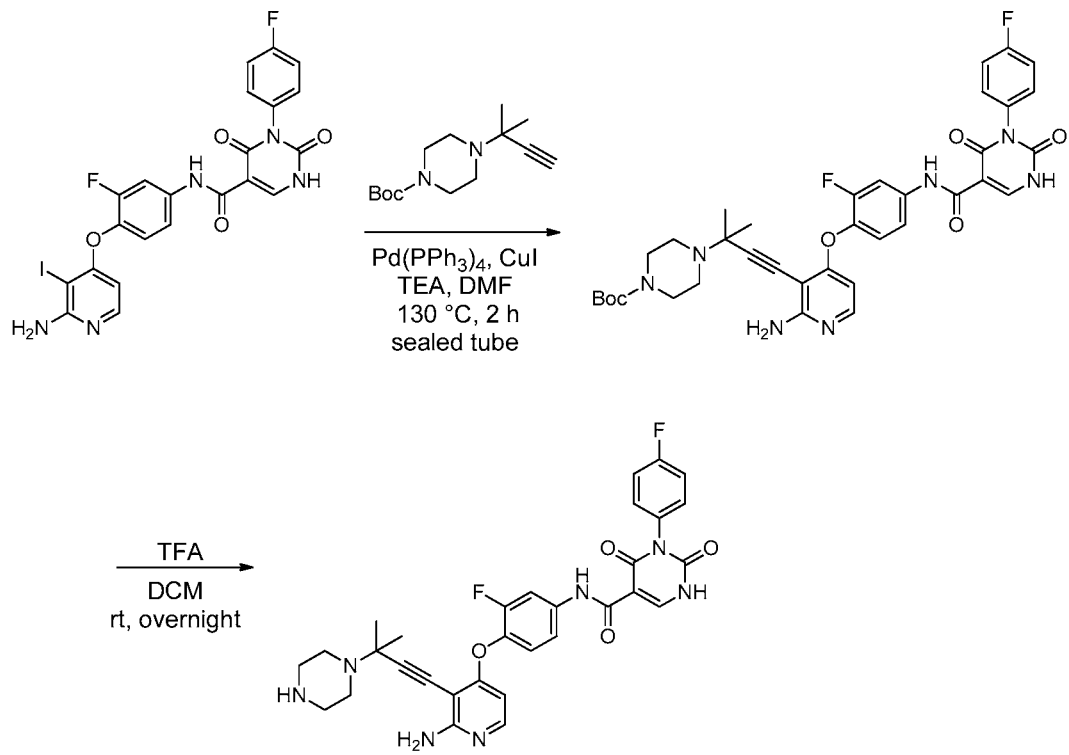
FIG. 49 is a chemical synthesis of N-(4-((2-amino-3-(3-methyl-3-(piperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention.

This example describes the synthesis of N-(4-((2-amino-3-(3-methyl-3-(piperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention. See FIG. 49.

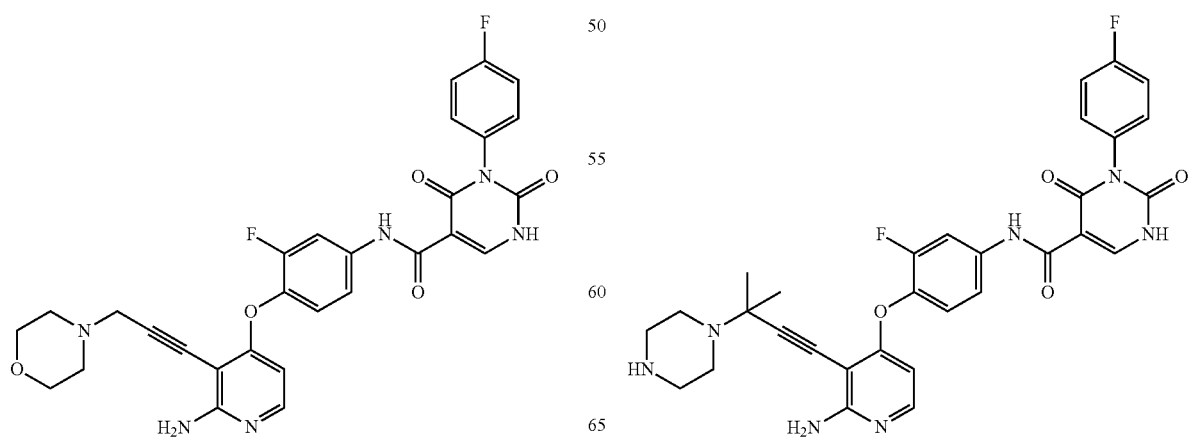

Step A: tert-butyl 4-(4-(2-amino-4-(2-fluoro-4-(3-(4-fluorophenyl)-2,4-dioxo-1,2,3,4-tetrahydropyrimidine-5-carboxamido)phenoxy)pyridin-3-yl)-2-methylbut-3-yn-2-yl)piperazine-1-carboxylate

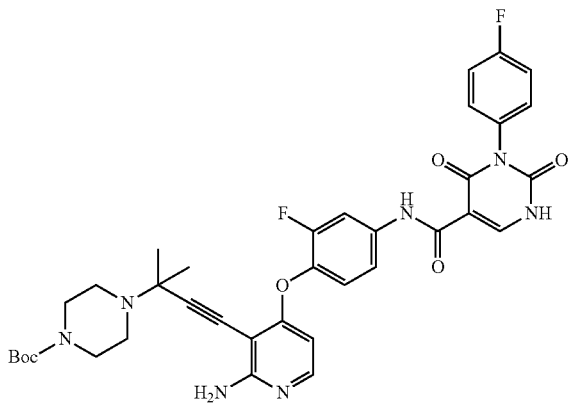

A mixture of N-(4-(2-amino-3-iodopyridin-4-yloxy)-3-fluorophenyl)-3-(4-fluorophenyl)-2,4-dioxo-1,2,3,4-tetrahydropyrimidine-5-carboxamide (intermediate 22, 200 mg, 0.35 mmol), tert-butyl 4-(2-methylbut-3-yn-2-yl)piperazine-1-carboxylate (131 mg, 0.52 mmol), copper(I) iodide (13.2 mg, 0.07 mmol), and TEA (189 µL, 1.39 mmol) in DMF (1.5 mL) was degassed with $N_2$. To reaction mixture was added $Pd(PPh_3)_4$ (40.0 mg, 0.04 mmol) and stirred for 2 h at 130° C. in sealed tube. After being cooled at room temperature, the reaction mixture was extracted with EtOAc, washed with brine, dried over $Na_2SO_4$, filtered and concentrated in vacuo. The residue was purified by column chromatography (EtOAc/MeOH=97/3) to afford the tert-butyl 4-(4-(2-amino-4-(2-fluoro-4-(3-(4-fluorophenyl)-2,4-dioxo-1,2,3,4-tetrahydropyrimidine-5-carboxamido)phenoxy)pyridin-3-yl)-2-methylbut-3-yn-2-yl)piperazine-1-carboxylate (25.5 mg, 10%) as a yellow solid. $^1$H-NMR (CD$_3$OD, Varian, 400 MHz): δ 1.40 (9H, s), 1.48 (6H, s), 2.67 (4H, m), 3.42 (4H, m), 6.03 (1H, d, J=6.0 Hz), 7.13 (1H, t, J=8.4 Hz), 7.23-7.25 (3H, m), 7.32-7.35 (2H, m), 7.75 (1H, d, J=6.4 Hz), 7.87-7.90 (1H, m), 8.53 (1H, s). * Protons of amine and amides were not observed.

Step B: N-(4-(2-amino-3-(3-methyl-3-(piperazin-1-yl)but-1-ynyl)pyridin-4-yloxy)-3-fluorophenyl)-3-(4-fluorophenyl)-2,4-dioxo-1,2,3,4-tetrahydropyrimidine-5-carboxamide

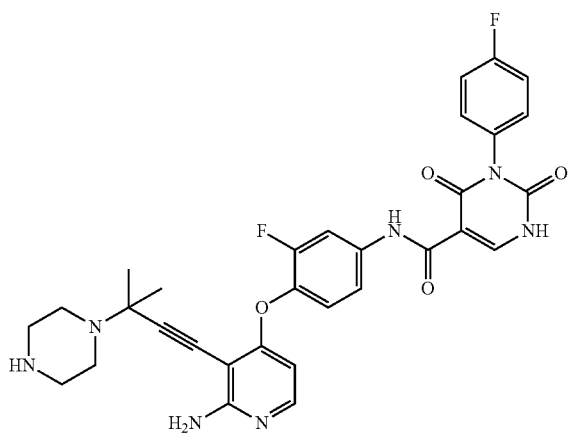 [SMILES: CC(C)(C#Cc1c(Oc2ccc(NC(=O)c3c[nH]c(=O)n(-c4ccc(F)cc4)c3=O)cc2F)ccnc1N)N1CCNCC1]

To a solution of tert-butyl 4-(4-(2-amino-4-(2-fluoro-4-(3-(4-fluorophenyl)-2,4-dioxo-1,2,3,4-tetrahydropyrimidine-5-carboxamido)phenoxy)pyridin-3-yl)-2-methylbut-3-yn-2-yl)piperazine-1-carboxylate (25.5 mg, 0.04 mmol) in DCM (1 mL) was added TFA (56.0 L, 0.73 mmol) at room temperature. The reaction mixture was stirred for overnight at room temperature. The reaction mixture was concentrated in vacuo. The residue was diluted with DCM, and then neutralized with TEA. The mixture was stirred for 10 min at room temperature and concentrated in vacuo. The residue was purified by prep-TLC on NH—SiO$_2$ (EtOAc/MeOH=9/1) to afford the N-(4-(2-amino-3-(3-methyl-3-(piperazin-1-yl)but-1-ynyl)pyridin-4-yloxy)-3-fluorophenyl)-3-(4-fluorophenyl)-2,4-dioxo-1,2,3,4-tetrahydropyrimidine-5-carboxamide (7.8 mg, 35%) as a yellow solid. $^1$H-NMR (CD$_3$OD, Varian, 400 MHz): δ 1.49 (6H, s), 2.88 (4H, m), 3.13 (4H, m), 6.04 (1H, d, J=6.0 Hz), 7.11 (1H, t, J=8.8 Hz), 7.23-7.30 (5H, m), 7.76 (1H, d, J=5.6 Hz), 7.88-7.89 (1H, m), 8.63 (1H, s). * Protons of amines and amides were not observed.

Example 53

Figure 50:
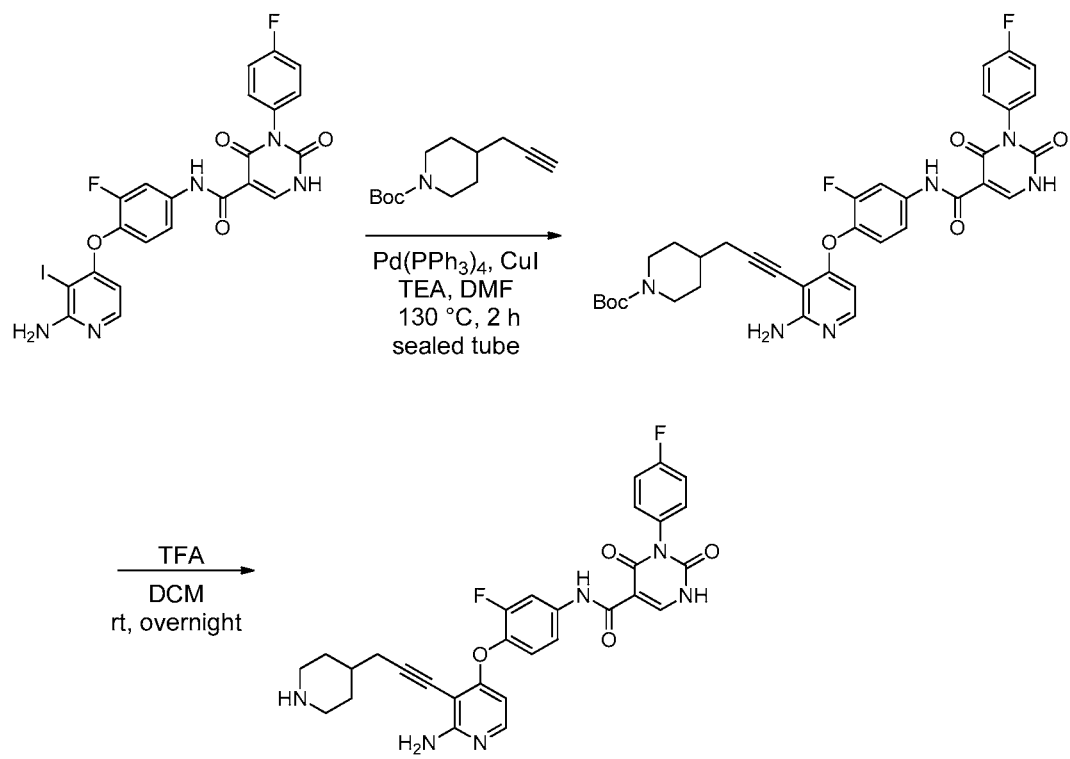
FIG. 50 is a chemical synthesis of N-(4-(2-amino-3-(3-(piperidin-4-yl)prop-1-ynyl)pyridin-4-yloxy)-3-fluorophenyl)-3-(4-fluorophenyl)-2,4-dioxo-1,2,3,4-tetrahydropyrimidine-5-carboxamide in an aspect of the invention.

This example describes the synthesis of N-(4-(2-amino-3-(3-(piperidin-4-yl)prop-1-ynyl)pyridin-4-yloxy)-3-fluorophenyl)-3-(4-fluorophenyl)-2,4-dioxo-1,2,3,4-tetrahydropyrimidine-5-carboxamide in an aspect of the invention. See FIG. 50.

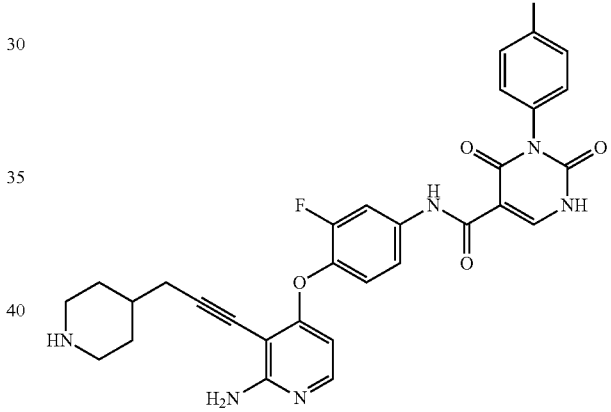

Step A: tert-butyl 4-(3-(2-amino-4-(2-fluoro-4-(3-(4-fluorophenyl)-2,4-dioxo-1,2,3,4-tetrahydropyrimidine-5-carboxamido)phenoxy)pyridin-3-yl)prop-2-ynyl)piperdine-1-carboxylate

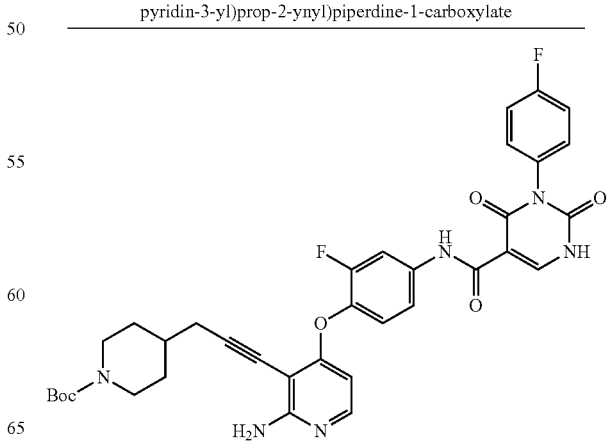

A mixture of N-(4-(2-amino-3-iodopyridin-4-yloxy)-3-fluorophenyl)-3-(4-fluorophenyl)-2,4-dioxo-1,2,3,4-tetrahydropyrimidine-5-carboxamide (intermediate 22, 200 mg, 0.35 mmol), tert-butyl 4-(prop-2-yn-1-yl)piperidine-1-carboxylate (116 mg, 0.52 mmol), copper(I) iodide (13.2 mg, 0.07 mmol), and TEA (0.19 mL, 1.39 mmol) in DMF (2 mL) was degassed with N$_2$. To reaction mixture was added Pd(PPh$_3$)$_4$ (40.0 mg, 0.04 mmol) and stirred for 2 h at 130° C. in sealed tube. After being cooled at room temperature, the reaction mixture was extracted with EtOAc, washed with brine, dried over Na$_2$SO$_4$, filtered and concentrated in vacuo. The residue was purified by column chromatography on SiO$_2$ (EtOAc only to EtOAc/MeOH=97/3) to afford the tert-butyl 4-(3-(2-amino-4-(2-fluoro-4-(3-(4-fluorophenyl)-2,4-dioxo-1,2,3,4-tetrahydropyrimidine-5-carboxamido)phenoxy)pyridin-3-yl)prop-2-ynyl)piperidine-1-carboxylate (77.9 mg, 33%) as a yellow solid. $^1$H-NMR (CD$_3$OD, Varian, 400 MHz): δ 1.16-1.26 (2H, m), 1.42 (9H, s), 1.72 (1H, brs), 1.80 (2H, d, J=13.2 Hz), 2.46 (2H, d, J=6.4 Hz), 2.72 (2H, brs), 4.03-4.10 (2H, m), 6.01 (1H, d, J=6.0 Hz), 7.125 (1H, t, J=8.6 Hz), 7.23-7.33 (5H, m), 7.72 (1H, m), 7.86-7.90 (1H, d, J=12.4 Hz), 8.54 (1H, s). * Protons of amine and amides were not observed.

Step B: N-(4-(2-amino-3-(3-(piperidin-4-yl)prop-1-ynyl)pyridin-4-yloxy)-3-fluorophenyl)-3-(4-fluorophenyl)-2,4-dioxo-1,2,3,4-tetrahydropyrimidine-5-carboxamide

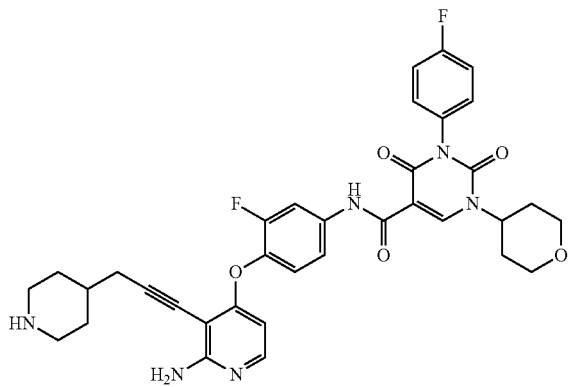

To a solution of tert-butyl 4-(3-(2-amino-4-(2-fluoro-4-(3-(4-fluorophenyl)-2,4-dioxo-1,2,3,4-tetrahydropyrimidine-5-carboxamido)phenoxy)pyridin-3-yl)prop-2-ynyl)piperidine-1-carboxylate (77.9 mg, 0.12 mmol) in DCM (1 mL) was added TFA (0.18 mL, 2.32 mmol) at room temperature. The reaction mixture was stirred for overnight at room temperature. The residue was diluted with DCM, and then neutralized with TEA. The mixture was stirred for 10 min at room temperature and concentrated in vacuo. The residue was purified by prep-TLC on SiO$_2$ (EtOAc/MeOH=4/1). The product was washed with water and extracted with EtOAc. The organic layer was concentrated in vacuo. The residue was dissolved in MeOH. Solid was removed and filtrate was concentrated in vacuo and dried under vacuum to afford the N-(4-(2-amino-3-(3-(piperidin-4-yl)prop-1-ynyl)pyridin-4-yloxy)-3-fluorophenyl)-3-(4-fluorophenyl)-2,4-dioxo-1,2,3,4-tetrahydropyrimidine-5-carboxamide (2.5 mg, 4%) as a yellow solid. $^1$H-NMR (CD$_3$OD, Varian, 400 MHz): δ 1.51-1.58 (2H, m), 1.93 (1H, m), 2.06-2.10 (2H, m), 2.58 (2H, d, J=6.4 Hz), 2.96-3.03 (2H, m), 3.37-3.40 (2H, m), 6.07 (1H, d, J=6.0 Hz), 7.18 (1H, t, J=8.8 Hz), 7.24-7.37 (5H, m), 7.73-7.75 (1H, m), 7.88-7.92 (1H, m), 8.52 (1H, s). * Protons of amine and amides were not observed.

Example 54

Figure 51:
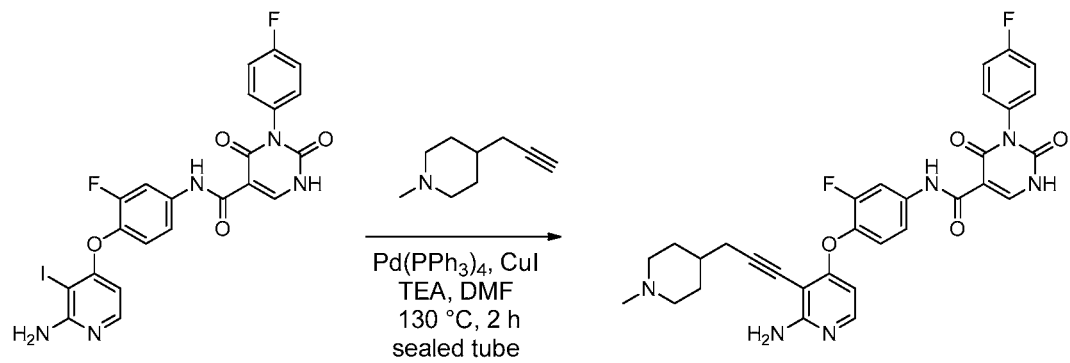
FIG. 51 is a chemical synthesis of N-(4-(2-amino-3-(3-(1-methylpiperidin-4-yl)prop-1-ynyl)pyridin-4-yloxy)-3-fluorophenyl)-3-(4-fluorophenyl)-2,4-dioxo-1,2,3,4-tetrahydropyrimidine-5-carboxamide in an aspect of the invention.

This example describes the synthesis of N-(4-(2-amino-3-(3-(1-methylpiperidin-4-yl)prop-1-ynyl)pyridin-4-yloxy)-3-fluorophenyl)-3-(4-fluorophenyl)-2,4-dioxo-1,2,3,4-tetrahydropyrimidine-5-carboxamide in an aspect of the invention. See FIG. 51.

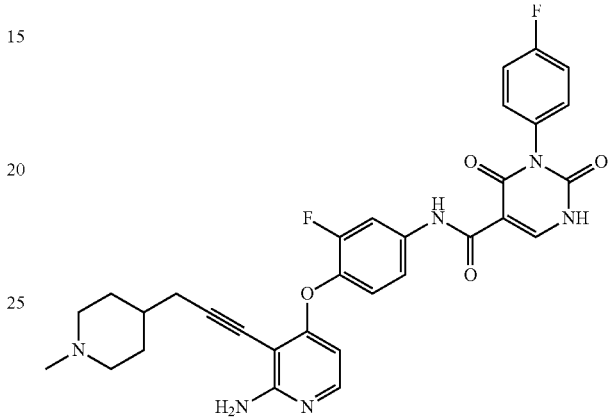

A mixture of N-(4-(2-amino-3-iodopyridin-4-yloxy)-3-fluorophenyl)-3-(4-fluorophenyl)-2,4-dioxo-1,2,3,4-tetrahydropyrimidine-5-carboxamide (intermediate 22, 100 mg, 0.17 mmol), 1-methyl-4-(prop-2-yn-1-yl)piperidine hydrochloride (45.0 mg, 0.26 mmol), copper(I) iodide (6.6 mg, 0.04 mmol), and TEA (94.0 μL, 0.70 mmol) in DMF (1 mL) was degassed with N$_2$. To reaction mixture was added Pd(PPh$_3$)$_4$ (20.0 mg, 0.02 mmol) and stirred for 2 h at 130° C. in a sealed tube. After being cooled at room temperature, the reaction mixture was extracted with EtOAc, washed with brine, dried over Na$_2$SO$_4$, filtered and concentrated in vacuo. The residue was purified by prep-TLC on NH—SiO$_2$ (EtOAc/MeOH=4/1). The product was purified by prep-TLC on SiO$_2$ (MeOH only) to afford the N-(4-(2-amino-3-(3-(1-methylpiperidin-4-yl)prop-1-ynyl)pyridin-4-yloxy)-3-fluorophenyl)-3-(4-fluorophenyl)-2,4-dioxo-1,2,3,4-tetrahydropyrimidine-5-carboxamide (1.8 mg, 1.7%) as a white solid. $^1$H-NMR (CD$_3$OD, Varian, 400 MHz): δ 1.44-1.54 (2H, m), 1.61-1.68 (1H, m), 1.92-1.96 (2H, m), 2.43-2.51 (7H, m), 3.12-3.15 (2H, m), 6.02 (1H, d, J=5.6 Hz), 7.08-7.12 (1H, m), 7.21-7.30 (5H, m), 7.72 (1H, d, J=5.6 Hz), 7.84-7.88 (1H, m), 8.66 (1H, s). * Protons of amine and amides were not observed.

Example 55

Figure 52:
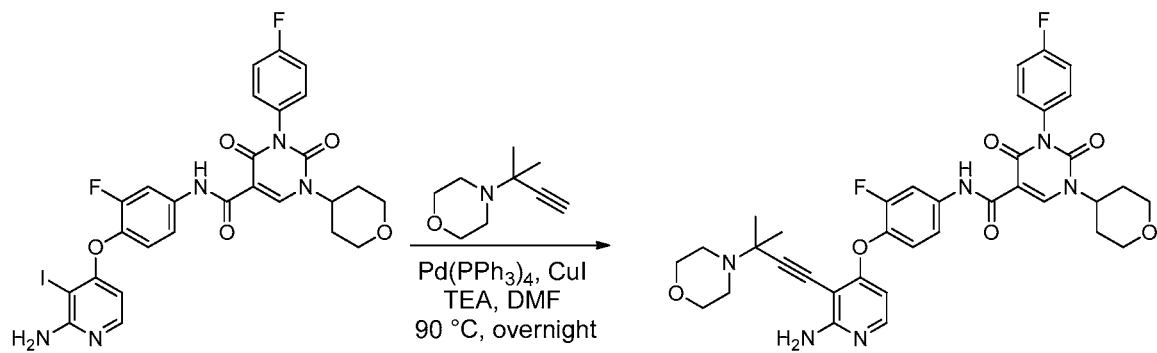
FIG. 52 is a chemical synthesis of N-(4-(2-amino-3-(3-methyl-3-morpholinobut-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention.

This example describes the synthesis of N-(4-(2-amino-3-(3-methyl-3-morpholinobut-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention. See FIG. 52.

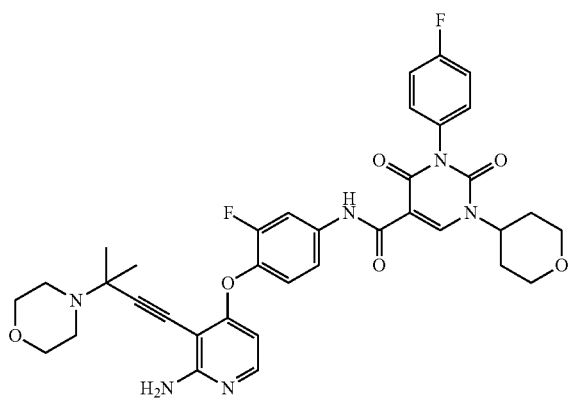 [SMILES: CC(C)(C#Cc1c(Oc2ccc(NC(=O)c3cn(C4CCOCC4)c(=O)n(-c4ccc(F)cc4)c3=O)cc2F)ccnc1N)N1CCOCC1]

A mixture of N-(4-(2-amino-3-iodopyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (intermediate 24, 50.0 mg, 0.08 mmol), 4-(2-methylbut-3-yn-2-yl)morpholine (17.0 mg, 0.11 mmol), copper(I) iodide (2.8 mg, 0.02 mmol), and TEA (41.0 μL, 0.30 mmol) in DMF (1 mL) was degassed with $N_2$. To reaction mixture was added Pd(PPh$_3$)$_4$ (8.7 mg, 7.56 μmol) and stirred for overnight at 90° C. After being cooled at room temperature, the reaction mixture was extracted with EtOAc, washed with brine, dried over $Na_2SO_4$, filtered and concentrated in vacuo. The residue was purified by column chromatography on SiO$_2$ (DCM/MeOH=95/5) to afford the N-(4-(2-amino-3-(3-methyl-3-morpholinobut-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (16.0 mg, 31%) as a yellow solid. $^1$H-NMR (CDCl$_3$, Varian, 400 MHz): δ 1.45 (6H, s), 1.95-2.05 (4H, m), 2.65-2.68 (4H, m), 3.52-3.57 (2H, m), 3.71-3.74 (4H, m), 4.14-4.18 (2H, m), 4.77-4.84 (1H, m), 5.04 (2H, s), 6.04 (1H, d, J=6.0 Hz), 7.06 (1H, t, J=8.8 Hz), 7.19-7.20 (1H, m), 7.24-7.25 (4H, m), 7.78-7.83 (2H, m), 8.68 (1H, s), 10.83 (1H, s).

Example 56

Figure 53:
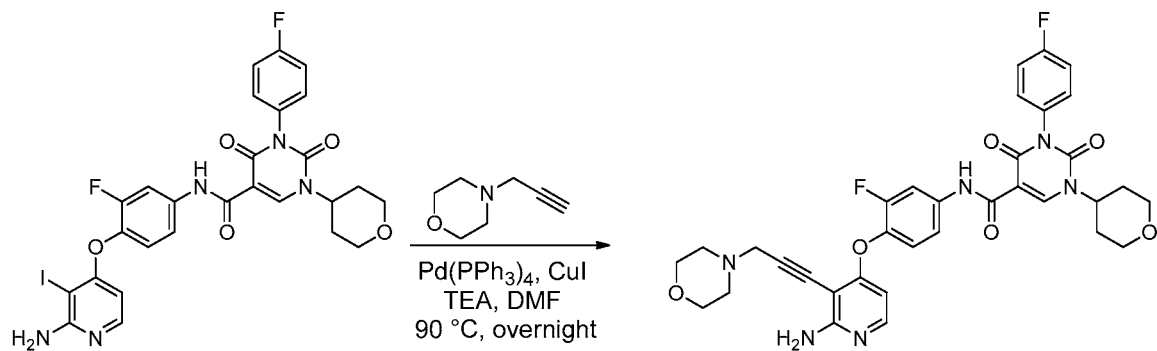
FIG. 53 is a chemical synthesis of N-(4-(2-amino-3-(3-morpholinoprop-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention.

This example describes the synthesis of N-(4-(2-amino-3-(3-morpholinoprop-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention. See FIG. 53.

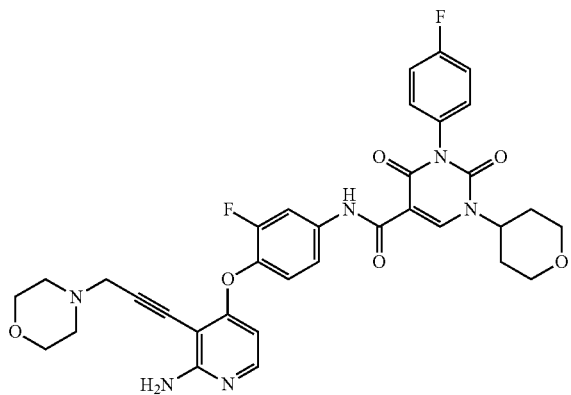 [SMILES: Nc1nccc(Oc2ccc(NC(=O)c3cn(C4CCOCC4)c(=O)n(-c4ccc(F)cc4)c3=O)cc2F)c1C#CCN1CCOCC1]

A mixture of N-(4-(2-amino-3-iodopyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (intermediate 24, 50.0 mg, 0.08 mmol), 4-(prop-2-yn-1-yl)morpholine (14.0 mg, 0.12 mmol), copper(I) iodide (2.8 mg, 0.02 mmol), and TEA (41.0 μL, 0.30 mmol) in DMF (1 mL) was degassed with $N_2$. To reaction mixture was added Pd(PPh$_3$)$_4$ (8.7 mg, 7.56 μmol) and stirred for overnight at 90° C. To a mixture was added copper(I) iodide (2.8 mg, 0.02 mmol), TEA (41.0 μL, 0.30 mmol) and Pd(PPh$_3$)$_4$ (8.7 mg, 7.56 μmol) and stirred for 7 h at 90° C. After being cooled at room temperature, the reaction mixture was diluted with EtOAc, washed with brine, dried over $Na_2SO_4$, filtered and concentrated in vacuo. The residue was purified by column chromatography on SiO$_2$ (DCM/MeOH=95/5). The product was purified by column chromatography on NH—SiO$_2$ (EtOAc only) to afford the N-(4-(2-amino-3-(3-morpholinoprop-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (18.0 mg, 37%) as a yellow solid. $^1$H-NMR (CDCl$_3$, Varian, 400 MHz): δ 1.95-2.07 (4H, m), 2.61-2.64 (4H, m), 3.51-3.57 (2H, m), 3.60 (2H, s), 3.73-3.75 (4H, m), 4.14-4.19 (2H, m), 4.78-4.84 (1H, m), 5.07 (2H, s), 5.98 (1H, d, J=5.6 Hz), 7.09 (1H, t, J=8.4 Hz), 7.19-7.22 (1H, m), 7.24-7.25 (4H, m), 7.78-7.83 (2H, m), 8.68 (1H, s), 10.85 (1H, s).

Example 57

Figure 54:
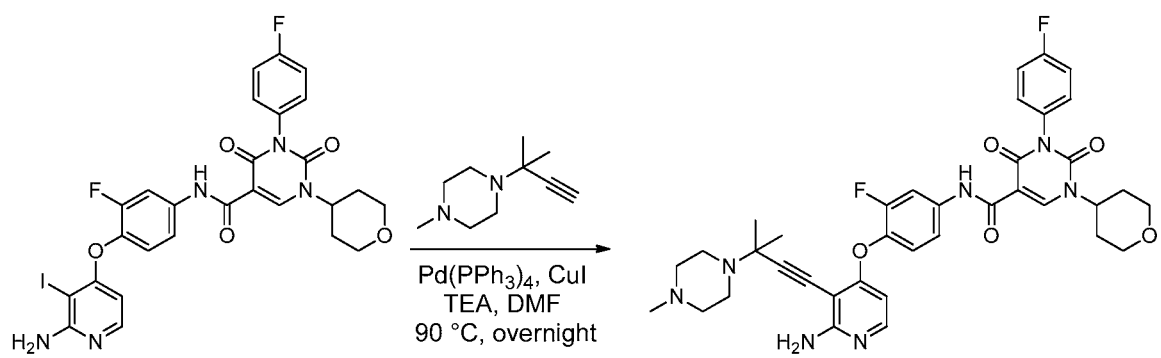
FIG. 54 is a chemical synthesis of N-(4-(2-amino-3-(3-methyl-3-(4-methylpiperazin-1-yl)but-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention.

This example describes the synthesis of N-(4-(2-amino-3-(3-methyl-3-(4-methylpiperazin-1-yl)but-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention. See FIG. 54.

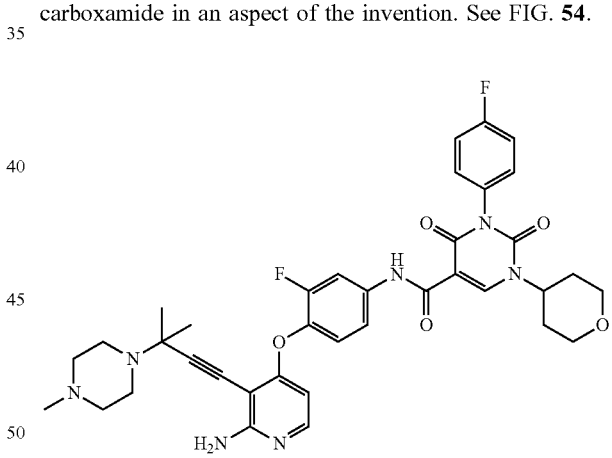

A mixture of N-(4-(2-amino-3-iodopyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (intermediate 24, 50.0 mg, 0.08 mmol), 1-methyl-4-(2-methylbut-3-yn-2-yl)piperazine (19.0 mg, 0.11 mmol), copper(I) iodide (2.88 mg, 0.02 mmol), and TEA (41.0 L, 0.30 mmol) in DMF (1 mL) was degassed with $N_2$. To reaction mixture was added Pd(PPh$_3$)$_4$ (8.7 mg, 7.56 μmol) and stirred for overnight at 90° C. After being cooled at room temperature, the reaction mixture was diluted with EtOAc, washed with brine, dried over $Na_2SO_4$, filtered and concentrated in vacuo. The residue was purified by column chromatography on NH—SiO$_2$ (EtOAc only) to afford the N-(4-(2-amino-3-(3-methyl-3-(4-methylpiperazin-1-yl)but-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (16.9 mg, 32%) as a yellow solid. ¹H-NMR (CDCl₃, Varian, 400 MHz): δ 1.45 (6H, s), 1.98-2.05 (4H, m), 2.26 (3H, s), 2.48 (4H, brs), 2.73 (4H, brs), 3.52-3.57 (2H, m), 4.14-4.17 (2H, m), 4.78-4.84 (1H, m), 5.04 (2H, s), 6.01 (1H, d, J=5.6 Hz), 7.07 (1H, t, J=8.8 Hz), 7.18-7.20 (1H, m), 7.24-7.25 (4H, m), 7.77-7.81 (2H, m), 8.68 (1H, s), 10.83 (1H, s).

Example 58

Figure 55:
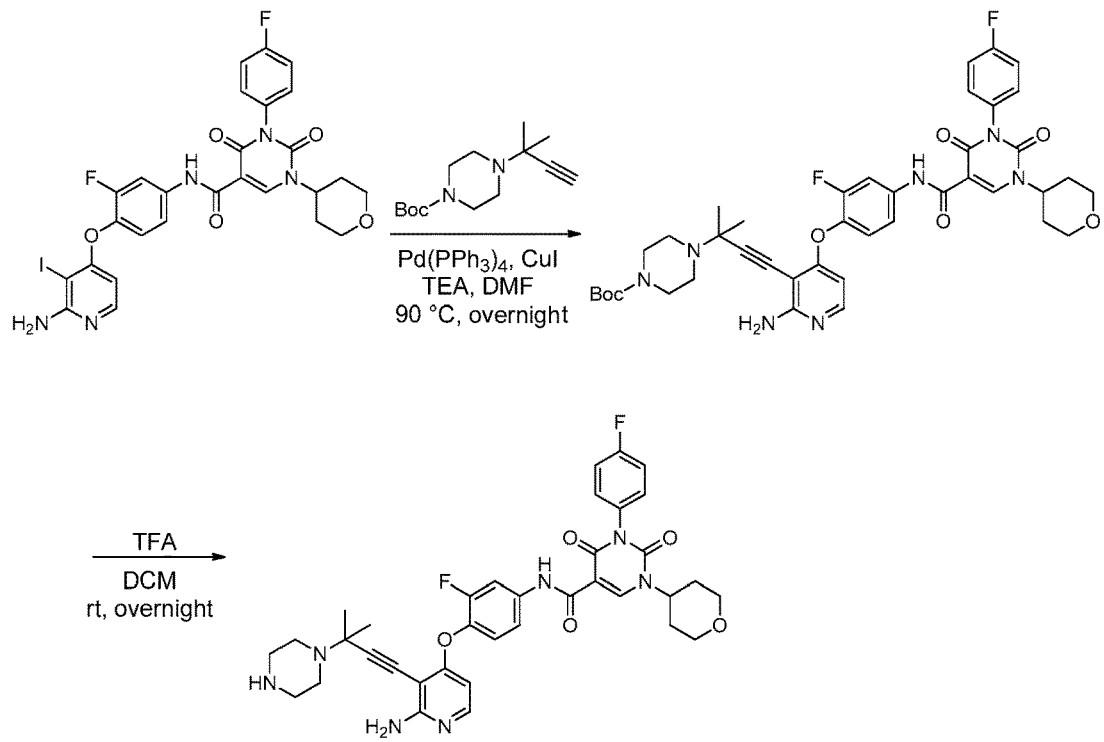
FIG. 55 is a chemical synthesis of N-(4-(2-amino-3-(3-methyl-3-(piperazin-1-yl)but-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention.

This example describes the synthesis of N-(4-(2-amino-3-(3-methyl-3-(piperazin-1-yl)but-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention. See FIG. 55.

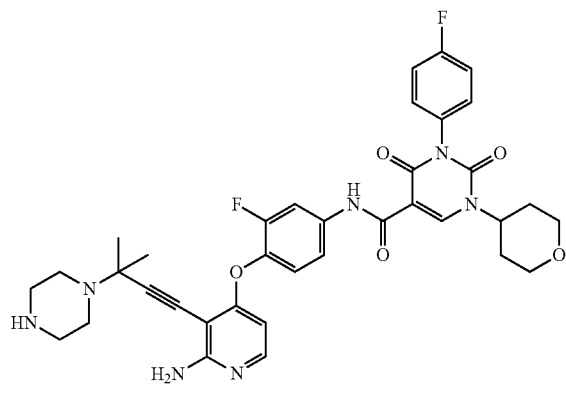 [SMILES: CC(C)(C#Cc1c(Oc2ccc(NC(=O)c3cn(C4CCOCC4)c(=O)n(-c4ccc(F)cc4)c3=O)cc2F)ccnc1N)N1CCNCC1]

Step A: tert-butyl 4-(4-(2-amino-4-(2-fluoro-4-(3-(4-fluorophenyl)-2,4-dioxo-1-(tetrahydro-2H-pyran-4-yl)-1,2,3,4-tetrahydropyrimidine-5-carboxamido)phenoxy)pyridin-3-yl)-2-methylbut-3-yn-2-yl)piperazine-1-carboxylate

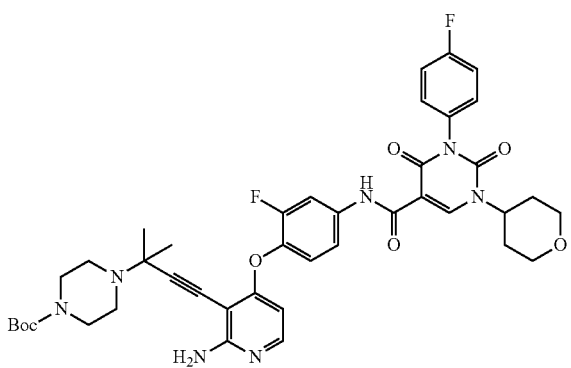

A mixture of N-(4-(2-amino-3-iodopyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (intermediate 24, 100 mg, 0.15 mmol), tert-butyl 4-(2-methylbut-3-yn-2-yl)piperazine-1-carboxylate (57.0 mg, 0.23 mmol), copper(I) iodide (5.76 mg, 0.03 mmol), and TEA (82.0 µL, 0.61 mmol) in DMF (2 mL) was degassed with N₂. To reaction mixture was added Pd(PPh₃)₄ (17.47 mg, 0.02 mmol) and stirred for overnight at 90° C. To a mixture was added tert-butyl 4-(2-methylbut-3-yn-2-yl)piperazine-1-carboxylate (57.0 mg, 0.23 mmol), copper(I) iodide (5.76 mg, 0.03 mmol), TEA (82.0 µL, 0.61 mmol) and Pd(PPh₃)₄ (17.47 mg, 0.02 mmol) and stirred for overnight at 90° C. After being cooled at room temperature, the reaction mixture was extracted with EtOAc, washed with brine, dried over Na₂SO₄, filtered and concentrated in vacuo. The residue was purified by column chromatography (EtOAc/MeOH=97/3) to afford the tert-butyl 4-(4-(2-amino-4-(2-fluoro-4-(3-(4-fluorophenyl)-2,4-dioxo-1-(tetrahydro-2H-pyran-4-yl)-1,2,3,4-tetrahydropyrimidine-5-carboxamido)phenoxy)pyridin-3-yl)-2-methylbut-3-yn-2-yl)piperazine-1-carboxylate (52.6 mg, 44%) as a beige solid. ¹H-NMR (CDCl₃, Varian, 400 MHz): δ 1.43 (9H, s), 1.50 (6H, s), 1.95-2.05 (4H, m), 2.62 (4H, m), 3.44 (4H, m), 3.54 (2H, t, J=11 Hz), 4.14-4.17 (2H, m), 4.78-4.84 (1H, s), 5.06 (2H, s), 6.03 (1H, brs), 7.06 (1H, t, J=8.0 Hz), 7.18-7.20 (1H, m), 7.24-7.26 (4H, m), 7.81-7.78 (2H, m), 8.64 (1H, s), 10.84 (1H, s).

Step B: N-(4-(2-amino-3-(3-methyl-3-(piperazin-1-yl)but-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide

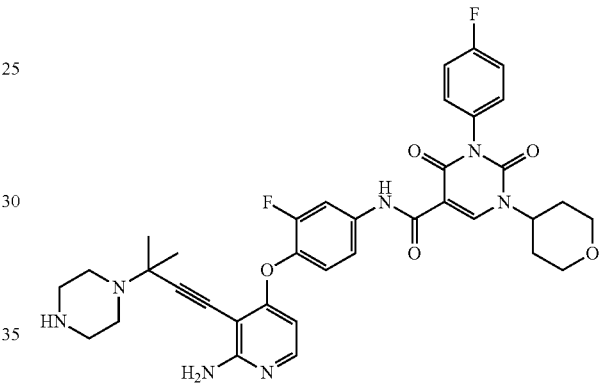

To a solution of tert-butyl 4-(4-(2-amino-4-(2-fluoro-4-(3-(4-fluorophenyl)-2,4-dioxo-1-(tetrahydro-2H-pyran-4-yl)-1,2,3,4-tetrahydropyrimidine-5-carboxamido)phenoxy)pyridin-3-yl)-2-methylbut-3-yn-2-yl)piperazine-1-carboxylate (52.6 mg, 0.07 mmol) in DCM (1 mL) was added TFA (0.10 mL, 1.34 mmol) at room temperature. The reaction mixture was stirred for overnight at room temperature. The residue was diluted with DCM, and then neutralized with TEA. The mixture was stirred for 10 min at room temperature and concentrated in vacuo. The residue was purified by column chromatography on NH—SiO₂ (EtOAc/MeOH=95/5) to afford the N-(4-(2-amino-3-(3-methyl-3-(piperazin-1-yl)but-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (24.0 mg, 52%) as a yellow solid. ¹H-NMR (CDCl₃, Varian, 400 MHz): δ 1.45 (6H, s), 1.98-2.04 (4H, m), 2.63 (4H, brs), 2.92 (4H, m), 3.51-3.57 (2H, m), 4.15-4.17 (2H, m), 4.78-4.84 (1H, m), 5.02 (2H, s), 6.05 (1H, d, J=6 Hz), 7.05 (1H, t, J=8.8 Hz), 7.18-7.20 (1H, m), 7.24-7.26 (4H, m), 7.77-7.81 (1H, m), 7.83 (1H, d, J=6.0 Hz), 8.68 (1H, s), 10.83 (1H, s). * NH peak was not observed.

Example 59

Figure 56:
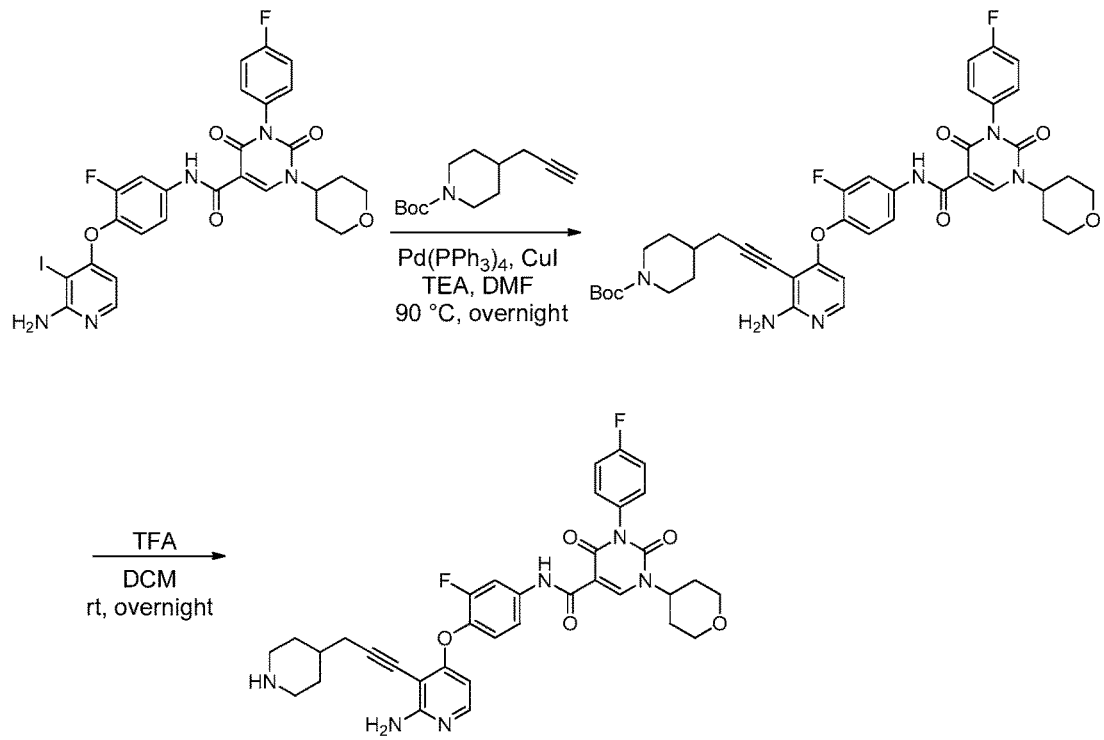
FIG. 56 is a chemical synthesis of N-(4-(2-amino-3-(3-(piperidin-4-yl)prop-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention.

This example describes the synthesis of N-(4-(2-amino-3-(3-(piperidin-4-yl)prop-1-ynyl)pyridin-4-yloxy)-3-fluorophenyl)-3-(4-fluorophenyl)-2,4-dioxo-1-(tetrahydro-2H- pyran-4-yl)-1,2,3,4-tetrahydropyrimidine-5-carboxamide in an aspect of the invention. See FIG. 56.

Step B: N-(4-(2-amino-3-(3-(piperidin-4-yl)prop-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide

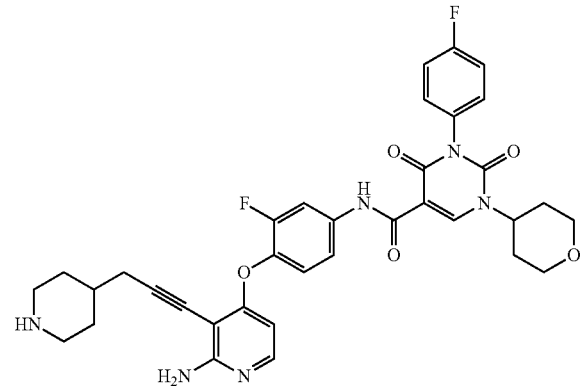 [SMILES: Nc1nccc(Oc2ccc(NC(=O)c3cn(C4CCOCC4)c(=O)n(-c4ccc(F)cc4)c3=O)cc2F)c1C#CCC1CCNCC1]

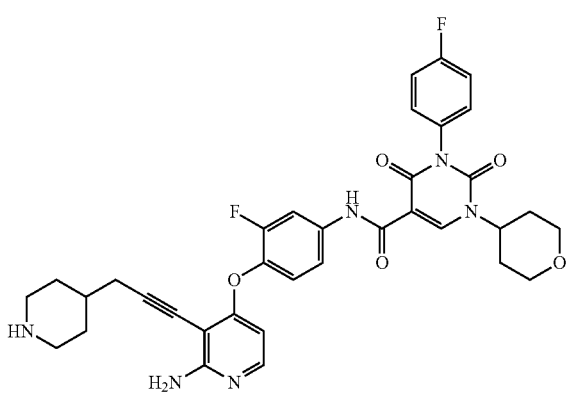

Step A: tert-butyl 4-(3-(2-amino-4-(2-fluoro-4-(3-(4-fluorophenyl)-2,4-dioxo-1-(tertahydro-2H-pyan-4-yl)-1,2,3,4-tetrahydropyrimidine-5-carboxamido)phenoxy)pyridin-3-yl)prop-2-ynyl)piperidine-1-carboxylate To a solution of tert-butyl 4-(3-(2-amino-4-(2-fluoro-4-(3-(4-fluorophenyl)-2,4-dioxo-1-(tetrahydro-2H-pyran-4-yl)-1,2,3,4-tetrahydropyrimidine-5-carboxamido)phenoxy)pyridin-3-yl)prop-2-ynyl)piperidine-1-carboxylate (49.3 mg, 0.07 mmol) in DCM (1 mL) was added TFA (0.10 mL, 1.30 mmol) at room temperature. The residue was diluted with DCM, and then neutralized with TEA. The mixture was stirred for 10 min at room temperature and concentrated in vacuo. The residue was purified by column chromatography on NH—SiO$_2$ (EtOAc/MeOH=9/1) to afford the N-(4-(2-amino-3-(3-(piperidin-4-yl)prop-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (27.0 mg, 64%) as a yellow solid. $^1$H-NMR (CDCl$_3$, Varian, 400 MHz): δ 1.20-1.23 (2H, m), 1.82 (2H, d, J=12.4 Hz), 1.98-2.07 (5H, m), 2.43 (2H, d, J=6.8 Hz), 2.57-2.62 (2H, m), 3.06-3.10 (2H, m), 3.52-3.57 (2H, m), 4.14-4.18 (2H, m), 4.78-4.84 (1H, m), 5.02 (2H, s), 5.99 (1H, d, J=6.0 Hz), 7.08 (1H, t, J=8.6 Hz), 7.18-7.20 (1H, m), 7.24-7.26 (4H, m), 7.78-7.81 (2H, m), 8.68 (1H, s), 10.84 (1H, s). * NH peak was not observed.

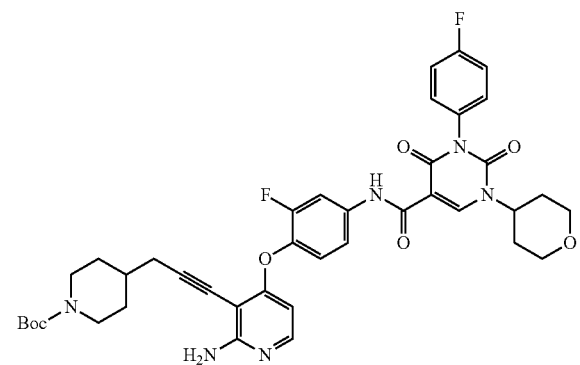

A mixture of N-(4-(2-amino-3-iodopyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (intermediate 24, 100 mg, 0.15 mmol), tert-butyl 4-(prop-2-yn-1-yl)piperidine-1-carboxylate (51.0 mg, 0.23 mmol), copper(I) iodide (5.76 mg, 0.03 mmol), and TEA (82.0 L, 0.61 mmol) in DMF (2 mL) was degassed with N$_2$. To reaction mixture was added Pd(PPh$_3$)$_4$ (17.47 mg, 0.02 mmol) and stirred for overnight at 90° C. After being cooled at room temperature, the reaction mixture was extracted with EtOAc, washed with brine, dried over Na$_2$SO$_4$, filtered and concentrated in vacuo. The residue was purified by column chromatography (EtOAc only) to afford the tert-butyl 4-(3-(2-amino-4-(2-fluoro-4-(3-(4-fluorophenyl)-2,4-dioxo-1-(tetrahydro-2H-pyran-4-yl)-1,2,3,4-tetrahydropyrimidine-5-carboxamido)phenoxy)pyridin-3-yl)prop-2-ynyl)piperidine-1-carboxylate (60.9 mg, 53%) as a yellow solid. $^1$H-NMR (CDCl$_3$, Varian, 400 MHz): δ 1.21-1.27 (2H, m), 1.44 (9H, s), 1.72 (1H, brs), 1.81 (2H, d, J=14 Hz), 1.98-2.05 (4H, m), 2.45 (2H, d, J=6.4 Hz), 2.69 (2H, brs), 3.52-3.57 (2H, m), 4.09-4.18 (4H, m), 4.78-4.84 (1H, m), 4.99 (2H, s), 5.98 (1H, d, J=6.0 Hz), 7.08 (1H, t, J=8.8 Hz), 7.19-7.21 (1H, m), 7.24-7.26 (4H, m), 7.79-7.81 (2H, m), 8.68 (1H, s), 10.84 (1H, s).

Example 60

Figure 57:
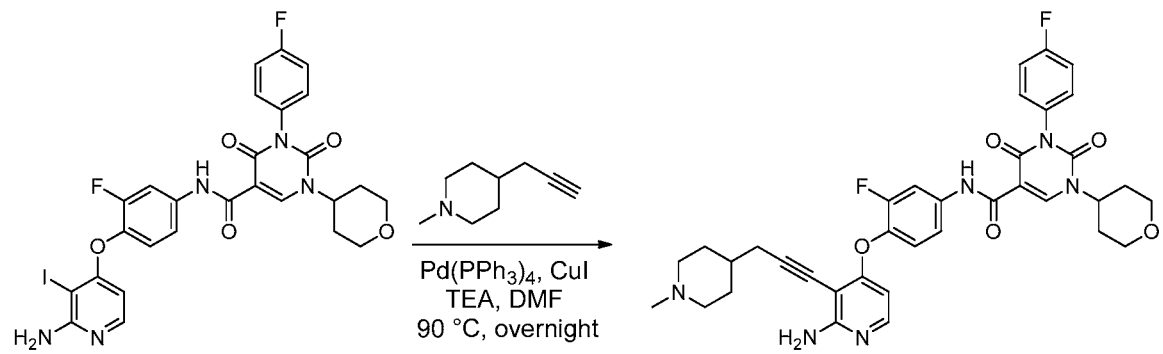
FIG. 57 is a chemical synthesis of N-(4-(2-amino-3-(3-(1-methylpiperidin-4-yl)prop-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention.

This example describes the synthesis of N-(4-(2-amino-3-(3-(1-methylpiperidin-4-yl)prop-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide in an aspect of the invention. See FIG. 57.

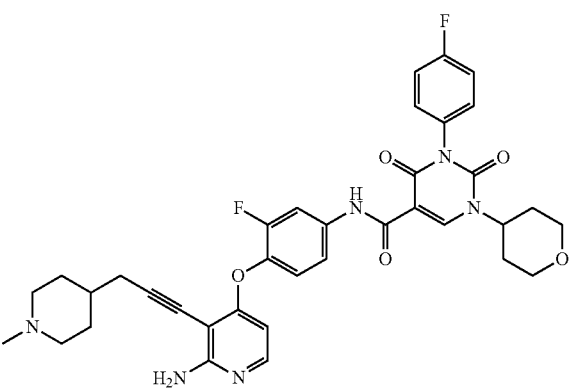 [SMILES: CN1CCC(CC#Cc2c(Oc3ccc(NC(=O)c4cn(C5CCOCC5)c(=O)n(-c5ccc(F)cc5)c4=O)cc3F)ccnc2N)CC1]

A mixture of N-(4-(2-amino-3-iodopyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (intermediate 24, 50.0 mg, 0.08 mmol), 1-methyl-4-(prop-2-yn-1-yl)piperidine hydrochloride (19.7 mg, 0.11 mmol), copper(I) iodide (2.88 mg, 0.02 mmol), and TEA (41.0 L, 0.30 mmol) in DMF (1 mL) was degassed with $N_2$. To reaction mixture was added Pd(PPh$_3$)$_4$ (8.74 mg, 7.56 µmol) and stirred for overnight at 90° C. in sealed tube. After being cooled at room temperature, the reaction mixture was extracted with EtOAc, washed with brine, dried over Na$_2$SO$_4$, filtered and concentrated in vacuo. The residue was purified by column chromatography on NH—SiO$_2$ (EtOAc/MeOH=97/3) to afford the N-(4-(2-amino-3-(3-(1-methylpiperidin-4-yl)prop-1-ynyl)pyridin-4-yloxy)-3-fluorophenyl)-3-(4-fluorophenyl)-2,4-dioxo-1-(tetrahydro-2H-pyran-4-yl)-1,2,3,4-tetrahydropyrimidine-5-carboxamide (15.8 mg, 31%) as a yellow solid. $^1$H-NMR (CDCl$_3$, Varian, 400 MHz): δ 1.33-1.43 (2H, m), 1.55 (1H, m), 1.82-2.05 (8H, m), 2.25 (3H, s), 2.43 (2H, d, J=6.4 Hz), 2.83-2.86 (2H, m), 3.52-3.57 (2H, m), 4.15-4.18 (2H, m), 4.80-4.84 (1H, m), 5.01 (2H, s), 5.97 (1H, d, J=5.6 Hz), 7.09 (1H, t, J=8.8 Hz), 7.20 (1H, d, J=8.0 Hz), 7.24-7.26 (4H, m), 7.78-7.81 (2H, m), 8.68 (1H, s), 10.84 (1H, s).

Example 61

Figure 58:
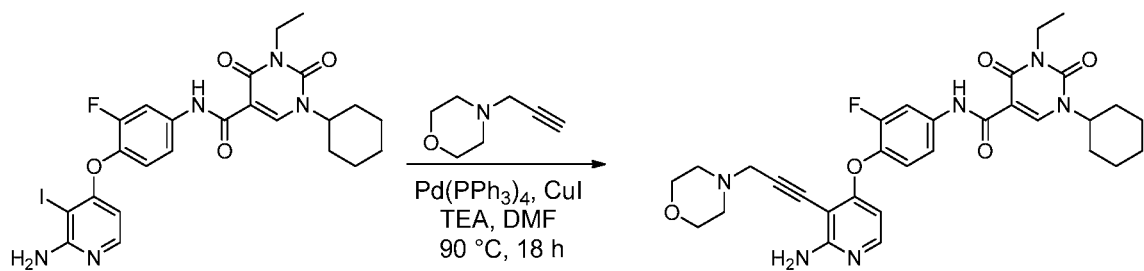
FIG. 58 is a chemical synthesis of N-(4-(2-amino-3-(3-morpholinoprop-1-ynyl)pyridin-4-yloxy)-3-fluorophenyl)-3-cyclohexyl-1-ethyl-2,4-dioxo-1,2,3,4-tetrahydropyrimidine-5-carboxamide in an aspect of the invention.

This example describes the synthesis of N-(4-(2-amino-3-(3-morpholinoprop-1-ynyl)pyridin-4-yloxy)-3-fluorophenyl)-3-cyclohexyl-1-ethyl-2,4-dioxo-1,2,3,4-tetrahydropyrimidine-5-carboxamide in an aspect of the invention. See FIG. 58.

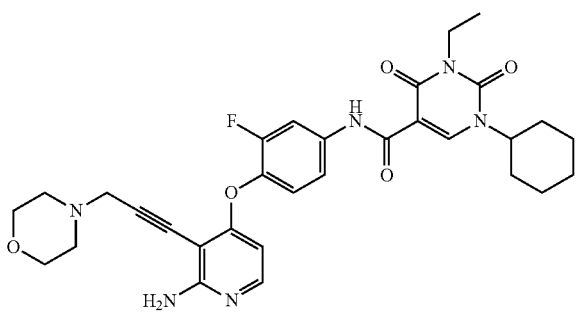 [SMILES: CCn1c(=O)c(C(=O)Nc2ccc(Oc3ccnc(N)c3C#CCN3CCOCC3)c(F)c2)cn(C2CCCCC2)c1=O]

To a solution of N-(4-(2-amino-3-iodopyridin-4-yloxy)-3-fluorophenyl)-3-cyclohexyl-1-ethyl-2,4-dioxo-1,2,3,4-tetrahydropyrimidine-5-carboxamide (Intermediate 26, 50.0 mg, 0.08 mmol) in DMF (1.7 mL) were added 4-(prop-2-ynyl)morpholine (10.6 mg, 0.08 mmol), copper(I) iodide (3.21 mg, 0.02 mmol) and TEA (46.0 µL, 0.34 mmol) at room temperature. The mixture was degassed by purging and re-filled with Ar in several times. After addition of Pd(PPh$_3$)$_4$ (9.74 mg, 8.43 µmol), the reaction mixture was heated at 90° C. for 18 hours. After cooled to room temperature, the reaction mixture was quenched with water and extracted with EtOAc. The organic layer was dried over Na$_2$SO$_4$, filtered, and concentrated in vacuo. The residue was purified by column chromatography on NH—SiO$_2$ (EtOAc only) to give the N-(4-(2-amino-3-(3-morpholinoprop-1-ynyl)pyridin-4-yloxy)-3-fluorophenyl)-3-cyclohexyl-1-ethyl-2,4-dioxo-1,2,3,4-tetrahydropyrimidine-5-carboxamide (26.8 mg, 54%) as an ivory solid. $^1$H-NMR (DMSO-d$_6$, Varian, 400 MHz): δ 0.79-0.84 (1H, m), 1.11-1.30 (6H, m), 1.55-1.66 (3H, m), 1.79 (2H, d, J=11.2 Hz), 2.32 (2H, q, J=12.0 Hz), 2.42-2.48 (5H, m), 3.54 (4H, s), 3.92 (2H, q, J=6.9 Hz), 4.70-4.80 (1H, m), 5.89 (1H, d, J=5.6 Hz), 6.26 (2H, s), 7.22-7.26 (1H, m), 7.44 (1H, d, J=9.2 Hz), 7.78 (1H, d, J=6.0 Hz), 7.92 (1H, d, J=12.4 Hz), 8.71 (1H, s), 11.1 (1H, s).

Example 62

Figure 59:
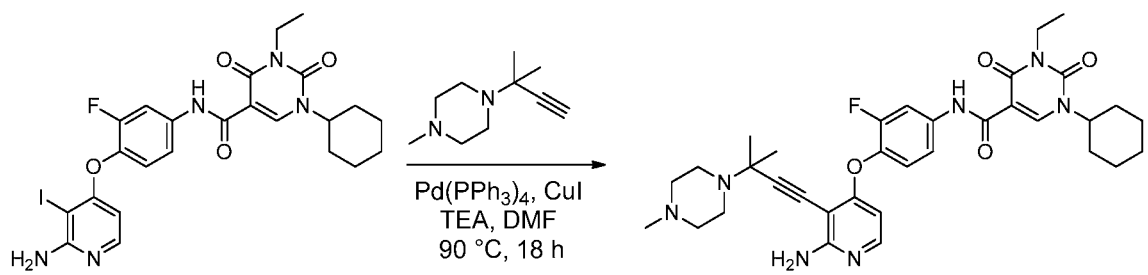
FIG. 59 is a chemical synthesis of N-(4-(2-amino-3-(3-methyl-3-(4-methylpiperazin-1-yl)but-1-ynyl)pyridin-4-yloxy)-3-fluorophenyl)-3-cyclohexyl-1-ethyl-2,4-dioxo-1,2,3,4-tetrahydropyridmidine-5-carboxamide in an aspect of the invention.

This example describes the synthesis of N-(4-(2-amino-3-(3-methyl-3-(4-methylpiperazin-1-yl)but-1-ynyl)pyridin-4-yloxy)-3-fluorophenyl)-3-cyclohexyl-1-ethyl-2,4-dioxo-1,2,3,4-tetrahydropyridmidine-5-carboxamide in an aspect of the invention. See FIG. 59.

To a solution of N-(4-(2-amino-3-iodopyridin-4-yloxy)-3-fluorophenyl)-3-cyclohexyl-1-ethyl-2,4-dioxo-1,2,3,4-tetrahydropyrimidine-5-carboxamide (Intermediate 26, 50.0 mg, 0.08 mmol) in DMF (1.7 mL) were added 1-methyl-4-(2-methylbut-3-yn-2-yl)piperazine (14.0 mg, 0.08 mmol), copper(I) iodide (3.21 mg, 0.02 mmol) and TEA (46.0 µL, 0.34 mmol) at room temperature. The mixture was degassed by purging and re-filled with Ar in several times. After addition of Pd(PPh$_3$)$_4$ (9.74 mg, 8.43 µmol), the reaction mixture was heated at 90° C. for 18 hours. After cooled to room temperature, the reaction mixture was quenched with water and extracted with EtOAc. The organic layer was dried over Na$_2$SO$_4$, filtered, and concentrated in vacuo. The residue was purified by column chromatography on NH—SiO$_2$ (EtOAc/MeOH=50/1) to give the N-(4-(2-amino-3-(3-methyl-3-(4-methylpiperazin-1-yl)but-1-ynyl)pyridin-4-yloxy)-3-fluorophenyl)-3-cyclohexyl-1-ethyl-2,4-dioxo-1,2,3,4-tetrahydropyridmidine-5-carboxamide (6.4 mg, 12%) as an ivory solid. $^1$H-NMR (DMSO-d$_6$, Varian, 400 MHz): δ 1.10-1.18 (2H, m), 1.22 (3H, t, J=6.8 Hz), 1.24-1.27 (1H, m), 1.33 (6H, s), 1.58-1.66 (3H, m), 1.75-1.84 (2H, m), 2.08 (3H, s), 2.22-2.38 (6H, m), 3.28-3.36 (4H, m), 3.92 (2H, q, J=7.2 Hz), 4.70-4.80 (1H, m), 5.98 (1H, d, J=6.0 Hz), 6.09 (2H, s), 7.18 (1H, t, J=9.6 Hz), 7.41 (1H, d, J=10.8 Hz), 7.80 (1H, d, J=6.4 Hz), 7.91 (1H, d, J=13.2 Hz), 8.70 (1H, s), 11.1 (1H, s).

Example 63

Figure 60:
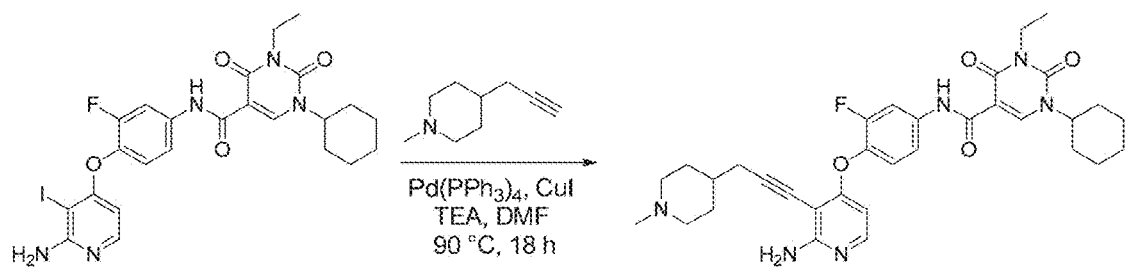
FIG. 60 is a chemical synthesis of N-(4-(2-amino-3-(methyl-3-morpholinbut-1-ynyl)pyridin-4-yloxy)-3-fluorophenyl)-3-cyclohexyl-1-ethyl-2,4-dioxo-1,2,3,4-tetrahydropyrimidine-5-carboxamide in an aspect of the invention.

This example describes the synthesis of N-(4-(2-amino-3-(3-(methyl-3-morpholinbut-1-ynyl)pyridin-4-yloxy)-3-fluorophenyl)-3-cyclohexyl-1-ethyl-2,4-dioxo-1,2,3,4-tetrahydropyrimidine-5-carboxamide in an aspect of the invention. See FIG. 60.

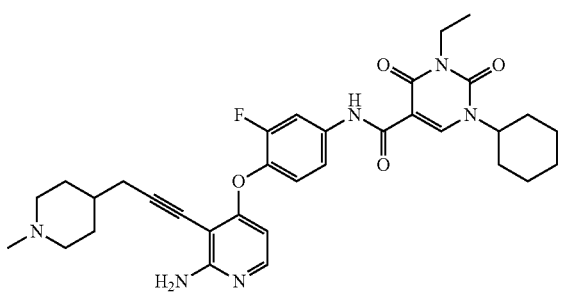 [SMILES: CCn1c(=O)c(C(=O)Nc2ccc(Oc3ccnc(N)c3C#CCC3CCN(C)CC3)c(F)c2)cn(C2CCCCC2)c1=O]

To a solution of N-(4-(2-amino-3-iodopyridin-4-yloxy)-3-fluorophenyl)-3-cyclohexyl-1-ethyl-2,4-dioxo-1,2,3,4-tetrahydropyrimidine-5-carboxamide (Intermediate 26, 50.0 mg, 0.08 mmol) in DMF (1.7 mL) were added 1-methyl-4-(prop-2-ynyl)piperidine (12.0 mg, 0.08 mmol), copper(I) iodide (3.21 mg, 0.02 mmol) and TEA (46.0 μL, 0.34 mmol) at room temperature. The mixture was degassed by purging and re-filled with Ar in several times. After addition of Pd(PPh$_3$)$_4$ (9.74 mg, 8.43 μmol), the reaction mixture was heated at 90° C. for 18 hours. After cooled to room temperature, the reaction mixture was quenched with water and extracted with EtOAc. The organic layer was dried over Na$_2$SO$_4$, filtered, and concentrated in vacuo. The residue was purified by column chromatography on NH—SiO$_2$ (EtOAc/MeOH=50/1) to give the N-(4-(2-amino-3-(3-(1-methylpiperidin-4-yl)prop-1-ynyl)pyridin-4-yloxy)-3-fluorophenyl)-3-cyclohexyl-1-ethyl-2,4-dioxo-1,2,3,4-tetrahydropyrimidine-5-carboxamide (1.0 mg, 2%) as a white solid. $^1$H-NMR (DMSO-d$_6$, Varian, 400 MHz): δ 1.10-1.18 (2H, m), 1.22 (3H, t, J=7.2 Hz), 1.27-1.30 (2H, m), 1.36-1.48 (1H, m), 1.55-1.69 (4H, m), 1.75-1.82 (3H, m), 2.10 (2H, s), 2.27-2.34 (2H, m), 2.39 (2H, d, J=7.2 Hz), 2.63-2.76 (2H, m), 3.30-3.33 (3H, m), 3.92 (2H, q, J=6.8 Hz), 4.70-4.80 (1H, m), 5.74 (1H, s), 5.90 (1H, d, J=6.0 Hz), 6.17 (2H, s), 7.22 (1H, t, J=9.0 Hz), 7.42 (1H, d, J=10.4 Hz), 7.75 (1H, d, J=6.0 Hz), 7.91 (1H, d, J=12.4 Hz), 8.71 (1H, s), 11.1 (1H, s).

Example 64

Figure 61:
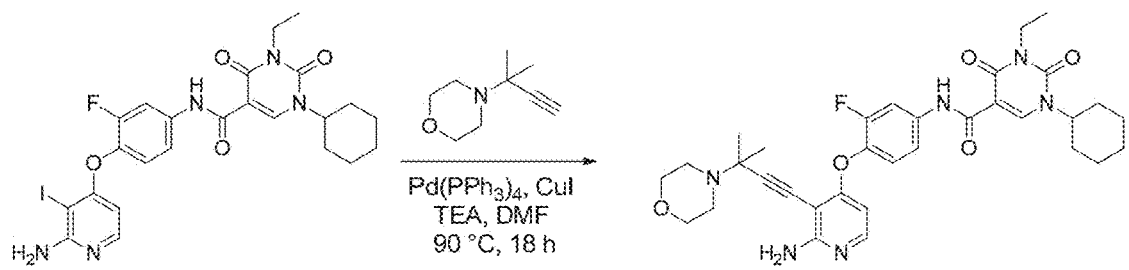
FIG. 61 is a chemical synthesis of N-(4-((2-amino-3-(3-methyl-3-(4-methylpiperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention.

This example describes the synthesis of N-(4-((2-amino-3-(3-methyl-3-(4-methylpiperazin-1-yl)but-1-yn-1-yl)pyridin-4-yl)oxy)-3-fluorophenyl)-1-(2-(dimethylamino)-2-oxoethyl)-3-(4-fluorophenyl)-2,4-dioxo-1,2,3,4-tetrahydropyrimidine-5-carboxamide in an aspect of the invention. See FIG. 61.

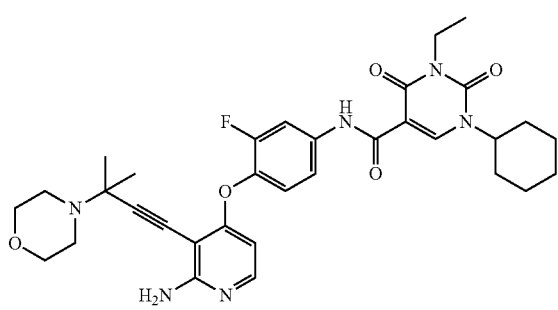 [SMILES: CCn1c(=O)c(C(=O)Nc2ccc(Oc3ccnc(N)c3C#CC(C)(C)N3CCOCC3)c(F)c2)cn(C2CCCCC2)c1=O]

To a solution of N-(4-(2-amino-3-iodopyridin-4-yloxy)-3-fluorophenyl)-3-cyclohexyl-1-ethyl-2,4-dioxo-1,2,3,4-tetrahydropyrimidine-5-carboxamide (Intermediate 26, 50.0 mg, 0.08 mmol) in DMF (1.7 mL) were added 4-(2-methylbut-3-yn-2-yl)morpholine (13.0 mg, 0.08 mmol), copper (I) iodide (3.21 mg, 0.02 mmol) and TEA (0.05 mL, 0.34 mmol) at room temperature. The mixture was degassed by purging and re-filled with Ar in several times. After addition of Pd(PPh$_3$)$_4$ (9.74 mg, 8.43 μmol), the reaction mixture was heated at 90° C. for 18 hours. After cooled to room temperature, the reaction mixture was quenched with water and extracted with EtOAc. The organic layer was dried over Na$_2$SO$_4$, filtered, and concentrated in vacuo. The residue was purified by column chromatography on SiO$_2$ (EtOAc only to EtOAc/MeOH=100/1) to give the N-(4-(2-amino-3-(3-(methyl-3-morpholinbut-1-ynyl)pyridin-4-yloxy)-3-fluorophenyl)-3-cyclohexyl-1-ethyl-2,4-dioxo-1,2,3,4-tetrahydropyrimidine-5-carboxamide (6.2 mg, 12%) as a white solid. $^1$H-NMR (DMSO-d$_6$, Varian, 400 MHz): δ 1.10-1.19 (1H, m), 1.22 (3H, t, J=7.0 Hz), 1.23-1.27 (1H, m), 1.34 (6H, s), 1.54-1.66 (3H, m), 1.77-1.88 (2H, m), 2.28-2.40 (4H, m), 3.30-3.32 (4H, m), 3.51-3.55 (3H, m), 3.92 (2H, q, J=6.4 Hz), 4.70-4.80 (1H, m), 5.99 (1H, d, J=5.6 Hz), 6.12 (2H, s), 7.18 (1H, t, J=9.0 Hz), 7.42 (1H, d, J=9.2 Hz), 7.81 (1H, d, J=5.6 Hz), 7.91 (1H, d, J=12.4 Hz), 8.70 (1H, s), 11.1 (1H, s).

Example 65

Figure 62:
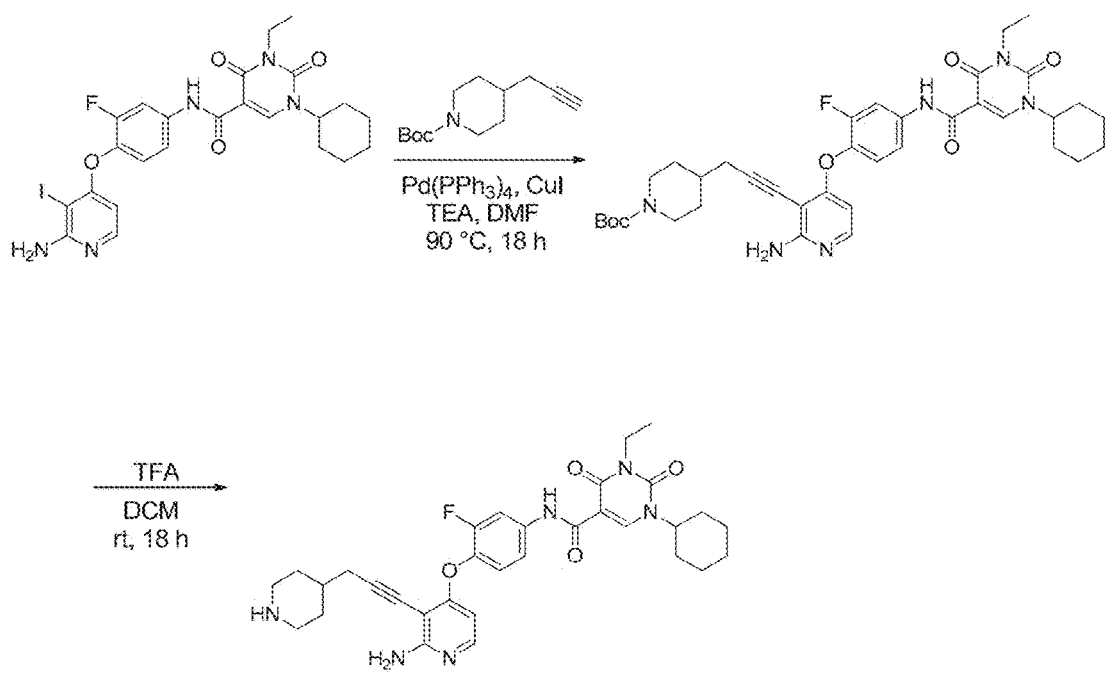
FIG. 62 is a chemical synthesis of N-(4-(2-amino-3-(3-(piperidin-4-yl)prop-1-ynyl)pyridin-4-yloxy)-3-fluorophenyl)-3-cyclohexyl-1-ethyl-2,4-dioxo-1,2,3,4-tetrahydropyrimidine-5-carboxamide in an aspect of the invention.

This example describes the synthesis of N-(4-(2-amino-3-(3-piperidin-4-yl)prop-1-ynyl)pyridin-4-yloxy)-3-fluorophenyl)-3-cyclohexyl-1-ethyl-2,4-dioxo-1,2,3,4-tetrahydropyrimidine-5-carboxamide in an aspect of the invention. See FIG. 62.

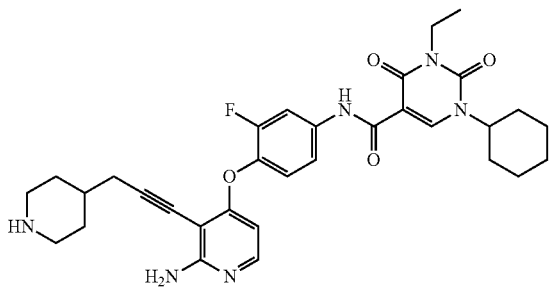 [SMILES: CCn1c(=O)c(C(=O)Nc2ccc(Oc3ccnc(N)c3C#CCC3CCNCC3)c(F)c2)cn(C2CCCCC2)c1=O]

Step A: tert-butyl 4-(3-(2-amino-4-(4-(3-cyclohexyl-1-ethyl-2,4-dioxo-1,2,3,4-tetrahydropyrimidine-5-carboxamido)-2-fluorophenoxy)pyridin-3-yl)prop-2-ynyl)piperidine-1-carboxylate

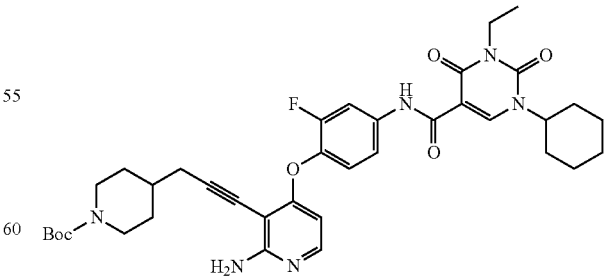

To a solution of N-(4-(2-amino-3-iodopyridin-4-yloxy)-3-fluorophenyl)-3-cyclohexyl-1-ethyl-2,4-dioxo-1,2,3,4-tetrahydropyrimidine-5-carboxamide (Intermediate 26, 110 mg, 0.18 mmol) in DMF (3.7 mL) were added tert-butyl 4-(prop-2-ynyl)piperidine-1-carboxylate (41.0 mg, 0.18 mmol), copper(I) iodide (7.06 mg, 0.04 mmol) and TEA (0.10 mL, 0.74 mmol) at room temperature. The mixture was degassed by purging and re-filled with Ar in several times. After addition of Pd(PPh$_3$)$_4$ (21.0 mg, 0.02 mmol), the reaction mixture was heated at 90° C. for 18 hours. After cooled to room temperature, the reaction mixture was quenched with water and extracted with EtOAc. The organic layer was dried over Na$_2$SO$_4$, filtered, and concentrated in vacuo. The residue was purified by column chromatography on SiO$_2$ (EtOAc/Hexanes=3/1 to EtOAc/Hexanes=5/1) to give the tert-butyl 4-(3-(2-amino-4-(4-(3-cyclohexyl-1-ethyl-2,4-dioxo-1,2,3,4-tetrahydropyrimidine-5-carboxamido)-2-fluorophenoxy)pyridin-3-yl)prop-2-ynyl)piperidine-1-carboxylate (31.0 mg, 24%) as a yellow solid. $^1$H-NMR (DMSO-d$_6$, Varian, 400 MHz): δ 1.01-1.18 (2H, m), 1.22 (3H, t, J=7.0 Hz), 1.27-1.31 (2H, m), 1.34 (9H, s), 1.56-1.69 (6H, m), 1.79 (2H, d, J=13.2 Hz), 2.27-2.38 (2H, m), 2.41 (2H, d, J=6.0 Hz), 3.30-3.32 (3H, m), 3.84-3.96 (4H, m), 4.70-4.80 (1H, m), 5.90 (1H, d, J=6.0 Hz), 6.19 (2H, s), 7.20 (1H, t, J=8.8 Hz), 7.42 (1H, d, J=7.6 Hz), 7.75 (1H, d, J=5.6 Hz), 7.92 (1H, dd, J=14.0, 2.0 Hz), 8.71 (1H, s), 11.1 (1H, s).

Step B: N-(4-(2-amino-3-(3-piperazin-4-yl)prop-1-ynyl)pyridin-4-yloxy)-3-fluorophenyl)-3-cyclohexyl-1-ethyl-2,4-dioxo-1,2,3,4-tetrahydropyrimidine-5-carboxamide

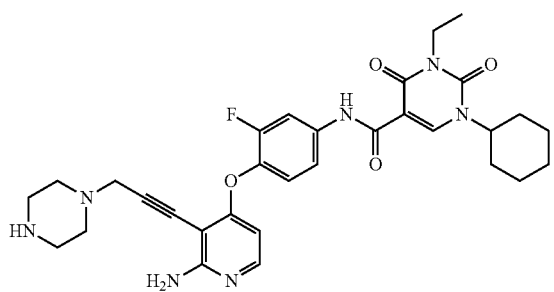

To a solution of tert-butyl 4-(3-(2-amino-4-(4-(3-cyclohexyl-1-ethyl-2,4-dioxo-1,2,3,4-tetrahydropyrimidine-5-carboxamido)-2-fluorophenoxy)pyridin-3-yl)prop-2-ynyl)piperidine-1-carboxylate (31.0 mg, 0.04 mmol) in DCM (1 mL) was added TFA (35.0 µL, 0.45 mmol) at room temperature. The reaction mixture was stirred for 18 hours at room temperature. After cooled to 0° C., the reaction mixture was quenched with sat. NaHCO$_3$ solution and extracted with DCM. The organic layer was dried over Na$_2$SO$_4$, filtered and concentrated in vacuo. The residue was triturated with DCM and Hexanes. The resulted solid was collected by filtration and dried under vacuum afford the N-(4-(2-amino-3-(3-piperidin-4-yl)prop-1-ynyl)pyridin-4-yloxy)-3-fluorophenyl)-3-cyclohexyl-1-ethyl-2,4-dioxo-1,2,3,4-tetrahydropyrimidine-5-carboxamide (11.9 mg, 45%) as a beige solid. $^1$H-NMR (DMSO-d$_6$, Varian, 400 MHz): δ 1.05-1.34 (8H, m), 1.53-1.71 (6H, m), 1.79 (2H, d, J=12.4 Hz), 2.28-2.50 (6H, m), 2.93 (2H, s), 3.92 (2H, q, J=7.2 Hz), 4.70-4.80 (1H, m), 5.88 (1H, d, J=6.0 Hz), 6.17 (2H, s), 7.22 (1H, t, J=8.8 Hz), 7.43 (1H, d, J=9.2 Hz), 7.75, (1H, d, J=6.0 Hz), 7.92 (1H, d, J=14.8 Hz), 8.70 (1H, s), 11.1 (1H, s). * A proton from NH was not observed.

Example 66

Figure 63:
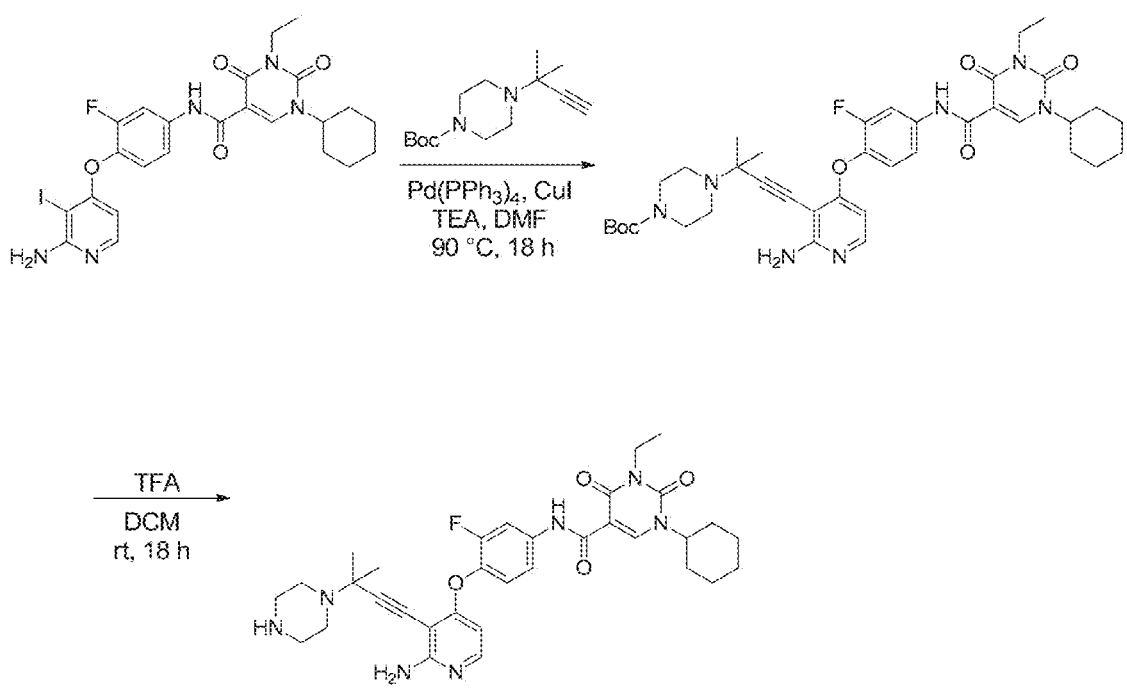
FIG. 63 is a chemical synthesis of N-(4-(2-amino-3-(3-methyl-3-(piperazin-1-yl)but-1-ynyl)pyridin-4-yloxy)-3-fluorophenyl)-3-cyclohexyl-1-ethyl-2,4-dioxo-1,2,3,4-tetrahydropyrimidine-5-carboxamide in an aspect of the invention.

This example describes the synthesis of N-(4-(2-amino-3-(3-methyl-3-(piperazin-1-yl)but-1-ynyl)pyridin-4-yloxy)-3-fluorophenyl)-3-cyclohexyl-1-ethyl-2,4-dioxo-1,2,3,4-tetrahydropyrimidine-5-carboxamide in an aspect of the invention. See FIG. 63.

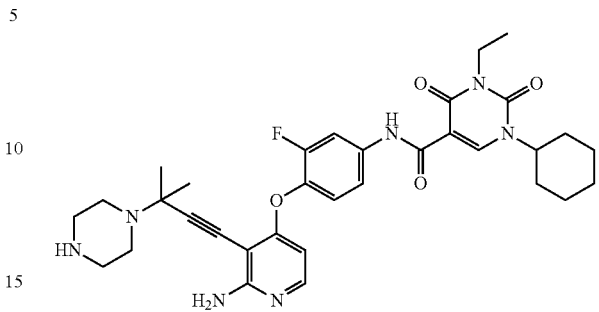

Step A: tert-butyl 4-(3-(2-amino-4-(4-(3-cyclohexyl-2,4-dioxo-1,2,3,4-tetrahydropyrimidine-5-carboxamido)-2-fluorophenoxy)pyridin-3-yl)-2-methylbut-3-yn-2-yl))piperazine-1-carboxylate.

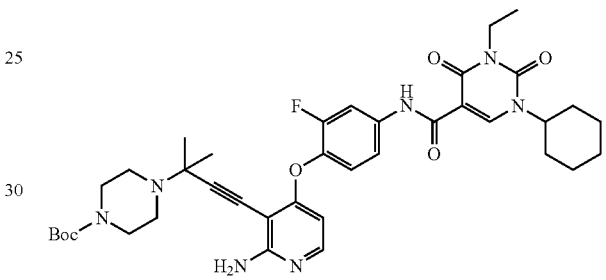

To a solution of N-(4-(2-amino-3-iodopyridin-4-yloxy)-3-fluorophenyl)-3-cyclohexyl-1-ethyl-2,4-dioxo-1,2,3,4-tetrahydropyrimidine-5-carboxamide (Intermediate 26, 120 mg, 0.20 mmol) in DMF (3.7 mL) were added tert-butyl 4-(2-methylbut-3-yn-2-yl)piperazine-1-carboxylate (51.0 mg, 0.20 mmol), copper(I) iodide (7.70 mg, 0.04 mmol) and TEA (0.11 mL, 0.81 mmol) at room temperature. The mixture was degassed by purging and re-filled with Ar in several times. After addition of Pd(PPh$_3$)$_4$ (23.0 mg, 0.02 mmol), the reaction mixture was heated at 90° C. for 18 hours. After cooled to room temperature, the reaction mixture was quenched with water and extracted with EtOAc. The organic layer was dried over Na$_2$SO$_4$, filtered, and concentrated in vacuo. The residue was purified by column chromatography on SiO$_2$ (EtOAc only to EtOAc/MeOH=50/1) to give the tert-butyl 4-(4-(2-amino-4-(4-(3-cyclohexyl-1-ethyl-2,4-dioxo-1,2,3,4-tetrahydropyrimidine-5-carboxamido)-2-fluorophenoxy)pyridin-3-yl)-2-methylbut-3-yn-2-yl))piperazine-1-carboxylate (30.0 mg, 21%) as an ivory solid. $^1$H-NMR (DMSO-d$_6$, Varian, 400 MHz): δ 1.11-1.19 (1H, m), 1.22 (3H, t, J=7.0 Hz), 1.22-1.27 (2H, m), 1.31 (9H, s), 1.36 (6H, s), 1.55-1.63 (3H, m), 1.79 (2H, d, J=11.6 Hz), 2.32 (2H, q, J=9.6 Hz), 2.48-2.44 (4H, m), 3.26 (4H, s), 3.92 (2H, q, J=7.2 Hz), 4.70-4.80 (1H, m), 5.96 (1H, d, J=6.0 Hz), 6.13 (2H, s), 7.17 (1H, t, J=9.0 Hz), 7.39 (1H, d, J=9.6 Hz), 7.80 (1H, d, J=6.0 Hz), 7.91 (1H, dd, J=14.8, 2.4 Hz), 8.70 (1H, s), 11.1 (1H, s).

215

Step B: N-(4-(2-amino-3-(3-methyl-3-(piperazin-1-yl)but-1-ynyl)pyridin-4-yloxy)-3-fluorophenyl)-3-cyclohexyl-1-ethyl-2,4-dioxo-1,2,3,4-tetrahydropyrimidine-5-carboxamide

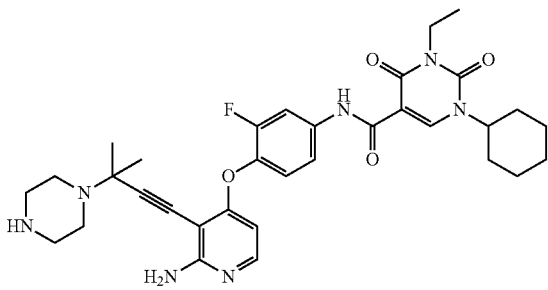 [SMILES: CCn1c(=O)c(C(=O)Nc2ccc(Oc3ccnc(N)c3C#CC(C)(C)N3CCNCC3)c(F)c2)cn(C2CCCCC2)c1=O]

To a solution of tert-butyl 4-(4-(2-amino-4-(4-(3-cyclohexyl-1-ethyl-2,4-dioxo-1,2,3,4-tetrahydropyrimidine-5-carboxamido)-2-fluorophenoxy)pyridin-3-yl)-2-methylbut-3-yn-2-yl))piperazine-1-carboxylate (30.0 mg, 0.04 mmol) in DCM (1 mL) was added TFA (32.0 µL, 0.42 mmol) at room temperature. The reaction mixture was stirred for 18 hours at room temperature. After cooled to 0° C., the reaction mixture was quenched with sat. NaHCO₃ solution and extracted with DCM. The organic layer was dried over Na₂SO₄, filtered and concentrated in vacuo. The residue was triturated with DCM and Hexanes. The resulted solid was collected by filtration and dried under vacuum afford the N-(4-(2-amino-3-(3-methyl-3-(piperazin-1-yl)but-1-ynyl)pyridin-4-yloxy)-3-fluorophenyl)-3-cyclohexyl-1-ethyl-2,4-dioxo-1,2,3,4-tetrahydropyrimidine-5-carboxamide (10.3 mg, 40%) as a yellow solid. $^1$H-NMR (DMSO-d₆, Varian, 400 MHz): δ 1.10-1.16 (1H, m), 1.22 (3H, t, J=7.0 Hz), 1.33 (6H, s), 1.52-1.67 (3H, m), 1.74-1.81 (2H, m), 2.27-2.39 (3H, m), 2.48-2.53 (3H, m), 2.77 (2H, s), 3.30-3.32 (4H, m), 3.92 (2H, q, J=7.6 Hz), 4.70-4.80 (1H, m), 5.98 (1H, d, J=5.2 Hz), 6.12 (2H, s), 7.19 (1H, t, J=9.0 Hz), 7.42 (1H, d, J=9.2 Hz), 7.81 (1H, d, J=6.0 Hz), 7.92 (1H, d, J=13.2 Hz), 8.70 (1H, s), 11.1 (1H, s). * A proton from NH was not observed.

Example 67

Figure 64:
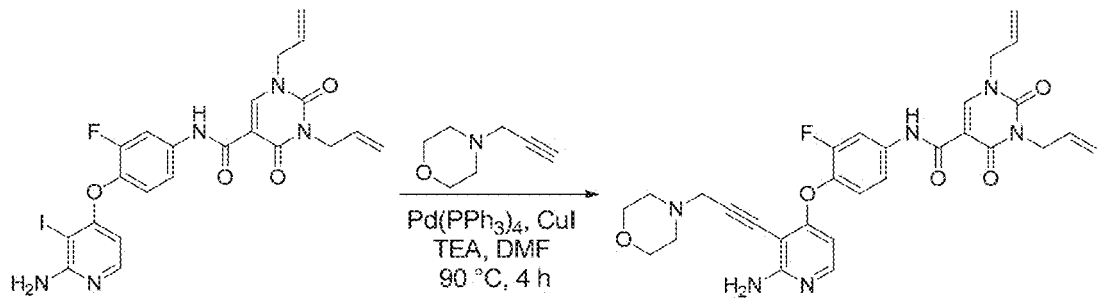
FIG. 64 is a chemical synthesis of 1,3-diallyl-N-(4-(2-amino-3-(3-morpholinoprop-1-ynyl)pyridin-4-yloxy)-3-fluorophenyl)-2,4-dioxo-1,2,3,4-tetrahydropyrimidine-5-carboxamide in an aspect of the invention.

This example describes the synthesis of 1,3-diallyl-N-(4-(2-amino-3-(3-morpholinoprop-1-ynyl)pyridin-4-yloxy)-3-fluorophenyl)-2,4-dioxo-1,2,3,4-tetrahydropyrimidine-5-carboxamide in an aspect of the invention. See FIG. 64.

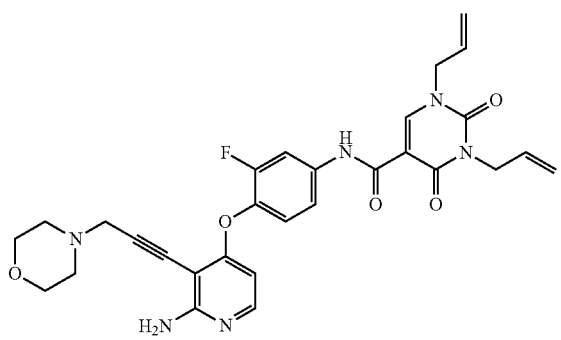 [SMILES: C=CCn1cc(C(=O)Nc2ccc(Oc3ccnc(N)c3C#CCN3CCOCC3)c(F)c2)c(=O)n(CC=C)c1=O]

A mixture of 1,3-diallyl-N-(4-(2-amino-3-iodopyridin-4-yloxy)-3-fluorophenyl)-2,4-dioxo-1,2,3,4-tetrahydropyrimidine-5-carboxamide (intermediate 28, 60.0 mg, 0.11 mmol), 4-(prop-2-ynyl))morpholine (20.0 mg, 0.16 mmol), copper

216

(I) iodide (4.1 mg, 0.02 mmol), and TEA (58.0 µL, 0.43 mmol) in DMF (1 mL) was degassed with N₂. To reaction mixture was added Pd(PPh₃)₄ (12.0 mg, 10.6 µmol) and stirred for 4 hours at 90° C. After being cooled at room temperature, the reaction mixture was extracted with EtOAc, washed with brine, dried over Na₂SO₄, filtered and concentrated in vacuo. The residue was purified by column chromatography on SiO₂ (EtOAc/MeOH=10/1) to afford the 1,3-diallyl-N-(4-(2-amino-3-(3-morpholinoprop-1-ynyl) pyridin-4-yloxy)-3-fluorophenyl)-2,4-dioxo-1,2,3,4-tetrahydropyrimidine-5-carboxamide (10.0 mg, 16%) as a yellow solid. $^1$H-NMR (DMSO-d₆, Varian, 400 MHz): δ 2.44 (4H, m), 3.53 (6H, m), 4.46-4.50 (2H, m), 4.57 (2H, d, J=5.6 Hz), 5.12-5.14 (2H, m), 5.22-5.27 (2H, m), 5.80-5.96 (3H, m), 6.24 (2H, brs), 7.24 (1H, t, J=9.2 Hz), 7.43 (1H, d, J=8.8 Hz), 7.79 (1H, d, J=5.6 Hz), 7.92 (1H, d, J=13.2 Hz), 8.68 (1H, m), 11.04 (1H, s).

Example 68

Figure 65:
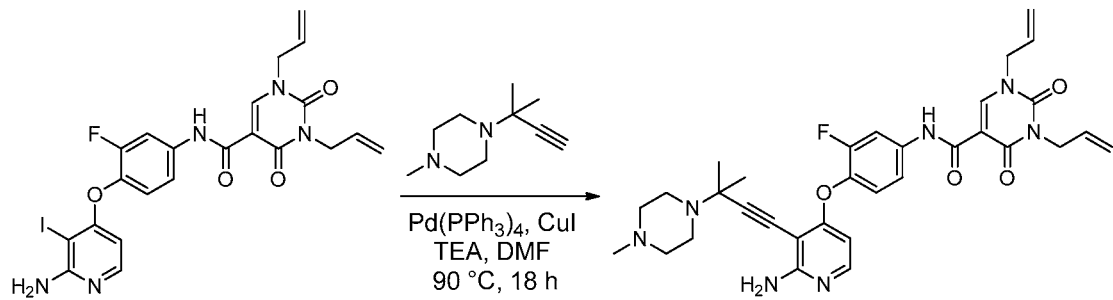
FIG. 65 is a chemical synthesis of 1,3-diallyl-N-(4-(2-amino-3-(3-methyl-3-(4-methylpiperazin-1-yl)but-1-ynyl)

This example describes the synthesis of 1,3-diallyl-N-(4-(2-amino-3-(3-methyl-3-(4-methylpiperazin-1-yl)but-1-ynyl)pyridin-4-yloxy)-3-fluorophenyl)-2,4-dioxo-1,2,3,4-tetrahydropyrimidine-5-carboxamide in an aspect of the invention. See FIG. 65.

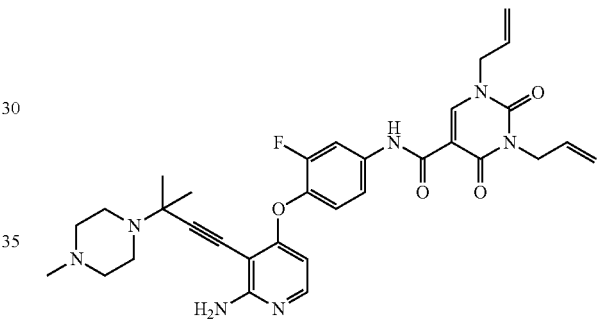

To a solution of 1,3-diallyl-N-(4-(2-amino-3-iodopyridin-4-yloxy)-3-fluorophenyl)-2,4-dioxo-1,2,3,4-tetrahydropyrimidine-5-carboxamide (Intermediate 28, 50.0 mg, 0.09 mmol) in DMF (1.8 mL) were added 1-methyl-4-(2-methylbut-3-yn-2-yl)piperazine (22.0 mg, 0.13 mmol), copper(I) iodide (3.38 mg, 0.02 mmol) and TEA (0.05 mL, 0.36 mmol) at room temperature. The mixture was degassed by purging and re-filled with Ar in several times. After addition of Pd(PPh₃)₄ (10.3 mg, 8.88 µmol), the reaction mixture was heated at 90° C. for 18 hours. After cooled to room temperature, the reaction mixture was quenched with water and extracted with EtOAc. The organic layer was dried over Na₂SO₄, filtered, and concentrated in vacuo. The residue was purified by column chromatography on NH—SiO₂ (EtOAc only) to give the 1,3-diallyl-N-(4-(2-amino-3-(3-methyl-3-(4-methylpiperazin-1-yl)but-1-ynyl)pyridin-4-yloxy)-3-fluorophenyl)-2,4-dioxo-1,2,3,4-tetrahydropyrimidine-5-carboxamide (8.0 mg, 15%) as a yellow solid. $^1$H-NMR (CDCl₃, Varian, 400 MHz): δ 1.47 (6H, s), 2.27 (3H, s), 2.50 (4H, s), 2.74 (4H, s), 4.52 (2H, d, J=5.6 Hz), 4.64 (2H, d, J=5.6 Hz), 5.01 (2H, s), 5.27 (2H, d, J=11.2 Hz), 5.34 (1H, d, J=5.6 Hz), 5.41 (1H, d, J=10.4 Hz), 5.96-5.88 (2H, m), 6.02 (1H, d, J=5.6 Hz), 7.10 (2H, t, J=8.4 Hz), 7.82 (2H, d, J=6.8 Hz), 8.48 (1H, s), 11.0 (1H, s).

Example 69

This example describes the synthesis of 1,3-diallyl-N-(4-(2-amino-3-(3-(1-methylpiperdin-4-yl)prop-1-ynyl)pyridin- 4-yloxy)-3-fluorophenyl)-2,4-dioxo-1,2,3,4-tetrahydropyrimidine-5-carboxamide in an aspect of the invention. See FIG. 66.

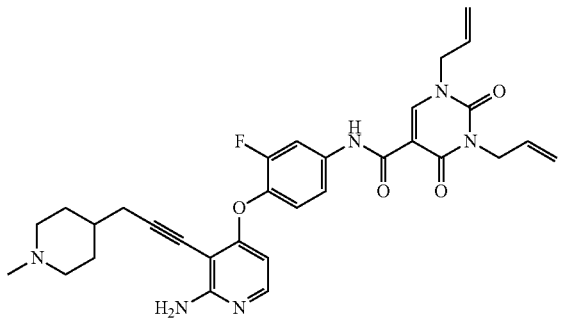 [SMILES: C=CCn1cc(C(=O)Nc2ccc(Oc3ccnc(N)c3C#CCC3CCN(C)CC3)c(F)c2)c(=O)n(CC=C)c1=O]

To a solution of 1,3-diallyl-N-(4-(2-amino-3-iodopyridin-4-yloxy)-3-fluorophenyl)-2,4-dioxo-1,2,3,4-tetrahydropyrimidine-5-carboxamide (Intermediate 28, 100 mg, 0.18 mmol) in DMF (1.8 mL) were added 1-methyl-4-(prop-2-ynyl)piperidine (37.0 mg, 0.27 mmol), copper(I) iodide (6.76 mg, 0.02 mmol) and TEA (0.10 mL, 0.71 mmol) at room temperature. The mixture was degassed by purging and re-filled with Ar in several times. After addition of Pd(PPh₃)₄ (21.0 mg, 0.02 mmol), the reaction mixture was heated at 90° C. for 18 hours. After cooled to room temperature, the reaction mixture was quenched with water and extracted with EtOAc. The organic layer was dried over Na₂SO₄, filtered, and concentrated in vacuo. The residue was purified by column chromatography on NH—SiO₂ (EtOAc/MeOH=50/1) to give the 1,3-diallyl-N-(4-(2-amino-3-(3-(1-methylpiperdin-4-yl)prop-1-ynyl)pyridin-4-yloxy)-3-fluorophenyl)-2,4-dioxo-1,2,3,4-tetrahydropyrimidine-5-carboxamide (1.0 mg, 1%) as a white solid. ¹H-NMR (CDCl₃, Varian, 400 MHz): δ 0.79-0.89 (1H, m), 1.35-1.44 (2H, m), 1.85 (2H, d, J=12.0 Hz), 1.93 (2H, t, J=11.4 Hz), 2.26 (3H, s), 2.45 (2H, d, J=6.4 Hz), 2.86 (2H, d, J=10.8 Hz), 4.53 (2H, d, J=5.6 Hz), 4.64 (2H, d, J=5.2 Hz), 5.01 (2H, s), 5.27 (2H, d, J=10.8 Hz), 5.34 (1H, d, J=6.0 Hz), 5.40 (2H, d, J=10.8 Hz), 5.99-5.88 (3H, m), 7.12 (1H, t, J=8.4 Hz), 7.84-7.78 (2H, m), 8.48 (1H, s), 11.0 (1H, s).

Example 70

This example describes the synthesis of 1,3-diallyl-N-(4-(2-amino-3-(3-methyl-3-morpholinobut-1-ynyl)pyridin-4-yloxy)-3-fluorophenyl)-2,4-dioxo-1,2,3,4-tetrahydropyrimidine-5-carboxamide in an aspect of the invention. See FIG. 67.

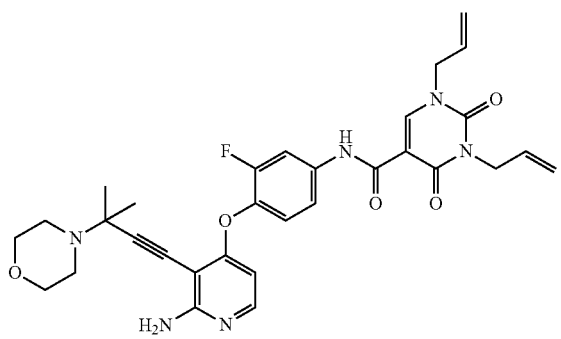 [SMILES: C=CCn1cc(C(=O)Nc2ccc(Oc3ccnc(N)c3C#CC(C)(C)N3CCOCC3)c(F)c2)c(=O)n(CC=C)c1=O]

To a solution of 1,3-diallyl-N-(4-(2-amino-3-iodopyridin-4-yloxy)-3-fluorophenyl)-2,4-dioxo-1,2,3,4-tetrahydropyrimidine-5-carboxamide (Intermediate 28, 100 mg, 0.18 mmol) in DMF (1.8 mL) were added 4-(2-methylbut-3-yn-2-yl)morpholine (41.0 mg, 0.27 mmol), copper(I) iodide (6.76 mg, 0.02 mmol) and TEA (97.0 μL, 0.71 mmol) at room temperature. The mixture was degassed by purging and re-filled with Ar in several times. After addition of Pd(PPh₃)₄ (21.0 mg, 0.02 mmol), the reaction mixture was heated at 90° C. for 18 hours. After cooled to room temperature, the reaction mixture was quenched with water and extracted with EtOAc. The organic layer was dried over Na₂SO₄, filtered, and concentrated in vacuo. The residue was purified by column chromatography on SiO₂ (EtOAc/MeOH=30/1) to give the 1,3-diallyl-N-(4-(2-amino-3-(3-methyl-3-morpholinobut-1-ynyl)pyridin-4-yloxy)-3-fluorophenyl)-2,4-dioxo-1,2,3,4-tetrahydropyrimidine-5-carboxamide (1.2 mg, 1%) as a white solid. ¹H-NMR (CDCl₃, Varian, 400 MHz): δ 1.47 (6H, s), 2.64-2.71 (4H, m), 3.71-3.79 (4H, m), 4.52 (2H, d, J=6.4 Hz), 4.64 (2H, d, J=5.6 Hz), 5.02 (2H, s), 5.27 (2H, d, J=10.4 Hz), 5.34 (1H, d, J=5.6 Hz), 5.41 (2H, d, J=11.2 Hz), 5.88-6.00 (1H, m), 6.04 (1H, d, J=6.0 Hz), 7.10 (2H, t, J=8.6 Hz), 7.85-7.81 (2H, m), 8.48 (1H, s), 11.0 (1H, s)

Example 71

This example describes the synthesis of 1,3-dialyl-N-(4-(2-amino-3-(3-(piperidin-4-yl)prop-1-ynyl)pyridin-4-yloxy)-3-fluorophenyl)-2,4-dioxo-1,2,3,4-tetrahydropyrimidine-5-carboxamide in an aspect of the invention. See FIG. 68.

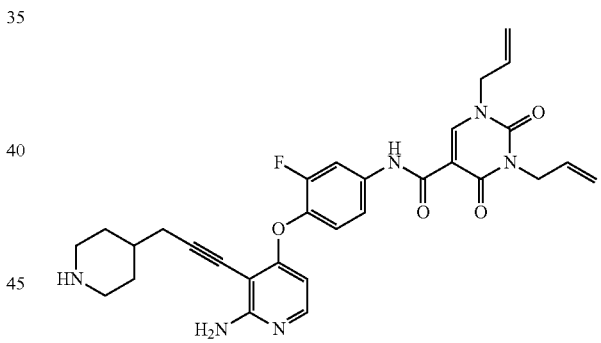

Step A: tert-butyl 4-(3-(2-amino-4-(4-(1,3-diallyl-2,4-dioxo-1,2,3,4-tetrahydropyrimidine-5-carboxamido)-2-fluorophenoxy)pyridin-3-yl)prop-2-ynyl)piperidine-1-carboxylate

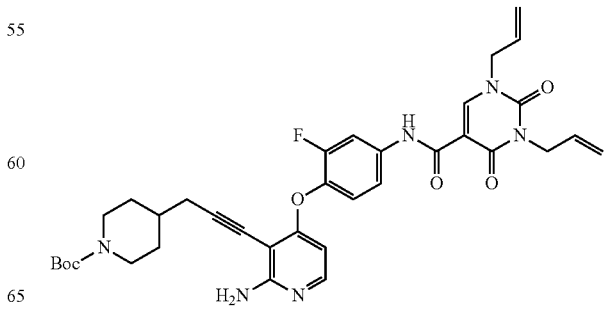

To a solution of 1,3-diallyl-N-(4-(2-amino-3-iodopyridin-4-yloxy)-3-fluorophenyl)-2,4-dioxo-1,2,3,4-tetrahydropyrimidine-5-carboxamide (Intermediate 28, 150 mg, 0.27 mmol) in DMF (5.3 mL) were added tert-butyl 4-(prop-2-ynyl)piperidine-1-carboxylate (89.0 mg, 0.40 mmol), copper (I) iodide (10.1 mg, 0.05 mmol) and TEA (0.15 mL, 1.07 mmol) at room temperature. The mixture was degassed by purging and re-filled with Ar in several times. After addition of Pd(PPh$_3$)$_4$ (31.0 mg, 0.03 mmol), the reaction mixture was heated at 90° C. for 18 hours. After cooled to room temperature, the reaction mixture was quenched with water and extracted with EtOAc. The organic layer was dried over Na$_2$SO$_4$, filtered, and concentrated in vacuo. The residue was purified by column chromatography on SiO$_2$ (EtOAc/MeOH=50/1) to give the tert-butyl 4-(3-(2-amino-4-(4-(1,3-diallyl-2,4-dioxo-1,2,3,4-tetrahydropyrimidine-5-carboxamido)-2-fluorophenoxy)pyridin-3-yl)prop-2-ynyl)piperidine-1-carboxylate (43.0 mg, 25%) as a yellow solid. $^1$H-NMR (CDCl$_3$, Varian, 400 MHz): δ 0.78-0.88 (1H, m), 1.21-1.29 (4H, m), 1.44 (9H, s), 1.65 (4H, s), 2.46 (2H, d, J=6.4 Hz), 4.52 (2H, d, J=6.0 Hz), 4.64 (2H, d, J=5.2 Hz), 5.02 (2H, s), 5.27 (2H, d, J=10.8 Hz), 5.34 (1H, d, J=5.6 Hz), 5.41 (2H, d, J=10.4 Hz), 5.88-5.98 (3H, m), 7.12 (1H, t, J=8.8 Hz), 7.48-7.55 (2H, m), 8.48 (1H, s), 11.0 (1H, s).

Step B: 1,3-dialyl-N-(4-(2-amino-3-(3-(piperidin-4-yl)prop-1-ynyl)pyridin-4-yloxy)-3-fluorophenyl)-2,4-dioxo-1,2,3,4-tetrahydropyrimidine-5-carboxamide

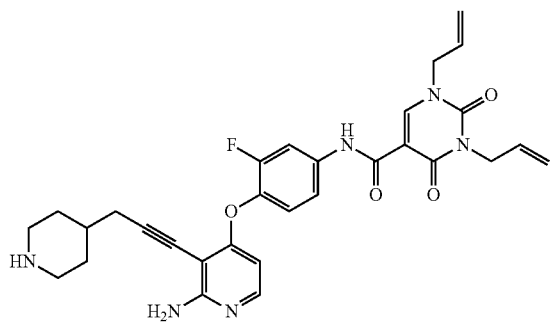 [SMILES: C=CCn1cc(C(=O)Nc2ccc(Oc3ccnc(N)c3C#CCC3CCNCC3)c(F)c2)c(=O)n(CC=C)c1=O]

To a solution of tert-butyl 4-(3-(2-amino-4-(4-(1,3-diallyl-2,4-dioxo-1,2,3,4-tetrahydropyrimidine-5-carboxamido)-2-fluorophenoxy)pyridin-3-yl)prop-2-ynyl)piperidine-1-carboxylate (43.0 mg, 0.06 mmol) in DCM (1.3 mL) was added TFA (50.0 µL, 0.65 mmol) at room temperature. The reaction mixture was stirred for 18 hours at room temperature. After cooled to 0° C., the reaction mixture was quenched with sat. NaHCO$_3$ solution and extracted with DCM. The organic layer was dried over Na$_2$SO$_4$, filtered and concentrated in vacuo. The residue was purified by column chromatography on NH—SiO$_2$ (EtOAc/MeOH=10/1) to give the 1,3-dialyl-N-(4-(2-amino-3-(3-(piperidin-4-yl)prop-1-ynyl)pyridin-4-yloxy)-3-fluorophenyl)-2,4-dioxo-1,2,3,4-tetrahydropyrimidine-5-carboxamide (3.3 mg, 9%) as a white solid. $^1$H-NMR (CDCl$_3$, Varian, 400 MHz): δ 1.24-1.30 (3H, m), 1.83 (2H, d, J=14.4 Hz), 2.44 (2H, d, J=6.4 Hz), 2.61 (2H, t, J=12.2 Hz), 3.09 (2H, d, J=11.6 Hz), 4.53 (2H, d, J=6.4 Hz), 4.64 (2H, d, J=6.0 Hz), 5.02 (2H, s), 5.27 (2H, d, J=10.8 Hz), 5.34 (1H, d, J=6.0 Hz), 5.41 (2H, d, J=10.4 Hz), 5.88-5.99 (2H, m), 6.00 (1H, d, J=6.0 Hz), 7.11 (1H, t, J=9.0 Hz), 7.80-7.83 (2H, m), 8.49 (1H, s), 11.0 (1H, s). * A proton from NH was not observed.

Example 72

This example illustrates an enzymatic assay to determine the inhibitory activity of exemplary compounds of Formula (I) in an embodiment of the invention.

All the kinase reactions were performed in 5 µL using tyrosine kinase buffer with 0.2 µg/µL poly (Glu4, Tyr1) substrate, 10 M ATP, serial dilution of the inhibitor, and incubated at room temperature for 60 min. After the indicated incubation times, 5 µL ADP-GLO™ reagent (Promega, Madison, WI) was added to the reactions and the plate was incubated at room temperature for 40 min. Then, 10 µL of kinase detection reagent was added and after an incubation time of 40 min, luminescence was recorded and IC$_{50}$ values were determined (Table 3). All 384-well assay plates were read using a GLOMAX™ Discover Microplate Luminometer from Promega (Madison, WI). To plot, analyze the data and calculate all kinase reaction biochemical values, both Microsoft Excel and Prism from GraphPad 7 Software (La Jolla, CA) were used.

TABLE 3

| | Enzymatic assay IC$_{50}$ (nM) | | |
|---|---|---|---|
| Ex. No | c-MET | AXL | MER |
| 33 | <1000 | <10000 | <100 |
| 34 | <10000 | <1000 | <100 |
| 35 | <10000 | <10000 | <100 |
| 36 | <10000 | <10000 | <1000 |
| 37 | <10000 | <100 | <10 |
| 38 | <10 | <100 | <10 |
| 39 | <100 | <100 | <100 |
| 40 | <1000 | <100 | <100 |
| 41 | <100 | <100 | <100 |
| 42 | <100 | <1000 | <100 |
| 43 | <10 | <10 | <10 |
| 44 | <10 | <10 | <10 |
| 45 | <1000 | <100 | <100 |
| 46 | <100 | <10 | <100 |
| 47 | <1000 | <10 | <100 |
| 48 | <100 | <100 | <1000 |
| 49 | <1000 | <100 | <100 |
| 50 | <100 | <10 | <100 |
| 51 | <100 | <100 | <100 |
| 52 | <1000 | <100 | <100 |
| 53 | <100 | <10 | <10 |
| 54 | <10 | <10 | <100 |
| 55 | <100 | <100 | <100 |
| 56 | <100 | <100 | <100 |
| 57 | <100 | <100 | <10 |
| 58 | <100 | <100 | <10 |
| 59 | <100 | <100 | <10 |
| 60 | <100 | <10 | <10 |
| 61 | <100 | <10 | <10 |
| 62 | <100 | <10 | <10 |
| 63 | <10 | <10 | <10 |
| 64 | <100 | <10 | <10 |
| 65 | <100 | <10 | <10 |
| 66 | <100 | <10 | <10 |
| 67 | <100 | <10 | <10 |
| 68 | <1000 | <1000 | <100 |
| 69 | <1000 | <100 | <100 |
| 70 | <1000 | <1000 | <10 |
| 71 | <100 | <100 | <10 |

Example 73

This example illustrates a cell viability assay of exemplary compounds of Formula (I) in an embodiment of the invention.

Cell viability assays were carried out by plating 1,000 cells per well of HCC827 or PC9 resistant cells, respectively, into white transparent-bottom 384-well plates. The cells were treated with each TKI across a 10-dose range from 1 nM to 10,000 nM. After 72 h of drug treatment, cell viability was measured using the CellTiter-Glo 2.0 assay (Promega, Madison, WI). EGFR TKIs (gefitinib, erlotinib, and osimertinib)-resistant cell lines that was derived from the parental EGFR TKIs-sensitive HCC827 or PC9 cell line was established by continuous exposure of cells to EGFR TKIs more than a period of 3 months. The resistant cell lines were designated PC9/ER, HCC827/ER, HCC827/GR and HCC827/OR. All of these resistant cells exhibited a 1,000-fold higher resistance to EGFR TKIs than the parental cells.

The efficacy of combinations of EGFR TKIs and inhibitor of Formula (I) in EGFR TKI-resistant cells is shown in Table 4.

TABLE 4

| | Relative cell viability; IC$_{50}$ (nM) | | | |
|---|---|---|---|---|
| Ex. No | PC9ER | HCC827ER | HCC827GR | HCC827OR |
| 33 | <1000 | <1000 | <1000 | <1000 |
| 34 | <10000 | <1000 | <1000 | <10000 |
| 35 | >10000 | <10000 | >10000 | <10000 |
| 36 | <10000 | <10000 | <10000 | <10000 |
| 37 | <10000 | <10000 | <10000 | <10000 |
| 38 | <10000 | <10000 | <10000 | <10000 |
| 39 | <100 | <100 | <100 | <100 |
| 40 | <100 | <100 | <100 | <1000 |
| 41 | <1000 | <1000 | <1000 | <1000 |
| 42 | <1000 | <100 | <100 | <1000 |
| 43 | <100 | <100 | <100 | <1000 |
| 44 | <1000 | <1000 | <100 | <1000 |
| 45 | <1000 | <1000 | <1000 | <10000 |
| 46 | <10000 | <10000 | <1000 | <10000 |
| 47 | <10000 | <10000 | <10000 | <10000 |
| 48 | <1000 | <1000 | <1000 | <1000 |
| 49 | <1000 | <10000 | <1000 | <10000 |
| 50 | <100 | <100 | <1000 | <100 |
| 51 | <1000 | <1000 | <10000 | <1000 |
| 52 | <10000 | <10000 | <10000 | >10000 |
| 53 | <10000 | <1000 | <10000 | <10000 |
| 54 | <1000 | <1000 | <1000 | <1000 |
| 55 | <1000 | <100 | <100 | <1000 |
| 56 | <1000 | <10 | <100 | <1000 |
| 57 | <1000 | <100 | <100 | <1000 |
| 58 | <1000 | <1000 | <1000 | <1000 |
| 59 | <1000 | <1000 | <1000 | <1000 |
| 60 | <100 | <100 | <100 | <100 |
| 61 | <1000 | <1000 | <1000 | <100 |
| 62 | <1000 | <100 | <1000 | <1000 |
| 63 | <1000 | <1000 | <10000 | <10000 |
| 64 | <1000 | <1000 | <1000 | <1000 |
| 65 | <1000 | <1000 | <1000 | <10000 |
| 66 | <1000 | <1000 | <1000 | <10000 |
| 67 | <1000 | <100 | <100 | <1000 |
| 68 | <10000 | <1000 | <1000 | <1000 |
| 69 | <1000 | <1000 | <1000 | <1000 |
| 70 | <10000 | <1000 | <1000 | <1000 |
| 71 | <1000 | <1000 | <1000 | <1000 |

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of Formula (I) or a pharmaceutically acceptable salt thereof:

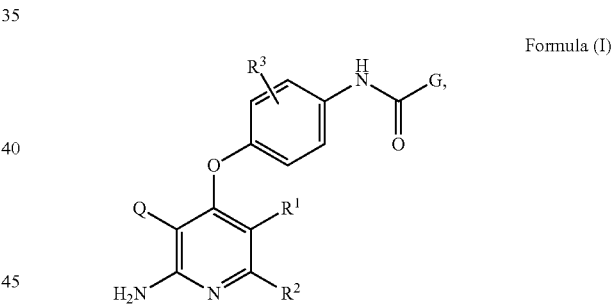

Formula (I)

wherein
$R^1$ is H, alkyl, haloalkyl, halo, or CN;
$R^2$ is H, alkyl, haloalkyl, halo, or CN;
$R^3$ is H or halo;
Q is unsubstituted alkyl, alkenyl, alkynyl, unsubstituted or substituted, cycloalkyl, unsubstituted or substituted, heterocyclyl, unsubstituted or substituted, heteroaryl, or unsubstituted or substituted, aryl, wherein said alkenyl or alkynyl is selected from the group consisting of:
—CH=CR$^4$(CX')$_m$(CH$_2$)$_n$NR$^5$R$^6$, —C≡C(CX')$_m$(CH$_2$)$_n$NR$^5$R$^6$,
—CH=CR$^4$(CX')$_m$(CH$_2$)$_n$CHR$^5$R$^6$, —C≡C(CX')$_m$(CH$_2$)$_n$CHR$^5$R$^6$,
—CH=CR$^4$(CX')$_m$(CH$_2$)$_n$NR$^7$OR$^8$, and —C≡C(CX')$_m$(CH$_2$)$_n$NR$^7$OR$^8$;
wherein
$R^4$ is hydrogen or halo;
X' is H$_2$, (C$_{1-6}$ alkyl)$_2$, or =O;
m is 0 or 1;
n is 0 or 1-3;

—NR⁵R⁶ either forms a 4-7 membered heterocyclic ring or does not form a ring structure, the heterocyclic ring being either heteroaryl or heterocyclyl ring, when —NR⁵R⁶ forms a 4-7 membered heterocyclic ring, the 4-7 membered heterocyclic ring includes an optional second heteroatom in addition to the nitrogen of —NR⁵R⁶ and is optionally substituted with one or more substituent groups independently selected from the group consisting of linear $C_1$-$C_6$ alkyl, branched $C_3$-$C_6$ alkyl, hydroxy, $C_1$-$C_6$ alkoxyalkyl, carboxylic acid, linear $C_1$-$C_4$ alkyl carboxylic acid, and branched $C_3$-$C_4$ alkyl carboxylic acid;

when —NR⁵R⁶ does not form a ring structure, R⁵ is selected from the group consisting of hydrogen, linear $C_1$-$C_6$ alkyl, and branched $C_3$-$C_6$ alkyl, and R⁶ is selected from the group consisting of hydrogen, linear $C_1$-$C_6$ alkyl optionally substituted with at least one fluoro or at least one hydroxy, branched $C_3$-$C_6$ alkyl optionally substituted with at least one fluoro or at least one hydroxy, and cycloalkyl optionally substituted with at least one fluoro or at least one hydroxy;

—CHR⁵R⁶ either forms a 4-7 membered heterocyclic ring or does not form a ring structure, the heterocyclic ring being either heteroaryl or heterocyclyl ring, when —CHR⁵R⁶ forms a 4-7 membered heterocyclic ring, the 4-7 membered heterocyclic ring includes one or two heteroatoms and is optionally substituted with one or more substituent groups independently selected from the group consisting of linear $C_1$-$C_6$ alkyl, branched $C_3$-$C_6$ alkyl, hydroxy, $C_1$-$C_6$ alkoxyalkyl, carboxylic acid, linear $C_1$-$C_4$ alkyl carboxylic acid, and branched $C_3$-$C_4$ alkyl carboxylic acid;

when —CHR⁵R⁶ does not form a ring structure, R⁵ is selected from the group consisting of hydrogen, linear $C_1$-$C_6$ alkyl, and branched $C_3$-$C_6$ alkyl, and R⁶ is selected from the group consisting of hydrogen, linear $C_1$-$C_6$ alkyl optionally substituted with at least one fluoro or at least one hydroxy, branched $C_3$-$C_6$ alkyl optionally substituted with at least one fluoro or at least one hydroxy, and cycloalkyl optionally substituted with at least one fluoro or at least one hydroxy;

—NR⁷OR⁸ does not form a ring structure, R⁷ is selected from the group consisting of hydrogen, linear $C_1$-$C_6$ alkyl, and branched $C_3$-$C_6$ alkyl, and R¹ is selected from the group consisting of hydrogen, linear $C_1$-$C_6$ alkyl optionally substituted with at least one fluoro, hydroxy, or alkoxy group, branched $C_3$-$C_6$ alkyl optionally substituted with at least one fluoro, hydroxy, or alkoxy group, and cycloalkyl optionally substituted with at least one fluoro, hydroxy, or alkoxy group;

G is

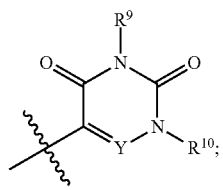

wherein

R⁹ is H, alkyl, substituted alkyl, alkenyl, substituted alkenyl, alkynyl, substituted alkynyl, cycloalkyl, aryl, substituted aryl, heteroaryl, substituted heteroaryl, heterocyclyl or heteroarylalkyl, where the heteroaryl group of heteroarylalkyl may be substituted or unsubstituted;

R¹⁰ is H, aryl, substituted aryl, heteroaryl, substituted heteroaryl, heterocyclyl, alkyl or cycloalkyl, cycloalkylalkyl, alkenyl or alkynyl, where alkyl, alkenyl or cycloalkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, substituted heteroaryl, carboxyl, oxo, carbamoyl, alkylcarbamoyl, dialkycarbamoyl, where the alkyl groups of dialkylcarbamoyl may be the same or different and heterocyclylcarbonyl; and Y is N, C—H, or C-alkyl.

2. The compound of claim 1 or a pharmaceutically acceptable salt thereof, wherein both R¹ and R² are hydrogen.

3. The compound of claim 1 or a pharmaceutically acceptable salt thereof, wherein R³ is a halo.

4. The compound of claim 1 or a pharmaceutically acceptable salt thereof, wherein Q is optionally substituted phenyl, optionally substituted heterocyclyl, or an alkenyl or alkynyl moiety selected from the group consisting of —CH═CR⁴(CX')$_m$(CH$_2$)$_n$NR⁵R⁶, —C≡C(CX')$_m$(CH$_2$)$_n$NR⁵R⁶, —CH═CR⁴(CX')$_m$(CH$_2$)$_n$CHR⁵R⁶, —C≡C(CX')$_m$(CH$_2$)$_n$CHR⁵R⁶, —CH═CR⁴(CX')$_m$(CH$_2$)$_n$NR⁷OR⁸, and —C≡C(CX')$_m$(CH$_2$)$_n$NR⁷OR⁸, wherein R⁴ is hydrogen or halo;

X' is H$_2$, (C$_{1-6}$ alkyl)$_2$, or ═O;

m is 0 or 1;

n is 0 or 1;

—NR⁵R⁶ is morpholinyl, piperazinyl, or piperidinyl, each of which is optionally substituted with one or more substituent groups independently selected from the group consisting of a nitrogen protecting group, alkyl, hydroxy, alkoxy, and alkoxyalkyl, —CHR⁵R⁶ is tetrahydropyranyl, morpholinyl, piperazinyl, or piperidinyl, each of which is optionally substituted with one or more substituent groups independently selected from the group consisting of a nitrogen protecting group, alkyl, hydroxy, alkoxy, and alkoxyalkyl, R⁷ is selected from the group consisting of hydrogen, linear $C_1$-$C_6$ alkyl, and branched $C_3$-$C_6$ alkyl, and R⁸ is selected from the group consisting of linear $C_1$-$C_6$ alkyl optionally substituted with at least one alkoxy group and branched $C_3$-$C_6$ alkyl optionally substituted with at least one alkoxy group.

5. The compound of claim 1 or a pharmaceutically acceptable salt thereof, wherein R⁹ is phenyl substituted with alkyl, haloalkyl, halo, and/or CN; and either (i) Y is C—H or (ii) Y is N.

6. The compound of claim 1 or a pharmaceutically acceptable salt thereof, wherein the compound of Formula (I) is a compound Formula (Ib):

Formula (Ib)

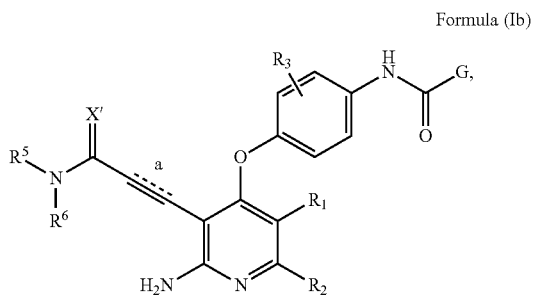

wherein ⩵ᵃ is —C≡C— or —CH=CH—.

7. The compound of claim 6 or a pharmaceutically acceptable salt thereof, wherein both $R^1$ and $R^2$ are hydrogen.

8. The compound of claim 6 or a pharmaceutically acceptable salt thereof, wherein $R^3$ is a halo.

9. The compound of claim 6 or a pharmaceutically acceptable salt thereof, wherein X' is $H_2$, $(C_{1-6}$ alkyl$)_2$, or =O; and —$NR^5R^6$ is morpholinyl, piperazinyl, or piperidinyl, each of which is optionally substituted with one or more substituent groups independently selected from the group consisting of a nitrogen protecting group, alkyl, hydroxy, alkoxy, and alkoxyalkyl.

10. The compound of claim 6 or a pharmaceutically acceptable salt thereof, wherein $R^9$ is phenyl substituted with alkyl, haloalkyl, halo, and/or CN; and either (i) Y is C—H or (ii) Y is N.

11. The compound of claim 1 or a pharmaceutically acceptable salt thereof, wherein the compound of Formula (I) is a compound Formula (Ic):

Formula (Ic)

wherein ⩵ᵃ is —C≡C— or —CH=CH—.

12. The compound of claim 11 or a pharmaceutically acceptable salt thereof, wherein both $R^1$ and $R^2$ are hydrogen.

13. The compound of claim 11 or a pharmaceutically acceptable salt thereof, wherein $R^3$ is a halo.

14. The compound of claim 11 or a pharmaceutically acceptable salt thereof, wherein X' is $H_2$, $(C_{1-6}$ alkyl$)_2$, or =O;

$R^7$ is selected from the group consisting of linear $C_1$-$C_6$ alkyl and branched $C_3$-$C_6$ alkyl, and $R^8$ is selected from the group consisting of linear $C_1$-$C_6$ alkyl and branched $C_3$-$C_6$ alkyl.

15. The compound of claim 11 or a pharmaceutically acceptable salt thereof, wherein $R^9$ is phenyl substituted with alkyl, haloalkyl, halo, and/or CN; and either (i) Y is C—H or (ii) Y is N.

16. A compound of claim 1 selected from

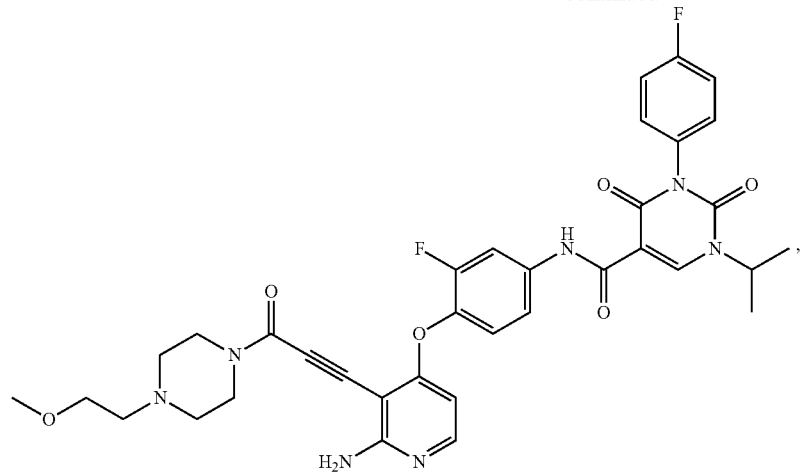
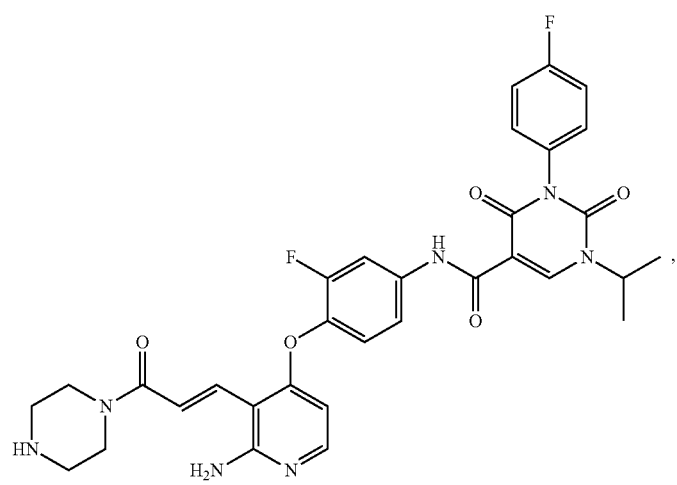
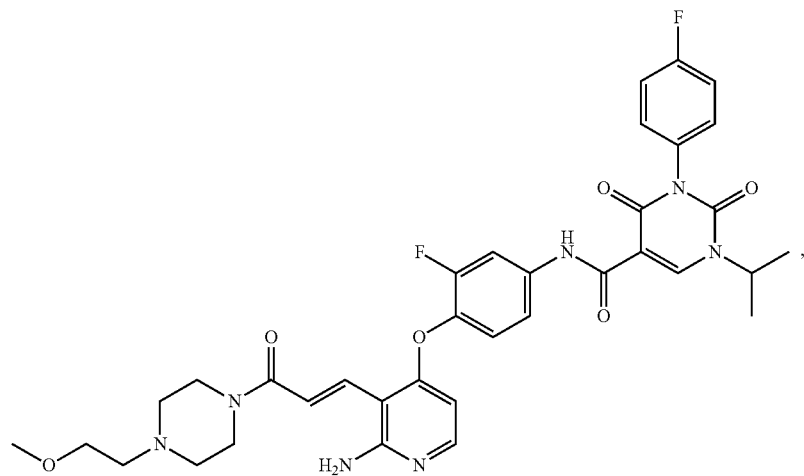

229
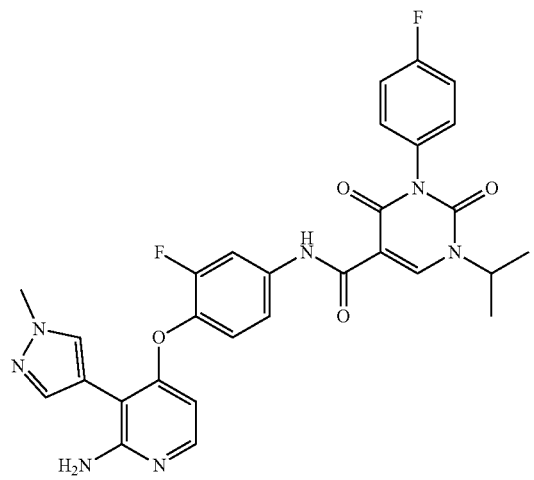
,
230
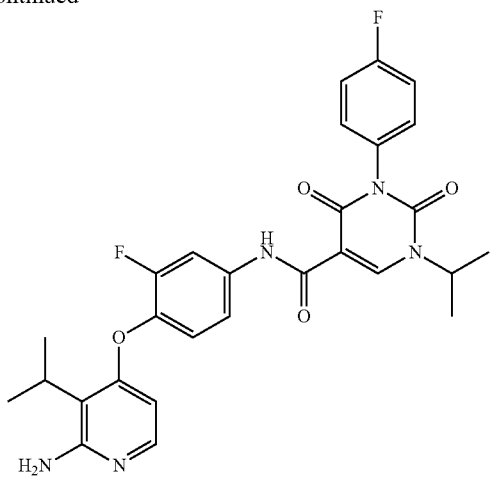
,
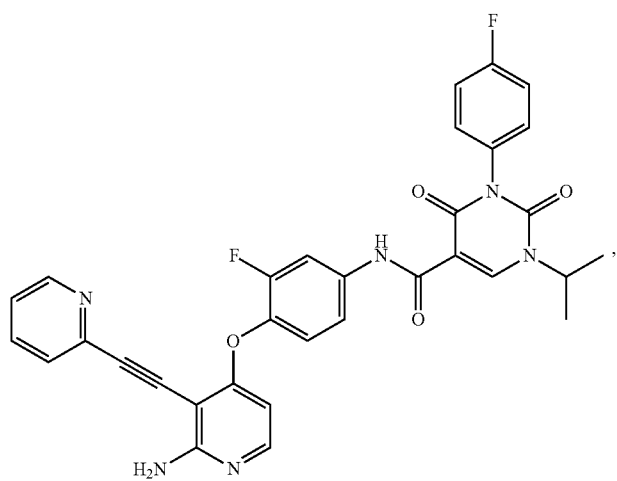
,
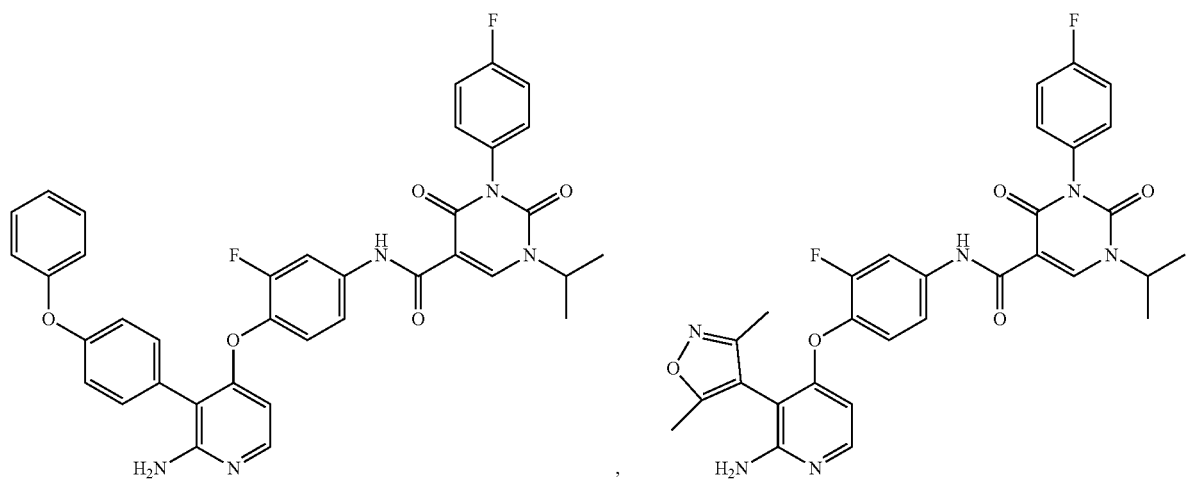
,

-continued
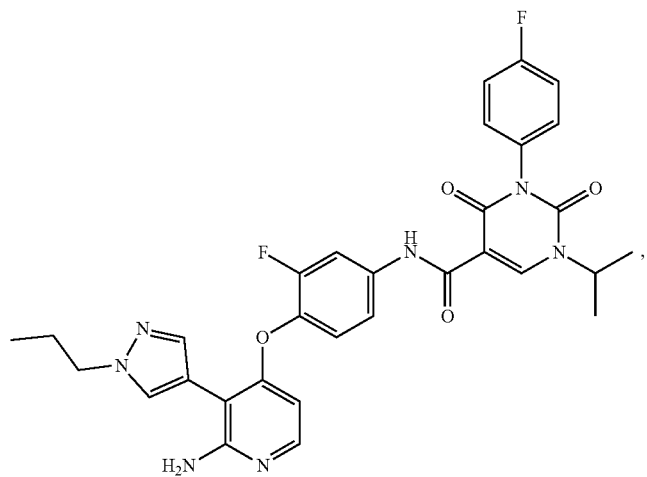
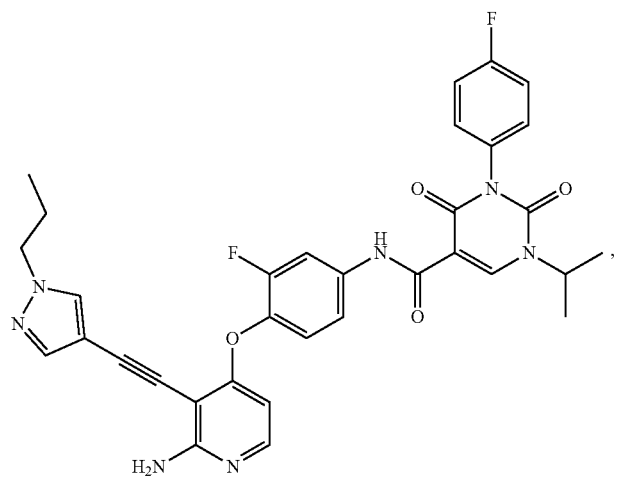
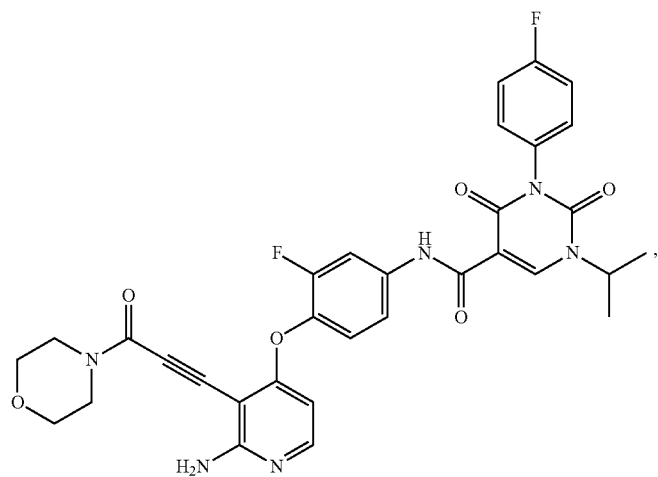

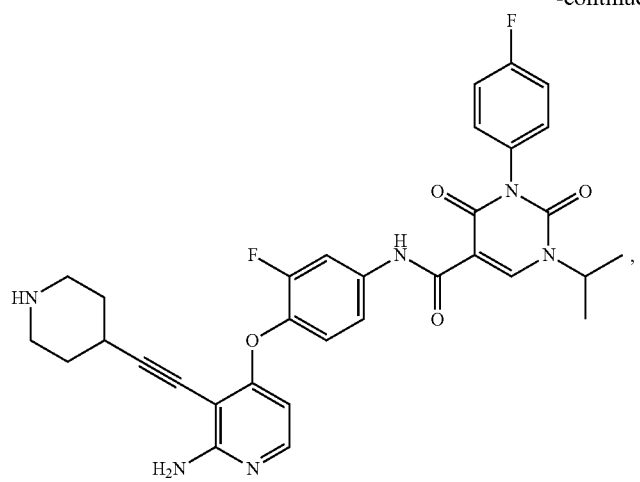
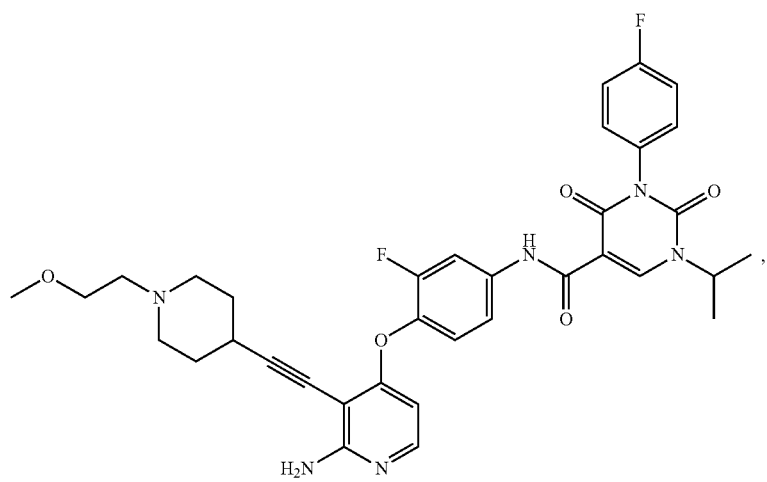
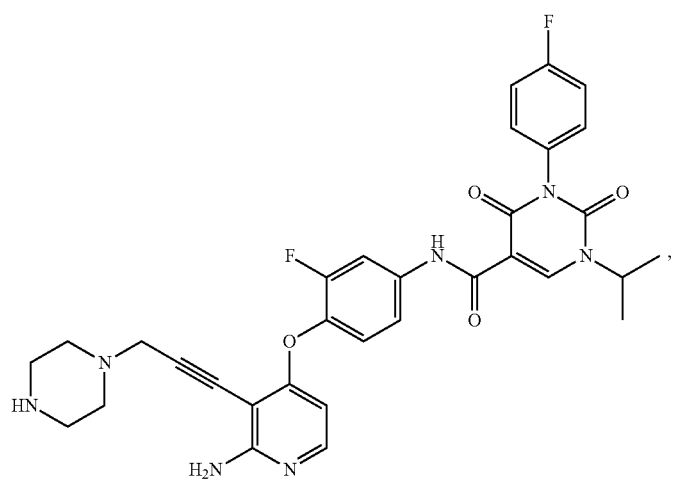

-continued
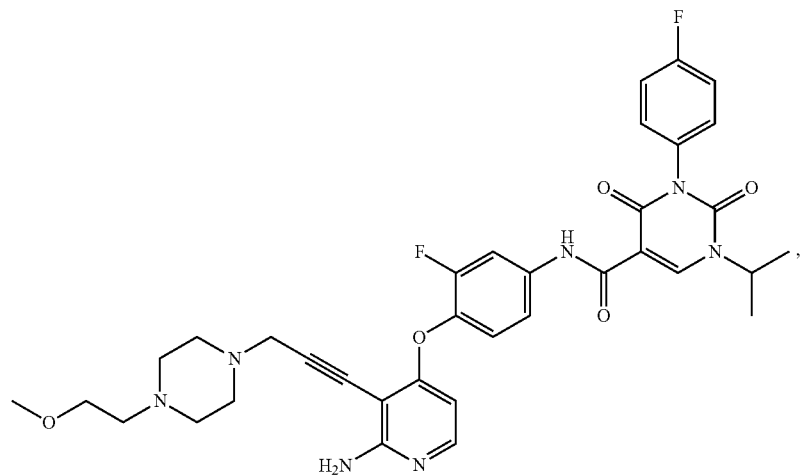
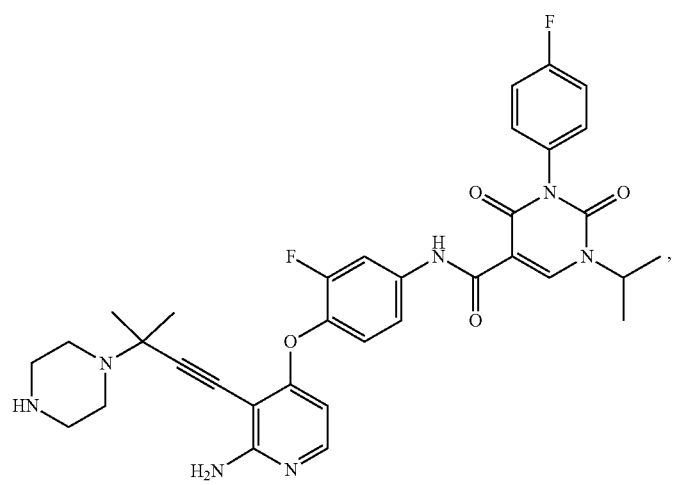
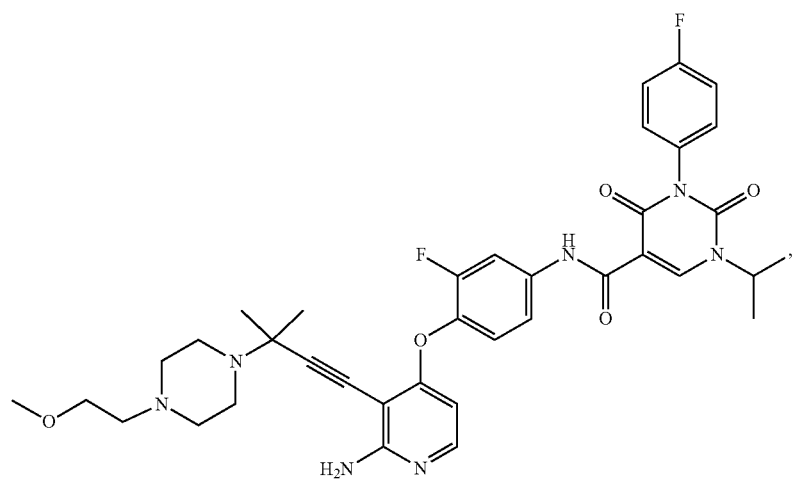

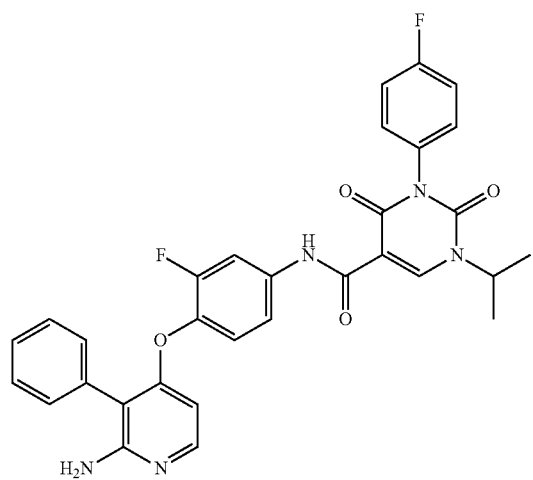
,
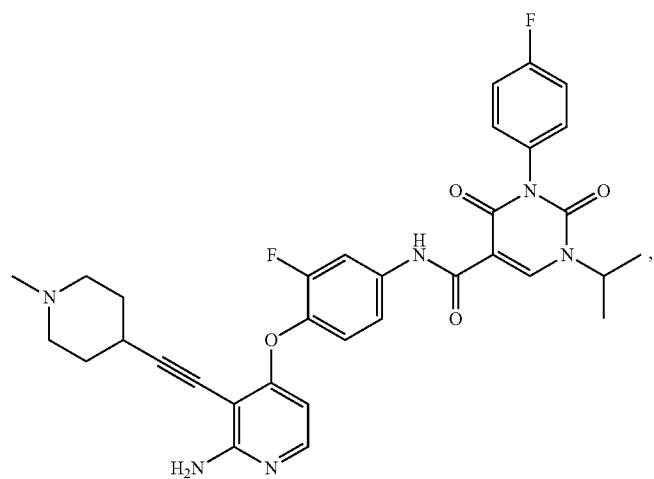
,
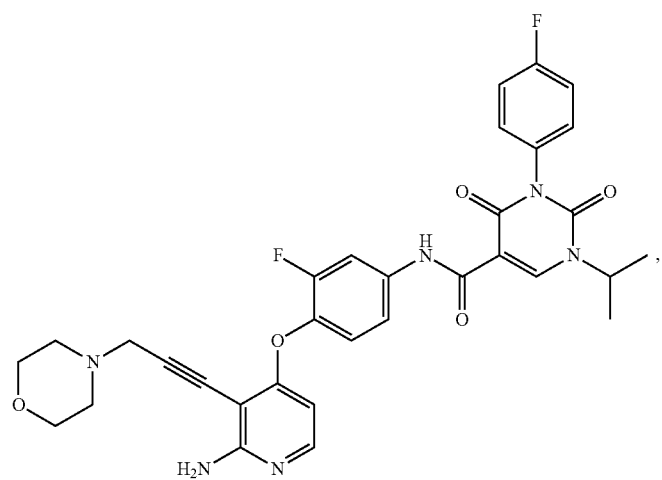
,

-continued
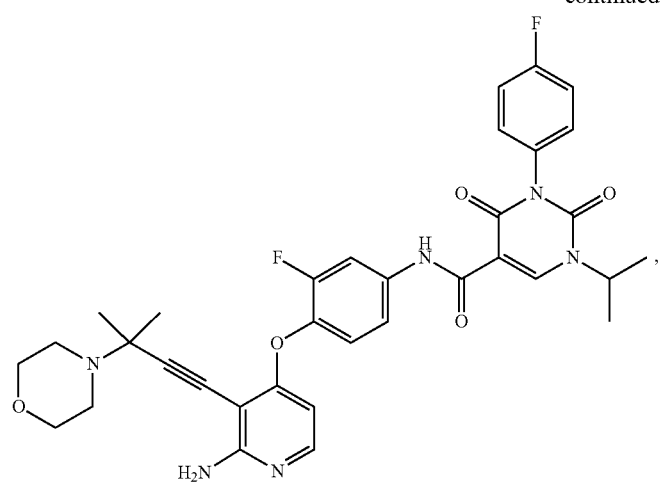
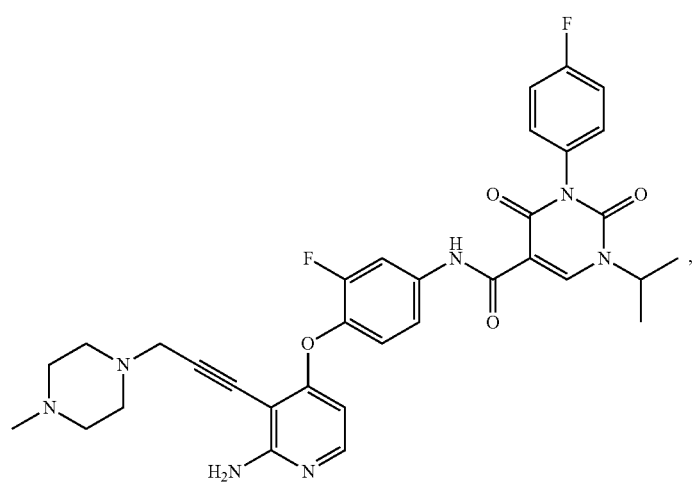
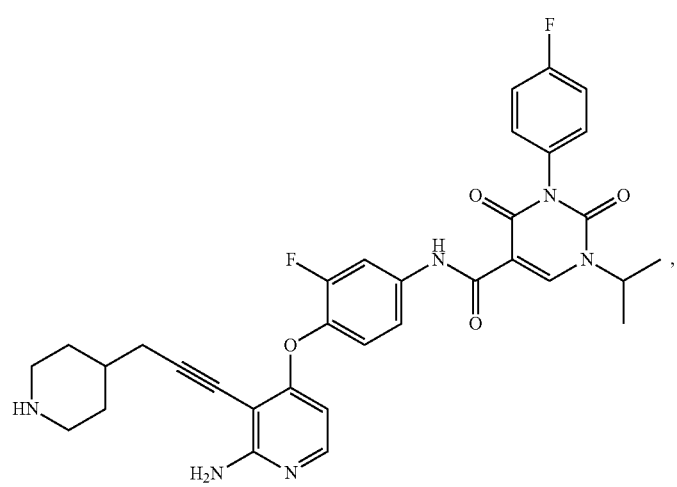

-continued
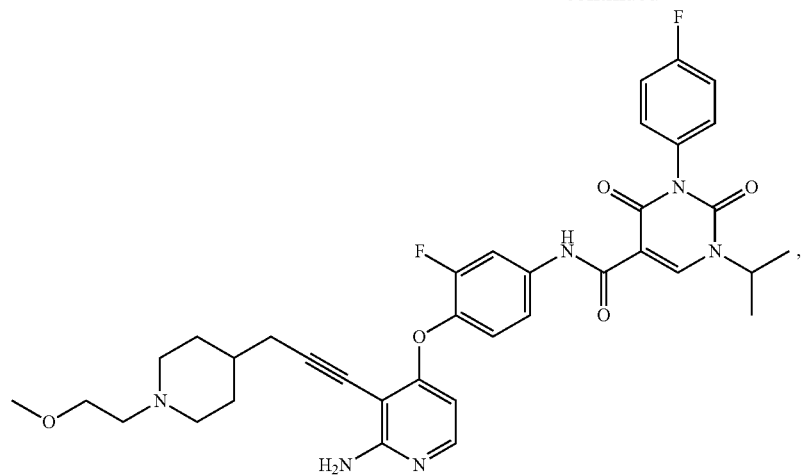
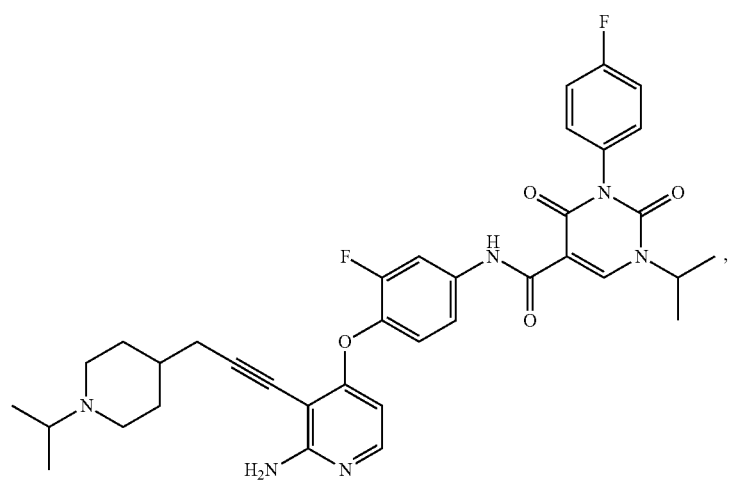
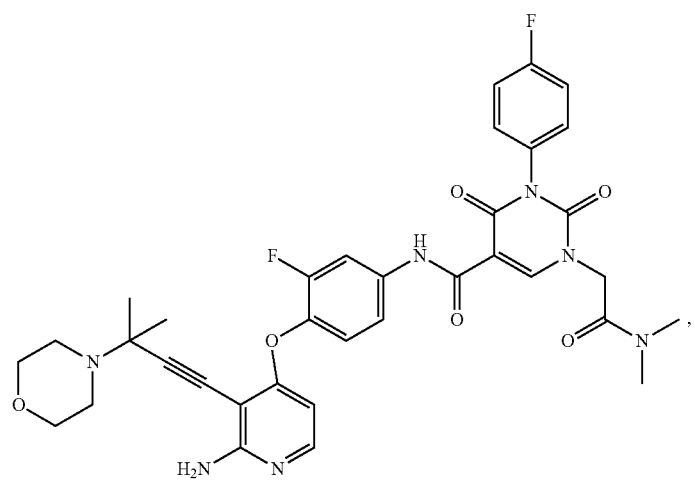

-continued
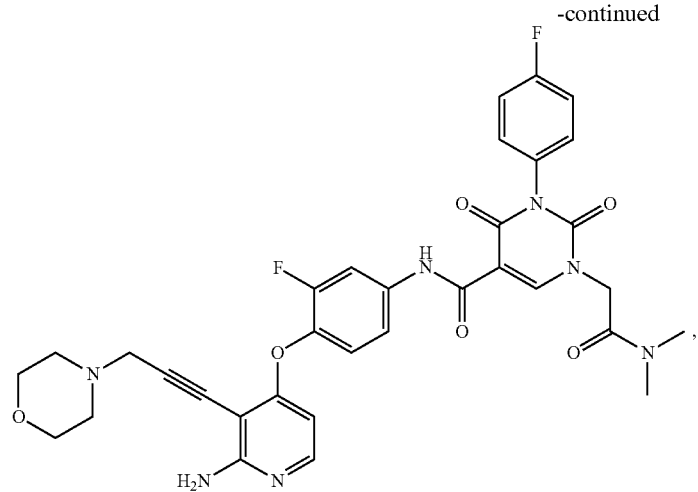
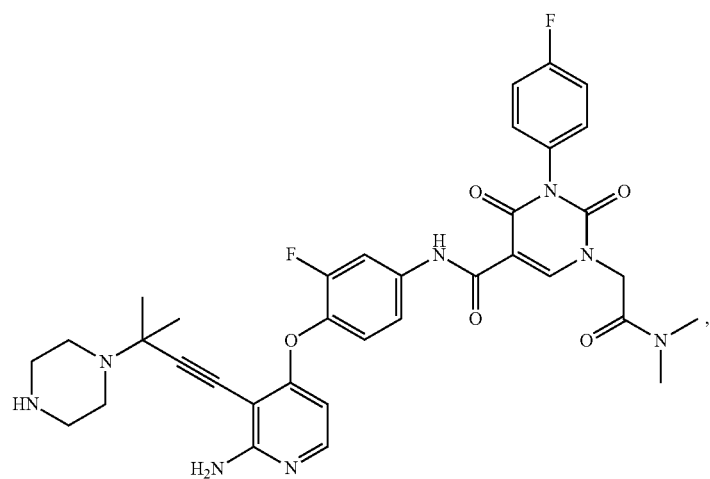
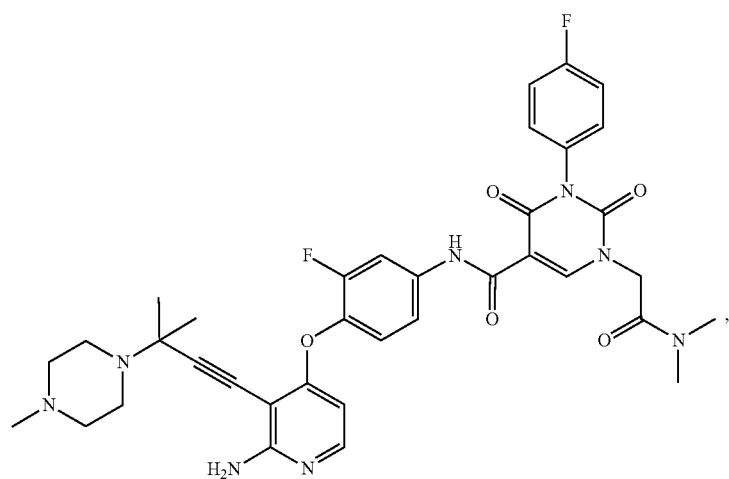

-continued
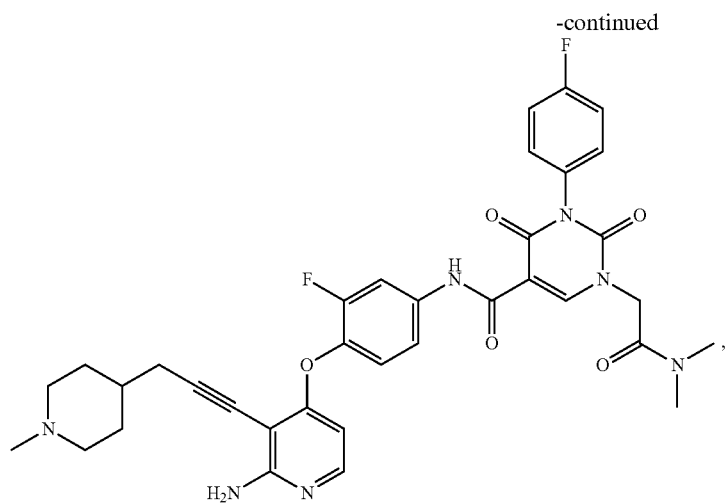
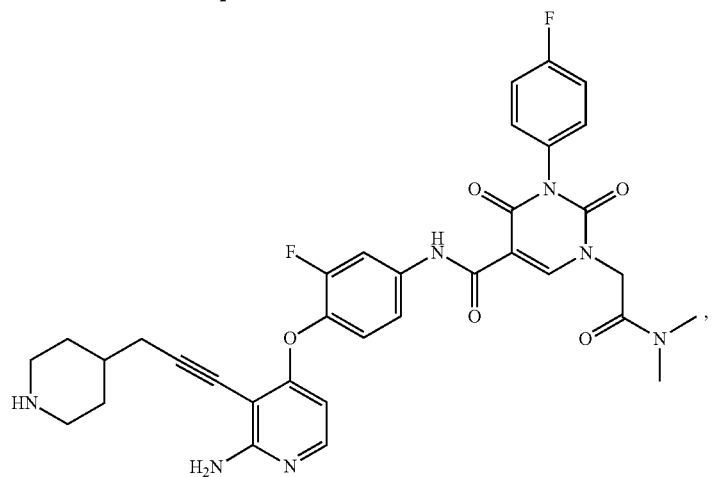
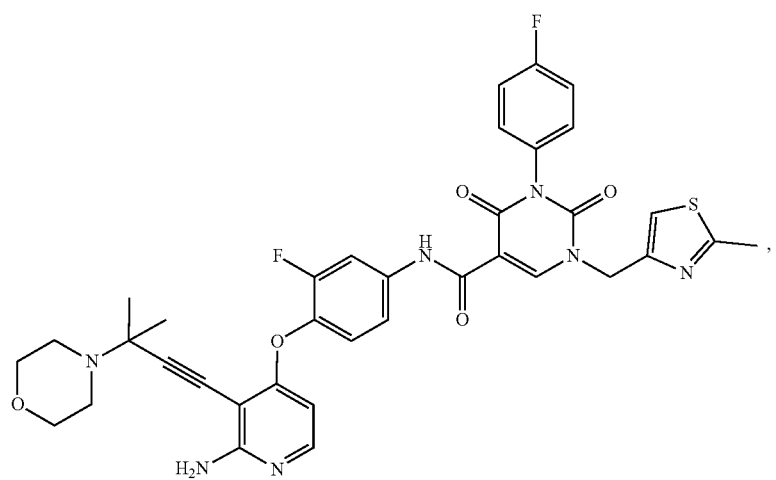

-continued
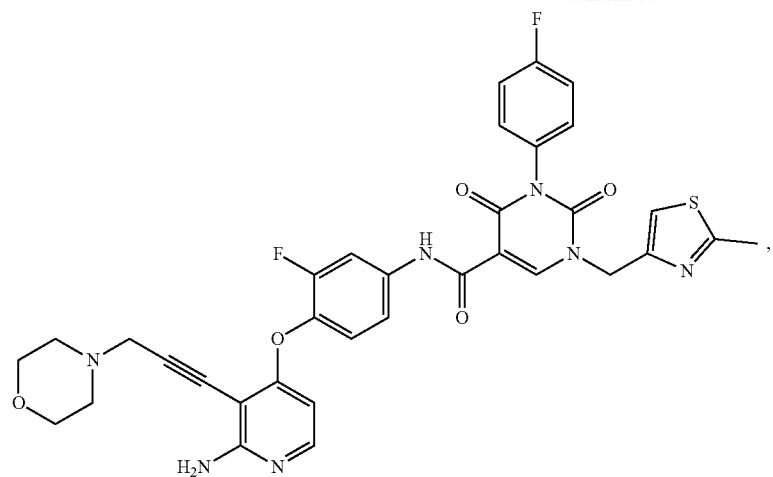
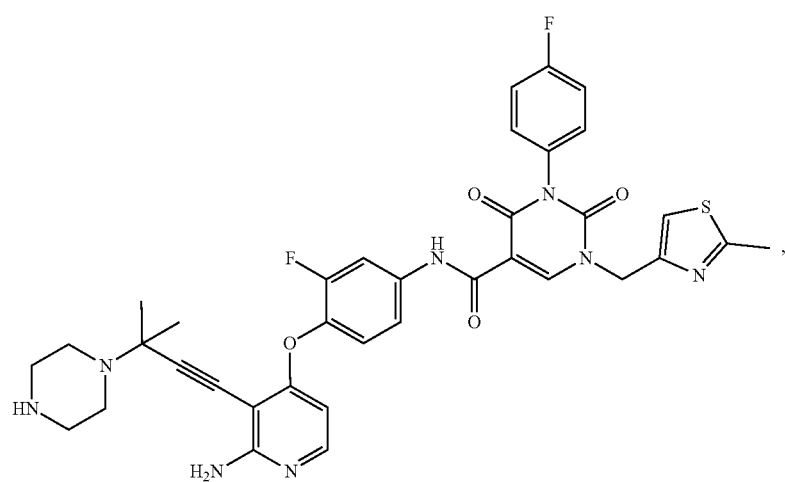
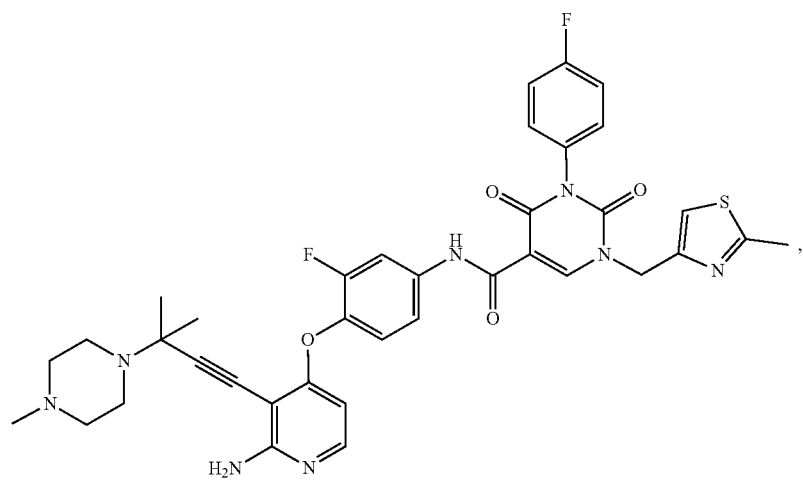

-continued
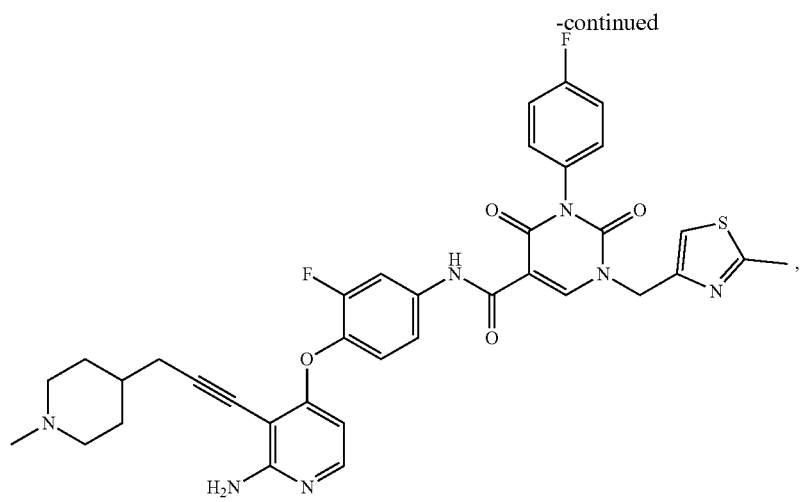
-continued
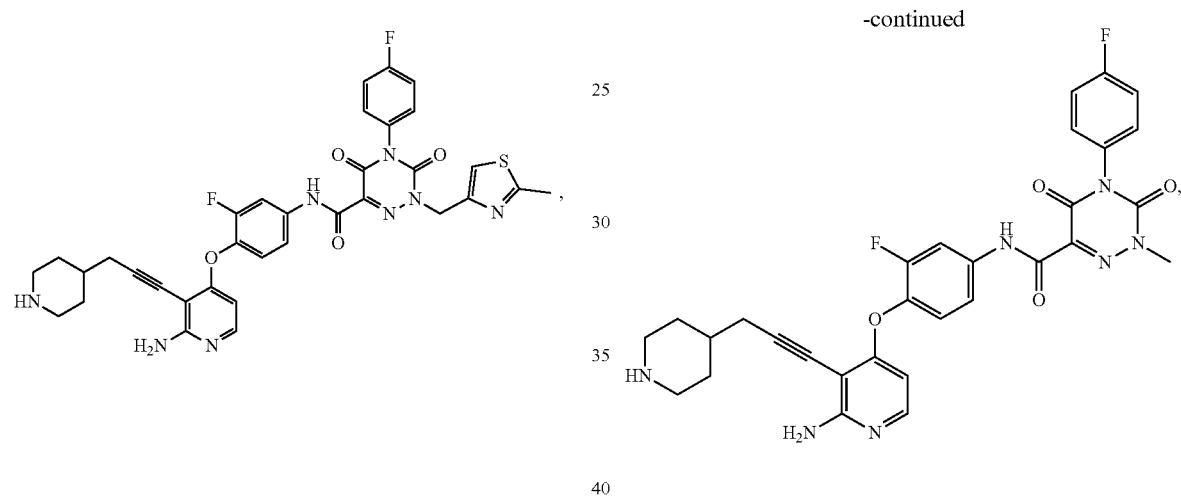
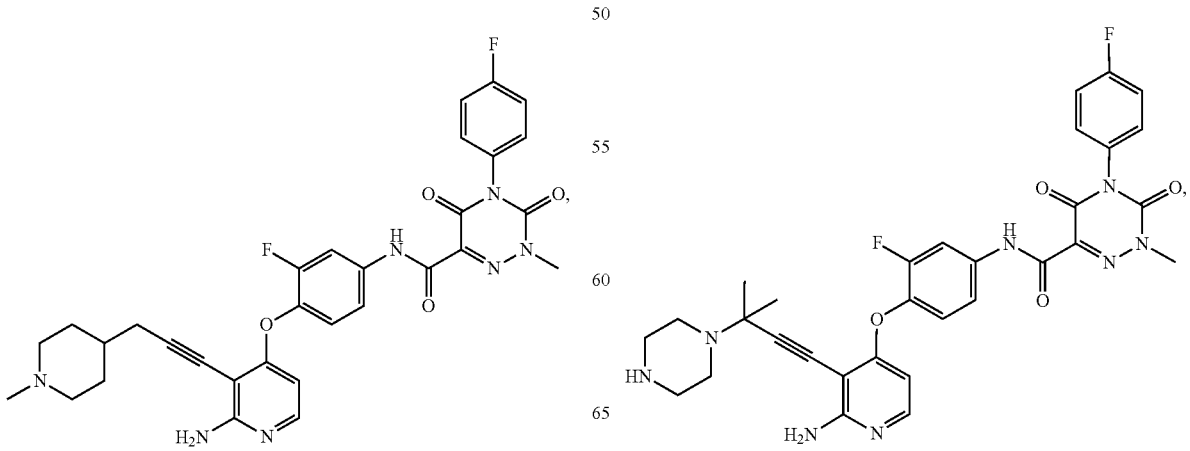

251
-continued
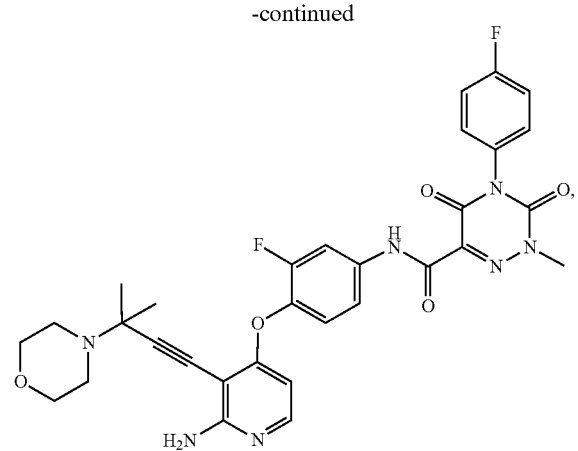
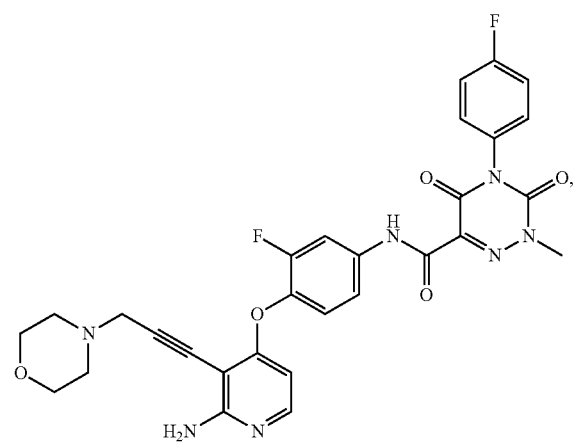
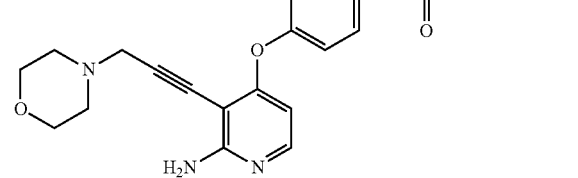
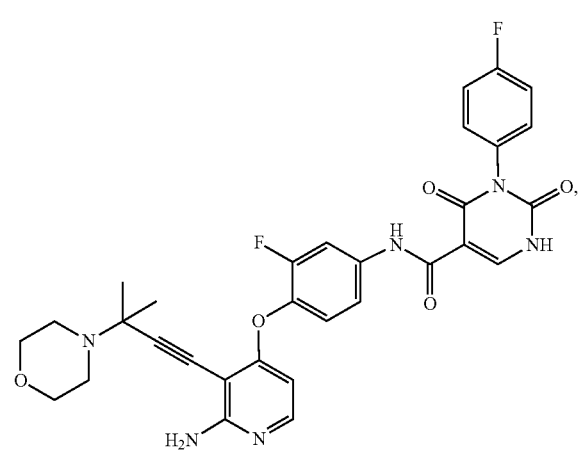
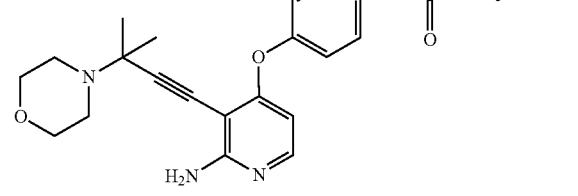
252
-continued
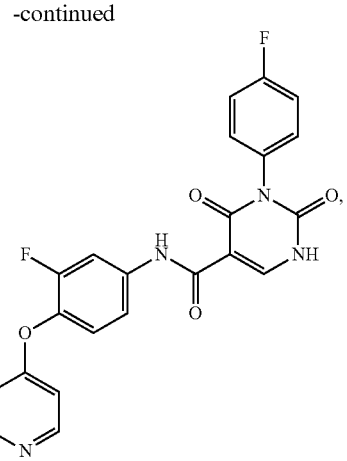
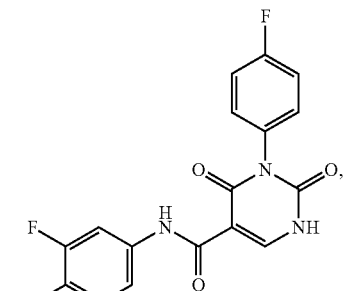
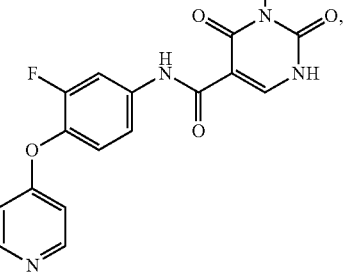
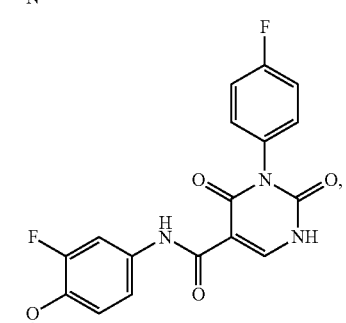
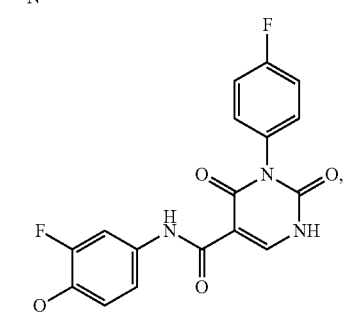

253
-continued
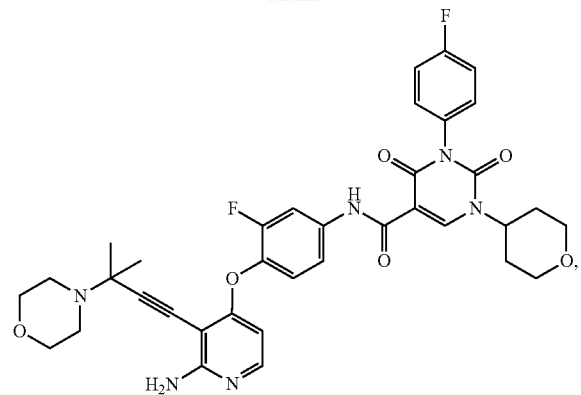
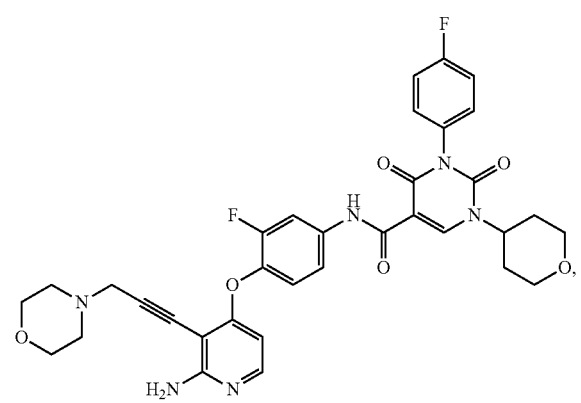
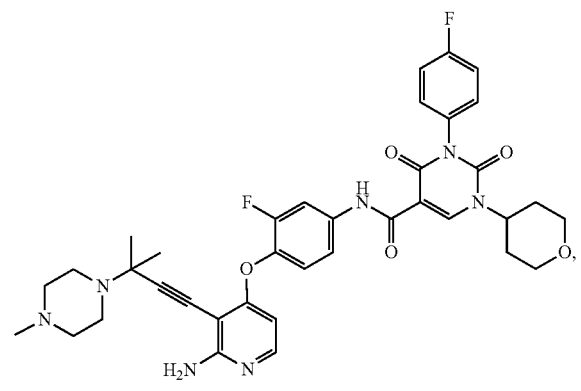
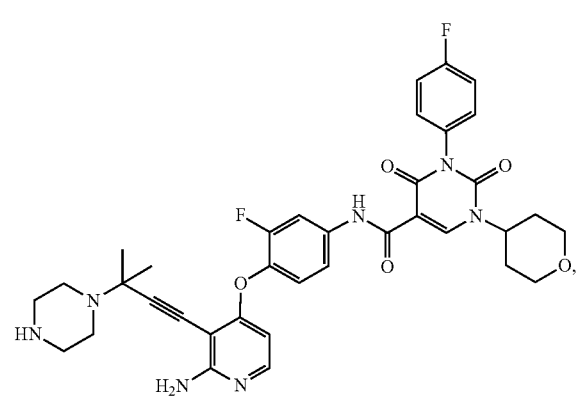
254
-continued
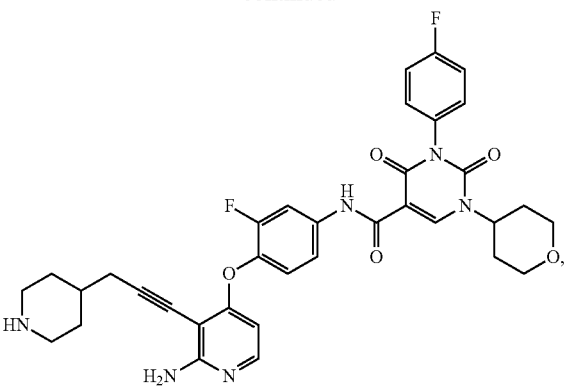

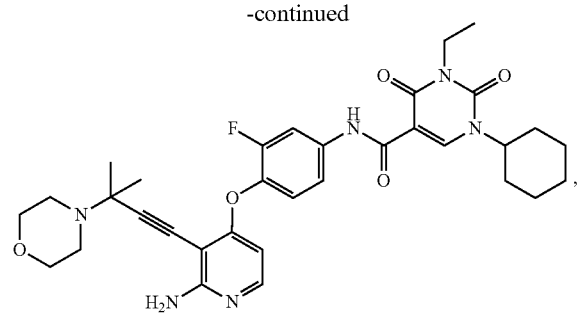

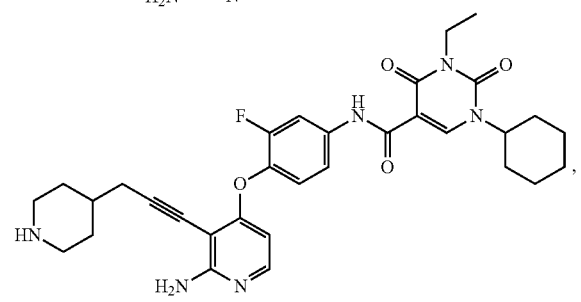

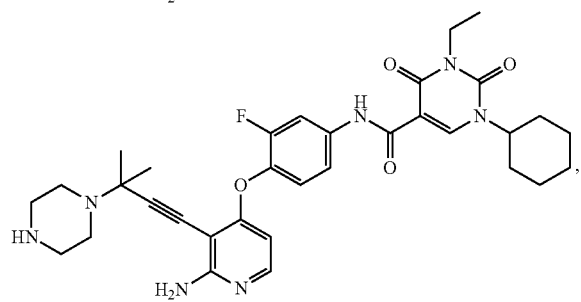

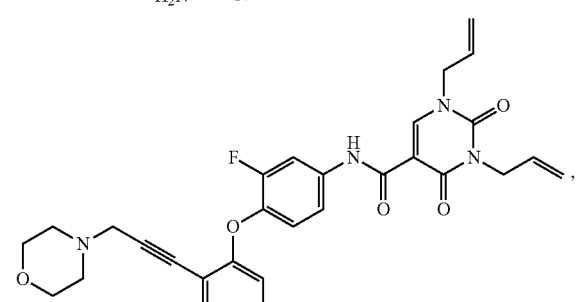

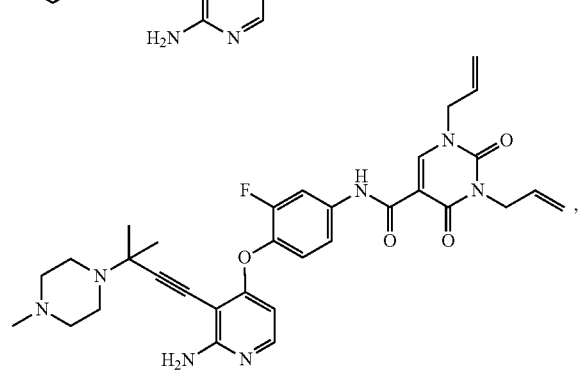

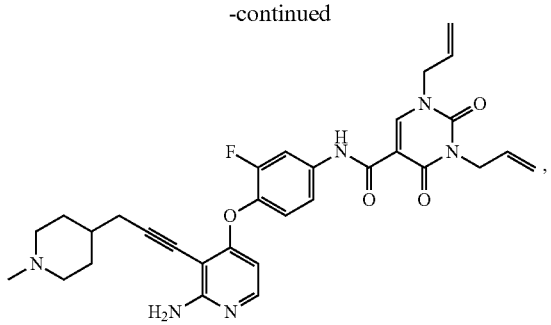

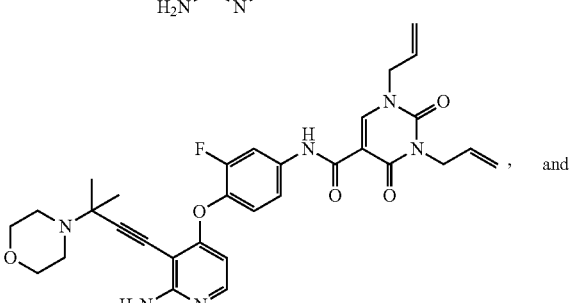

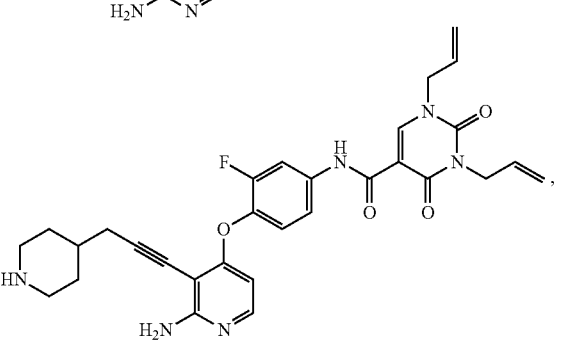

, and

, or a pharmaceutically acceptable salt thereof.

17. A pharmaceutical composition comprising at least one compound of claim 1 or a pharmaceutically acceptable salt thereof and a pharmaceutically acceptable carrier.

18. A method of treating or prophylaxis of an AXL-, Mer- and/or c-Met-mediated disease in a subject, wherein the disease is selected from the group consisting of papillary thyroid carcinoma, pancreatic cancer, lung cancer, colon cancer, breast carcinoma, neuroblastoma, pain, cachexia, dermatitis, and asthma, the method comprising administering a pharmaceutically effective amount of the compound of claim 1 or a pharmaceutically acceptable salt thereof to a subject in need of such treatment.

19. The method of claim 18, wherein the lung cancer is non-small cell lung cancer.

20. A method of inhibiting a AXL, Mer, and/or c-Met enzyme in a cell, the method comprising administering a pharmaceutically effective amount of the compound of claim 1 or a pharmaceutically acceptable salt thereof to a cell in need of such inhibition.

\* \* \* \* \*